United States Patent
Zhang et al.

(10) Patent No.: US 12,350,368 B2
(45) Date of Patent: Jul. 8, 2025

(54) DELIVERY OF LARGE PAYLOADS

(71) Applicants: The Broad Institute, Inc., Cambridge, MA (US); Massachusetts Institute of Technology, Cambridge, MA (US); Trustees of Tufts College, Medford, MA (US)

(72) Inventors: Feng Zhang, Cambridge, MA (US); Sourav Choudhury, Cambridge, MA (US); Qiaobing Xu, Medford, MA (US)

(73) Assignees: The Broad Institute, Inc., Cambridge, MA (US); Massachusetts Institute of Technology, Cambridge, MA (US); Trustees of Tufts College, Medford, MA (US)

( * ) Notice: Subject to any disclaimer, the term of this patent is extended or adjusted under 35 U.S.C. 154(b) by 1641 days.

(21) Appl. No.: 16/604,711

(22) PCT Filed: Apr. 16, 2018

(86) PCT No.: PCT/US2018/027793
§ 371 (c)(1),
(2) Date: Oct. 11, 2019

(87) PCT Pub. No.: WO2018/191750
PCT Pub. Date: Oct. 18, 2018

(65) Prior Publication Data
US 2020/0405639 A1 Dec. 31, 2020

Related U.S. Application Data

(60) Provisional application No. 62/485,625, filed on Apr. 14, 2017.

(51) Int. Cl.
| | |
|---|---|
| C12N 5/00 | (2006.01) |
| A61K 9/1271 | (2025.01) |
| A61K 39/00 | (2006.01) |
| C12N 9/22 | (2006.01) |
| C12N 15/10 | (2006.01) |
| C12N 15/86 | (2006.01) |

(52) U.S. Cl.
CPC .......... *A61K 9/1271* (2013.01); *C12N 9/22* (2013.01); *C12N 15/102* (2013.01); *C12N 15/86* (2013.01); *C12N 2750/14133* (2013.01); *C12N 2750/14142* (2013.01); *C12N 2750/14143* (2013.01)

(58) Field of Classification Search
None
See application file for complete search history.

(56) References Cited

U.S. PATENT DOCUMENTS

| | | |
|---|---|---|
| 5,580,859 A | 12/1996 | Felgner et al. |
| 5,589,466 A | 12/1996 | Felgner et al. |
| 5,593,972 A | 1/1997 | Weiner et al. |
| 5,846,946 A | 12/1998 | Huebner et al. |
| 6,740,525 B2 | 5/2004 | Roelvink et al. |
| 6,911,199 B2 | 6/2005 | Vigne et al. |
| 7,256,036 B2 | 8/2007 | Legrand et al. |
| 7,259,015 B2 | 8/2007 | Kingsman et al. |
| 7,303,910 B2 | 12/2007 | Bebbington et al. |
| 7,344,872 B2 | 3/2008 | Gao et al. |
| 7,351,585 B2 | 4/2008 | Mitrophanous et al. |
| 7,745,651 B2 | 6/2010 | Heyes et al. |
| 7,799,565 B2 | 9/2010 | MacLachlan et al. |
| 7,803,397 B2 | 9/2010 | Heyes et al. |
| 7,838,658 B2 | 11/2010 | MacLachlan et al. |
| 7,901,708 B2 | 3/2011 | MacLachlan et al. |
| 7,915,399 B2 | 3/2011 | MacLachlan et al. |
| 7,982,027 B2 | 7/2011 | MacLachlan et al. |
| 8,058,069 B2 | 11/2011 | Yaworski et al. |
| 8,071,082 B2 | 12/2011 | Zugates et al. |
| 8,101,741 B2 | 1/2012 | MacLachlan et al. |
| 8,188,263 B2 | 5/2012 | MacLachlan et al. |
| 8,236,943 B2 | 8/2012 | Lee et al. |
| 8,283,333 B2 | 10/2012 | Yaworski et al. |
| 8,404,658 B2 | 3/2013 | Hajjar et al. |
| 8,454,972 B2 | 6/2013 | Nabel et al. |
| 8,697,359 B1 | 4/2014 | Zhang |
| 8,771,945 B1 | 7/2014 | Zhang |
| 8,795,965 B2 | 8/2014 | Zhang |

(Continued)

FOREIGN PATENT DOCUMENTS

| | | |
|---|---|---|
| EP | 1 519 714 A1 | 4/2005 |
| EP | 1 664 316 A1 | 6/2006 |

(Continued)

OTHER PUBLICATIONS

Luyao Wang et al, (International Journal of Molecular Sciences, 2016, p. 626).*

(Continued)

*Primary Examiner* — Agnieszka Boesen
(74) *Attorney, Agent, or Firm* — F. Brent Nix, Esq.; Johnson, Marcou, Isaacs & Nix, LLC; Erin M. Daly, Esq.

(57) ABSTRACT

The disclosure includes non-naturally occurring or engineered CRISPR systems and proteins, associated with a delivery system comprising a virus component and a lipid component. The disclosure includes CRISPR proteins associated with capsid proteins, e.g., AAV VP1VP2, and/or VP3, on the surface of or internal to the AAV, along with compositions, systems and complexes involving the AAV-CRISPR protein, nucleic acid molecules and vectors encoding the same, deliver}-systems, and uses therefor.

31 Claims, 23 Drawing Sheets

Specification includes a Sequence Listing.

(56) References Cited

U.S. PATENT DOCUMENTS

| | | |
|---|---|---|
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,410,129 B2 | 8/2016 | Ranki et al. |
| 2002/0150626 A1 | 10/2002 | Kohane et al. |
| 2004/0013648 A1 | 1/2004 | Kingsman et al. |
| 2005/0019923 A1 | 1/2005 | Uchegbu et al. |
| 2005/0123596 A1 | 6/2005 | Kohane et al. |
| 2006/0281180 A1 | 12/2006 | Radcliffe et al. |
| 2007/0025970 A1 | 2/2007 | Kingsman et al. |
| 2007/0054961 A1 | 3/2007 | Maden et al. |
| 2008/0267903 A1 | 10/2008 | Uchegbu et al. |
| 2009/0007284 A1 | 1/2009 | Radcliffe et al. |
| 2009/0017543 A1 | 1/2009 | Wilkes et al. |
| 2009/0111106 A1 | 4/2009 | Mitrophanous et al. |
| 2009/0215879 A1 | 8/2009 | Diprimio et al. |
| 2010/0129793 A1 | 5/2010 | Mirkin et al. |
| 2010/0317109 A1 | 12/2010 | Maden et al. |
| 2011/0023139 A1 | 1/2011 | Weinstein et al. |
| 2011/0117189 A1 | 5/2011 | Mazzone et al. |
| 2011/0212179 A1 | 9/2011 | Liu |
| 2011/0293571 A1 | 12/2011 | Widdowson et al. |
| 2011/0293703 A1 | 12/2011 | Mahon et al. |
| 2012/0251618 A1 | 10/2012 | Schrum et al. |
| 2012/0295960 A1 | 11/2012 | Palfi et al. |
| 2013/0244279 A1 | 9/2013 | de Fougerolles et al. |
| 2013/0245107 A1 | 9/2013 | de Fougerolles et al. |
| 2013/0252281 A1 | 9/2013 | de Fougerolles et al. |
| 2013/0302401 A1 | 11/2013 | Zhang |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0301951 A1 | 10/2014 | Liu et al. |
| 2014/0308304 A1 | 10/2014 | Manoharan et al. |
| 2014/0310830 A1 | 10/2014 | Zhang et al. |
| 2014/0328759 A1 | 11/2014 | Cullis et al. |
| 2014/0348900 A1 | 11/2014 | Zhu |
| 2015/0071903 A1 | 3/2015 | Liu et al. |
| 2015/0105538 A1 | 4/2015 | Chromy et al. |
| 2015/0118216 A1 | 4/2015 | Liu et al. |
| 2015/0140070 A1 | 5/2015 | Heartlein et al. |
| 2015/0232883 A1 | 8/2015 | Dahlman et al. |
| 2015/0250725 A1 | 9/2015 | Bader et al. |
| 2016/0082126 A1 | 3/2016 | Xu et al. |
| 2016/0129120 A1 | 5/2016 | Xu et al. |
| 2016/0174546 A1 | 6/2016 | Berg et al. |
| 2016/0200779 A1 | 7/2016 | Liu et al. |
| 2016/0244761 A1 | 8/2016 | Payne et al. |
| 2016/0251648 A1 | 9/2016 | Wang et al. |
| 2016/0257951 A1 | 9/2016 | Koizumi et al. |
| 2016/0367686 A1 | 12/2016 | Anderson et al. |
| 2017/0079916 A1 | 3/2017 | Khan et al. |
| 2017/0306335 A1 | 10/2017 | Zhang et al. |

FOREIGN PATENT DOCUMENTS

| | | |
|---|---|---|
| EP | 1 766 035 A1 | 3/2007 |
| EP | 1 781 593 A2 | 5/2007 |
| EP | 2 784 162 A1 | 10/2014 |
| EP | 2 771 468 B1 | 2/2015 |
| EP | 2 784 162 B1 | 4/2015 |
| EP | 2 764 103 A2 | 8/2015 |
| WO | 2005/121348 A1 | 12/2005 |
| WO | 2008/042973 A2 | 4/2008 |
| WO | 2013/093648 A2 | 6/2013 |
| WO | 2014/018423 A2 | 1/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/186348 A2 | 11/2014 |
| WO | 2014/186366 A1 | 11/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2015/065964 A1 | 5/2015 |
| WO | 2015/089419 A2 | 6/2015 |
| WO | 2015/089462 A1 | 6/2015 |
| WO | 2015/089486 A2 | 6/2015 |
| WO | 2016/027264 A1 | 2/2016 |
| WO | 2018035387 A1 | 2/2018 |
| WO | 2018035388 A1 | 2/2018 |

OTHER PUBLICATIONS

Yin et al. (Nature Biotechnology, 2016, vol. 34, p. 328-334).*
Condezo et al. (Journal of Virology, 2015, vol. 89, p. 9653-9664).*
Al-Jamal et al., (Accounts of Chemical Research, 2011, p. 1094-1104).*
2011.*
The Broad Institute Inc., "Notification of Transmittal of the International Search Report and the Written Opinion of the International Searching Authority, or the Declaration for PCT/US2018/027793", Oct. 31, 2018, 17 pages.
Fein, et al., "Cationic Lipid Formulations Alter the In Vivo Tropism of AAV2/9 Vector in Lung", Molecular Therapy, vol. 17, No. 12, Dec. 28, 2009, pp. 2078-2087.
Wang, et al., "In Vivo Delivery Systems for Therapeutic Genome Editing", International Journal of Molecular Statistics, vol. 17, No. 626, 2016, 19 pages.
Yin, et al., "Therapeutic Genome Editing by Combined Viral and Non-Viral Delivery of CRISPR System Components in Vivo", Nature Biotechnology, vol. 34, No. 3, Feb. 1, 2016, pp. 328-333.
The Broad Institute, Inc., "Notification Concerning Transmittal of International Preliminary Report on Patentability for PCT/US2018/027793", Oct. 24, 2019, 9 pages.
Gao, et al., "Antibody-Targeted Immunoliposomes for Cancer Treatment", Mini-Reviews in Medicinal Chemistry, vol. 13, No. 14, Dec. 2013, 2026-2035.
Grimm, et al., "In Vitro and In Vivo Gene Therapy Vector Evolution via Multispecies Interbreeding and Retargeting of Adeno-Associated Viruses", Journal of Virology, vol. 82, No. 12, Jun. 2008, 5887-5911.
Lux, et al., "Green Fluorescent Protein-Tagged Adeno-Associated Virus Particles Allow the Study of Cytosolic and Nuclear Trafficking", Journal of Virology, vol. 79, No. 18, Sep. 2005, 11776-11787.
Manjappa, et al., "Antibody Derivatization and Conjugation Strategies: Application in Preparation of Stealth Immunoliposome to

(56) References Cited

OTHER PUBLICATIONS

Target Chemotherapeutics to Tumor", Journal of Controlled Release, vol. 150, No. 1, Feb. 28, 2011, 2-22.

Matthews, et al., "Capsid-Incorporation of Antigens into Adenovirus Capsid Proteins for a Vaccine Approach", Molecular Pharmaceutics, vol. 8, No. 1, Feb. 7, 2011, 3-11.

Molavi, et al., "Anti-CD30 Antibody Conjugated Liposomal Doxorubicin with Significantly Improved Therapeutic Efficacy against Anaplastic Large Cell Lymphoma", Biomaterials, vol. 34, No. 34, Nov. 2013, 8718-8725.

Munch, et al., "Displaying High-Affinity Ligands on Adeno-Associated Viral Vectors Enables Tumor Cell-Specific and Safe Gene Transfer", Molecular Therapy, vol. 21, No. 1, Jan. 2013, 109-118.

Nance, et al., "Perspective on Adeno-Associated Virus Capsid Modification for Duchenne Muscular Dystrophy Gene Therapy", Human Gene Therapy, vol. 26, No. 12, Dec. 2015, 786-800.

Rybniker, et al., "Incorporation of Antigens into Viral Capsids Augments Immunogenicity of Adeno-Associated Virus Vector-Based Vaccines", Journal of Virology, vol. 86, No. 24, Dec. 2012, 13800-13804.

Sofou, et al., "Antibody-Targeted Liposomes in Cancer Therapy and Imaging", Expert Opinion on Drug Delivery, vol. 5, No. 2, Feb. 2008, 189-204.

Sonoke, et al., "Galactose-Modified Cationic Liposomes as a Liver-Targeting Delivery System for Small Interfering RNA", Biological and Pharmaceutical Bulletin, vol. 34, No. 8, 2011, 1338-1342.

Surace, et al., "Lipoplexes Targeting the CD44 Hyaluronic Acid Receptor for Efficient Transfection of Breast Cancer Cells", Molecular Pharmaceutics, vol. 6, No. 4, Jul.-Aug. 2009, 1062-1073.

Torchilin, et al., "Antibody-Modified Liposomes for Cancer Chemotherapy", Expert Opinion on Drug Delivery, vol. 5. No. 9, Sep. 2008, 1003-10025.

Wang, et al., "A Combinatorial Library of Unsaturated Lipidoids for Efficient Intracellular Gene Delivery", ACS Synthetic Biology, vol. 1, No. 9, May 25, 2012, 403-407.

Wang, et al., "Efficient Delivery of Genome-Editing Proteins using Bioreducible Lipid Nanoparticles", Proceedings of the National Academy of Sciences of the United States of America, vol. 113, No. 11, Mar. 15, 2016, 2868-2873.

Warrington, et al., "Adeno-Associated Virus Type 2 VP2 Capsid Protein is Nonessential and can Tolerate Large Peptide Insertions at Its N Terminus", Journal of Virology, vol. 78, No. 12, Jun. 2004, 6595-6609.

* cited by examiner

Mangeot, et.al. Mol. Ther. 2011

A.

B.

C.

D.

E.

DELIVERY OF LARGE PAYLOADS

RELATED APPLICATIONS AND INCORPORATION BY REFERENCE

This application claims priority to and benefit of U.S. Provisional Patent Application 62/485,625 filed Apr. 14, 2017.

All documents cited herein or in any applications cited herein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FEDERAL FUNDING LEGEND

This invention was made with government support under grant numbers MH100706 and MH110049 awarded by the National Institutes of Health. The government has certain rights in the invention.

FIELD OF THE INVENTION

The present inventions generally relate to delivery of large payloads and includes novel delivery particles, particularly using lipid and viral particle, and also novel viral capsids, both suitable to deliver large payloads, such as Clustered Regularly Interspaced Short Palindromic Repeats (CRISPR), CRISPR protein (e.g., Cas, Cas9, Cpf1, Cas13a, Cas13b and the like), CRISPR-Cas or CRISPR system or CRISPR-Cas complex, components thereof, nucleic acid molecules, e.g., vectors, involving the same and uses of all of the foregoing, amongst other aspects.

BACKGROUND OF THE INVENTION

Advances in genome sequencing techniques and analysis methods have significantly accelerated the ability to catalog and map genetic factors associated with a diverse range of biological functions and diseases. Precise genome targeting technologies are needed to enable systematic reverse engineering of causal genetic variations by allowing selective perturbation of individual genetic elements, as well as to advance synthetic biology, biotechnological, and medical applications. There remains a need for new genome engineering technologies.

Citation or identification of any document in this application is not an admission that such document is available as prior art to the present invention.

SUMMARY OF THE INVENTION

There exists a pressing need for alternative and robust systems and techniques for sequence targeting with a wide array of applications. This invention addresses this need and provides related advantages. CRISPR systems, such as the CRISPR/Cas or the CRISPR-Cas system (both terms may be used interchangeably throughout this application) do not require the generation of customized proteins to target specific sequences but rather a single CRISPR enzyme can be programmed by a short RNA molecule to recognize a specific nucleic acid target, such as DNA or RNA target, in other words the CRISPR enzyme can be recruited to a specific nucleic acid target using said short RNA molecule. Adding the CRISPR system to the repertoire of genome sequencing techniques and analysis methods may significantly simplify the methodology and accelerate the ability to catalog and map genetic factors associated with a diverse range of biological functions and diseases. To utilize the CRISPR system effectively for genome editing without deleterious effects, it is critical to understand aspects of engineering and optimization of these genome engineering tools, which are aspects of the claimed invention.

In an aspect, the invention provides a particle delivery system comprising a hybrid virus capsid protein or hybrid viral outer protein, wherein the hybrid virus capsid or outer protein comprises a virus capsid or outer protein attached to at least a portion of a non-capsid protein or peptide. The genetic material of a virus is stored within a viral structure called the capsid. The capsid of certain viruses are enclosed in a membrane called the viral envelope. The viral envelope is made up of a lipid bilayer embedded with viral proteins including viral glycoproteins. As used herein, an "envelope protein" or "outer protein" means a protein exposed at the surface of a viral particle that is not a capsid protein. For example envelope or outer proteins typically comprise proteins embedded in the envelope of the virus. Non-limiting examples of outer or envelope proteins include, without limit, gp41 and gp 120 of HIV, hemagglutinin, neuraminidase and M2 proteins of influenza virus.

In an embodiment of the delivery system, the non-capsid protein or peptide has a molecular weight of up to a megadalton, or has a molecular weight in the range of 110 to 160 kDa, 160 to 200 kDa, 200 to 250 kDa, 250 to 300 kDa, 300 to 400 kDa, or 400 to 500 kDa, the non-capsid protein or peptide comprises a CRISPR protein.

In an embodiment of the delivery system, the virus is an Adenoviridae or a Parvoviridae or a retrovirus or a Rhabdoviridae or an enveloped virus having a glycoprotein protein (G protein).

In an embodiment of the delivery system, the virus is an adeno-associated virus (AAV) or an adenovirus.

In an embodiment of the delivery system, the virus is lentivirus or murine leukemia virus (MuMLV).

In an embodiment of the delivery system, the virus is VSV or rabies virus.

In an embodiment of the delivery system, the capsid or outer protein comprises a capsid protein having VP1, VP2 or VP3.

In an embodiment of the delivery system, the capsid protein is VP3, and the non-capsid protein is inserted into or attached to VP3 loop 3 or loop 6.

In an embodiment of the delivery system, the virus is delivered to the interior of a cell.

In an embodiment of the delivery system, the capsid or outer protein and the non-capsid protein can dissociate after delivery into a cell.

In an embodiment of the delivery system, the capsid or outer protein is attached to the protein by a linker.

In an embodiment of the delivery system, the linker comprises amino acids.

In an embodiment of the delivery system, the linker is a chemical linker.

In an embodiment of the delivery system, the linker is cleavable.

In an embodiment of the delivery system, the linker is biodegradable.

In an embodiment of the delivery system, the linker comprises (GGGGS) 1-3, ENLYFQG, or a disulfide.

In an embodiment, the delivery system comprises a protease or nucleic acid molecule(s) encoding a protease that is expressed, said protease being capable of cleaving the linker, whereby there can be cleavage of the linker. In an embodiment of the invention, a protease is delivered with a particle component of the system, for example packaged, mixed with, or enclosed by lipid and/or capsid. Entry of the particle into a cell is thereby accompanied or followed by cleavage and dissociation of payload from particle. In certain embodiments, an expressible nucleic acid encoding a protease is delivered, whereby at entry or following entry of the particle into a cell, there is protease expression, linker cleavage, and dissociation of payload from capsid. In certain embodiments, dissociation of payload occurs with viral replication. In certain embodiments, dissociation of payload occurs in the absence of productive virus replication.

In an embodiment of the delivery system, each terminus of a CRISPR protein is attached to the capsid or outer protein by a linker.

In an embodiment of the delivery system, the non-capsid protein is attached to the exterior portion of the capsid or outer protein.

In an embodiment of the delivery system, the non-capsid protein is attached to the interior portion of the capsid or outer protein.

In an embodiment of the delivery system, the capsid or outer protein and the non-capsid protein are a fusion protein.

In an embodiment of the delivery system, the non-capsid protein is encapsulated by the capsid or outer protein.

In an embodiment of the delivery system, the non-capsid protein is attached to a component of the capsid protein or a component of the outer protein prior to formation of the capsid or the outer protein.

In an embodiment of the delivery system, the protein is attached to the capsid or outer protein after formation of the capsid or outer protein.

In an embodiment, the delivery system comprises a targeting moiety, such as active targeting of a lipid entity of the invention, e.g., lipid particle or nanoparticle or liposome or lipid bylayer of the invention comprising a targeting moiety for active targeting.

With regard to targeting moieties, mention is made of Deshpande et al, "Current trends in the use of liposomes for tumor targeting," Nanomedicine (Lond). 8 (9), doi: 10.2217/nnm.13.118 (2013), and the documents it cites, all of which are incorporated herein by reference. Mention is also made of WO/2016/027264, and the documents it cites, all of which are incorporated herein by reference. And mention is made of Lorenzer et al, "Going beyond the liver: Progress and challenges of targeted delivery of siRNA therapeutics," Journal of Controlled Release, 203:1-15 (2015), and the documents it cites, all of which are incorporated herein by reference.

An actively targeting lipid particle or nanoparticle or liposome or lipid bylayer delivery system (generally as to embodiments of the invention, "lipid entity of the invention" delivery systems) are prepared by conjugating targeting moieties, including small molecule ligands, peptides and monoclonal antibodies, on the lipid or liposomal surface; for example, certain receptors, such as folate and transferrin (Tf) receptors (TfR), are overexpressed on many cancer cells and have been used to make liposomes tumor cell specific. Liposomes that accumulate in the tumor microenvironment can be subsequently endocytosed into the cells by interacting with specific cell surface receptors. To efficiently target liposomes to cells, such as cancer cells, it is useful that the targeting moiety have an affinity for a cell surface receptor and to link the targeting moiety in sufficient quantities to have optimum affinity for the cell surface receptors; and determining these aspects are within the ambit of the skilled artisan. In the field of active targeting, there are a number of cell-, e.g., tumor-, specific targeting ligands.

Also as to active targeting, with regard to targeting cell surface receptors such as cancer cell surface receptors, targeting ligands on liposomes can provide attachment of liposomes to cells, e.g., vascular cells, via a noninternalizing epitope; and, this can increase the extracellular concentration of that which is being delivered, thereby increasing the amount delivered to the target cells. A strategy to target cell surface receptors, such as cell surface receptors on cancer cells, such as overexpressed cell surface receptors on cancer cells, is to use receptor-specific ligands or antibodies. Many cancer cell types display upregulation of tumor-specific receptors. For example, TfRs and folate receptors (FRs) are greatly overexpressed by many tumor cell types in response to their increased metabolic demand. Folic acid can be used as a targeting ligand for specialized delivery owing to its ease of conjugation to nanocarriers, its high affinity for FRs and the relatively low frequency of FRs, in normal tissues as compared with their overexpression in activated macrophages and cancer cells, e.g., certain ovarian, breast, lung, colon, kidney and brain tumors. Overexpression of FR on macrophages is an indication of inflammatory diseases, such as psoriasis, Crohn's disease, rheumatoid arthritis and atherosclerosis; accordingly, folate-mediated targeting of the invention can also be used for studying, addressing or treating inflammatory disorders, as well as cancers. Folate-linked lipid particles or nanoparticles or liposomes or lipid by layers of the invention ("lipid entity of the invention") deliver their cargo intracellularly through receptor-mediated endocytosis. Intracellular trafficking can be directed to acidic compartments that facilitate cargo release, and, most importantly, release of the cargo can be altered or delayed until it reaches the cytoplasm or vicinity of target organelles. Delivery of cargo using a lipid entity of the invention having a targeting moiety, such as a folate-linked lipid entity of the invention, can be superior to nontargeted lipid entity of the invention. The attachment of folate directly to the lipid head groups may not be favorable for intracellular delivery of folate-conjugated lipid entity of the invention, since they may not bind as efficiently to cells as folate attached to the lipid entity of the invention surface by a spacer, which may can enter cancer cells more efficiently. A lipid entity of the invention coupled to folate can be used for the delivery of complexes of lipid, e.g., liposome, e.g., anionic liposome and virus or capsid or envelope or virus outer protein, such as those herein discussed such as adenovirous or AAV. Tf is a monomeric serum glycoprotein of approximately 80 KDa involved in the transport of iron throughout the body. Tf binds to the TfR and translocates into cells via receptor-mediated endocytosis. The expression of TfR can be higher in certain cells, such as tumor cells (as compared with normal cells and is associated with the increased iron demand in rapidly proliferating cancer cells. Accordingly, the invention comprehends a TfR-targeted lipid entity of the invention, e.g., as to liver cells, liver cancer, breast cells such as breast cancer cells, colon such as colon cancer cells, ovarian cells such as ovarian cancer cells, head, neck and lung cells, such as head, neck and non-small-cell lung cancer cells, cells of the mouth such as oral tumor cells.

Also as to active targeting, a lipid entity of the invention can be multifunctional, i.e., employ more than one targeting moiety such as CPP, along with Tf; a bifunctional system; e.g., a combination of Tf and poly-L-arginine which can provide transport across the endothelium of the blood-brain barrier. EGFR, is a tyrosine kinase receptor belonging to the ErbB family of receptors that mediates cell growth, differentiation and repair in cells, especially non-cancerous cells, but EGF is overexpressed in certain cells such as many solid tumors, including colorectal, non-small-cell lung cancer, squamous cell carcinoma of the ovary, kidney, head, pancreas, neck and prostate, and especially breast cancer. The invention comprehends EGFR-targeted monoclonal antibody(ies) linked to a lipid entity of the invention. HER-2 is often overexpressed in patients with breast cancer, and is also associated with lung, bladder, prostate, brain and stomach cancers. HER-2, encoded by the ERBB2 gene. The invention comprehends a HER-2-targeting lipid entity of the invention, e.g., an anti-HER-2-antibody (or binding fragment thereof)-lipid entity of the invention, a HER-2-targeting-PEGylated lipid entity of the invention (e.g., having an anti-HER-2-antibody or binding fragment thereof), a HER-2-targeting-maleimide-PEG polymer-lipid entity of the invention (e.g., having an anti-HER-2-antibody or binding fragment thereof). Upon cellular association, the receptor-antibody complex can be internalized by formation of an endosome for delivery to the cytoplasm. With respect to receptor-mediated targeting, the skilled artisan takes into consideration ligand/target affinity and the quantity of receptors on the cell surface, and that PEGylation can act as a barrier against interaction with receptors. The use of antibody-lipid entity of the invention targeting can be advantageous. Multivalent presentation of targeting moieties can also increase the uptake and signaling properties of antibody fragments. In practice of the invention, the skilled person takes into account ligand density (e.g., high ligand densities on a lipid entity of the invention may be advantageous for increased binding to target cells). Preventing early by macrophages can be addressed with a sterically stabilized lipid entity of the invention and linking ligands to the terminus of molecules such as PEG, which is anchored in the lipid entity of the invention (e.g., lipid particle or nanoparticle or liposome or lipid by layer). The microenvironment of a cell mass such as a tumor microenvironment can be targeted; for instance, it may be advantageous to target cell mass vasculature, such as the the tumor vasculature microenvironment. Thus, the invention comprehends targeting VEGF. VEGF and its receptors are well-known proangiogenic molecules and are well-characterized targets for antiangiogenic therapy. Many small-molecule inhibitors of receptor tyrosine kinases, such as VEGFRs or basic FGFRs, have been developed as anticancer agents and the invention comprehends coupling any one or more of these peptides to a lipid entity of the invention, e.g., phage IVO peptide(s) (e.g., via or with a PEG terminus), tumor-homing peptide APRPG such as APRPG-PEG-modified. VCAM, the vascular endothelium plays a key role in the pathogenesis of inflammation, thrombosis and atherosclerosis. CAMs are involved in inflammatory disorders, including cancer, and are a logical target, E- and P-selectins, VCAM-1 and ICAMs. Can be used to target a lipid entity of the invention, e.g., with PEGylation. Matrix metalloproteases (MMPs) belong to the family of zinc-dependent endopeptidases. They are involved in tissue remodeling, tumor invasiveness, resistance to apoptosis and metastasis. There are four MMP inhibitors called TIMP1-4, which determine the balance between tumor growth inhibition and metastasis; a protein involved in the angiogenesis of tumor vessels is MT1-MMP, expressed on newly formed vessels and tumor tissues. The proteolytic activity of MT1-MMP cleaves proteins, such as fibronectin, elastin, collagen and laminin, at the plasma membrane and activates soluble MMPs, such as MMP-2, which degrades the matrix. An antibody or fragment thereof such as a Fab' fragment can be used in the practice of the invention such as for an antihuman MT1-MMP monoclonal antibody linked to a lipid entity of the invention, e.g., via a spacer such as a PEG spacer. αβ-Integrins or integrins are a group of transmembrane glycoprotein receptors that mediate attachment between a cell and its surrounding tissues or extracellular matrix. Integrins contain two distinct chains (heterodimers) called a-and-subunits. The tumor tissue-specific expression of integrin receptors can be been utilized for targeted delivery in the invention, e.g., whereby the targeting moiety can be an RGD peptide such as a cyclic RGD. Aptamers are ssDNA or RNA oligonucleotides that impart high affinity and specific recognition of the target molecules by electrostatic interactions, hydrogen bonding and hydro phobic interactions as opposed to the Watson-Crick base pairing, which is typical for the bonding interactions of oligonucleotides. Aptamers as a targeting moiety can have advantages over antibodies: aptamers can demonstrate higher target antigen recognition as compared with antibodies; aptamers can be more stable and smaller in size as compared with antibodies; aptamers can be easily synthesized and chemically modified for molecular conjugation; and aptamers can be changed in sequence for improved selectivity and can be developed to recognize poorly immunogenic targets. Such moieties as a sgc8 aptamer can be used as a targeting moiety (e.g., via covalent linking to the lipid entity of the invention, e.g., via a spacer, such as a PEG spacer). The targeting moiety can be stimuli-sensitive, e.g., sensitive to an externally applied stimuli, such as magnetic fields, ultrasound or light; and pH-triggering can also be used, e.g., a labile linkage can be used between a hydrophilic moiety such as PEG and a hydrophobic moiety such as a lipid entity of the invention, which is cleaved only upon exposure to the relatively acidic conditions characteristic of the particular environment or microenvironment such as an endocytic vacuole or the acidotic tumor mass. pH-sensitive copolymers can also be incorporated in embodiments of the invention can provide shielding; diortho esters, vinyl esters, cysteine-cleavable lipopolymers, double esters and hydrazones are a few examples of pH-sensitive bonds that are quite stable at pH 7.5, but are hydrolyzed relatively rapidly at pH 6 and below, e.g., a terminally alkylated copolymer of N-isopropylacrylamide and methacrylic acid that copolymer facilitates destabilization of a lipid entity of the invention and release in compartments with decreased pH value; or, the invention comprehends ionic polymers for generation of a pH-responsive lipid entity of the invention (e.g., poly (methacrylic acid), poly(diethylaminoethyl methacrylate), poly(acrylamide) and poly(acrylic acid)). Temperature-triggered delivery is also within the ambit of the invention. Many pathological areas, such as inflamed tissues and tumors, show a distinctive hyperthermia compared with normal tissues. Utilizing this hyperthermia is an attractive strategy in cancer therapy since hyperthermia is associated with increased tumor permeability and enhanced uptake. This technique involves local heating of the site to increase microvascular pore size and blood flow, which, in turn, can result in an increased extravasation of embodiments of the invention. Temperature-sensitive lipid entity of the invention can be prepared from thermosensitive lipids or polymers with a low critical solution temperature. Above the low critical solution temperature (e.g., at site such as tumor site or inflamed tissue site), the polymer precipitates, disrupting the liposomes to release. Lipids with a specific gel-to-liquid phase transition temperature are used to prepare these lipid entities of the invention; and a lipid for a thermosensitive embodiment can be dipalmitoylphosphatidylcholine. Thermosensitive polymers can also facilitate destabilization followed by release, and a useful thermosensitive polymer is poly(N-isopropylacrylamide). Another temperature triggered system can employ lysolipid temperature-sensitive liposomes. The invention also comprehends redox-triggered delivery: The difference in redox potential between normal and inflamed or tumor tissues, and between the intra- and extra-cellular environments has been exploited for delivery; e.g., GSH is a reducing agent abundant in cells, especially in the cytosol, mitochondria and nucleus. The GSH concentrations in blood and extracellular matrix are just one out of 100 to one out of 1000 of the intracellular concentration, respectively. This high redox potential difference caused by GSH, cysteine and other reducing agents can break the reducible bonds, destabilize a lipid entity of the invention and result in release of payload. The disulfide bond can be used as the cleavable/reversible linker in a lipid entity of the invention, because it causes sensitivity to redox owing to the dissulfeto-thiol reduction reaction; a lipid entity of the invention can be made reduction sensitive by using two (e.g., two forms of a disulfide-conjugated multifunctional lipid as cleavage of the disulfide bond (e.g., via tris(2-carboxyethyl) phosphine, dithiothreitol, L-cysteine or GSH), can cause removal of the hydrophilic head group of the conjugate and alter the membrane organization leading to release of payload. Calcein release from reduction-sensitive lipid entity of the invention containing a disulfide conjugate can be more useful than a reduction-insensitive embodiment. Enzymes can also be used as a trigger to release payload. Enzymes, including MMPs (e.g. MMP2), phospholipase A2, alkaline phosphatase, transglutaminase or phosphatidylinositol-specific phospholipase C, have been found to be overexpressed in certain tissues, e.g., tumor tissues. In the presence of these enzymes, specially engineered enzyme-sensitive lipid entity of the invention can be disrupted and release the payload. An MMP2-cleavable octapeptide (Gly-Pro-Leu-Gly-Ile-Ala-Gly-Gln) can be incorporated into a linker, and can have antibody targeting, e.g., antibody 2C5. The invention also comprehends light- or energy-triggered delivery, e.g., the lipid entity of the invention can be light-sensitive, such that light or energy can facilitate structural and conformational changes, which lead to direct interaction of the lipid entity of the invention with the target cells via membrane fusion, photo-isomerism, photofragmentation or photopolymerization; such a moiety therefor can be benzoporphyrin photosensitizer. Ultrasound can be a form of energy to trigger delivery; a lipid entity of the invention with a small quantity of particular gas, including air or perfluorated hydrocarbon can be triggered to release with ultrasound, e.g., low-frequency ultrasound (LFUS). Magnetic delivery: A lipid entity of the invention can be magnetized by incorporation of magnetites, such as $Fe_3O_4$ or $\gamma\text{-}Fe_2O_3$, e.g., those that are less than 10 nm in size. Targeted delivery can be then by exposure to a magnetic field.

Also as to active targeting, the invention also comprehends intracellular delivery. Since liposomes follow the endocytic pathway, they are entrapped in the endosomes (pH 6.5-6) and subsequently fuse with lysosomes (pH<5), where they undergo degradation that results in a lower therapeutic potential. The low endosomal pH can be taken advantage of to escape degradation. Fusogenic lipids or peptides, which destabilize the endosomal membrane after the conformational transition/activation at a lowered pH. Amines are protonated at an acidic pH and cause endosomal swelling and rupture by a buffer effect Unsaturated dioleoylphosphatidylethanolamine (DOPE) readily adopts an inverted hexagonal shape at a low pH, which causes fusion of liposomes to the endosomal membrane. This process destabilizes a lipid entity containing DOPE and releases the cargo into the cytoplasm; fusogenic lipid GALA, cholesteryl-GALA and PEG-GALA may show a highly efficient endosomal release; a pore-forming protein listeriolysin O may provide an endosomal escape mechanism; and, histidine-rich peptides have the ability to fuse with the endosomal membrane, resulting in pore formation, and can buffer the proton pump causing membrane lysis.

Also as to active targeting, cell-penetrating peptides (CPPs) facilitate uptake of macromolecules through cellular membranes and, thus, enhance the delivery of CPP-modified molecules inside the cell. CPPs can be split into two classes: amphipathic helical peptides, such as transportan and MAP, where lysine residues are major contributors to the positive charge; and Arg-rich peptides, such as TATp, Antennapedia or penetratin. TATp is a transcription-activating factor with 86 amino acids that contains a highly basic (two Lys and six Arg among nine residues) protein transduction domain, which brings about nuclear localization and RNA binding. Other CPPs that have been used for the modification of liposomes include the following: the minimal protein transduction domain of Antennapedia, a *Drosophila* homeoprotein, called penetratin, which is a 16-mer peptide (residues 43-58) present in the third helix of the homeodomain; a 27-amino acid-long chimeric CPP, containing the peptide sequence from the amino terminus of the neuropeptide galanin bound via the Lys residue, mastoparan, a wasp venom peptide; VP22, a major structural component of HSV-1 facilitating intracellular transport and transportan (18-mer) amphipathic model peptide that translocates plasma membranes of mast cells and endothelial cells by both energy-dependent and -independent mechanisms. The invention comprehends a lipid entity of the invention modified with CPP(s), for intracellular delivery that may proceed via energy dependent macropinocytosis followed by endosomal escape. The invention further comprehends organelle-specific targeting. A lipid entity of the invention surface-functionalized with the triphenylphosphonium (TPP) moiety or a lipid entity of the invention with a lipophilic cation, rhodamine 123 can be effective in delivery of cargo to mitochondria. DOPE/sphingomyelin/stearyl-octa-arginine can delivers cargos to the mitochondrial interior via membrane fusion. A lipid entity of the invention surface modified with a lysosomotropic ligand, octadecyl rhodamine B can deliver cargo to lysosomes. Ceramides are useful in inducing lysosomal membrane permeabilization; the invention comprehends intracellular delivery of a lipid entity of the invention having a ceramide. The invention further comprehends a lipid entity of the invention targeting the nucleus, e.g., via a DNA-intercalating moiety. The invention also comprehends multifunctional liposomes for targeting, i.e., attaching more than one functional group to the surface of the lipid entity of the invention, for instance to enhances accumulation in a desired site and/or promotes organelle-specific delivery and/or target a particular type of cell and/or respond to the local stimuli such as temperature (e.g., elevated), pH (e.g., decreased), respond to externally applied stimuli such as a magnetic field, light, energy, heat or ultrasound and/or promote intracellular delivery of the cargo. All of these are considered actively targeting moieties.

An embodiment of the invention includes the delivery system comprising an actively targeting lipid particle or nanoparticle or liposome or lipid bylayer delivery system; or comprising a lipid particle or nanoparticle or liposome or lipid bylayer comprising a targeting moiety whereby there is active targeting or wherein the targeting moiety is an actively targeting moiety. A targeting moiety can be one or more targeting moieties, and a targeting moiety can be for any desired type of targeting such as, e.g., to target a cell such as any herein-mentioned; or to target an organelle such as any herein-mentioned; or for targeting a response such as to a physical condition such as heat, energy, ultrasound, light, pH, chemical such as enzymatic, or magnetic stimuli; or to target to achieve a particular outcome such as delivery of payload to a particular location, such as by cell penetration.

It should be understood that as to each possible targeting or active targeting moiety herein-discussed, there is an aspect of the invention wherein the delivery system comprises such a targeting or active targeting moiety. Likewise, the following table provides exemplary targeting moieties that can be used in the practice of the invention an as to each an aspect of the invention provides a delivery system that comprises such a targeting moiety.

| Targeting Moiety | Target Molecule | Target Cell or Tissue |
|---|---|---|
| folate | folate receptor | cancer cells |
| transferrin | transferrin receptor | cancer cells |
| Antibody CC52 | rat CC531 | rat colon adenocarcinoma CC531 |
| anti-HER2 antibody | HER2 | HER2-overexpressing tumors |
| anti-GD2 | GD2 | neuroblastoma, melanoma |
| anti-EGFR | EGFR | tumor cells overexpressing EGFR |
| pH-dependent fusogenic peptide diINF-7 | | ovarian carcinoma |
| anti-VEGFR | VEGF Receptor | tumor vasculature |
| anti-CD19 | CD19 (B cell marker) | leukemia, lymphoma |
| cell-penetrating peptide | | blood-brain barrier |
| cyclic arginine-glycine-aspartic acid-tyrosine-cysteine peptide (c(RGDyC)-LP) | $\alpha v \beta 3$ | glioblastoma cells, human umbilical vein endothelial cells, tumor angiogenesis |
| ASSHN peptide | | endothelial progenitor cells; anti-cancer |
| PR_b peptide | $\alpha_5\beta_1$ integrin | cancer cells |
| AG86 peptide | $\alpha_6\beta_4$ integrin | cancer cells |
| KCCYSL (P6.1 peptide) | HER-2 receptor | cancer cells |
| affinity peptide LN (YEVGHRC) | Aminopeptidase N (APN/CD13) | APN-positive tumor |
| synthetic somatostatin analogue | Somatostatin receptor 2 (SSTR2) | breast cancer |
| anti-CD20 monoclonal antibody | B-lymphocytes | B cell lymphoma |

Thus, in an embodiment of the delivery system, the targeting moiety comprises a receptor ligand, such as, for example, hyaluronic acid for CD44 receptor, galactose for hepatocytes, or antibody or fragment thereof such as a binding antibody fragment against a desired surface receptor, and as to each of a targeting moiety comprising a receptor ligand, or an antibody or fragment thereof such as a binding fragment thereof, such as against a desired surface receptor, there is an aspect of the invention wherein the delivery system comprises a targeting moiety comprising a receptor ligand, or an antibody or fragment thereof such as a binding fragment thereof, such as against a desired surface receptor, or hyaluronic acid for CD44 receptor, galactose for hepatocytes (see, e.g., Surace et al, "Lipoplexes targeting the CD44 hyaluronic acid receptor for efficient transfection of breast cancer cells," J. Mol Pharm 6 (4): 1062-73; doi: 10.1021/mp800215d (2009); Sonoke et al, "Galactose-modified cationic liposomes as a liver-targeting delivery system for small interfering RNA," Biol Pharm Bull. 34 (8): 1338-42 (2011); Torchilin, "Antibody-modified liposomes for cancer chemotherapy," Expert Opin. Drug Deliv. 5 (9), 1003-1025 (2008); Manjappa et al, "Antibody derivatization and conjugation strategies: application in preparation of stealth immunoliposome to target chemotherapeutics to tumor," J. Control. Release 150 (1), 2-22 (2011); Sofou S "Antibody-targeted liposomes in cancer therapy and imaging," Expert Opin. Drug Deliv. 5 (2): 189-204 (2008); Gao J et al, "Antibody-targeted immunoliposomes for cancer treatment," Mini. Rev. Med. Chem. 13 (14): 2026-2035 (2013); Molavi et al, "Anti-CD30 antibody conjugated liposomal doxorubicin with significantly improved therapeutic efficacy against anaplastic large cell lymphoma," Biomaterials 34 (34): 8718-25 (2013), each of which and the documents cited therein are hereby incorporated herein by reference).

Moreover, in view of the teachings herein the skilled artisan can readily select and apply a desired targeting moiety in the practice of the invention as to a lipid entity of the invention. The invention comprehends an embodiment wherein the delivery system comprises a lipid entity having a targeting moiety.

In an embodiment of the delivery system, the protein comprises a CRISPR protein, or portion thereof.

In some embodiments a non-capsid protein or protein that is not a virus outer protein or a virus envelope (sometimes herein shorthanded as "non-capsid protein"), such as a CRISPR protein or portion thereof, can have one or more functional moiety (ies) thereon, such as a moiety for targeting or locating, such as an NLS or NES, or an activator or repressor.

In an embodiment of the delivery system, a protein or portion thereof can comprise a tag.

In an aspect, the invention provides a virus particle comprising a capsid or outer protein having one or more hybrid virus capsid or outer proteins comprising the virus capsid or outer protein attached to at least a portion of a non-capsid protein or a CRISPR protein.

In an aspect, the invention provides an in vitro method of delivery comprising contacting the delivery system with a cell, optionally a eukaryotic cell, whereby there is delivery into the cell of constituents of the delivery system.

In an aspect, the invention provides an in vitro, a research or study method of delivery comprising contacting the delivery system with a cell, optionally a eukaryotic cell, whereby there is delivery into the cell of constituents of the delivery system, obtaining data or results from the contacting, and transmitting the data or results.

In an aspect, the invention provides a cell from or of an in vitro method of delivery, wherein the method comprises contacting the delivery system with a cell, optionally a eukaryotic cell, whereby there is delivery into the cell of constituents of the delivery system, and optionally obtaining data or results from the contacting, and transmitting the data or results.

In an aspect, the invention provides a cell from or of an in vitro method of delivery, wherein the method comprises contacting the delivery system with a cell, optionally a eukaryotic cell, whereby there is delivery into the cell of constituents of the delivery system, and optionally obtaining data or results from the contacting, and transmitting the data or results; and wherein the cell product is altered compared to the cell not contacted with the delivery system, for example altered from that which would have been wild type of the cell but for the contacting.

In an embodiment, the cell product is non-human or animal.

In one aspect, the invention provides a particle delivery system comprising a composite virus particle, wherein the composite virus particle comprises a lipid, a virus capsid protein, and at least a portion of a non-capsid protein or peptide. The non-capsid peptide or protein can have a molecular weight of up to one megadalton.

In one embodiment, the particle delivery system comprises a virus particle adsorbed to a liposome or lipid particle or nanoparticle. In one embodiment, a virus is adsorbed to a liposome or lipid particle or nanoparticle either through electrostatic interactions, or is covalently linked through a linker. The lipid particle or nanoparticles (1 mg/ml) dissolved in either sodium acetate buffer (pH 5.2) or pure $H_2O$ (pH 7) are positively charged. The isoelectric point of most viruses is in the range of 3.5-7. They have a negatively charged surface in either sodium acetate buffer (pH 5.2) or pure $H_2O$. The electrostatic interaction between the virus and the liposome or synthetic lipid nanoparticle is the most significant factor driving adsorption. By modifying the charge density of the lipid nanoparticle, e.g. inclusion of neutral lipids into the lipid nanoparticle, it is possible to modulate the interaction between the lipid nanoparticle and the virus, hence modulating the assembly. In one embodiment, the liposome comprises a cationic lipid.

In one embodiment, the liposome of the particle delivery system comprises a CRISPR system component.

In one aspect, the invention provides a delivery system comprising one or more hybrid virus capsid proteins in combination with a lipid particle, wherein the hybrid virus capsid protein comprises at least a portion of a virus capsid protein attached to at least a portion of a non-capsid protein.

In one embodiment, the virus capsid protein of the delivery system is attached to a surface of the lipid particle. When the lipid particle is a bilayer, e.g., a liposome, the lipid particle comprises an exterior hydrophilic surface and an interior hydrophilic surface. In one embodiment, the virus capsid protein is attached to a surface of the lipid particle by an electrostatic interaction or by hydrophobic interaction.

In one embodiment, the particle delivery system has a diameter of 50-1000 nm, preferably 100-1000 nm.

In one embodiment, the delivery system comprises a non-capsid protein or peptide, wherein the non-capsid protein or peptide has a molecular weight of up to a megadalton. In one embodiment, the non-capsid protein or peptide has a molecular weight in the range of 110 to 160 kDa, 160 to 200 kDa, 200 to 250 kDa, 250 to 300 kDa, 300 to 400 kDa, or 400 to 500 kDa.

In one embodiment, the delivery system comprises a non-capsid protein or peptide, wherein the protein or peptide comprises a CRISPR protein or peptide. In one embodiment, the protein or peptide comprises a Cas9, a Cpf1 or a C2c2/Cas13a.

In one embodiment, a composite virus particle of the delivery system comprises a lipid, wherein the lipid comprises at least one cationic lipid.

In one embodiment, the delivery system comprises a lipid particle, wherein the lipid particle comprises at least one cationic lipid.

In one embodiment, a particle of the delivery system comprises a lipid layer, wherein the lipid layer comprises at least one cationic lipid.

As used herein, a "composite virus particle" means a virus particle that includes, at a minimum, at least a portion of a virus capsid protein, one or more lipids and a non-capsid protein or peptide. The lipid can be part of a liposome and the virus particle can be adsorbed to the liposome. In certain embodiments, the virus particle is attached to the lipid directly. Alternatively, the virus particle is attached to the lipid via a linker moiety. As used herein, "at least a portion of" means at least 50%, for example, 50%, 55%, 60%, 65%, 70%, 75%, 80%, 85%, 90% or 99%. "At least a portion of", as it refers to a virus capsid protein or a non-capsid protein, means of a length that is sufficient to allow the two proteins to attach, either directly or via a linker. "At least a portion of", as it refers to an outer protein or a non-capsid protein, means of a length that is sufficient to allow the two proteins to attach, either directly or via a linker. As used herein, a "lipid particle" is a particle comprised of lipid molecules. As used herein, a "lipid layer" means a layer of lipid molecules arranged side-by-side, preferably with charged groups aligned to one surface. For example, a biological membrane typically comprises two lipid layers, with hydrophobic regions arranged tail-to-tail, and charged regions exposed to an aqueous environment. Using a linker to covalently attach the skilled person from knowledge in the art and this disclosure can obtain 5-100% virus or capsid or virus outer protein or envelope attached to non-capsid or non-virus outer protein or non-envelope protein.

The lipid, lipid particle, or lipid bylayer or lipid entity of the invention can be prepared by methods well known in the art. See Wang et al., ACS Synthetic Biology, 1, 403-07 (2012); Wang et al., PNAS, 113 (11) 2868-2873 (2016); Manoharan, et al., WO 2008/042973; Zugates et al., U.S. Pat. No. 8,071,082; Xu et al., WO 2014/186366 A1 (US20160082126). Xu et provides a way to make a nanocomplex for the delivery of saporin wherein the nanocomplex comprising saporin and a lipid-like compound, and wherein the nanocomplex has a particle size of 50 nm to 1000 nm; the saporin binds to the lipid-like compound via non-covalent interaction or covalent bonding; and the lipid-like compound has a hydrophilic moiety, a hydrophobic moiety, and a linker joining the hydrophilic moiety and the hydrophobic moiety, the hydrophilic moiety being optionally charged and the hydrophobic moiety having 8 to 24 carbon atoms. Xu et al., WO 2014/186348 (US20160129120) provides examples of nanocomplexes of modified peptides or proteins comprising a cationic delivery agent and an anionic pharmaceutical agent, wherein the nanocomplex has a particle size of 50 to 1000 nm, the cationic delivery agent binds to the anionic pharmaceutical agent, and the anionic pharmaceutical agent is a modified peptide or protein formed of a peptide and a protein and an added chemical moiety that contains an anionic group. The added chemical moiety is linked to the peptide or protein via an amide group, an ester group, an ether group, a thioether group, a disulfide group, a hydrazone group, a sulfenate ester group, an amidine group, a urea group, a carbamate group, an imidoester group, or a carbonate group. More particularly these documents provide examples of lipid or lipid-like compounds that can be used to make the particle delivery system of the present invention, including compounds of the formula β1-K$_1$-A-K$_2$—B$_2$, in which A, the hydrophilic moiety, is

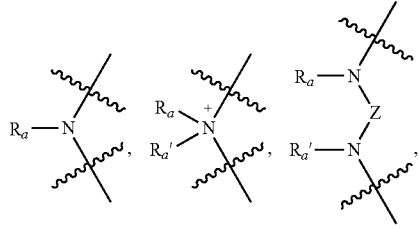

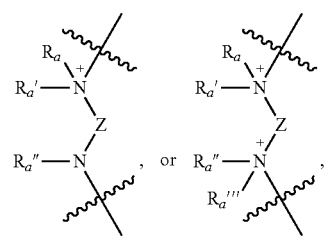

each of R$_a$, R$_a$', R$_a$", and R$_a$'" independently, being a C$_1$-C$_{20}$ monovalent aliphatic radical, a C$_1$-C$_{20}$ monovalent heteroaliphatic radical, a monovalent aryl radical, or a monovalent heteroaryl radical; and Z being a C$_1$-C$_{20}$ bivalent aliphatic radical, a C$_1$-C$_{20}$ bivalent heteroaliphatic radical, a bivalent aryl radical, or a bivalent heteroaryl radical; each of β1, the hydrophobic moiety, and B$_2$, also the hydrophobic moiety, independently, is a C$_{12-20}$ aliphatic radical or a C$_{12-20}$ heteroaliphatic radical; and each of K$_1$, the linker, and K$_2$, also the linker, independently, is O, S, Si, C$_1$-C$_6$ alkylene

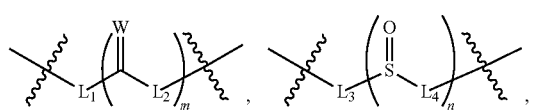

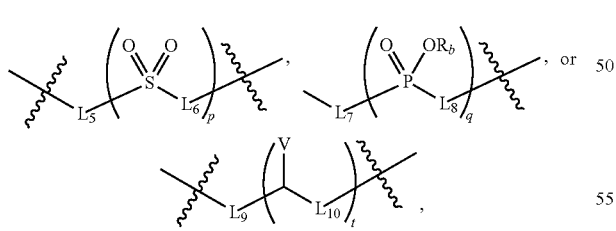

in which each of m, n, p, q, and t, independently, is 1-6; W is O, S, or NR$_C$; each of L$_1$, L$_3$, L$_5$, L$_7$, and L$_9$, independently, is a bond, O, S, or NR$_d$; each of L$_2$, L$_4$, L$_6$, L$_8$, and L$_{10}$, independently, is a bond, O, S, or NR$_e$; and V is OR$_f$, SR$_g$, or NR$_h$R$_i$, each of R$_b$, R$_c$, R$_a$, R$_e$, R$_f$, R$_g$, R$_h$, and R$_i$, independently, being H, OH, a C$_1$-C$_{10}$ oxyaliphatic radical, a C$_1$-C$_{10}$ monovalent aliphatic radical, a C$_1$-C$_{10}$ monovalent heteroaliphatic radical, a monovalent aryl radical, or a monovalent heteroaryl radical and specific compounds:

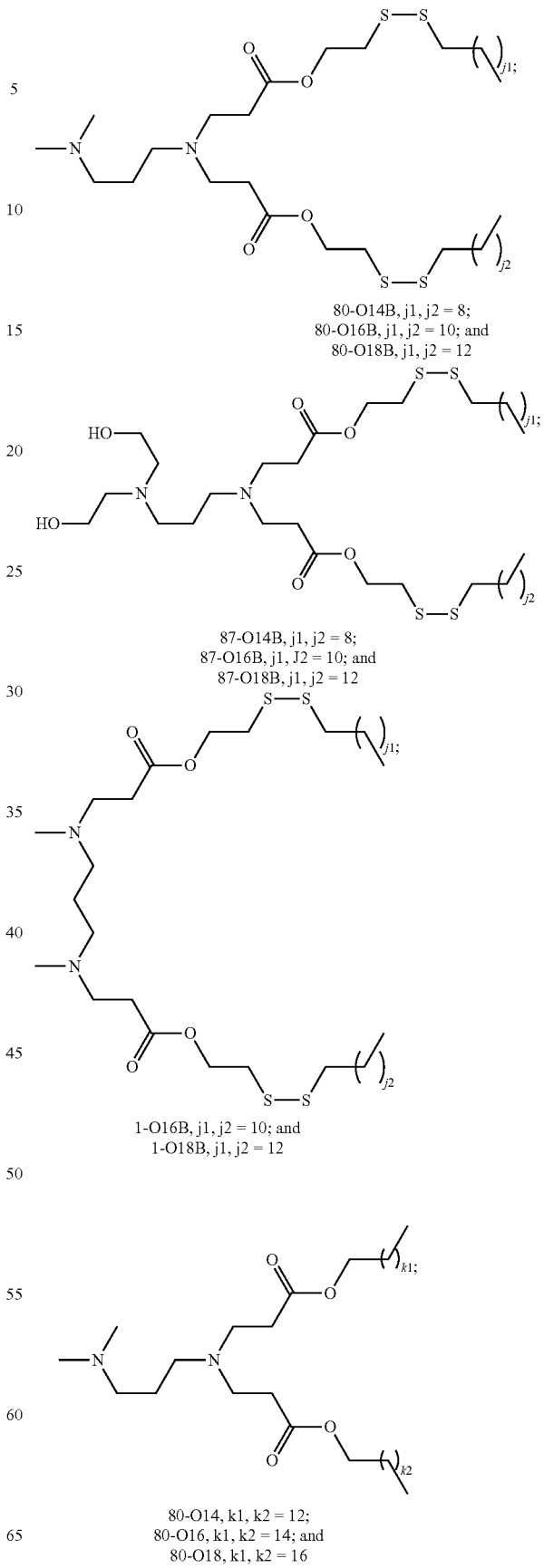

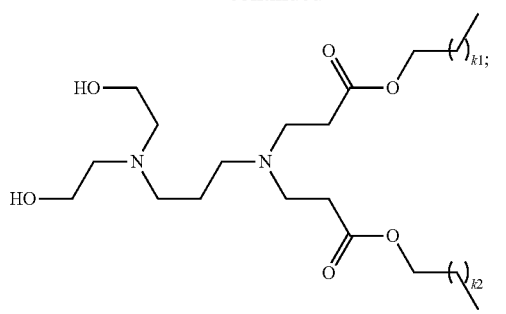

87-O14, k1, k2 = 12;
87-O16, k1, k2 = 14; and
87-O18, k1, k2 = 16.

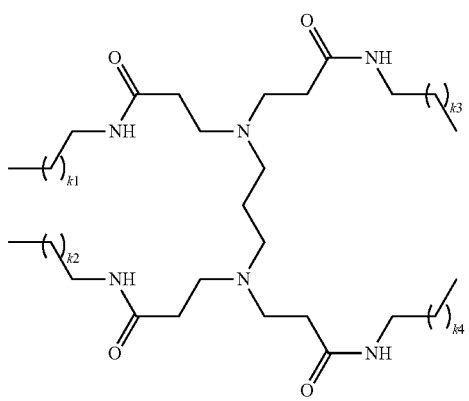

1-N16, k1, k2, k3, k4 = 14
1-N18, k1 = 12, k2 = 13, k3 = 15, and k4 = 16;

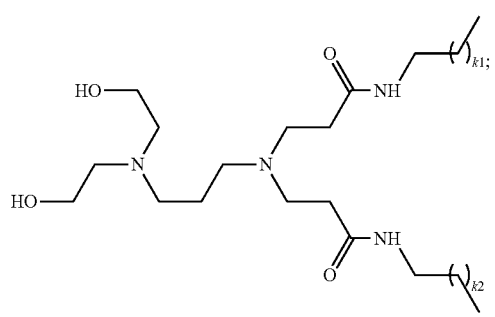

87-N17, k1 = 13 and k2 = 15;
87-N16, k1, k2 = 14; and
87-N18, k1, k2 = 16.

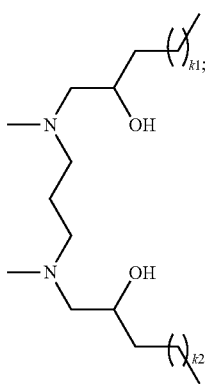

EC16-1, k1, k2 = 14

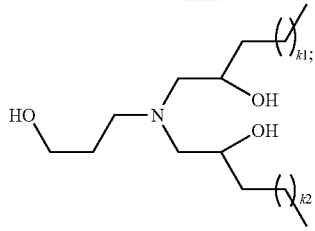

EC16-3, k1, k2 = 14

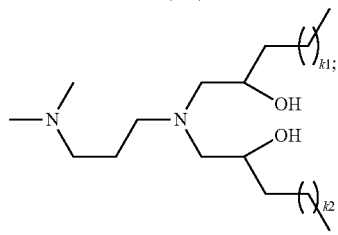

EC16-12, k1, k2 = 14

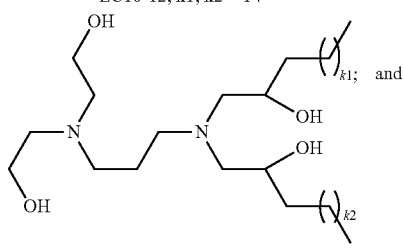

EC16-14, k1, k2 = 14

EC16-63

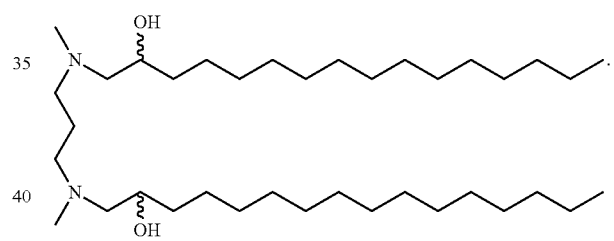

Additional examples of cationic lipid that can be used to make the particle delivery system of the invention can be found in US20150140070, wherein the cationic lipid has the formula

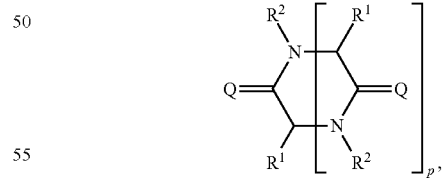

wherein p is an integer between 1 and 9, inclusive; each instance of Q is independently O, S, or $NR^Q$; $R^Q$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii) or (iii); each instance of $R^1$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, halogen, —OR$^{A1}$, —N(R$^{A1}$)$_2$, —SR$^{A1}$, or a group of formula:

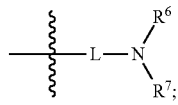

L is an optionally substituted alkylene, optionally substituted alkenylene, optionally substituted alkynylene, optionally substituted heteroalkylene, optionally substituted heteroalkenylene, optionally substituted heteroalkynylene, optionally substituted carbocyclylene, optionally substituted heterocyclylene, optionally substituted arylene, or optionally substituted heteroarylene, or combination thereof, and each of R$^6$ and R$^7$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of formula (i), (ii) or (iii); each occurrence of R$^{A1}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, a nitrogen protecting group when attached to a nitrogen atom, or two RAI groups, together with the nitrogen atom to which they are attached, are joined to form an optionally substituted heterocyclic or optionally substituted heteroaryl ring; each instance of R$^2$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii), or (iii); Formulae (i), (ii), and (iii) are:

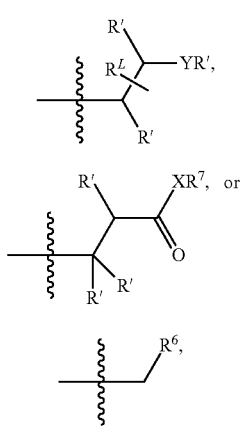

each instance of R' is independently hydrogen or optionally substituted alkyl; X is O, S, or NR$^X$; R$^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; Y is O, S, or NR); RY is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; R$^P$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom; R$^L$ is optionally substituted C$_{1-50}$ alkyl, optionally substituted C$_{2-50}$ alkenyl, optionally substituted C$_{2-50}$ alkynyl, optionally substituted heteroC$_{1-50}$ alkyl, optionally substituted heteroC$_{2-50}$ alkenyl, optionally substituted heteroC$_{2-50}$ alkynyl, or a polymer; provided that at least one instance of R$^Q$, R$^2$, R$^6$, or R$^7$ is a group of the formula (i), (ii), or (iii); in Liu et al., (US 20160200779, US 20150118216, US 20150071903, and US 20150071903), which provide examples of cationic lipids to include polyethylenimine, polyamidoamine (PAMAM) starburst dendrimers, Lipofectin (a combination of DOTMA and DOPE), Lipofectase, LIPOFECTAMINE® (e.g., LIPOFECTAMINE® 2000, LIPOFECTAMINE® 3000, LIPOFECTAMINE® RNAiMAX, LIPOFECTAMINE® LTX), SAINT-RED (Synvolux Therapeutics, Groningen Netherlands), DOPE, Cytofectin (Gilead Sciences, Foster City, Calif.), and Eufectins (JBL, San Luis Obispo, Calif.). Exemplary cationic liposomes can be made from N-[1-(2,3-dioleoloxy)-propyl]-N,N,N-trimethylammonium chloride (DOTMA), N-[1-(2,3-dioleoloxy)-propyl]-N,N,N-trimethylammonium methylsulfate (DOTAP), 3.beta.-[N—(N',N'-dimethylaminoethane) carbamoyl]cholesterol (DC-Chol), 2,3,-dioleyloxy-N-[2 (sperminecarboxamido)ethyl]-N,N-dimethyl-1-propanamin-ium trifluoroacetate (DOSPA), 1,2-dimyristyloxypropyl-3-dimethyl-hydroxyethyl ammonium bromide; and dimethyldioctadecylammonium bromide (DDAB); in WO2013/093648 which provides cationic lipids of formula

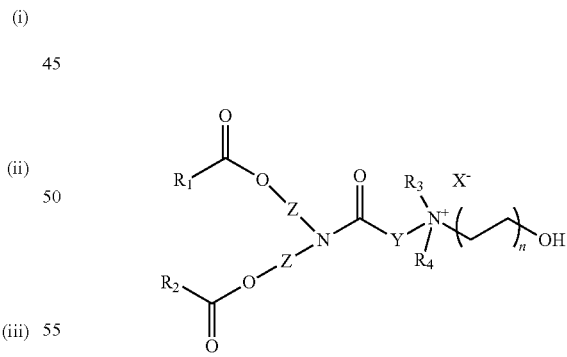

in which Z=an alkyl linker, C$_2$-C$_4$ alkyl, Y=an alkyl linker, C$_1$-C$_6$ alkyl, R$^1$ and R$_2$ are each independently C$_{10}$-C$_{30}$alkyl, C$_{10}$-C$_{30}$alkenyl, or C$_{10}$-C$_{30}$alkynyl, C$_{10}$-C$_{30}$alkyl, C$_{10}$-C$_{30}$alkyl, C$_{12}$-C$_{18}$alkyl, C$_{13}$-C$_{17}$alkyl, C$_{13}$alkyl, C$_{10}$-C$_{30}$alkenyl, C$_{10}$-C$_{20}$oalkenyl. C$_{12}$-C$_{18}$alkenyl, C$_{13}$-C$_{17}$alkenyl, C$_{17}$alkenyl; R3 and R4 are each independently hydrogen, C$_1$-C$_6$ alkyl, or —CH$_2$CH$_2$OH, C$_1$-C$_6$ alkyl, C$_1$-C$_3$alkyl; n is 1-6; and X is a counterion, including any nitrogen counterion, as that term is readily understood in the art, and specific cationic lipids including

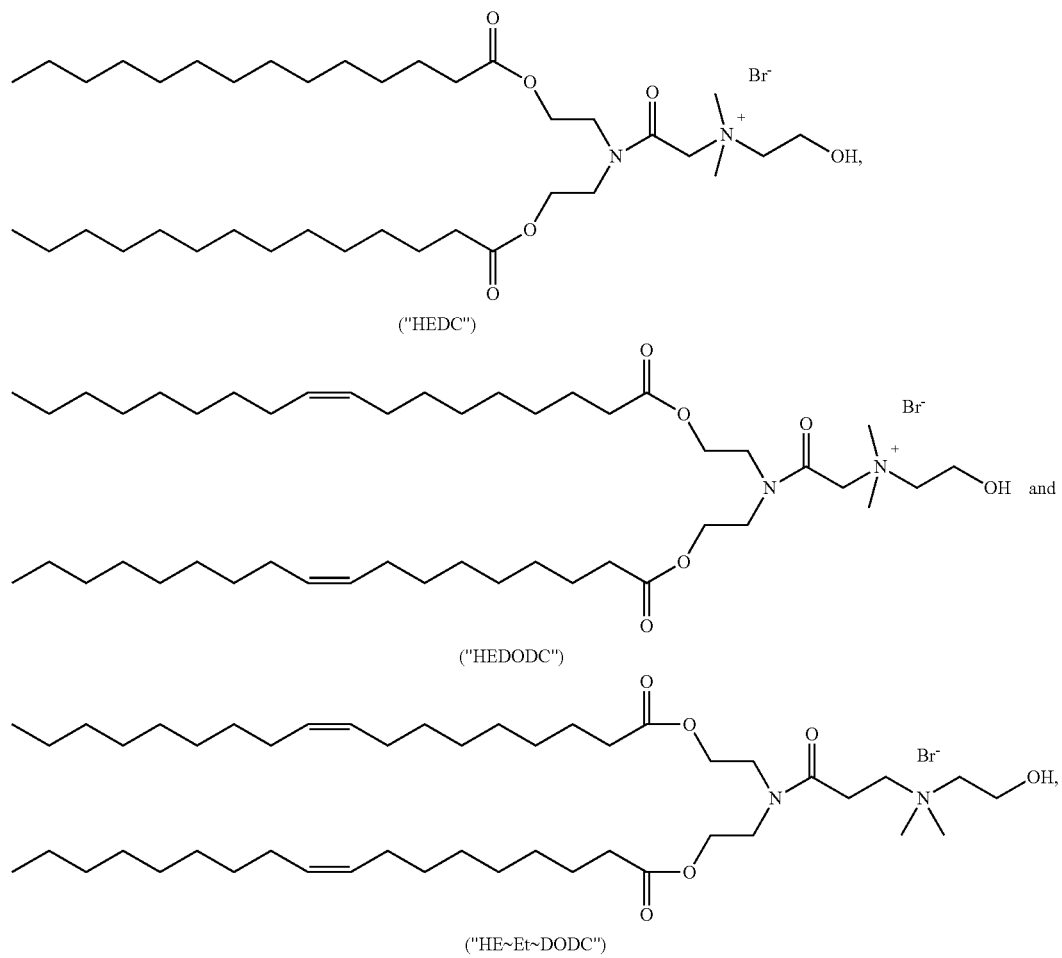

("HEDC")

("HEDODC")

("HE~Et~DODC")

WO2013/093648 also provides examples of other cationic charged lipids at physiological pH including N,N-dioleyl-N,N-dimethylammonium chloride (DODAC), N,N-distearyl-N,N-dimethylammonium bromide (DDAB); N-(1,2-dimyristyloxyprop-3-yl)-N,N-dimethyl-N-hydroxyethylammonium bromide (DMRIE) and dioctadecylamidoglycyl carboxyspermidine (DOGS); in US20160257951, which provides cationic lipids with a general formula

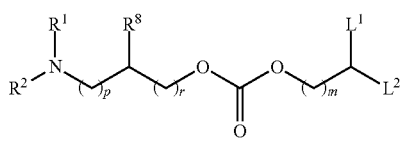

or a pharmacologically acceptable salt thereof, wherein $R^1$ and $R^2$ are each independently a hydrogen atom, a $C_1$-$C_6$ alkyl group optionally substituted with one or more substituents selected from substituent group a, a $C_2$-$C_6$ alkenyl group optionally substituted with one or more substituents selected from substituent group α, a $C_2$-$C_6$ alkynyl group optionally substituted with one or more substituents selected from substituent group α, or a $C_3$-$C_7$cycloalkyl group optionally substituted with one or more substituents selected from substituent group α, or $R^1$ and $R^2$ form a 3- to 10-membered heterocyclic ring together with the nitrogen atom bonded thereto, wherein the heterocyclic ring is optionally substituted with one or more substituents selected from substituent group a and optionally contains one or more atoms selected from a nitrogen atom, an oxygen atom, and a sulfur atom, in addition to the nitrogen atom bonded to $R^1$ and $R^2$, as atoms constituting the heterocyclic ring; $R^8$ is a hydrogen atom or a $C_1$-$C_6$ alkyl group optionally substituted with one or more substituents selected from substituent group α; or $R^1$ and $R^8$ together are the group —$(CH_2)_q$; substituent group a consists of a halogen atom, an oxo group, a hydroxy group, a sulfanyl group, an amino group, a cyano group, a $C_1$-$C_6$ alkyl group, a $C_1$-$C_6$ halogenated alkyl group, a $C_1$-$C_6$ alkoxy group, a $C_1$-$C_6$ alkylsulfanyl group, a $C_1$-$C_6$ alkylamino group, and a $C_1$-$C_7$alkanoyl group; $L_1$ is a $C_{10}$-$C_{24}$ alkyl group optionally substituted with one or more substituents selected from substituent group β1, a $C_{10}$-$C_{24}$ alkenyl group optionally substituted with one or more substituents selected from substituent group β1, a $C_3$-$C_{24}$ alkynyl group optionally substituted with one or more substituents selected from substituent group β1, or a ($C_1$-$C_{10}$ alkyl)-$(Q)_k$-($C_1$-$C_{10}$ alkyl) group optionally substituted with one or more substituents selected from substituent group β1; $L^2$ is, independently of $L_1$, a $C_{10}$-$C_{24}$ alkyl group optionally substituted with one or more substituents selected from substituent group β1, a $C_{10}$-$C_{24}$ alkenyl group optionally substituted with one or more substituents selected from substituent group β1, a C₃-C₂₄ alkynyl group optionally substituted with one or more substituents selected from substituent group β1, a (C₁-C₁₀ alkyl)-(Q)$_k$—(C₁-C₁₀ alkyl) group optionally substituted with having one or more substituents selected from substituent group β1, a (C₁₀-C₂₄ alkoxy)methyl group optionally substituted with one or more substituents selected from substituent group β1, a (C₁₀-C₂₄ alkenyl)oxymethyl group optionally substituted with one or more substituents selected from substituent group β1, a (C₃-C₂₄ alkynyl)oxymethyl group optionally substituted with one or more substituents selected from substituent group β1, or a (C₁-C₁₀ alkyl)-(Q)$_k$—(C₁-C₁₀ alkoxy)methyl group optionally substituted with one or more substituents selected from substituent group β1; substituent group β1 consists of a halogen atom, an oxo group, a cyano group, a C₁-C₆ alkyl group, a C₁-C₆ halogenated alkyl group, a C₁-C₆ alkoxy group, a C₁-C₆ alkylsulfanyl group, a C₁-C₇ alkanoyl group, a C₁-C₇alkanoyloxy group, a C₃-C₇alkoxyalkoxy group, a (C₁-C₆ alkoxy) carbonyl group, a (C₁-C₆ alkoxy) carboxyl group, a (C₁-C₆ alkoxy) carbamoyl group, and a (C₁-C₆ alkylamino) carboxyl group; Q is a group of formula:

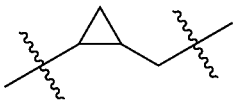 [SMILES: *CC1CC1*]

when L₁ and L² are each substituted with one or more substituents selected from substituent group β1 and substituent group B₁ is a C₁-C₆ alkyl group, a C₁-C₆ alkoxy group, a C₁-C₆ alkylsulfanyl group, a C₁-C₇ alkanoyl group, or a C₁-C₇ alkanoyloxy group, the substituent or substituents selected from substituent group β1 in L' and the substituent or substituents selected from substituent group β1 in L² optionally bind to each other to form a cyclic structure; k is 1, 2, 3, 4, 5, 6, or 7; m is 0 or 1; p is 0, 1, or 2; q is 1, 2, 3, or 4; and r is 0, 1, 2, or 3, provided that p+r is 2 or larger, or q+r is 2 or larger, and specific cationic lipids including

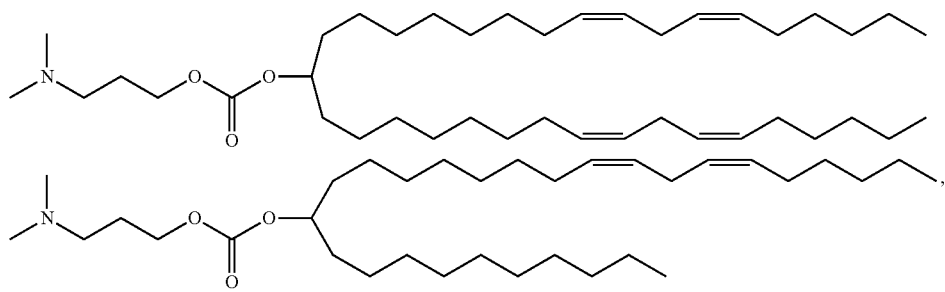

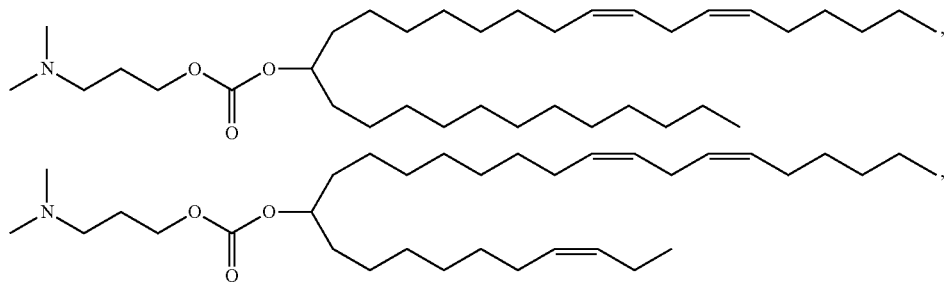

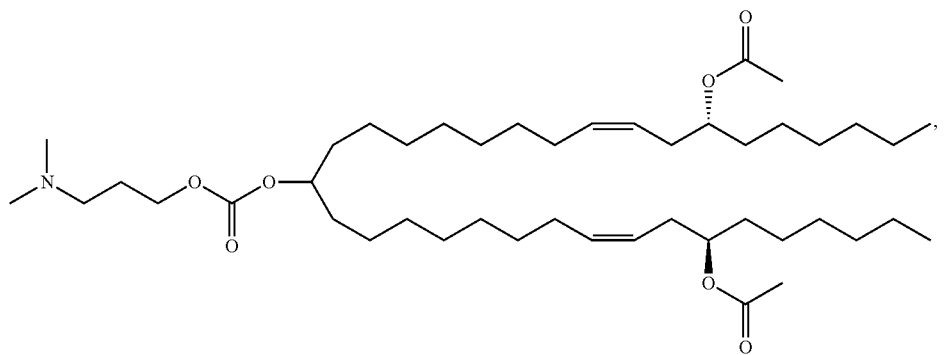

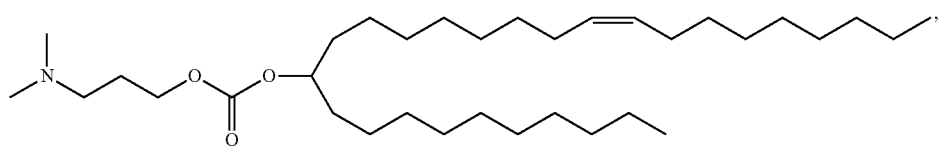

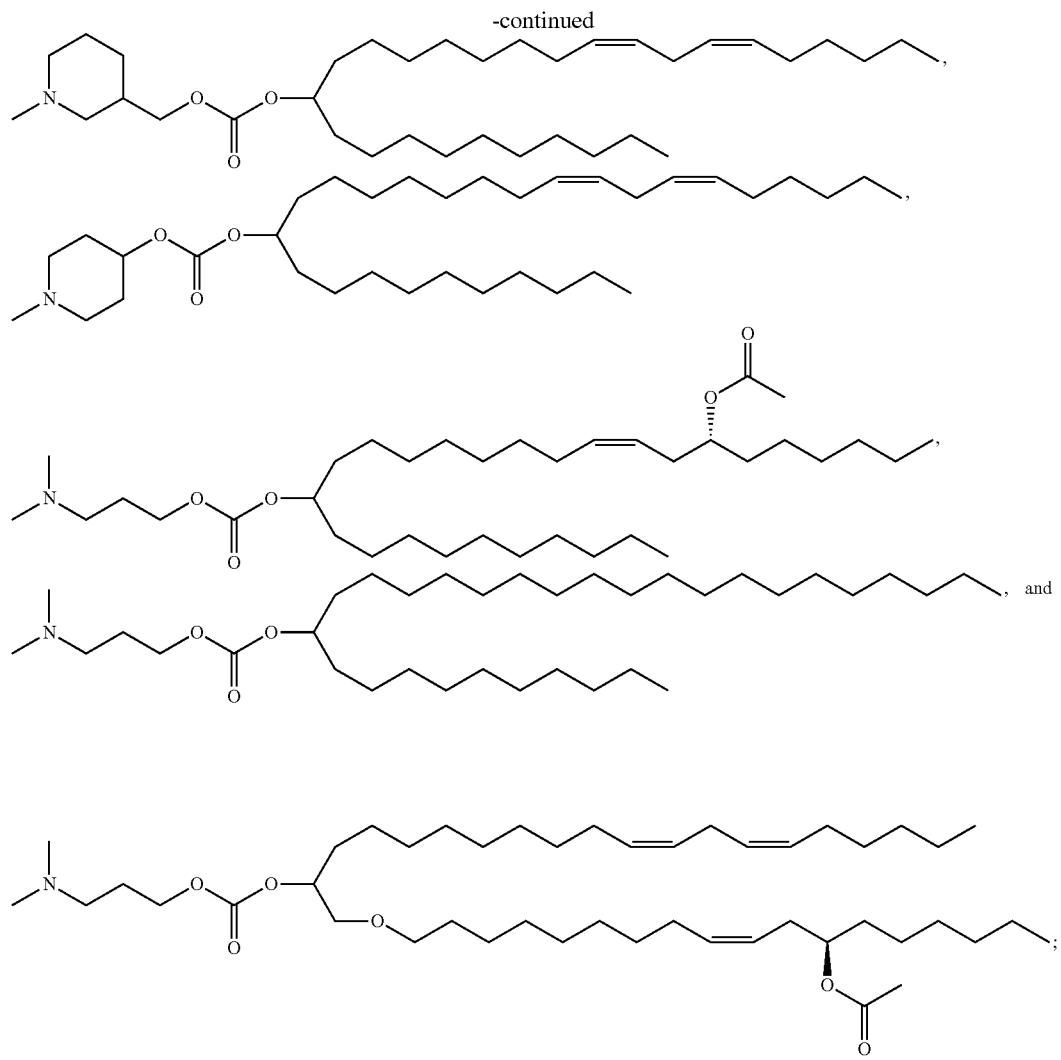

and in US 20160244761, which provides cationic lipids that include 1,2-distearyloxy-N,N-dimethyl-3-aminopropane (DSDMA), 1,2-dioleyloxy-N,N-dimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA), 1,2-di-.gamma.-linolenyloxy-N,N-dimethylaminopropane (.gamma.-DLenDMA), 1,2-dilinoleyloxy-keto-N,N-dimethyl-3-aminopropane (DLin-K-DMA), 1,2-dilinoleyl-4-(2-dimethylaminoethyl)-[1,3]-dioxolane (DLin-K—C$_2$-DMA) (also known as DLin-C$_2$K-DMA, XTC2, and C$_2$K), 2,2-dilinoleyl-4-(3-dimethylaminopropyl)-[1,3]-dioxolane (DLin-K—C$_3$-DMA), 2,2-dilinoleyl-4-(4-dimethylaminobutyl)-[1,3]-dioxolane (DLin-K—C$_4$-DMA), 1,2-dilinolenyloxy-4-(2-dimethylaminoethyl)-[1,3]-dioxolane (DLen-C$_2$K-DMA), 1,2-di-.gamma.-linolenyloxy-4-(2-dimethylaminoethyl)-[1,3]-dioxolane (.gamma.-DLen-C$_2$K-DMA), dilinoleylmethyl-3-dimethylaminopropionate (DLin-M-C$_2$-DMA) (also known as MC2), (6Z,9Z,28Z,31Z)-heptatriaconta-6,9,28,31-tetraen-19-yl 4-(dimethylamino)butanoate (DLin-M-C$_3$-DMA) (also known as MC3) and 3-(dilinoleylmethoxy)-N,N-dimethylpropan-1-amine (DLin-MP-DMA) (also known as 1-B1 1).

In one embodiment, the lipid compound is preferably a bio-reducible material, e.g., a bio-reducible polymer and a bio-reducible lipid-like compound.

In embodiment, the lipid compound comprises a hydrophilic head, and a hydrophobic tail, and optionally a linker.

In one embodiment, the hydrophilic head contains one or more hydrophilic functional groups, e.g., hydroxyl, carboxyl, amino, sulfhydryl, phosphate, amide, ester, ether, carbamate, carbonate, carbamide and phosphodiester. These groups can form hydrogen bonds and are optionally positively or negatively charged, in particular at physiological conditions such as physiological pH.

In one embodiment, the hydrophobic tail is a saturated or unsaturated, linear or branched, acyclic or cyclic, aromatic or nonaromatic hydrocarbon moiety, wherein the saturated or unsaturated, linear or branched, acyclic or cyclic, aromatic or nonaromatic hydrocarbon moiety optionally contains a disulfide bond and/or 8-24 carbon atoms. One or more of the carbon atoms can be replaced with a heteroatom, such as N, O, P, B, S, Si, Sb, Al, Sn, As, Se, and Ge. The lipid or lipid-like compounds containing disulfide bond can be bioreducible.

In one embodiment, the linker of the lipid or lipid-like compound links the hydrophilic head and the hydrophobic tail. The linker can be any chemical group that is hydrophilic or hydrophobic, polar or non-polar, e.g., O, S, Si, amino, alkylene, ester, amide, carbamate, carbamide, carbonate phosphate, phosphite, sulfate, sulfite, and thiosulfate.

The lipid or lipid-like compounds described above include the compounds themselves, as well as their salts and solvates, if applicable. A salt, for example, can be formed between an anion and a positively charged group (e.g., amino) on a lipid-like compound. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group (e.g., carboxylate) on a lipid-like compound. Suitable cations include sodium ion, potassium ion, magnesium ion, calcium ion, and an ammonium cation such as tetramethylammonium ion. The lipid-like compounds also include those salts containing quaternary nitrogen atoms. A solvate refers to a complex formed between a lipid-like compound and a pharmaceutically acceptable solvent. Examples of pharmaceutically acceptable solvents include water, ethanol, isopropanol, ethyl acetate, acetic acid, and ethanolamine.

In one embodiment, the lipid, lipid particle or lipid layer of the delivery system further comprises a wild-type capsid protein.

In one embodiment, a weight ratio of hybrid capsid protein to wild-type capsid protein is from 1:10 to 1:1, for example, 1:1, 1:2, 1:3, 1:4, 1:5, 1:6, 1:7, 1:8, 1:9 and 1:10.

In one embodiment, the virus of the delivery system is an Adenoviridae or a Parvoviridae or a Rhabdoviridae or an enveloped virus having a glycoprotein protein. In one embodiment, the virus is an adeno-associated virus (AAV) or an adenovirus or a VSV or a rabies virus. In one embodiment, the virus is a retrovirus or a lentivirus. In one embodiment, the virus is murine leukemia virus (MuMLV).

In one embodiment, the virus capsid protein of the delivery system comprises VP1, Sn, VP2 or VP3.

In one embodiment, the virus capsid protein of the delivery system is VP3, and the non-capsid protein is inserted into or tethered or connected to VP3 loop 3 or loop 6.

In one embodiment, the virus of the delivery system is delivered to the interior of a cell.

In one embodiment, the virus capsid protein and the non-capsid protein are capable of dissociating after delivery into a cell.

In one aspect of the delivery system, the virus capsid protein is attached to the non-capsid protein by a linker. In one embodiment, the linker comprises amino acids. In one embodiment, the linker is a chemical linker. In another embodiment, the linker is cleavable or biodegradable. In one embodiment, the linker comprises $(GGGGS)_{1-3}$, ENLYFQG, or a disulfide.

In one embodiment of the delivery system, each terminus of the non-capsid protein is attached to the capsid protein by a linker moiety.

In one embodiment, the non-capsid protein is attached to the exterior portion of the virus capsid protein. As used herein, "exterior portion" as it refers to a virus capsid protein means the outer surface of the virus capsid protein when it is in a formed virus capsid.

In one embodiment, the non-capsid protein is attached to the interior portion of the capsid protein or is encapsulated within the lipid particle. As used herein, "interior portion" as it refers to a virus capsid protein means the inner surface of the virus capsid protein when it is in a formed virus capsid. In one embodiment, the virus capsid protein and the non-capsid protein are a fusion protein.

In one embodiment, the fusion protein is attached to the surface of the lipid particle.

In one embodiment, the non-capsid protein is attached to the virus capsid protein prior to formation of the capsid.

In one embodiment, the non-capsid protein is attached to the virus capsid protein after formation of the capsid.

In one embodiment, the non-capsid protein comprises a targeting moiety.

In one embodiment, the targeting moiety comprises a receptor ligand.

In an embodiment, the non-capsid protein comprises a tag.

In an embodiment, the non-capsid protein comprises one or more heterologous nuclear localization signals(s) (NLSs).

In an embodiment, the protein or peptide comprises a Type II CRISPR protein or a Type VI CRISPR protein.

In an embodiment, the delivery system further comprises guide RNS, optionally complexed with the CRISPR protein.

In an embodiment, the delivery system comprises a protease or nucleic acid molecule(s) encoding a protease that is expressed, whereby the protease cleaves the linker. In certain embodiments, there is protease expression, linker cleavage, and dissociation of payload from capsid in the absence of productive virus replication.

In an aspect, the invention provides a delivery system comprising a first hybrid virus capsid protein and a second hybrid virus capsid protein, wherein the first hybrid virus capsid protein comprises a virus capsid protein attached to a first part of a protein, and wherein the second hybrid virus capsid protein comprises a second virus capsid protein attached to a second part of the protein, wherein the first part of the protein and the second part of the protein are capable of associating to form a functional protein.

In an aspect, the invention provides a delivery system comprising a first hybrid virus capsid protein and a second hybrid virus capsid protein, wherein the first hybrid virus capsid protein comprises a virus capsid protein attached to a first part of a CRISPR protein, and wherein the second hybrid virus capsid protein comprises a second virus capsid protein attached to a second part of a CRISPR protein, wherein the first part of the CRISPR protein and the second part of the CRISPR protein are capable of associating to form a functional CRISPR protein.

In an embodiment of the delivery system, the first hybrid virus capsid protein and the second virus capsid protein are on the surface of the same virus particle.

In an embodiment of the delivery system, the first hybrid virus capsule protein is located at the interior of a first virus particle and the second hybrid virus capsid protein is located at the interior of a second virus particle.

In an embodiment of the delivery system, the first part of the protein or CRISPR protein is linked to a first member of a ligand pair, and the second part of the protein or CRISPR protein is linked to a second member of a ligand pair, wherein the first part of the ligand pair binds to the second part of the ligand pair in a cell. In an embodiment, the binding of the first part of the ligand pair to the second part of the ligand pair is inducible.

In an embodiment of the delivery system, either or both of the first part of the protein or CRISPR protein and the second part of the protein or CRISPR protein comprise one or more NLSs.

In an embodiment of the delivery system, either or both of the first part of the protein or CRISPR protein and the second part of the protein or CRISPR protein comprise one or more nuclear export signals (NESs).

In one aspect, the invention provides a delivery system for a non-naturally occurring or engineered CRISPR system, component, protein or complex. The delivery system comprises a non-naturally occurring or engineered CRISPR system, component, protein or complex, associated with a virus structural component and a lipid component. The delivery system can further comprise a targeting molecule, for example a targeting molecule that preferentially guides the delivery system to a cell type or interest, or a cell expressing a target protein of interest. The targeting molecule may be associated with or attached to the virus component or the lipid component. In certain embodiments, the virus component preferentially guides the delivery system to the target of interest.

In certain embodiments, the virus structural component comprises one or more capsid proteins including an entire capsid. In certain embodiments, such as wherein a viral capsid comprises multiple copies of different proteins, the delivery system can provide one or more of the same protein or a mixture of such proteins. For example, AAV comprises 3 capsid proteins, VP1, Sn, VP2, and VP3, thus delivery systems of the invention can comprise one or more of VP1, Sn, and/or one or more of VP2, and/or one or more of VP3. Accordingly, the present invention is applicable to a virus within the family Adenoviridae, such as Atadenovirus, e.g., Ovine atadenovirus D, Aviadenovirus, e.g., Fowl aviadenovirus A, Ichtadenovirus, e.g., Sturgeon ichtadenovirus A, Mastadenovirus (which includes adenoviruses such as all human adenoviruses), e.g., Human mastadenovirus C, and Siadenovirus, e.g., Frog siadenovirus A. Thus, a virus of within the family Adenoviridae is contemplated as within the invention with discussion herein as to adenovirus applicable to other family members. Target-specific AAV capsid variants can be used or selected. Non-limiting examples include capsid variants selected to bind to chronic myelogenous leukemia cells, human CD34 PBPC cells, breast cancer cells, cells of lung, heart, dermal fibroblasts, melanoma cells, stem cell, glioblastoma cells, coronary artery endothelial cells and keratinocytes. See, e.g., Buning et al, 2015, Current Opinion in Pharmacology 24, 94-104. From teachings herein and knowledge in the art as to modifications of adenovirus (see, e.g., U.S. Pat. Nos. 9,410,129, 7,344,872, 7,256,036, 6,911,199, 6,740,525; Matthews, "Capsid-Incorporation of Antigens into Adenovirus Capsid Proteins for a Vaccine Approach," Mol Pharm, 8 (1): 3-11 (2011)), as well as regarding modifications of AAV, the skilled person can readily obtain a modified adenovirus that has a large payload protein or a CRISPR-protein, despite that heretofore it was not expected that such a large protein could be provided on an adenovirus. And as to the viruses related to adenovirus mentioned herein, as well as to the viruses related to AAV mentioned herein, the teachings herein as to modifying adenovirus and AAV, respectively, can be applied to those viruses without undue experimentation from this disclosure and the knowledge in the art.

In an embodiment of the invention, the delivery system comprises a virus protein or particle adsorbed to a lipid component, such as, for example, a liposome. In certain embodiments, a CRISPR system, component, protein or complex is associated with the virus protein or particle. In certain embodiments, a CRISPR system, component, protein or complex is associated with the lipid component. In certain embodiments, one CRISPR system, component, protein or complex is associated with the virus protein or particle, and a second CRISPR system, component, protein, or complex is associated with the lipid component. As used herein, associated with includes, but is not limited to, linked to, adhered to, adsorbed to, enclosed in, enclosed in or within, mixed with, and the like. In certain embodiments, the virus component and the lipid component are mixed, including but not limited to the virus component dissolved in or inserted in a lipid bilayer. In certain embodiments, the virus component and the lipid component are associated but separate, including but not limited a virus protein or particle adsorbed or adhered to a liposome. In embodiments of the invention that further comprise a targeting molecule, the targeting molecule can be associated with a virus component, a lipid component, or a virus component and a lipid component.

In another aspect, the invention provides a non-naturally occurring or engineered CRISPR protein associated with Adeno Associated Virus (AAV), e.g., an AAV comprising a CRISPR protein as a fusion, with or without a linker, to or with an AAV capsid protein such as VP1, Sn, VP2, and/or VP3; and, for shorthand purposes, such a non-naturally occurring or engineered CRISPR protein is herein termed a "AAV-CRISPR protein" More in particular, modifying the knowledge in the art, e.g., Rybniker et al., "Incorporation of Antigens into Viral Capsids Augments Immunogenicity of Adeno-Associated Virus Vector-Based Vaccines," J Virol. December 2012; 86 (24): 13800-13804, Lux K, et al. 2005. Green fluorescent protein-tagged adeno-associated virus particles allow the study of cytosolic and nuclear trafficking. J. Virol. 79:11776-11787, Munch R C, et al. 2012. "Displaying high-affinity ligands on adeno-associated viral vectors enables tumor cell-specific and safe gene transfer." Mol. Ther. [Epub ahead of print.] doi: 10.1038/mt.2012.186 and Warrington K H, Jr, et al. 2004. Adeno-associated virus type 2 VP2 capsid protein is nonessential and can tolerate large peptide insertions at its N terminus. J. Virol. 78:6595-6609, each incorporated herein by reference, one can obtain a modified AAV capsid of the invention. It will be understood by those skilled in the art that the modifications described herein if inserted into the AAV cap gene may result in modifications in the VP1, Sn, VP2 and/or VP3 capsid subunits. Alternatively, the capsid subunits can be expressed independently to achieve modification in only one or two of the capsid subunits (VP1, Sn, VP2, VP3, VP1, Sn+VP2, VP1, Sn+VP3, or VP2+VP3). One can modify the cap gene to have expressed at a desired location a non-capsid protein advantageously a large payload protein, such as a CRISPR-protein. Likewise, these can be fusions, with the protein, e.g., large payload protein such as a CRISPR-protein fused in a manner analogous to prior art fusions. See, e.g., US Patent Publication 20090215879; Nance et al., "Perspective on Adeno-Associated Virus Capsid Modification for Duchenne Muscular Dystrophy Gene Therapy," Hum Gene Ther. 26 (12): 786-800 (2015) and documents cited therein, incorporated herein by reference. The skilled person, from this disclosure and the knowledge in the art can make and use modified AAV or AAV capsid as in the herein invention, and through this disclosure one knows now that large payload proteins can be fused to the AAV capsid. Applicants provide AAV capsid-CRISPR protein (e.g., Cas, Cas9, dCas9, Cpf1, Cas13a, Cas13b) fusions and those AAV-capsid CRISPR protein (e.g., Cas, Cas9) fusions can be a recombinant AAV that contains nucleic acid molcule(s) encoding or providing CRISPR-Cas or CRISPR system or complex RNA guide(s), whereby the CRISPR protein (e.g., Cas, Cas9) fusion delivers a CRISPR-Cas or CRISPR system complex (e.g., the CRISPR protein or Cas or Cas9 is provided by the fusion, e.g., VP1, Sn, VP2, pr VP3 fusion, and the guide RNA is provided by the coding of the recombinant virus, whereby in vivo, in a cell, the CRISPR-Cas or CRISPR system is assembled from the nucleic acid molecule(s) of the recombinant providing the guide RNA and the outer surface of the virus providing the CRISPR-Enzyme or Cas or Cas9. Such as complex may herein be termed an "AAV-CRISPR system" or an "AAV-CRISPR-Cas" or "AAV-CRISPR complex" or AAV-CRISPR-Cas complex." Accordingly, the instant invention is also applicable to a virus in the genus Dependoparvovirus or in the family Parvoviridae, for instance, AAV, or a virus of Amdoparvovirus, e.g., Carnivore amdoparvovirus 1, a virus of Aveparvovirus, e.g., Galliform aveparvovirus 1, a virus of Bocaparvovirus, e.g., Ungulate bocaparvovirus 1, a virus of Copiparvovirus, e.g., Ungulate copiparvovirus 1, a virus of Dependoparvovirus, e.g., Adeno-associated dependoparvovirus A, a virus of Erythroparvovirus, e.g., Primate erythroparvovirus 1, a virus of Protoparvovirus, e.g., Rodent protoparvovirus 1, a virus of Tetraparvovirus, e.g., Primate tetraparvovirus 1. Thus, a virus of within the family Parvoviridae or the genus Dependoparvovirus or any of the other foregoing genera within Parvoviridae is contemplated as within the invention with discussion herein as to AAV applicable to such other viruses.

In one aspect, the invention provides a non-naturally occurring or engineered composition comprising a CRISPR enzyme which is part of or tethered to a AAV capsid domain, i.e., VP1, Sn, VP2, or VP3 domain of Adeno-Associated Virus (AAV) capsid. In some embodiments, part of or tethered to a AAV capsid domain includes associated with associated with a AAV capsid domain. In some embodiments, the CRISPR enzyme may be fused to the AAV capsid domain. In some embodiments, the fusion may be to the N-terminal end of the AAV capsid domain. As such, in some embodiments, the C-terminal end of the CRISPR enzyme is fused to the N-terminal end of the AAV capsid domain. In some embodiments, an NLS and/or a linker (such as a GlySer linker) may be positioned between the C-terminal end of the CRISPR enzyme and the N-terminal end of the AAV capsid domain. In some embodiments, the fusion may be to the C-terminal end of the AAV capsid domain. In some embodiments, this is not preferred due to the fact that the VP1, Sn, VP2 and VP3 domains of AAV are alternative splices of the same RNA and so a C-terminal fusion may affect all three domains. In some embodiments, the AAV capsid domain is truncated. In some embodiments, some or all of the AAV capsid domain is removed. In some embodiments, some of the AAV capsid domain is removed and replaced with a linker (such as a GlySer linker), typically leaving the N-terminal and C-terminal ends of the AAV capsid domain intact, such as the first 2, 5 or 10 amino acids. In this way, the internal (non-terminal) portion of the VP3 domain may be replaced with a linker. It is particularly preferred that the linker is fused to the CRISPR protein. A branched linker may be used, with the CRISPR protein fused to the end of one of the branches. This allows for some degree of spatial separation between the capsid and the CRISPR protein. In this way, the CRISPR protein is part of (or fused to) the AAV capsid domain.

Alternatively, the CRISPR enzyme may be fused in frame within, i.e. internal to, the AAV capsid domain. Thus in some embodiments, the AAV capsid domain again preferably retains its N-terminal and C-terminal ends. In this case, a linker is preferred, in some embodiments, either at one or both ends of the CRISPR enzyme. In this way, the CRISPR enzyme is again part of (or fused to) the AAV capsid domain. In certain embodiments, the positioning of the CRISPR enzyme is such that the CRISPR enzyme is at the external surface of the viral capsid once formed. In one aspect, the invention provides a non-naturally occurring or engineered composition comprising a CRISPR enzyme associated with a AAV capsid domain of Adeno-Associated Virus (AAV) capsid. Here, associated may mean in some embodiments fused, or in some embodiments bound to, or in some embodiments tethered to. The CRISPR protein may, in some embodiments, be tethered to the VP1, Sn, VP2, or VP3 domain. This may be via a connector protein or tethering system such as the biotin-streptavidin system. In one example, a biotinylation sequence (15 amino acids) could therefore be fused to the CRISPR protein. When a fusion of the AAV capsid domain, especially the N-terminus of the AAV AAV capsid domain, with streptavidin is also provided, the two will therefore associate with very high affinity. Thus, in some embodiments, provided is a composition or system comprising a CRISPR protein-biotin fusion and a streptavidin-AAV capsid domain arrangement, such as a fusion. The CRISPR protein-biotin and streptavidin-AAV capsid domain forms a single complex when the two parts are brought together. NLSs may also be incorporated between the CRISPR protein and the biotin; and/or between the streptavidin and the AAV capsid domain.

An alternative tether may be to fuse or otherwise associate the AAV capsid domain to an adaptor protein which binds to or recognizes to a corresponding RNA sequence or motif. In some embodiments, the adaptor is or comprises a binding protein which recognizes and binds (or is bound by) an RNA sequence specific for said binding protein. In some embodiments, a preferred example is the MS2 (see Konermann et al. December 2014, cited infra, incorporated herein by reference) binding protein which recognizes and binds (or is bound by) an RNA sequence specific for the MS2 protein.

With the AAV capsid domain associated with the adaptor protein, the CRISPR protein may, in some embodiments, be tethered to the adaptor protein of the AAV capsid domain. The CRISPR protein may, in some embodiments, be tethered to the adaptor protein of the AAV capsid domain via the CRISPR enzyme being in a complex with a modified guide, see Konermann et al. The modified guide is, in some embodiments, a sgRNA. In some embodiments, the modified guide comprises a distinct RNA sequence; see, e.g., PCT/US14/70175, incorporated herein by reference.

In some embodiments, distinct RNA sequence is an aptamer. Thus, corresponding aptamer-adaptor protein systems are preferred. One or more functional domains may also be associated with the adaptor protein. An example of a preferred arrangement would be:

[AAV AAV capsid domain-adaptor protein]-[modified guide-CRISPR protein]

In certain embodiments, the positioning of the CRISPR protein is such that the CRISPR protein is at the internal surface of the viral capsid once formed. In one aspect, the invention provides a non-naturally occurring or engineered composition comprising a CRISPR protein associated with an internal surface of an AAV capsid domain. Here again, associated may mean in some embodiments fused, or in some embodiments bound to, or in some embodiments tethered to. The CRISPR protein may, in some embodiments, be tethered to the VP1, Sn, VP2, or VP3 domain such that it locates to the internal surface of the viral capsid once formed. This may be via a connector protein or tethering system such as the biotin-streptavidin system as described above.

When the CRISPR protein fusion is designed so as to position the CRISPR protein at the internal surface of the capsid once formed, the CRISPR protein will fill most or all of internal volume of the capsid. Alternatively the CRISPR protein may be modified or divided so as to occupy a less of the capsid internal volume. Accordingly, in certain embodiments, the invention provides a CRISRP protein divided in two portions, one portion comprises in one viral particle or capsid and the second portion comprised in a second viral particle or capsid. In certain embodiments, by splitting the CRISPR protein in two portions, space is made available to link one or more heterologous domains to one or both CRISPR protein portions.

Split CRISPR proteins are set forth herein and in documents incorporated herein by reference in further detail herein. In certain embodiments, each part of a split CRISRP proteins are attached to a member of a specific binding pair, and when bound with each other, the members of the specific binding pair maintain the parts of the CRISPR protein in proximity. In certain embodiments, each part of a split CRISPR protein is associated with an inducible binding pair. An inducible binding pair is one which is capable of being switched "on" or "off" by a protein or small molecule that binds to both members of the inducible binding pair. In general, according to the invention, CRISPR proteins may preferably split between domains, leaving domains intact. Preferred, non-limiting examples of such CRISPR proteins include, without limitation, Cas9, Cpf1, C2c2, Cas13a, Cas13b, and orthologues. Preferred, non-limiting examples of split points include, with reference to SpCas9: a split position between 202A/203S; a split position between 255F/256D; a split position between 310E/311I; a split position between 534R/535K; a split position between 572E/573C; a split position between 713S/714G; a split position between 1003L/104E; a split position between 1054G/1055E; a split position between 1114N/1115S; a split position between 1152K/1153S; a split position between 1245K/1246G; or a split between 1098 and 1099.

In some embodiments, any AAV serotype is preferred. In some embodiments, the VP2 domain associated with the CRISPR enzyme is an AAV serotype 2 VP2 domain. In some embodiments, the VP2 domain associated with the CRISPR enzyme is an AAV serotype 8 VP2 domain. The serotype can be a mixed serotype as is known in the art. A tabulation of certain AAV serotypes as to these cells (see Grimm, D. et al, J. Virol. 82:5887-5911 (2008)) is as follows:

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

The CRISPR enzyme may form part of a CRISPR-Cas system, which further comprises a guide RNA (sgRNA) comprising a guide sequence capable of hybridizing to a target sequence in a genomic locus of interest in a cell. In some embodiments, the functional CRISPR-Cas system binds to the target sequence. In some embodiments, the functional CRISPR-Cas system may edit the genomic locus to alter gene expression. In some embodiments, the functional CRISPR-Cas system may comprise further functional domains.

In some embodiments, the CRISPR enzyme is a Cas9. In some embodiments, the CRISPR enzyme is an Sp Cas9. In some embodiments, the CRISPR enzyme is an Sa Cas9. In some embodiments, the CRISPR enzyme is an St or Fn Cas9, although other orthologs are envisaged. Sp and Sa Cas9s are particularly preferred, in some embodiments.

In some embodiments, the CRISPR enzyme is external to the capsid or virus particle. In the sense that it is not inside the capsid (enveloped or encompassed with the capsid), but is externally exposed so that it can contact the target genomic DNA). In some embodiments, the CRISPR enzyme cleaves both strands of DNA to produce a double strand break (DSB). In some embodiments, the CRISPR enzyme is a nickase. In some embodiments, the CRISPR enzyme is a dual nickase. In some embodiments, the CRISPR enzyme is a deadCas9. In some general embodiments, the CRISPR enzyme is associated with one or more functional domains. In some more specific embodiments, the CRISPR enzyme is a deadCas9 and is associated with one or more functional domains. In some embodiments, the CRISPR enzyme comprises a Rec2 or HD2 truncation. In some embodiments, the CRISPR enzyme is associated with the AAV VP2 domain by way of a fusion protein. In some embodiments, the CRISPR enzyme is fused to Destabilization Domain (DD). In other words, the DD may be associated with the CRISPR enzyme by fusion with said CRISPR enzyme. The AAV can then, by way of nucleic acid molecule(s) deliver the stabilizing ligand (or such can be otherwise delivered) In some embodiments, the enzyme may be considered to be a modified CRISPR enzyme, wherein the CRISPR enzyme is fused to at least one destabilization domain (DD) and VP2. In some embodiments, the association may be considered to be a modification of the VP2 domain. Where reference is made herein to a modified VP2 domain, then this will be understood to include any association discussed herein of the VP2 domain and the CRISPR enzyme. In some embodiments, the AAV VP2 domain may be associated (or tethered) to the CRISPR enzyme via a connector protein, for example using a system such as the streptavidin-biotin system. As such, provided is a fusion of a CRISPR enzyme with a connector protein specific for a high affinity ligand for that connector, whereas the AAV VP2 domain is bound to said high affinity ligand. For example, streptavidin may be the connector fused to the CRISPR enzyme, while biotin may be bound to the AAV VP2 domain. Upon co-localization, the streptavidin will bind to the biotin, thus connecting the CRISPR enzyme to the AAV VP2 domain. The reverse arrangement is also possible. In some embodiments, a biotinylation sequence (15 amino acids) could therefore be fused to the AAV VP2 domain, especially the N-terminus of the AAV VP2 domain. A fusion of the CRISPR enzyme with streptavidin is also preferred, in some embodiments. In some embodiments, the biotinylated AAV capsids with streptavidin-CRISPR enzyme are assembled in vitro. This way the AAV capsids should assemble in a straightforward manner and the CRISPR enzyme-streptavidin fusion can be added after assembly of the capsid. In other embodiments a biotinylation sequence (15 amino acids) could therefore be fused to the CRISPR enzyme, together with a fusion of the AAV VP2 domain, especially the N-terminus of the AAV VP2 domain, with streptavidin. For simplicity, a fusion of the CRISPR enzyme and the AAV VP2 domain is preferred in some embodiments. In some embodiments, the fusion may be to the N-terminal end of the CRISPR enzyme. In other words, in some embodiments, the AAV and CRISPR enzyme are associated via fusion. In some embodiments, the AAV and CRISPR enzyme are associated via fusion including a linker. Suitable linkers are discussed herein, but include Gly Ser linkers. Fusion to the N-term of AAV VP2 domain is preferred, in some embodiments. In some embodiments, the CRISPR enzyme comprises at least one Nuclear Localization Signal (NLS). In an aspect, the present invention provides a polynucleotide encoding the present CRISPR enzyme and associated AAV VP2 domain.

Viral delivery vectors, for example modified viral delivery vectors, are hereby provided. While the AAV may advantageously be a vehicle for providing RNA of the CRISPR-Cas Complex or CRISPR system, another vector may also deliver that RNA, and such other vectors are also herein discussed. In one aspect, the invention provides a non-naturally occurring modified AAV having a VP2-CRISPR enzyme capsid protein, wherein the CRISPR enzyme is part of or tethered to the VP2 domain. In some preferred embodiments, the CRISPR enzyme is fused to the VP2 domain so that, in another aspect, the invention provides a non-naturally occurring modified AAV having a VP2-CRISPR enzyme fusion capsid protein. The following embodiments apply equally to either modified AAV aspect, unless otherwise apparent. Thus, reference herein to a VP2-CRISPR enzyme capsid protein may also include a VP2-CRISPR enzyme fusion capsid protein. In some embodiments, the VP2-CRISPR enzyme capsid protein further comprises a linker. In some embodiments, the VP2-CRISPR enzyme capsid protein further comprises a linker, whereby the VP2-CRISPR enzyme is distanced from the remainder of the AAV. In some embodiments, the VP2-CRISPR enzyme capsid protein further comprises at least one protein complex, e.g., CRISPR complex, such as CRISPR-Cas9 complex guide RNA that targets a particular DNA, TALE, etc. A CRISPR complex, such as CRISPR-Cas system comprising the VP2-CRISPR enzyme capsid protein and at least one CRISPR complex, such as CRISPR-Cas9 complex guide RNA that targets a particular DNA, is also provided in one aspect. In general, in some embodiments, the AAV further comprises a repair template. It will be appreciated that comprises here may mean encompassed thin the viral capsid or that the virus encodes the comprised protein. In some embodiments, one or more, preferably two or more guide RNAs, may be comprised/encompassed within the AAV vector. Two may be preferred, in some embodiments, as it allows for multiplexing or dual nickase approaches. Particularly for multiplexing, two or more guides may be used. In fact, in some embodiments, three or more, four or more, five or more, or even six or more guide RNAs may be comprised/encompassed within the AAV. More space has been freed up within the AAV by virtue of the fact that the AAV no longer needs to comprise/encompass the CRISPR enzyme. In each of these instances, a repair template may also be provided comprised/encompassed within the AAV. In some embodiments, the repair template corresponds to or includes the DNA target.

In a further aspect, the present invention provides compositions comprising the CRISPR enzyme and associated AAV VP2 domain or the polynucleotides or vectors described herein. Also provides are CRISPR-Cas systems comprising guide RNAs.

Also provided is a method of treating a subject in need thereof, comprising inducing gene editing by transforming the subject with the polynucleotide encoding the system or any of the present vectors. A suitable repair template may also be provided, for example delivered by a vector comprising said repair template. In some embodiments, a single vector provides the CRISPR enzyme through (association with the viral capsid) and at least one of: guide RNA; and/or a repair template. Also provided is a method of treating a subject in need thereof, comprising inducing transcriptional activation or repression by transforming the subject with the polynucleotide encoding the present system or any of the present vectors, wherein said polynucleotide or vector encodes or comprises the catalytically inactive CRISPR enzyme and one or more associated functional domains. Compositions comprising the present system for use in said method of treatment are also provided. A kit of parts may be provided including such compositions. Use of the present system in the manufacture of a medicament for such methods of treatment are also provided.

Also provided is a pharmaceutical composition comprising the CRISPR enzyme which is part of or tethered to a VP2 domain of Adeno-Associated Virus (AAV) capsid; or the non-naturally occurring modified AAV; or a polynucleotide encoding them.

Also provided is a complex of the CRISPR enzyme with a guideRNA, such as sgRNA. The complex may further include the target DNA.

A split CRISPR enzyme, most preferably Cas9, approach may be used. The so-called 'split Cas9' approach Split Cas9 allows for the following. The Cas9 is split into two pieces and each of these are fused to one half of a dimer. Upon dimerization, the two parts of the Cas9 are brought together and the reconstituted Cas9 has been shown to be functional. Thus, one part of the split Cas9 may be associated with one VP2 domain and second part of the split Cas9 may be associated with another VP2 domain. The two VP2 domains may be in the same or different capsid. In other words, the split parts of the Cas9 could be on the same virus particle or on different virus particles.

In some embodiments, one or more functional domains may be associated with or tethered to CRISPR enzyme and/or may be associated with or tethered to modified guides via adaptor proteins. These can be used irrespective of the fact that the CRISPR enzyme may also be tethered to a virus outer protein or capsid or envelope, such as a VP2 domain or a capsid, via modified guides with aptamer RAN sequences that recognize correspond adaptor proteins.

In some embodiments, one or more functional domains comprise a transcriptional activator, repressor, a recombinase, a transposase, a histone remodeler, a demethylase, a DNA methyltransferase, a cryptochrome, a light inducible/controllable domain, a chemically inducible/controllable domain, an epigenetic modifying domain, or a combination thereof. Advantageously, the functional domain comprises an activator, repressor or nuclease.

In some embodiments, a functional domain can have methylase activity, demethylase activity, transcription activation activity, transcription repression activity, transcription release factor activity, histone modification activity, RNA cleavage activity or nucleic acid binding activity, or activity that a domain identified herein has.

Examples of activators include P65, a tetramer of the herpes simplex activation domain VP16, termed VP64, optimized use of VP64 for activation through modification of both the sgRNA design and addition of additional helper molecules, MS2, P65 and HSF1in the system called the synergistic activation mediator (SAM) (Konermann et al, "Genome-scale transcriptional activation by an engineered CRISPR-Cas9 complex," Nature 517 (7536): 583-8 (2015)); and examples of repressors include the KRAB (Kruppel-associated box) domain of Kox1 or SID domain (e.g. SID4X); and an example of a nuclease or nuclease domain suitable for a functional domain comprises Fok1.

Suitable functional domains for use in practice of the invention, such as activators, repressors or nucleases are also discussed in documents incorporated herein by reference, including the patents and patent publications herein-cited and incorporated herein by reference regarding general information on CRISPR-Cas Systems.

In some embodiments, the CRISPR enzyme comprises or consists essentially of or consists of a localization signal as, or as part of, the linker between the CRISPR enzyme and the AAV capsid, e.g., VP2. HA or Flag tags are also within the ambit of the invention as linkers as well as Glycine Serine linkers as short as GS up to (GGGGS) 3. In this regard it is mentioned that tags that can be used in embodiments of the invention include affinity tags, such as chitin binding protein (CBP), maltose binding protein (MBP), glutathione-S-transferase (GST), poly(His) tag; solubilization tags such as thioredoxin (TRX) and poly (NANP), MBP, and GST; chromatography tags such as those consisting of polyanionic amino acids, such as FLAG-tag; epitope tags such as V5-tag, Myc-tag, HA-tag and NE-tag; fluorescence tags, such as GFP and mCherry; protein tags that may allow specific enzymatic modification (such as biotinylation by biotin ligase) or chemical modification (such as reaction with FLASH-EDT2 for fluorescence imaging).

Also provided is a method of treating a subject, e.g, a subject in need thereof, comprising inducing gene editing by transforming the subject with the AAV-CRISPR enzyme advantageously encoding and expressing in vivo the remaining portions of the CRISPR system (e.g., RNA, guides). A suitable repair template may also be provided, for example delivered by a vector comprising said repair template. Also provided is a method of treating a subject, e.g., a subject in need thereof, comprising inducing transcriptional activation or repression by transforming the subject with the AAV-CRISPR enzyme advantageously encoding and expressing in vivo the remaining portions of the CRISPR system (e.g., RNA, guides); advantageously in some embodiments the CRISPR enzyme is a catalytically inactive CRISPR enzyme and comprises one or more associated functional domains. Where any treatment is occurring ex vivo, for example in a cell culture, then it will be appreciated that the term 'subject' may be replaced by the phrase "cell or cell culture."

Compositions comprising the present system for use in said method of treatment are also provided. A kit of parts may be provided including such compositions. Use of the present system in the manufacture of a medicament for such methods of treatment are also provided. Use of the present system in screening is also provided by the present invention, e.g., gain of function screens. Cells which are artificially forced to overexpress a gene are be able to down regulate the gene over time (re-establishing equilibrium) e.g. by negative feedback loops. By the time the screen starts the unregulated gene might be reduced again.

In one aspect, the invention provides an engineered, non-naturally occurring CRISPR-Cas system comprising a AAV-Cas protein and a guide RNA that targets a DNA molecule encoding a gene product in a cell, whereby the guide RNA targets the DNA molecule encoding the gene product and the Cas protein cleaves the DNA molecule encoding the gene product, whereby expression of the gene product is altered; and, wherein the Cas protein and the guide RNA do not naturally occur together. The invention comprehends the guide RNA comprising a guide sequence fused to a tracr sequence. In an embodiment of the invention the Cas protein is a type II CRISPR-Cas protein and in a preferred embodiment the Cas protein is a Cas9 protein. The invention further comprehends the coding for the Cas protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

In another aspect, the invention provides an engineered, non-naturally occurring vector system comprising one or more vectors comprising a first regulatory element operably linked to a CRISPR-Cas system guide RNA that targets a DNA molecule encoding a gene product and a AAV-Cas protein. The components may be located on same or different vectors of the system, or may be the same vector whereby the AAV-Cas protein also delivers the RNA of the CRISPR system. The guide RNA targets the DNA molecule encoding the gene product in a cell and the AAV-Cas protein may cleaves the DNA molecule encoding the gene product (it may cleave one or both strands or have substantially no nuclease activity), whereby expression of the gene product is altered; and, wherein the AAV-Cas protein and the guide RNA do not naturally occur together. The invention comprehends the guide RNA comprising a guide sequence fused to a tracr sequence. In an embodiment of the invention the AAV-Cas protein is a type II AAV-CRISPR-Cas protein and in a preferred embodiment the AAV-Cas protein is a AAV-Cas9 protein. The invention further comprehends the coding for the AAV-Cas protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

In one aspect, the invention provides a vector system comprising one or more vectors. In some embodiments, the system comprises: (a) a first regulatory element operably linked to a tracr mate sequence and one or more insertion sites for inserting one or more guide sequences upstream of the tracr mate sequence, wherein when expressed, the guide sequence directs sequence-specific binding of a AAV-CRISPR complex to a target sequence in a eukaryotic cell, wherein the CRISPR complex comprises a AAV-CRISPR enzyme complexed with (1) the guide sequence that is hybridized to the target sequence, and (2) the tracr mate sequence that is hybridized to the tracr sequence; and (b) said AAV-CRISPR enzyme comprising at least one nuclear localization sequence and/or at least one NES; wherein components (a) and (b) are located on or in the same or different vectors of the system. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a AAV-CRISPR complex to a different target sequence in a eukaryotic cell. In some embodiments, the system comprises the tracr sequence under the control of a third regulatory element, such as a polymerase III promoter. In some embodiments, the tracr sequence exhibits at least 50%, 60%, 70%, 80%, 90%, 95%, or 99% of sequence complementarity along the length of the tracr mate sequence when optimally aligned. Determining optimal alignment is within the purview of one of skill in the art. For example, there are publically and commercially available alignment algorithms and programs such as, but not limited to, ClustalW, Smith-Waterman in matlab, Bowtie, Geneious, Biopython and SeqMan. In some embodiments, the AAV-CRISPR complex comprises one or more nuclear localization sequences of sufficient strength to drive accumulation of said CRISPR complex in a detectable amount in the nucleus of a eukaryotic cell. Without wishing to be bound by theory, it is believed that a nuclear localization sequence is not necessary for AAV-CRISPR complex activity in eukaryotes, but that including such sequences enhances activity of the system, especially as to targeting nucleic acid molecules in the nucleus and/or having molecules exit the nucleus. In some embodiments, the AAV-CRISPR enzyme is a type II AAV-CRISPR system enzyme. In some embodiments, the AAV-CRISPR enzyme is a AAV-Cas9 enzyme. In some embodiments, the AAV-Cas9 enzyme is derived from S. pneumoniae, S. pyogenes, S. thermophiles, F. novicida or S. aureus Cas9 (e.g., a Cas9 of one of these organisms modified to have or be associated with at least one AAV), and may include further mutations or alterations or be a chimeric Cas9. The enzyme may be a AAV-Cas9 homolog or ortholog. In some embodiments, the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). Again, the RNA of the CRISPR System, while advantageously delivered via the AAV-CRISPR enzyme can also be delivered separately, e.g. via a separate vector.

The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R—U5' segment in LTR of HTLV-I (Mol. Cell. Biol., Vol. 8 (1), p. 466-472, 1988); SV40 enhancer; and the intron sequence between exons 2 and 3 of rabbit β-globin (Proc. Natl. Acad. Sci. USA., Vol. 78 (3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Advantageous vectors include lentiviruses and adeno-associated viruses, and types of such vectors can also be selected for targeting particular types of cells.

In one aspect, the invention provides an AAV-CRISPR enzyme comprising one or more nuclear localization sequences and/or NES. In some embodiments, said AAV-CRISPR enzyme includes a regulatory element that drives transcription of component(s) of the CRISPR system (e.g., RNA, such as guide RNA and/or HR template nucleic acid molecule) in a eukaryotic cell such that said AAV-CRISPR enzyme delivers the CRISPR system accumulates in a detectable amount in the nucleus of the eukaryotic cell and/or is exported from the nucleus. In some embodiments, the regulatory element is a polymerase II promoter. In some embodiments, the AAV-CRISPR enzyme is a type II AAV-CRISPR system enzyme. In some embodiments, the AAV-CRISPR enzyme is a AAV-Cas9 enzyme. In some embodiments, the AAV-Cas9 enzyme is derived from *S. pneumoniae, S. pyogenes, S. thermophilus, F. novicida* or *S. aureus* Cas9 (e.g., modified to have or be associated with at least one AAV), and may include further alteration or mutation of the Cas9, and can be a chimeric Cas9. In some embodiments, the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks or substantially DNA strand cleavage activity (e.g., no more than 5% nuclease activity as compared with a wild type enzyme or enzyme not having the mutation or alteration that decreases nuclease activity).

In one aspect, the invention provides a AAV-CRISPR enzyme comprising one or more nuclear localization sequences of sufficient strength to drive accumulation of said AAV-CRISPR enzyme in a detectable amount in the nucleus of a eukaryotic cell. In some embodiments, the AAV-CRISPR enzyme is a type II AAV-CRISPR system enzyme. In some embodiments, the AAV-CRISPR enzyme is a AAV-Cas9 enzyme. In some embodiments, the AAV-Cas9 enzyme is derived from *S. pneumoniae, S. pyogenes, S. thermophilus, F. novicida* or *S. aureus* Cas9 (e.g., modified to have or be associated with at least one AAV), and may include further alteration or mutation of the Cas9, and can be a chimeric Cas9. In some embodiments, the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks or substantially DNA strand cleavage activity (e.g., no more than 5% nuclease activity as compared with a wild type enzyme or enzyme not having the mutation or alteration that decreases nuclease activity).

In one aspect, the invention provides a eukaryotic host cell comprising (a) a first regulatory element operably linked to a tracr mate sequence and one or more insertion sites for inserting one or more guide sequences upstream of the tracr mate sequence, wherein when expressed, the guide sequence directs sequence-specific binding of a AAV-CRISPR complex to a target sequence in a eukaryotic cell, wherein the AAV-CRISPR complex comprises a AAV-CRISPR enzyme complexed with (1) the guide sequence that is hybridized to the target sequence, and (2) the tracr mate sequence that is hybridized to the tracr sequence; and/or (b) a said AAV-CRISPR enzyme optionally comprising at least one nuclear localization sequence and/or NES. In some embodiments, the host cell comprises components (a) and (b). In some embodiments, component (a), component (b), or components (a) and (b) are stably integrated into a genome of the host eukaryotic cell. In some embodiments, component (b) includes or contains component (a). In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a AAV-CRISPR complex to a different target sequence in a eukaryotic cell. In some embodiments, the eukaryotic host cell further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. In some embodiments, the AAV-CRISPR enzyme comprises one or more nuclear localization sequences and/or nuclear export sequences of sufficient strength to drive accumulation of said CRISPR enzyme in a detectable amount in of the nucleus of a eukaryotic cell. In some embodiments, the AAV-CRISPR enzyme is a type II CRISPR system enzyme. In some embodiments, the CRISPR enzyme is a Cas9 enzyme. In some embodiments, the AAV-Cas9 enzyme is derived from *S. pneumoniae, S. pyogenes, S. thermophilus, F. novicida* or *S. aureus* Cas9 (e.g., modified to have or be associated with at least one AAV), and may include further alteration or mutation of the Cas9, and can be a chimeric Cas9. In some embodiments, the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks or substantially DNA strand cleavage activity (e.g., no more than 5% nuclease activity as compared with a wild type enzyme or enzyme not having the mutation or alteration that decreases nuclease activity). In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In an aspect, the invention provides a non-human eukaryotic organism; preferably a multicellular eukaryotic organism, comprising a eukaryotic host cell according to any of the described embodiments. In other aspects, the invention provides a eukaryotic organism; preferably a multicellular eukaryotic organism, comprising a eukaryotic host cell according to any of the described embodiments. The organism in some embodiments of these aspects may be an animal; for example a mammal. Also, the organism may be an arthropod such as an insect. The organism also may be a plant. Further, the organism may be a fungus. Advantageously the organism is a host of AAV.

In one aspect, the invention provides a kit comprising one or more of the components described herein. In some embodiments, the kit comprises a vector system and instructions for using the kit. In some embodiments, the vector system comprises (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and/or (b) said AAV-CRISPR enzyme optionally comprising a nuclear localization sequence. In some embodiments, the kit comprises components (a) and (b) located on or in the same or different vectors of the system, e.g., (a) can be contained in (b). In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the system further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. In some embodiments, the CRISPR enzyme comprises one or more nuclear localization sequences of sufficient strength to drive accumulation of said CRISPR enzyme in a detectable amount in the nucleus of a eukaryotic cell. In some embodiments, the CRISPR enzyme is a type II CRISPR system enzyme. In some embodiments, the CRISPR enzyme is a Cas9 enzyme. In some embodiments, the Cas9 enzyme is derived from *S. pneumoniae, S. pyogenes, S. thermophilus, F. novicida* or *S. aureus* Cas9 (e.g., modified to have or be associated with at least one AAV), and may include further alteration or mutation of the Cas9, and can be a chimeric Cas9. In some embodiments, the coding for the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks or substantially DNA strand cleavage activity (e.g., no more than 5% nuclease activity as compared with a wild type enzyme or enzyme not having the mutation or alteration that decreases nuclease activity). In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length.

In one aspect, the invention provides a method of modifying a target polynucleotide in a eukaryotic cell. In some embodiments, the method comprises allowing a AAV-CRISPR complex to bind to the target polynucleotide, e.g., to effect cleavage of said target polynucleotide, thereby modifying the target polynucleotide, wherein the AAV-CRISPR complex comprises a AAV-CRISPR enzyme complexed with a guide sequence hybridized to a target sequence within said target polynucleotide, wherein said guide sequence is linked to a tracr mate sequence which in turn hybridizes to a tracr sequence. In some embodiments, said cleavage comprises cleaving one or two strands at the location of the target sequence by said AAV-CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein one or more vectors comprise the AAV-CRISPR enzyme and one or more vectors drive expression of one or more of: the guide sequence linked to the tracr mate sequence, and the tracr sequence. In some embodiments, said AAV-CRISPR enzyme drive expression of one or more of: the guide sequence linked to the tracr mate sequence, and the tracr sequence. In some embodiments such AAV-CRISPR enzyme are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of a polynucleotide in a eukaryotic cell. In some embodiments, the method comprises allowing a AAV-CRISPR complex to bind to the polynucleotide such that said binding results in increased or decreased expression of said polynucleotide; wherein the AAV-CRISPR complex comprises a AAV-CRISPR enzyme complexed with a guide sequence hybridized to a target sequence within said polynucleotide, wherein said guide sequence is linked to a tracr mate sequence which in turn hybridizes to a tracr sequence. In some embodiments, the method further comprises delivering one or more vectors to said eukaryotic cells, wherein the one or more vectors are the AAV-CRISPR enzyme and/or drive expression of one or more of: the guide sequence linked to the tracr mate sequence, and the tracr sequence.

In one aspect, the invention provides a method of generating a model eukaryotic cell comprising a mutated disease gene. In some embodiments, a disease gene is any gene associated an increase in the risk of having or developing a disease. In some embodiments, the method comprises (a) introducing one or more vectors into a eukaryotic cell, wherein the one or more vectors comprise the AAV-CRISPR enzyme and/or drive expression of one or more of: a guide sequence linked to a tracr mate sequence, and a tracr sequence; and (b) allowing a AAV-CRISPR complex to bind to a target polynucleotide, e.g., to effect cleavage of the target polynucleotide within said disease gene, wherein the AAV-CRISPR complex comprises the AAV-CRISPR enzyme complexed with (1) the guide sequence that is hybridized to the target sequence within the target polynucleotide, and (2) the tracr mate sequence that is hybridized to the tracr sequence, thereby generating a model eukaryotic cell comprising a mutated disease gene. Thus, in some embodiments the AAV-CRISPR enzyme contains nucleic acid molecules for and drives expression of one or more of: a guide sequence linked to a tracr mate sequence, and a tracr sequence and/or a Homologous Recombination template and/or a stabilizing ligand if the CRISPR enzyme has a destabilization domain. In some embodiments, said cleavage comprises cleaving one or two strands at the location of the target sequence by said AAV-CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

In one aspect, the invention provides a method for developing a biologically active agent that modulates a cell signaling event associated with a disease gene. In some embodiments, a disease gene is any gene associated an increase in the risk of having or developing a disease. In some embodiments, the method comprises (a) contacting a test compound with a model cell of any one of the described embodiments; and (b) detecting a change in a readout that is indicative of a reduction or an augmentation of a cell signaling event associated with said mutation in said disease gene, thereby developing said biologically active agent that modulates said cell signaling event associated with said disease gene.

In one aspect, the invention provides a recombinant polynucleotide comprising a guide sequence upstream of a tracr mate sequence, wherein the guide sequence when expressed directs sequence-specific binding of a AAV-CRISPR complex to a corresponding target sequence present in a eukaryotic cell. The polynucleotide can be carried within and expressed in vivo from the AAV-CRISPR enzyme. In some embodiments, the target sequence is a viral sequence present in a eukaryotic cell. In some embodiments, the target sequence is a proto-oncogene or an oncogene.

In one aspect the invention provides for a method of selecting one or more cell(s) by introducing one or more mutations in a gene in the one or more cell(s), the method comprising: introducing one or more vectors into the cell(s), wherein the one or more vectors comprise a AAV-CRISPR enzyme and/or drive expression of one or more of: a guide sequence linked to a tracr mate sequence, a tracr sequence, and an editing template; wherein, for example that which is being expressed is within and expressed in vivo by the AAV-CRISPR enzyme and/or the editing template comprises the one or more mutations that abolish AAV-CRISPR enzyme cleavage; allowing homologous recombination of the editing template with the target polynucleotide in the cell(s) to be selected; allowing a CRISPR complex to bind to a target polynucleotide to effect cleavage of the target polynucleotide within said gene, wherein the AAV-CRISPR complex comprises the AAV-CRISPR enzyme complexed with (1) the guide sequence that is hybridized to the target sequence within the target polynucleotide, and (2) the tracr mate sequence that is hybridized to the tracr sequence, wherein binding of the AAV-CRISPR complex to the target polynucleotide induces cell death, thereby allowing one or more cell(s) in which one or more mutations have been introduced to be selected. In a preferred embodiment, the AAV-CRISPR enzyme is AAV-Cas9. In another aspect of the invention the cell to be selected may be a eukaryotic cell. Aspects of the invention allow for selection of specific cells without requiring a selection marker or a two-step process that may include a counter-selection system. The cell(s) may be prokaryotic or eukaryotic cells.

With respect to mutations of the AAV-CRISPR enzyme, when the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. In an aspect the invention provides as to any or each or all embodiments herein-discussed wherein the AAV-CRISPR enzyme comprises at least one or more, or at least two or more mutations, wherein the at least one or more mutation or the at least two or more mutations is as to D10, E762, H840, N854, N863, or D986 according to SpCas9 protein, e.g., D10A, E762A, H840A, N854A, N863A and/or D986A as to SpCas9, or N580 according to SaCas9, e.g., N580A as to SaCas9, or any corresponding mutation(s) in a Cas9 of an ortholog to Sp or Sa, or the CRISPR enzyme comprises at least one mutation wherein at least H840 or N863A as to Sp Cas9 or N580A as to Sa Cas9 is mutated; e.g., wherein the CRISPR enzyme comprises H840A, or D10A and H840A, or D10A and N863A, according to SpCas9 protein, or any corresponding mutation(s) in a Cas9 of an ortholog to Sp protein or Sa protein.

Aspects of the invention encompass a non-naturally occurring or engineered composition that may comprise a guide RNA (sgRNA) comprising a guide sequence capable of hybridizing to a target sequence in a genomic locus of interest in a cell and a AAV-CRISPR enzyme that may comprise at least one or more nuclear localization sequences, wherein the AAV-CRISPR enzyme comprises one or two or more mutations, such that the enzyme has altered or diminished nuclease activity compared with the wild type enzyme, wherein at least one loop of the sgRNA is modified by the insertion of distinct RNA sequence(s) that bind to one or more adaptor proteins, and wherein the adaptor protein further recruits one or more heterologous functional domains. In an embodiment of the invention the AAV-CRISPR enzyme comprises one or two or more mutations in a residue selected from the group comprising, consisting essentially of, or consisting of D10, E762, H840, N854, N863, or D986. In a further embodiment the AAV-CRISPR enzyme comprises one or two or more mutations selected from the group comprising D10A, E762A, H840A, N854A, N863A or D986A. In another embodiment, the functional domain comprise, consist essentially of a transcriptional activation domain, e.g., VP64. In another embodiment, the functional domain comprise, consist essentially of a transcriptional repressor domain, e.g., KRAB domain, SID domain or a SID4X domain. In embodiments of the invention, the one or more heterologous functional domains have one or more activities selected from the group comprising, consisting essentially of, or consisting of methylase activity, demethylase activity, transcription activation activity, transcription repression activity, transcription release factor activity, histone modification activity, RNA cleavage activity and nucleic acid binding activity. In further embodiments of the invention the cell is a eukaryotic cell or a mammalian cell or a human cell. In further embodiments, the adaptor protein is selected from the group comprising, consisting essentially of, or consisting of MS2, PP7, QB, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, PRR1. In another embodiment, the at least one loop of the sgRNA is tetraloop and/or loop2. An aspect of the invention encompasses methods of modifying a genomic locus of interest to change gene expression in a cell by introducing into the cell any of the compositions described herein. An aspect of the invention is that the above elements are comprised in a single composition or comprised in individual compositions, e.g., the AAV-CRISPR enzyme delivers the enzyme as discussed as well as the guide. These compositions may advantageously be applied to a host to elicit a functional effect on the genomic level. In general, the sgRNA are modified in a manner that provides specific binding sites (e.g., aptamers) for adapter proteins comprising one or more functional domains (e.g., via fusion protein) to bind to. The modified sgRNA are modified such that once the sgRNA forms a AAV-CRISPR complex (i.e. AAV-CRISPR enzyme binding to sgRNA and target) the adapter proteins bind and, the functional domain on the adapter protein is positioned in a spatial orientation which is advantageous for the attributed function to be effective. For example, if the functional domain comprise, consist essentially of a transcription activator (e.g., VP64 or p65), the transcription activator is placed in a spatial orientation which allows it to affect the transcription of the target. Likewise, a transcription repressor will be advantageously positioned to affect the transcription of the target and a nuclease (e.g., Fok1) will be advantageously positioned to cleave or partially cleave the target. Again, the AAV-CRISPR enzyme can deliver both the enzyme and the modified guide. The skilled person will understand that modifications to the sgRNA which allow for binding of the adapter+functional domain but not proper positioning of the adapter+functional domain (e.g., due to steric hindrance within the three dimensional structure of the CRISPR complex) are modifications which are not intended. The one or more modified sgRNA may be modified at the tetra loop, the stem loop 1, stem loop 2, or stem loop 3, as described herein, preferably at either the tetra loop or stem loop 2, and most preferably at both the tetra loop and stem loop 2.

As explained herein the functional domains may be, for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). In some cases it is advantageous that additionally at least one NLS is provided. In some instances, it is advantageous to position the NLS at the N terminus. When more than one functional domain is included, the functional domains may be the same or different.

The sgRNA may be designed to include multiple binding recognition sites (e.g., aptamers) specific to the same or different adapter protein. The sgRNA may be designed to bind to the promoter region −1000-+1 nucleic acids upstream of the transcription start site (i.e. TSS), preferably −200 nucleic acids. This positioning improves functional domains which affect gene activation (e.g., transcription activators) or gene inhibition (e.g., transcription repressors). The modified sgRNA may be one or more modified sgRNAs targeted to one or more target loci (e.g., at least 1 sgRNA, at least 2 sgRNA, at least 5 sgRNA, at least 10 sgRNA, at least 20 sgRNA, at least 30 sg RNA, at least 50 sgRNA) comprised in a composition.

Further, the AAV-CRISPR enzyme with diminished nuclease activity is most effective when the nuclease activity is inactivated (e.g., nuclease inactivation of at least 70%, at least 80%, at least 90%, at least 95%, at least 97%, or 100% as compared with the wild type enzyme; or to put in another way, a AAV-Cas9 enzyme or AAV-CRISPR enzyme having advantageously about 0% of the nuclease activity of the non-mutated or wild type Cas9 enzyme or CRISPR enzyme, or no more than about 3% or about 5% or about 10% of the nuclease activity of the non-mutated or wild type Cas9 enzyme or CRISPR enzyme). This is possible by introducing mutations into the RuvC and HNH nuclease domains of the SpCas9 and orthologs thereof. For example utilizing mutations in a residue selected from the group comprising, consisting essentially of, or consisting of D10, E762, H840, N854, N863, or D986 and more preferably introducing one or more of the mutations selected from the group comprising, consisting essentially of, or consisting of D10A, E762A, H840A, N854A, N863A or D986A. A preferable pair of mutations is D10A with H840A, more preferable is D10A with N863A of SpCas9 and orthologs thereof. The inactivated CRISPR enzyme may have associated (e.g., via fusion protein) one or more functional domains, e.g., at least one destabilizing domain; or, for instance like those as described herein for the modified sgRNA adaptor proteins, including for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1, MyoD1. In the event that Fok1 is provided, it is advantageous that multiple Fok1 functional domains are provided to allow for a functional dimer and that sgRNAs are designed to provide proper spacing for functional use (Fok1) as specifically described in Tsai et al. Nature Biotechnology, Vol. 32, Number 6, June 2014). The adaptor protein may utilize known linkers to attach such functional domains. In some cases it is advantageous that additionally at least one NLS is provided. In some instances, it is advantageous to position the NLS at the N terminus. When more than one functional domain is included, the functional domains may be the same or different. In general, the positioning of the one or more functional domain on the inactivated AAV-CRISPR enzyme is one which allows for correct spatial orientation for the functional domain to affect the target with the attributed functional effect. For example, if the functional domain is a transcription activator (e.g., VP64 or p65), the transcription activator is placed in a spatial orientation which allows it to affect the transcription of the target. Likewise, a transcription repressor will be advantageously positioned to affect the transcription of the target, and a nuclease (e.g., Fok1) will be advantageously positioned to cleave or partially cleave the target. This may include positions other than the N—/C-terminus of the AAV-CRISPR enzyme. Positioning the functional domain in the Rec1 domain, the Rec2 domain, the HNH domain, or the PI domain of the SpCas9 protein or any ortholog corresponding to these domains is advantageous; and again, it is mentioned that the functional domain can be a DD. Positioning of the functional domains to the Rec1 domain or the Rec2 domain, of the SpCas9 protein or any ortholog corresponding to these domains, in some instances may be preferred. Positioning of the functional domains to the Rec1 domain at position 553, Rec1 domain at 575, the Rec2 domain at any position of 175-306 or replacement thereof, the HNH domain at any position of 715-901 or replacement thereof, or the PI domain at position 1153 of the SpCas9 protein or any ortholog corresponding to these domains, in some instances may be preferred. Fok1 functional domain may be attached at the N terminus. When more than one functional domain is included, the functional domains may be the same or different.

An adaptor protein may be any number of proteins that binds to an aptamer or recognition site introduced into the modified sgRNA and which allows proper positioning of one or more functional domains, once the sgRNA has been incorporated into the AAV-CRISPR complex, to affect the target with the attributed function. As explained in detail in this application such may be coat proteins, preferably bacteriophage coat proteins. The functional domains associated with such adaptor proteins (e.g., in the form of fusion protein) may include, for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1, MyoD1. In the event that the functional domain is a transcription activator or transcription repressor it is advantageous that additionally at least an NLS is provided and preferably at the N terminus. When more than one functional domain is included, the functional domains may be the same or different. The adaptor protein may utilize known linkers to attach such functional domains. Such linkers may be used to associate the AAV (e.g., capsid or VP2) with the CRISPR enzyme or have the CRISPR enzyme comprise the AAV (or vice versa).

Thus, sgRNA, e.g., modified sgRNA, the inactivated AAV-CRISPR enzyme (with or without functional domains), and the binding protein with one or more functional domains, may each individually be comprised in a composition and administered to a host individually or collectively. Alternatively, these components may be provided in a single composition for administration to a host, e.g., the AAV-CRISPR enzyme can deliver the RNA or guide or sgRNA or modified sgRNA and/or other components of the CRISPR system. Administration to a host may be performed via viral vectors, advantageously using the AAV-CRISPR enzyme as the delivery vehicle, although other vehicles can be used to deliver components other than the enzyme of the CRISPR system, and such viral vectors can be, for example, lentiviral vector, adenoviral vector, AAV vector. Several variations are appropriate to elicit a genomic locus event, including DNA cleavage, gene activation, or gene deactivation. Using the provided compositions, the person skilled in the art can advantageously and specifically target single or multiple loci with the same or different functional domains to elicit one or more genomic locus events. The compositions may be applied in a wide variety of methods for screening in libraries in cells and functional modeling in vivo (e.g., gene activation of lincRNA and identification of function; gain-of-function modeling; loss-of-function modeling; the use the compositions of the invention to establish cell lines and transgenic animals for optimization and screening purposes).

In an aspect, the invention provides a particle delivery system or the delivery system or the virus particle of any one of any one of the above embodiments or the cell of any one of the above embodiments for use in medicine or in therapy; or for use in a method of modifying an organism or a non-human organism by manipulation of a target sequence in a genomic locus associated with a disease or disorder; or for use in a method of treating or inhibiting a condition caused by one or more mutations in a genetic locus associated with a disease in a eukaryotic organism or a non-human organism.; or for use in in vitro, ex vivo or in vivo gene or genome editing; or for use in in vitro, ex vivo or in vivo gene therapy.

In an aspect, the invention provides a pharmaceutical composition comprising the particle delivery system or the delivery system or the virus particle of any one of the above embodiment or the cell of any one of the above embodiment.

In an aspect, the invention provides a method of treating or inhibiting a condition or a disease caused by one or more mutations in a genomic locus in a eukaryotic organism or a non-human organism comprising manipulation of a target sequence within a coding, non-coding or regulatory element of said genomic locus in a target sequence in a subject or a non-human subject in need thereof comprising modifying the subject or a non-human subject by manipulation of the target sequence and wherein the condition or disease is susceptible to treatment or inhibition by manipulation of the target sequence comprising providing treatment comprising delivering a composition comprising the particle delivery system or the delivery system or the virus particle of any one of the above embodiment or the cell of any one of the above embodiment.

In an aspect, the invention provides use of the particle delivery system or the delivery system or the virus particle of any one of the above embodiment or the cell of any one of the above embodiment in ex vivo or in vivo gene or genome editing; or for use in in vitro, ex vivo or in vivo gene therapy.

In an aspect, the invention provides use of the particle delivery system or the delivery system or the virus particle of any one of the above embodiment or the cell of any one of the above embodiment in the manufacture of a medicament for in vitro, ex vivo or in vivo gene or genome editing or for use in in vitro, ex vivo or in vivo gene therapy or for use in a method of modifying an organism or a non-human organism by manipulation of a target sequence in a genomic locus associated with a disease or in a method of treating or inhibiting a condition or disease caused by one or more mutations in a genomic locus in a eukaryotic organism or a non-human organism.

In an aspect, the invention provides a method of individualized or personalized treatment of a genetic disease in a subject in need of such treatment comprising:
  (a) introducing one or more mutations ex vivo in a tissue, organ or a cell line, or in vivo in a transgenic non-human mammal, comprising delivering to cell(s) of the tissue, organ, cell or mammal a composition comprising the particle delivery system or the delivery system or the virus particle of any one of the above embodiment or the cell of any one of the above embodiment, wherein the specific mutations or precise sequence substitutions are or have been correlated to the genetic disease;
  (b) testing treatment(s) for the genetic disease on the cells to which the vector has been delivered that have the specific mutations or precise sequence substitutions correlated to the genetic disease; and
  (c) treating the subject based on results from the testing of treatment(s) of step (b).

In an aspect, the invention provides a method of modeling a disease associated with a genomic locus in a eukaryotic organism or a non-human organism comprising manipulation of a target sequence within a coding, non-coding or regulatory element of said genomic locus comprising delivering a non-naturally occurring or engineered composition comprising a viral vector system comprising one or more viral vectors operably encoding a composition for expression thereof, wherein the composition comprises particle delivery system or the delivery system or the virus particle of any one of the above embodiments or the cell of any one of the above embodiment.

In an aspect, the method provides a method of modifying an organism or a non-human organism by manipulation of a target sequence in a genomic locus of interest comprising administering a composition comprising the particle delivery system or the delivery system or the virus particle of any one of the above embodiment or the cell of any one of the above embodiment.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53 (c) EPC and Rule 28 (b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

As used herein, "enzyme" comprises active enzyme as well as inactive or dead enzyme.

As used herein, "enzyme" and "protein" are used interchangeably.

These and other embodiments are disclosed or are obvious from and encompassed by, the following Detailed Description.

| | |
|---|---|
| Packaging A0060 | VP3 only loop3 Cre 1:10 |
| Packaging A0061 | VP3 only loop3 Cre 1:1 |
| Packaging A0062 | VP3 only loop3 Cas9 1:10 |
| Packaging A0063 | VP3 only loop3 Cas9 1:1 |
| Packaging A0064 | VP3 only loop4 Cre 1:10 |
| Packaging A0065 | VP3 only loop4 Cre 1:1 |
| A0068 | VSVG Cas9 gesicle |
| A0069 | VSVG Cre gesicle |
| A0070 | RVG Cas9 gesicle |
| A0071 | RVG Cre gesicle |
| Packaging A0072 | AAV9 loop6 (His)6 1:10 |
| Packaging A0073 | AAV9 loop6 (His)6 1:1 |
| Packaging A0074 | VP3 only loop4 Cas9 1:10 |
| Packaging A0075 | VP3 only loop4 Cas9 1:1 |
| A0084 | VSVG-CRE |
| A0085 | DNase treatment |
| A0086 | (+G − S) |
| A0087 | (−G + S) |

Figure 1:
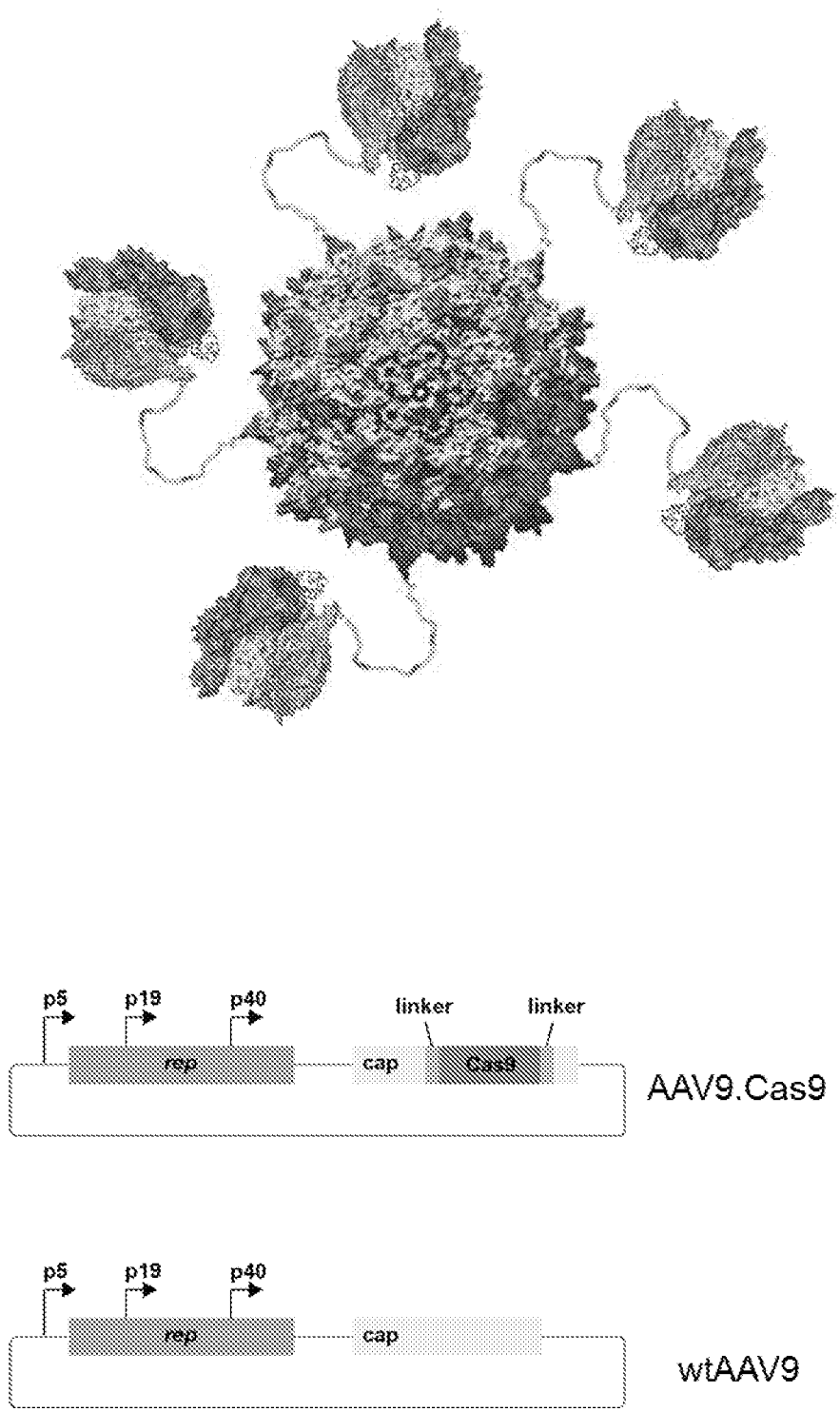
FIG. 1 shows illustrations of AAV-CRISPR protein of the invention, wherein Cas9 protein is fused or tethered to VP3, for example at the N-terminus of VP3. Cas9 is attached to some, but not all VP3 subunits to avoid steric blocking of cell entry sites on AAV surface. In the AAV9.Cas9 vector, a Cas9 protein fused or tethered to the C-term of VP1, Sn, VP2 or VP3 is depicted.
Figure 2A:
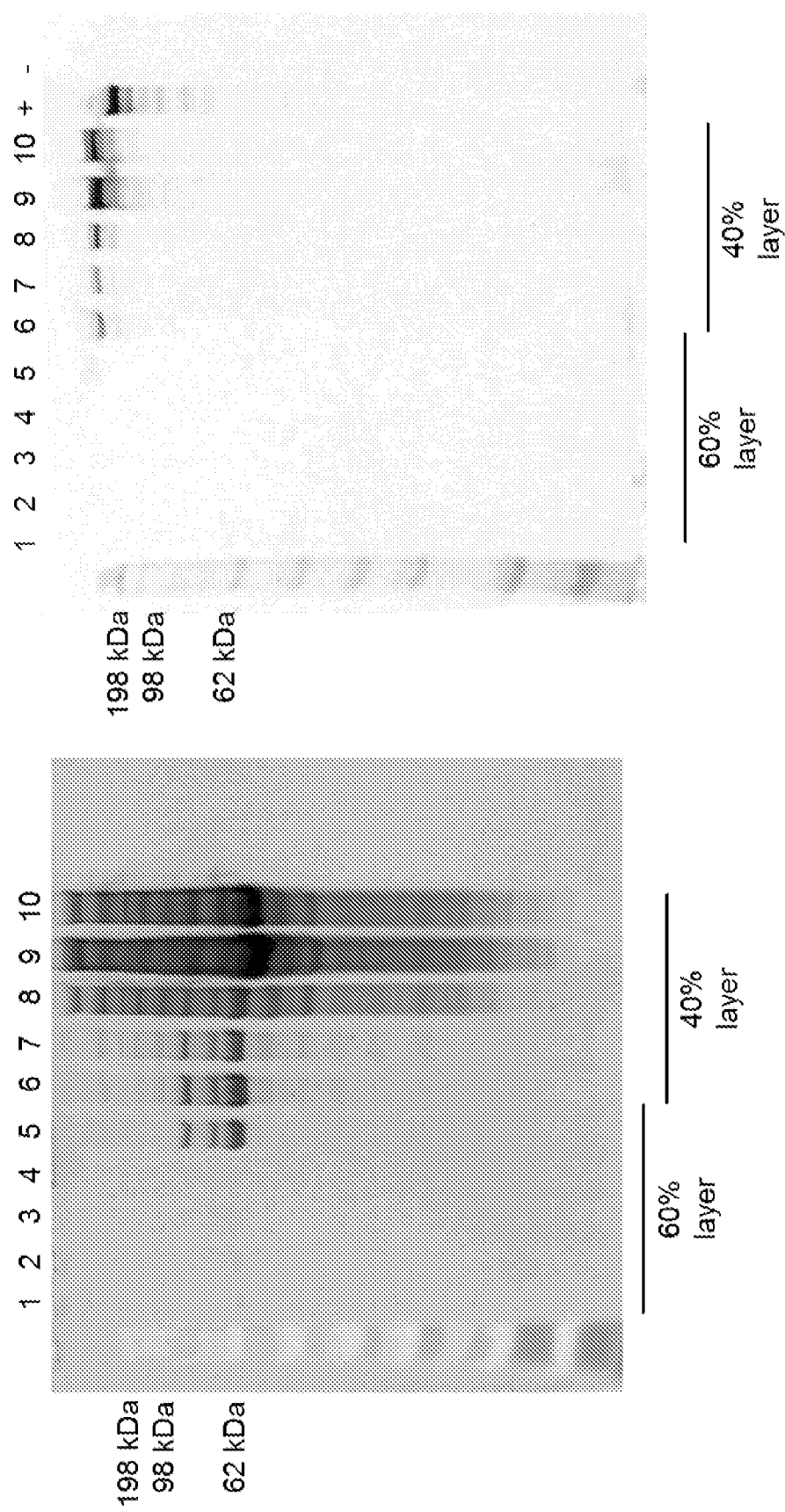
FIG. 2A-2B shows a Western blot confirming expression of Cas9-VP3 fusion proteins in cells transfected with plasmids encoding for Cas9 and Cas9-VP3 fusions (AAVCas9: wt 1:6). (A) Left panel: SYPRO Ruby protein staining of fractions from AAVCas9: wt 1:6. Right panel: Anti-SpCas9 blotting of fractions from AAVCas9: wt 1:6. (B) Left panel: SYPRO Ruby protein staining of fractions from wtAAV9. Right panel: Anti-SpCas9 blotting of fractions from wtAAV9.
Figure 2B:
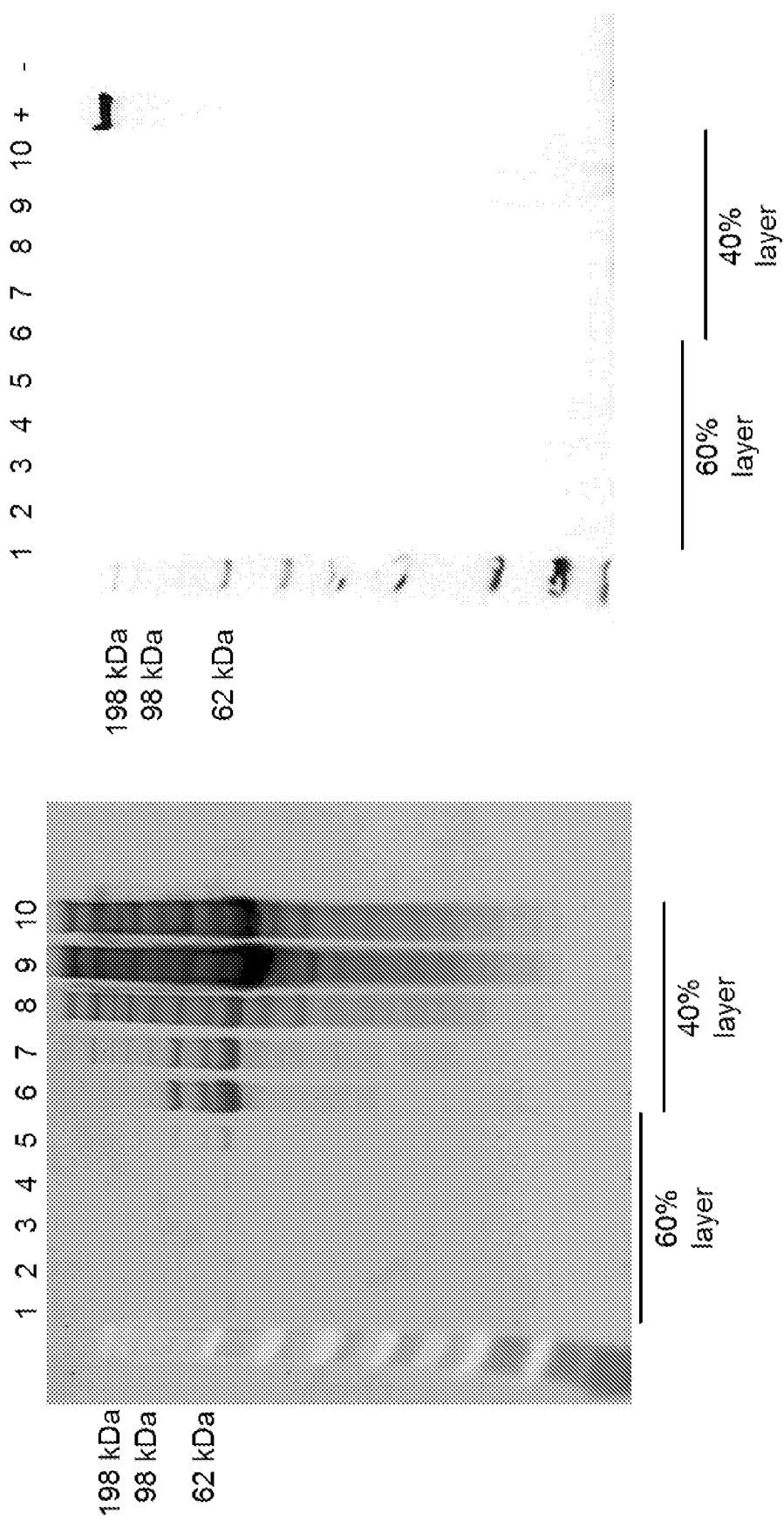
Figure 3:
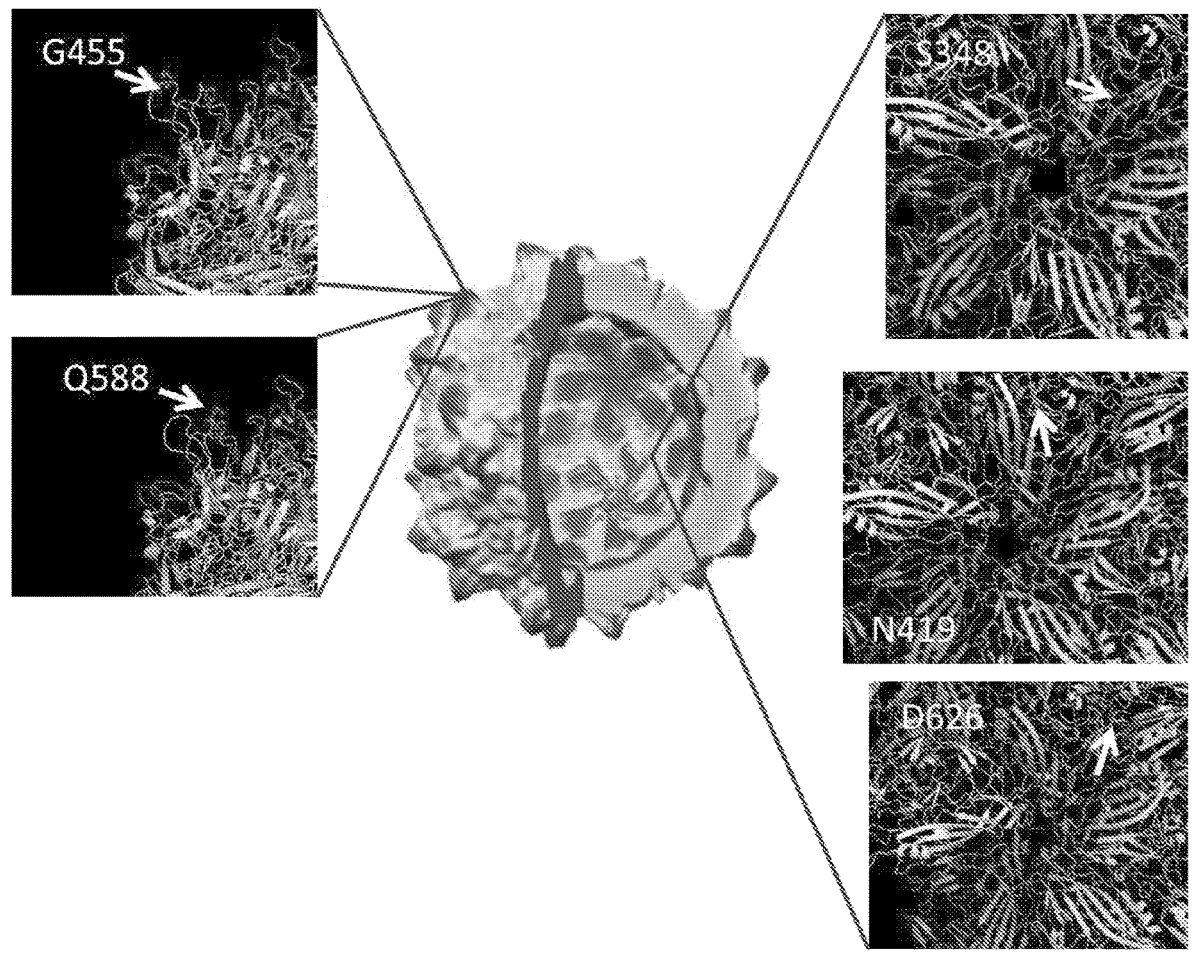
FIG. 3 illustrates exterior loops and interior sites in AAV9 VP3 for protein insertion.
Figure 4:
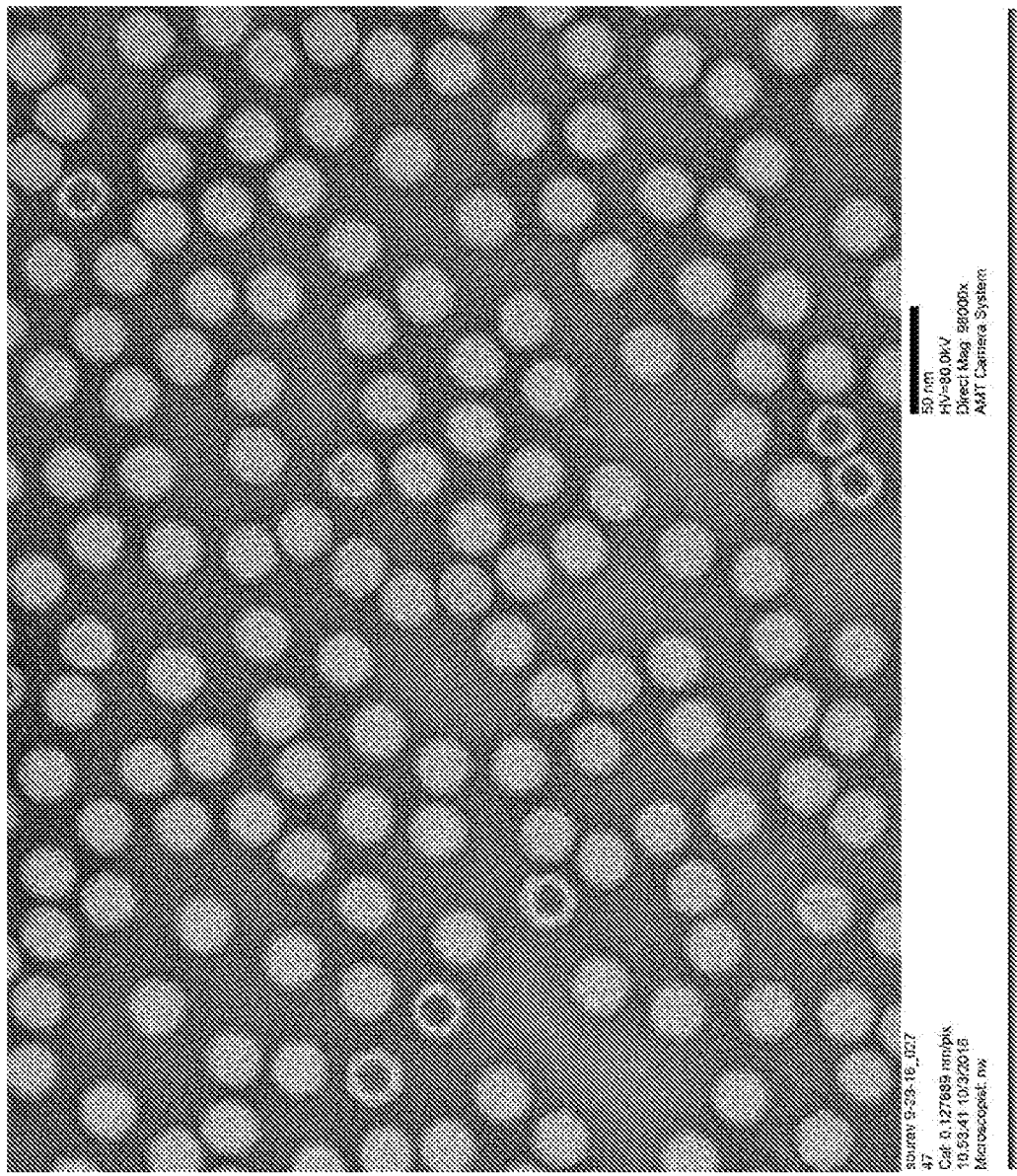
FIG. 4 depicts electron micrography of wtAAV. Dark particle centers indication empty particles.
Figure 5:
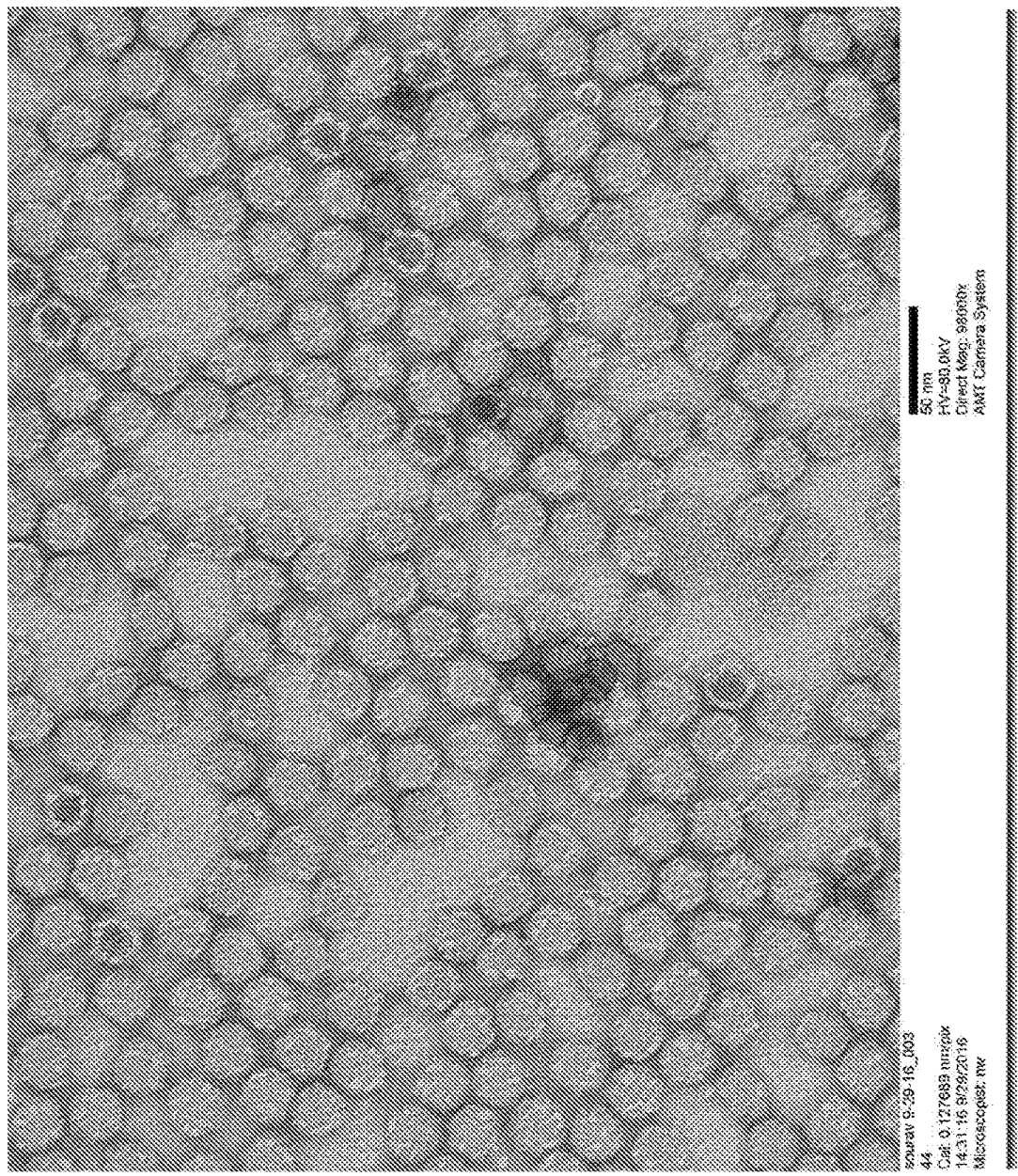
FIG. 5 depicts electron micrography of AAV.Cas9 virus particles comprising 50wtAAV: 10AAVCas9.
Figure 6:
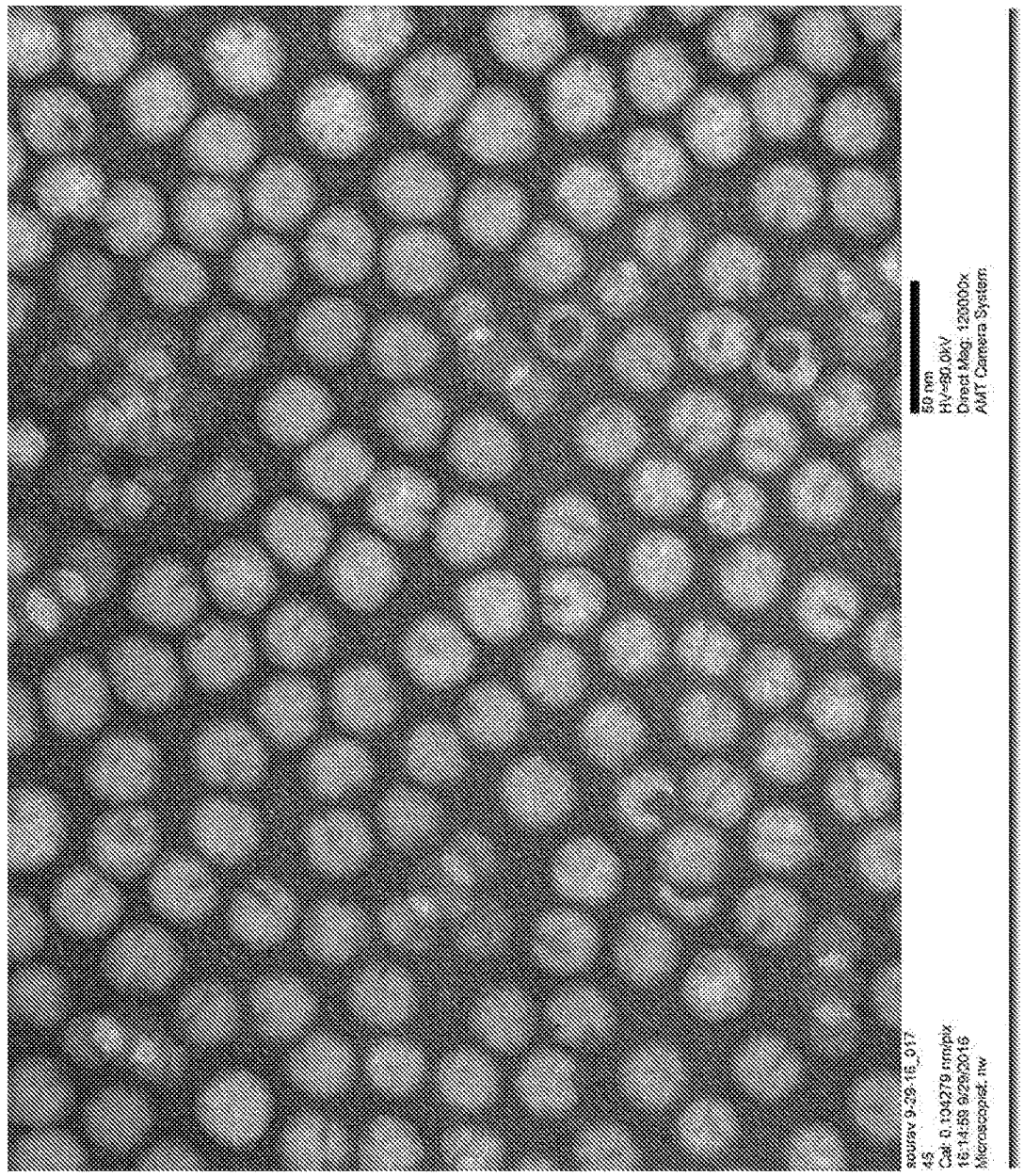
FIG. 6 depicts electron micrography of AAV.Cas9 virus particles comprising 30wtAAV: 30AAVCas9.
Figure 7A:
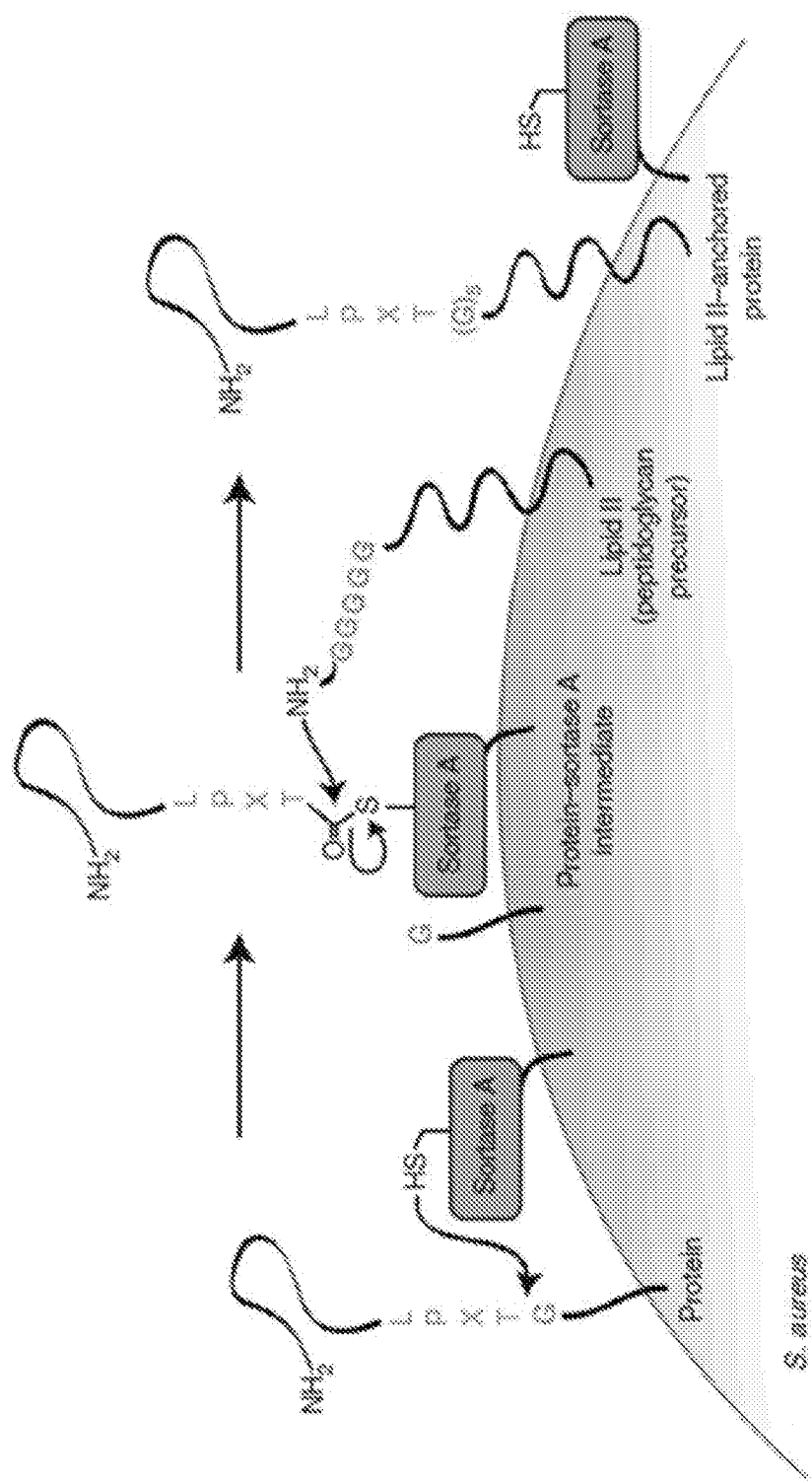
FIG. 7A-7B depicts sortase-mediated protein linkage. (A) schematic of proteins anchored to a cell wall via sortase in Gram-positive bacteria is shown (see, Guimares, et al., Nat. Prot. 2013). (B) linkage of Cas9 to AAV by TEV-sortase method. CRISPR protein modified at its C terminus with the LPXTG sortase-recognition motif followed by a handle for purification (often His6) is incubated with sortase A. Sortase cleaves the threonine-glycine bond and forms an acyl intermediate with threonine. Addition of TEV-cleaved AAV ("probe") comprising N-terminal glycine residues ligates the AAV to the C terminus of the CRISPR protein (see, Guimares, et al., Nat. Prot. 2013).
Figure 7B:
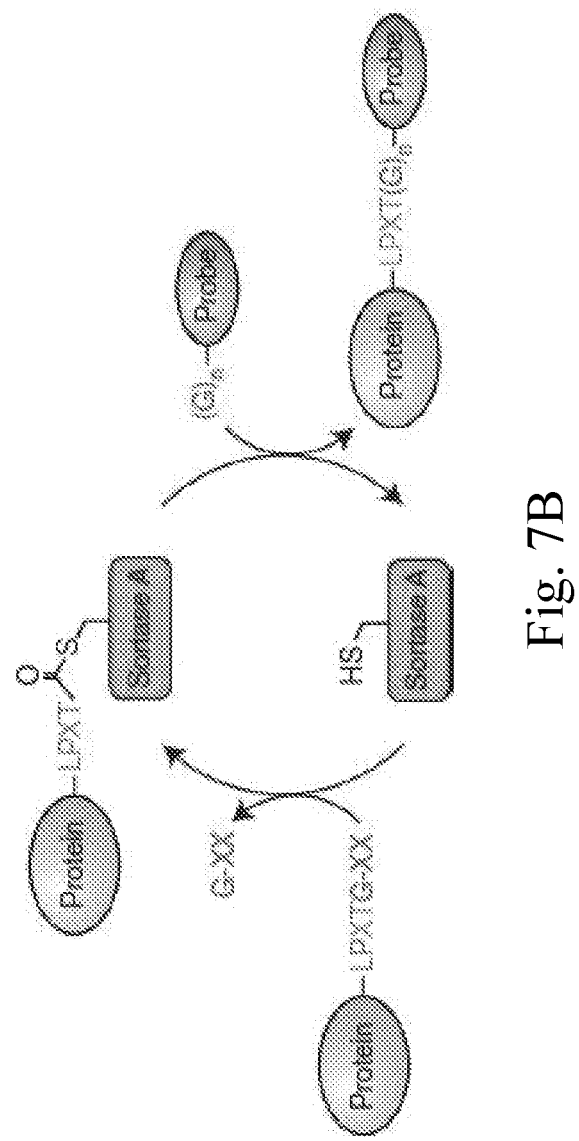
Figure 8:
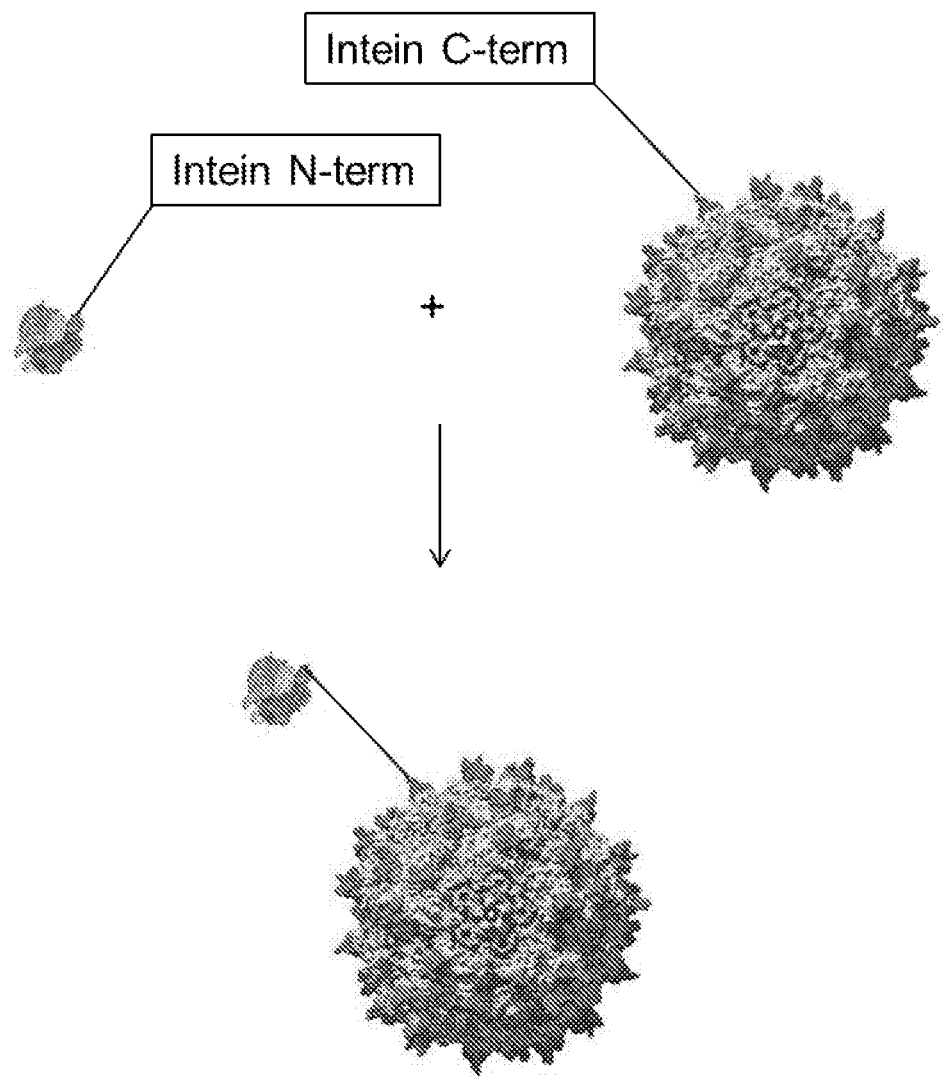
FIG. 8 depicts linkage of Cas9 to AAV by split intein reconstitution.
Figure 9A:
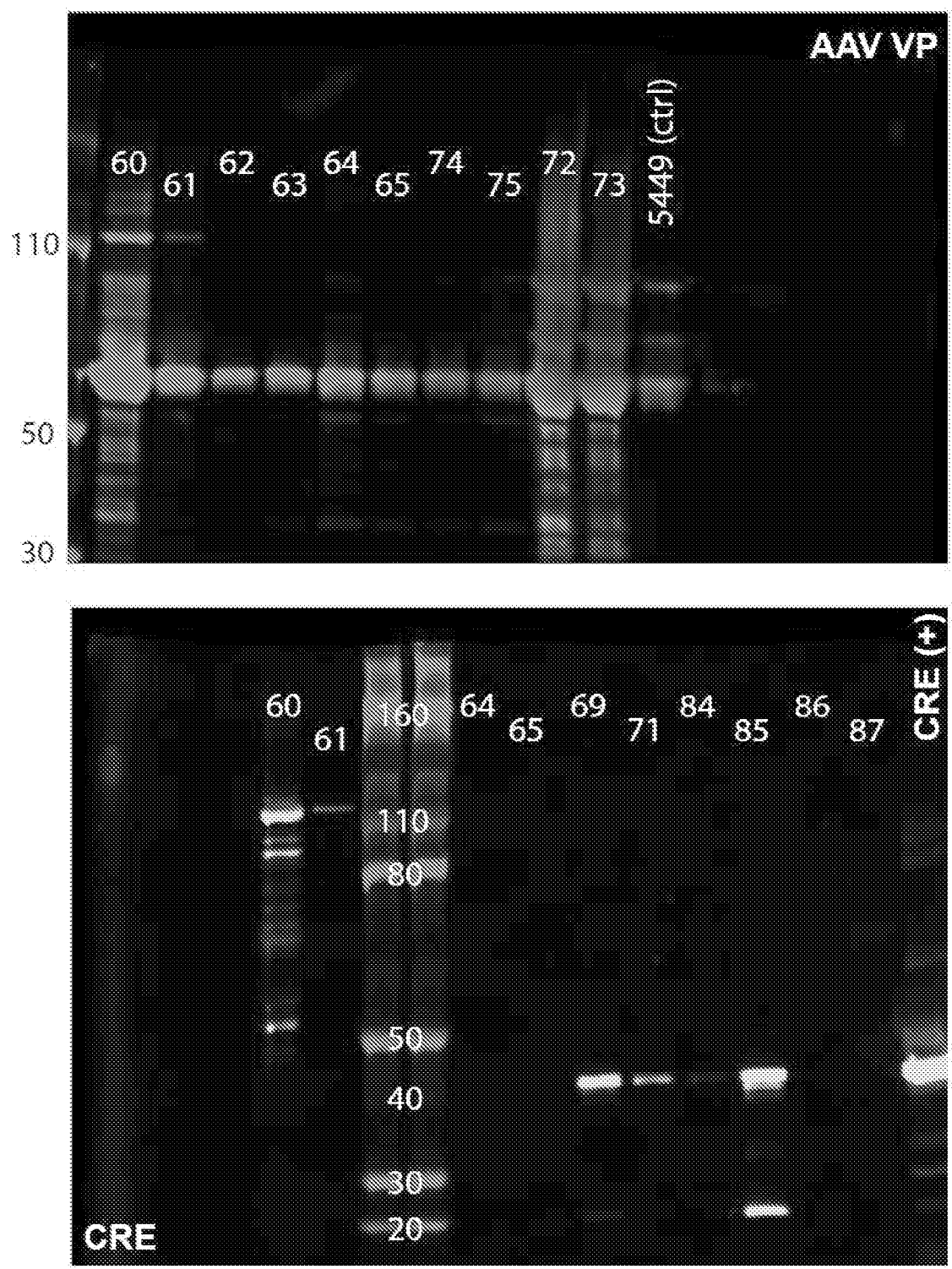
FIG. 9A-9B shows interior packaging of proteins.
Figure 9B:
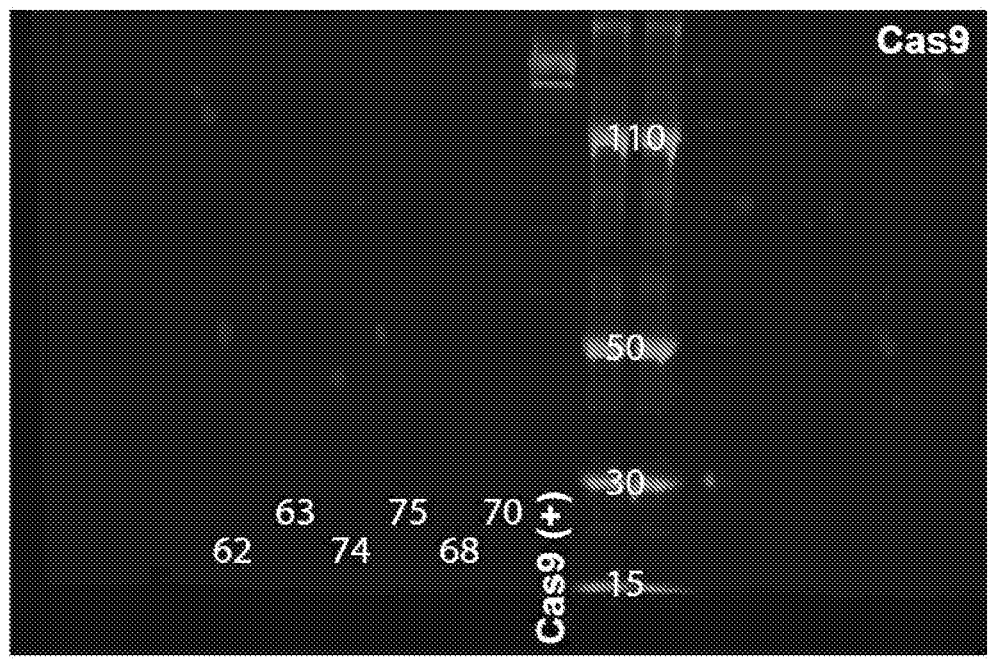
Figure 9B:
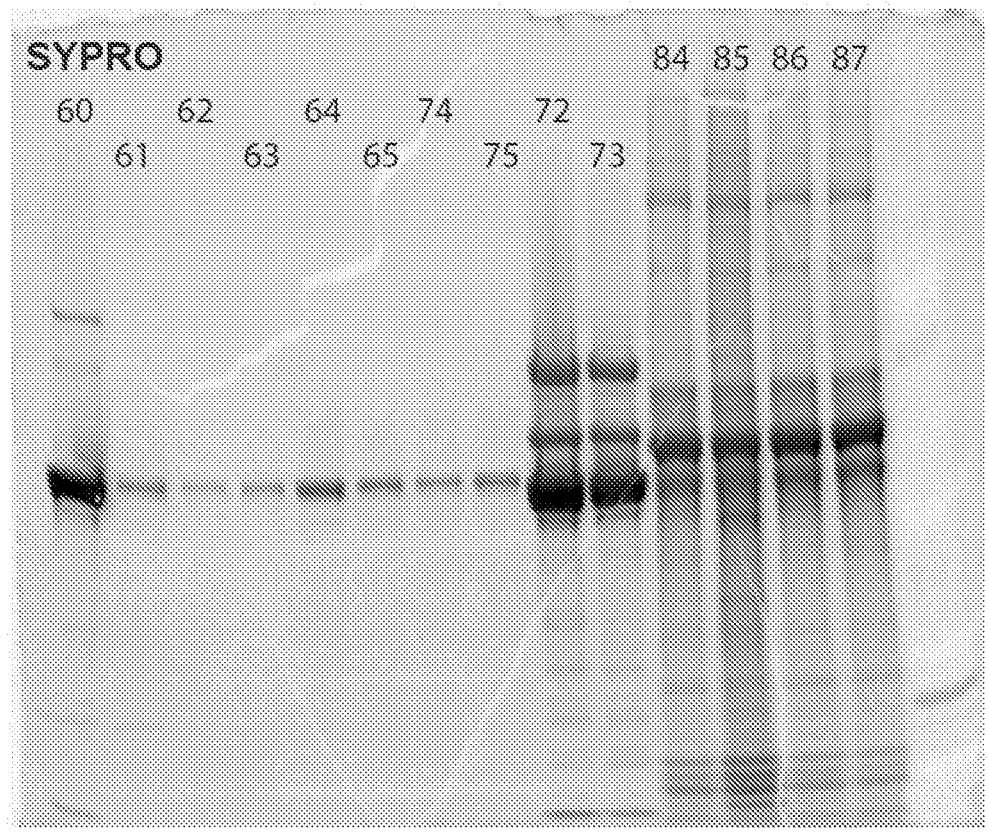
Figure 10:
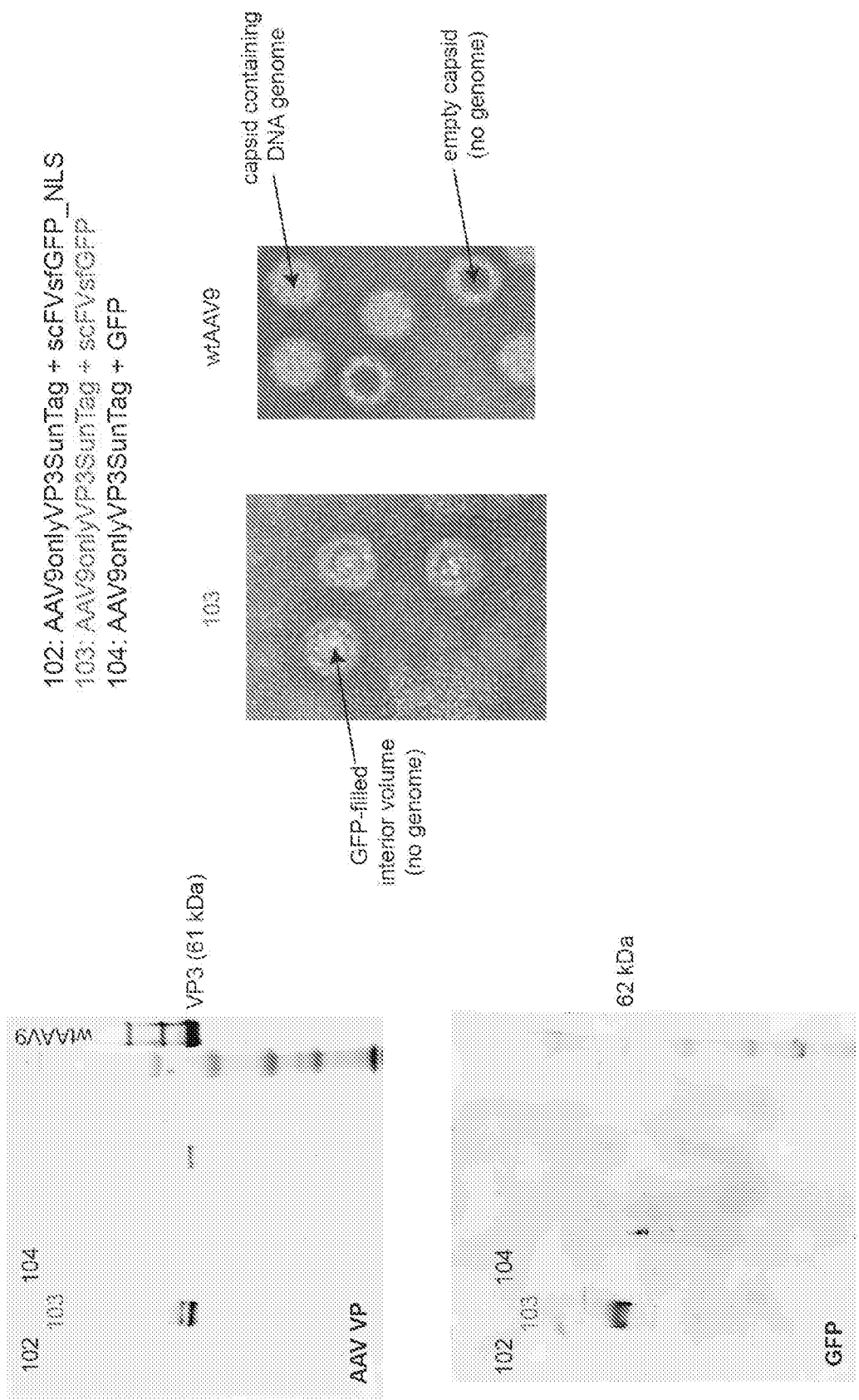

FIG. 10 shows Interior SunTag-GFP. Western blots detect VP3 (top left) and GFP (bottom left) for native VP3 and VP3-GFP fusion. Electron micrographs show GFP-filled capsid (103).

Figure 11:
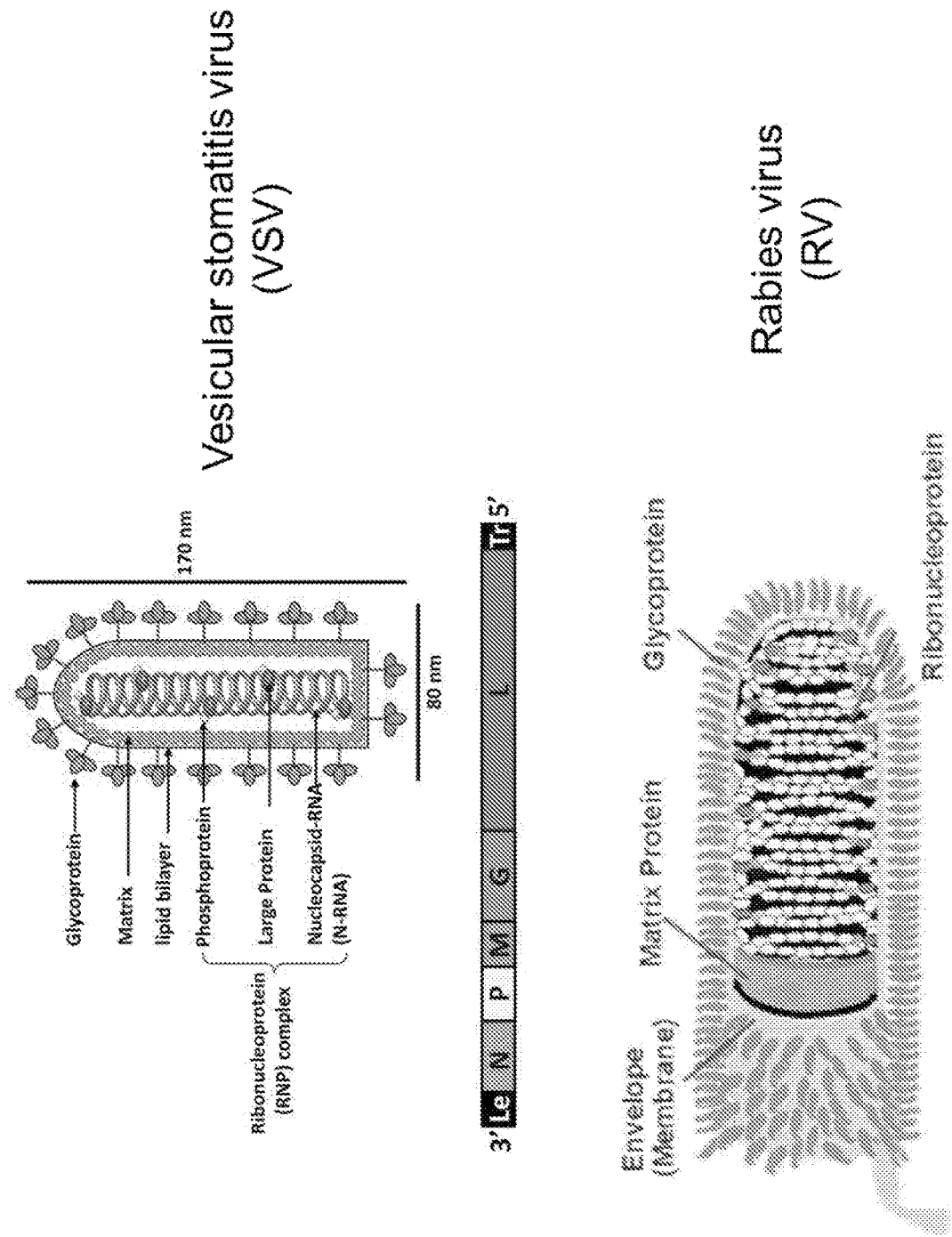

FIG. 11 depicts Vesicular stomatitis virus (VSV) and Rabies virus (RV) sources of packaging vesicles.

Figure 12:
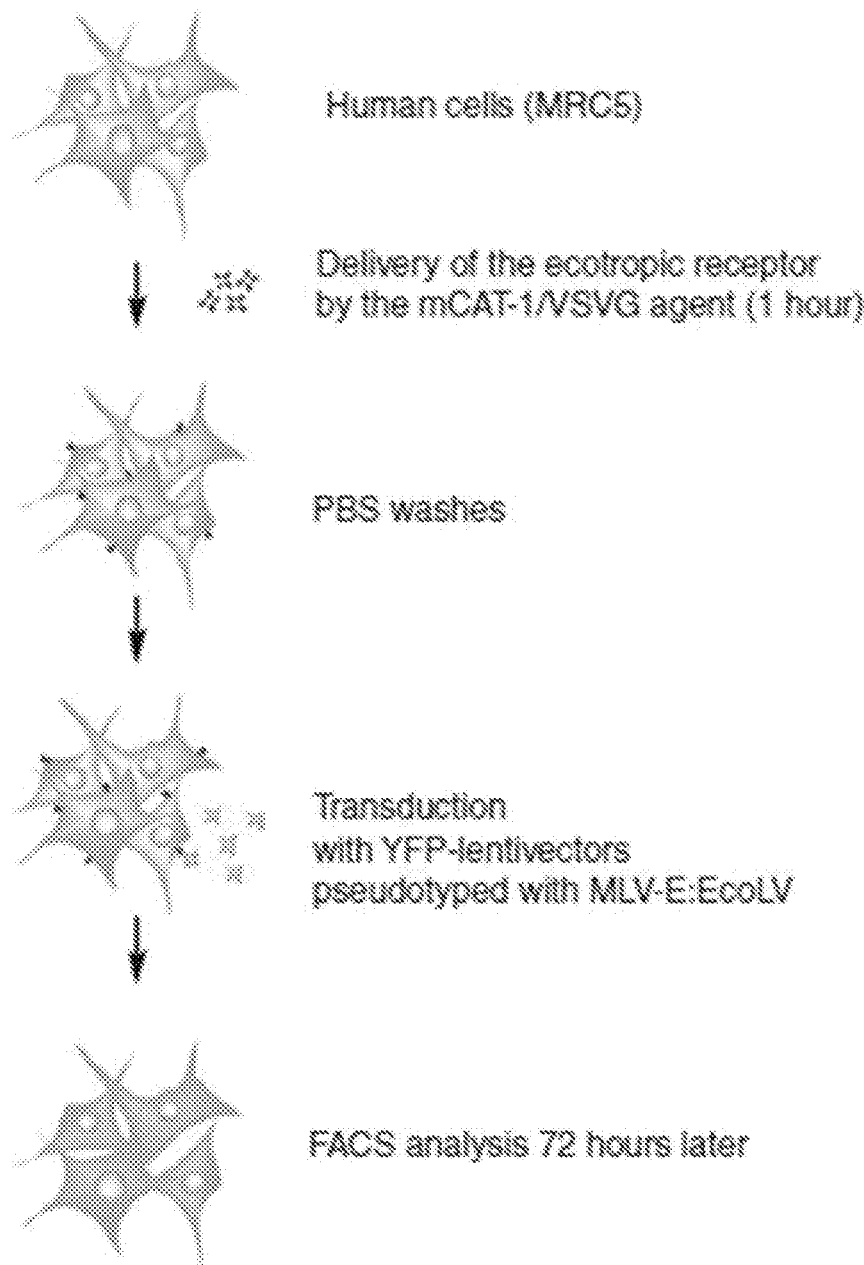

FIG. 12 shows a schematic for transduction of cells with lentiviral vectors packaged in vesicular stomatitis virus-G (VSVG) vesicles. (Cronin et al., Curr Gene Ther. 5 (4): 387-398 (2005)).

Figure 13:
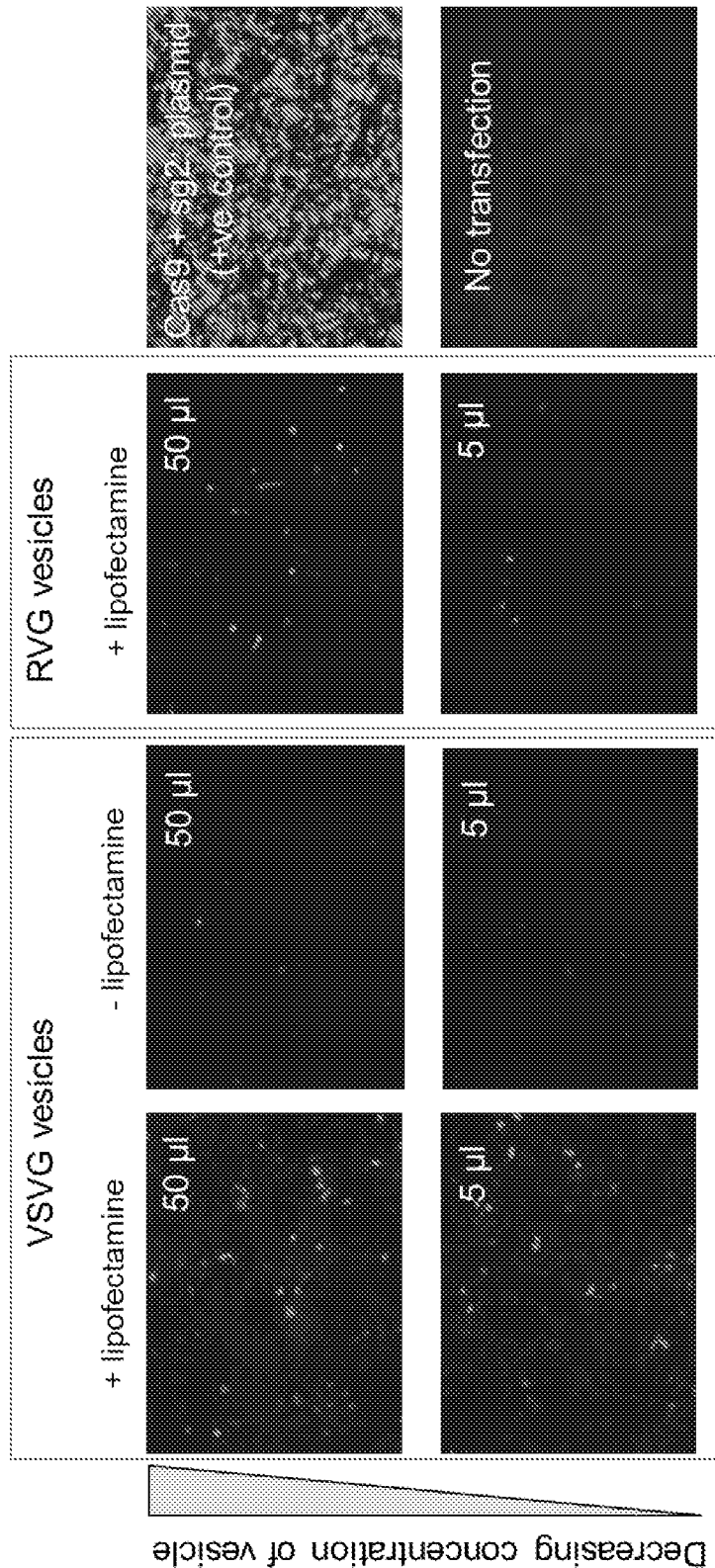

FIG. 13 depicts infection of TLR19 cells with VSVG and RVG vesicles harboring Cas9 and sgRNA inducing frameshift mutations to allow mCherry expression. Cas9 RNP vesicles were synthesized by contransfection of VSVG (or RVG) with eSpCas9 (1.1) and GFPg2 plasmid.

Figure 14:
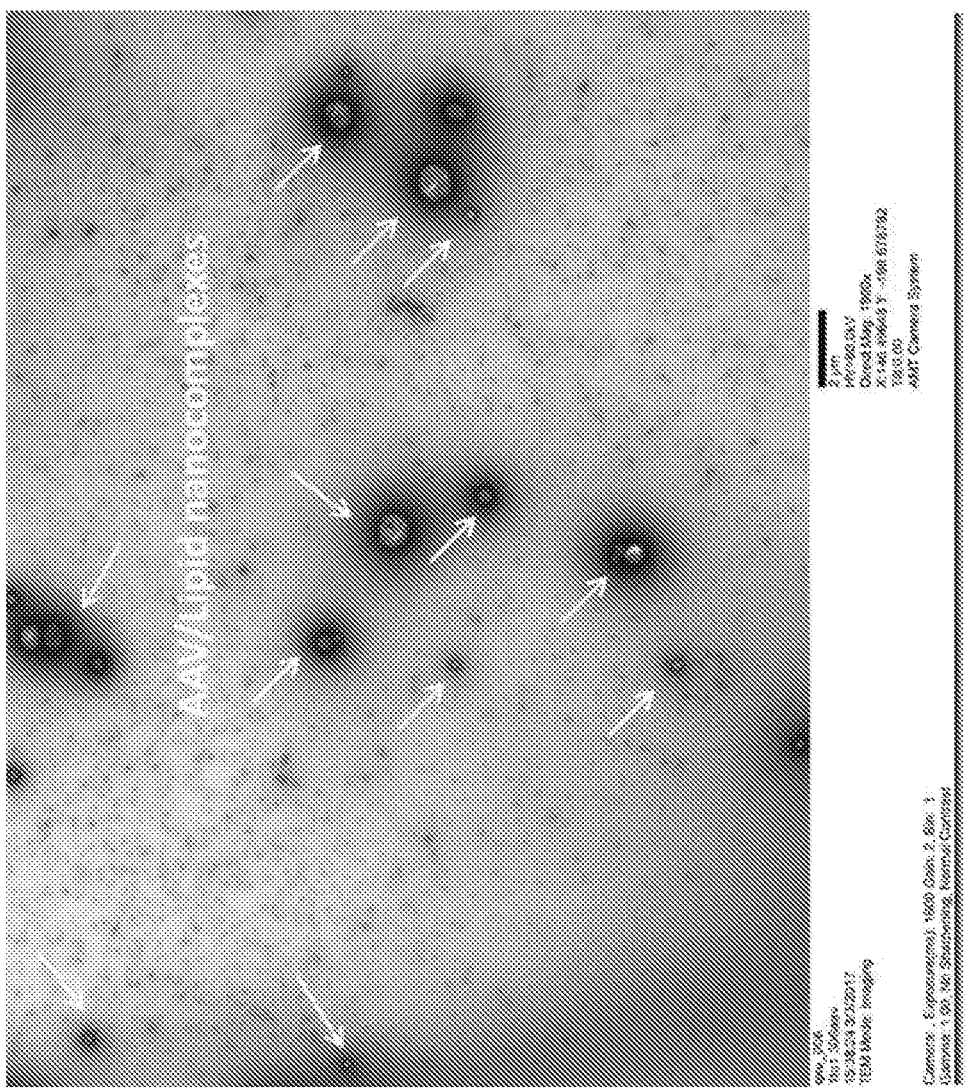

FIG. 14 depicts AAV/Lipid complexes with TEM imaging.

Figure 15:
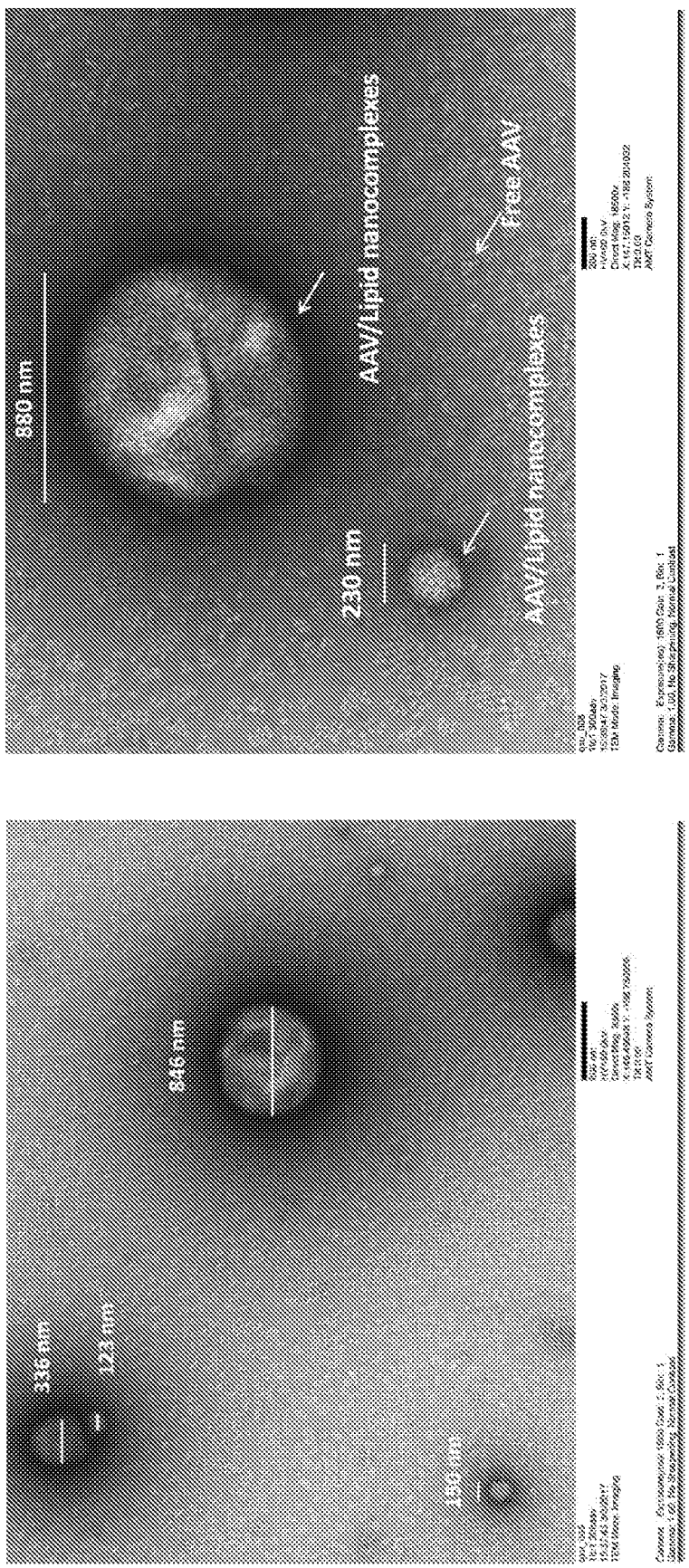

FIG. 15 depicts AAV particles adhered to lipid particles to form AAV/Lipid complexes with TEM imaging.

Figure 16A:
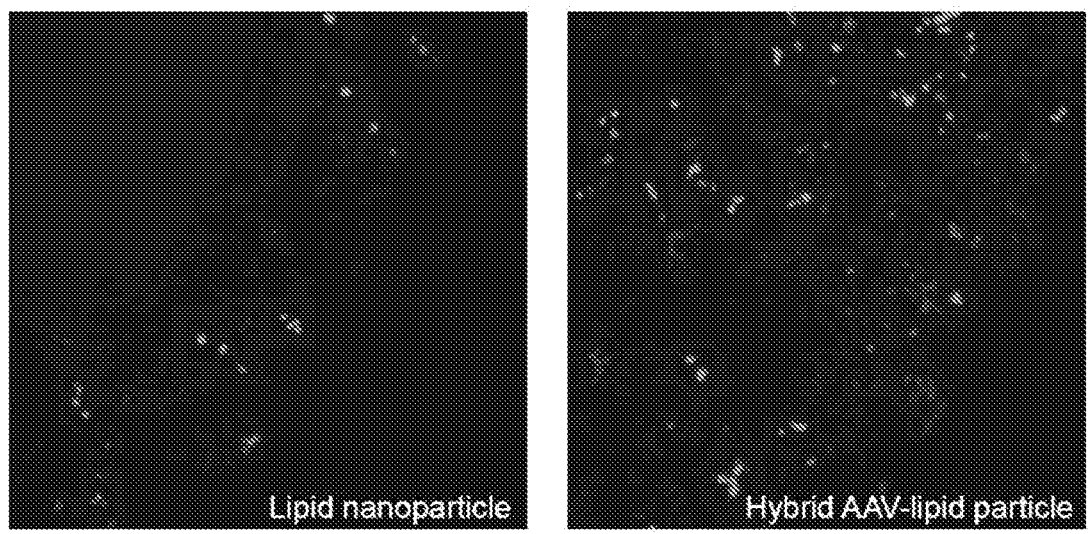
Figure 16B:
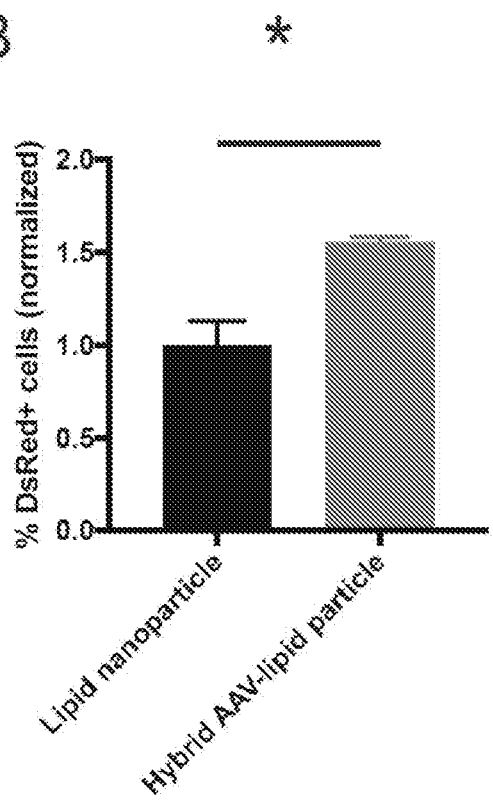

FIG. 16A-16B shows hybrid AAV-lipid particles mediate greater protein delivery in vitro compared to lipid nanoparticles. (A) Fluorescent imaging of DsRed+ cells. Successful delivery of CRE protein turns a cell DsRed+. (B) Quantification of DsRed+ cells by FACS analysis.

Figure 17A:
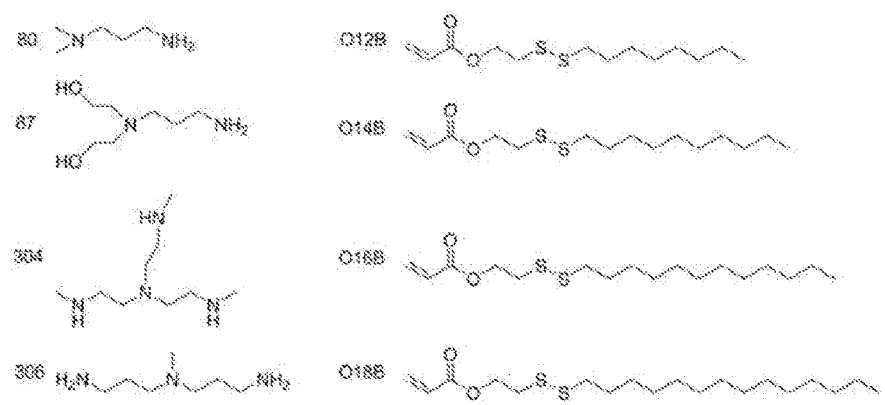
Figure 17B:
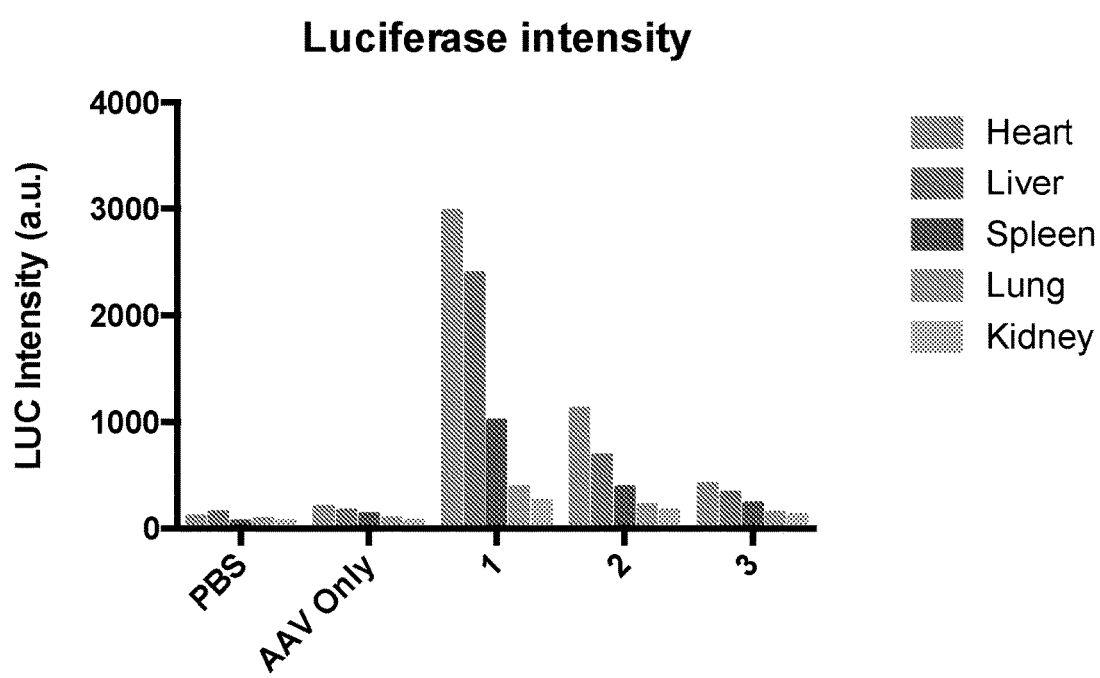

FIG. 17A-17B shows administration of luciferase AAV2/ lipid complexes. FIG. 17A: exemplary chemical structures of amines and acrylates of lipids of the invention. FIG. 17A: luciferase expression in the indicated organs 10 days after administration of a luciferase AAV2 vector alone of formulated with lipid 306-O16B-3 in the following amounts: Group 1:2.9×10$^{11}$ AAV, 10 µg lipid; Group 2:2.9×10$^{11}$ AAV, 50 µg lipid; Group 3:2.9×10$^{11}$ AAV, 100 µg lipid.

Figure 18A:
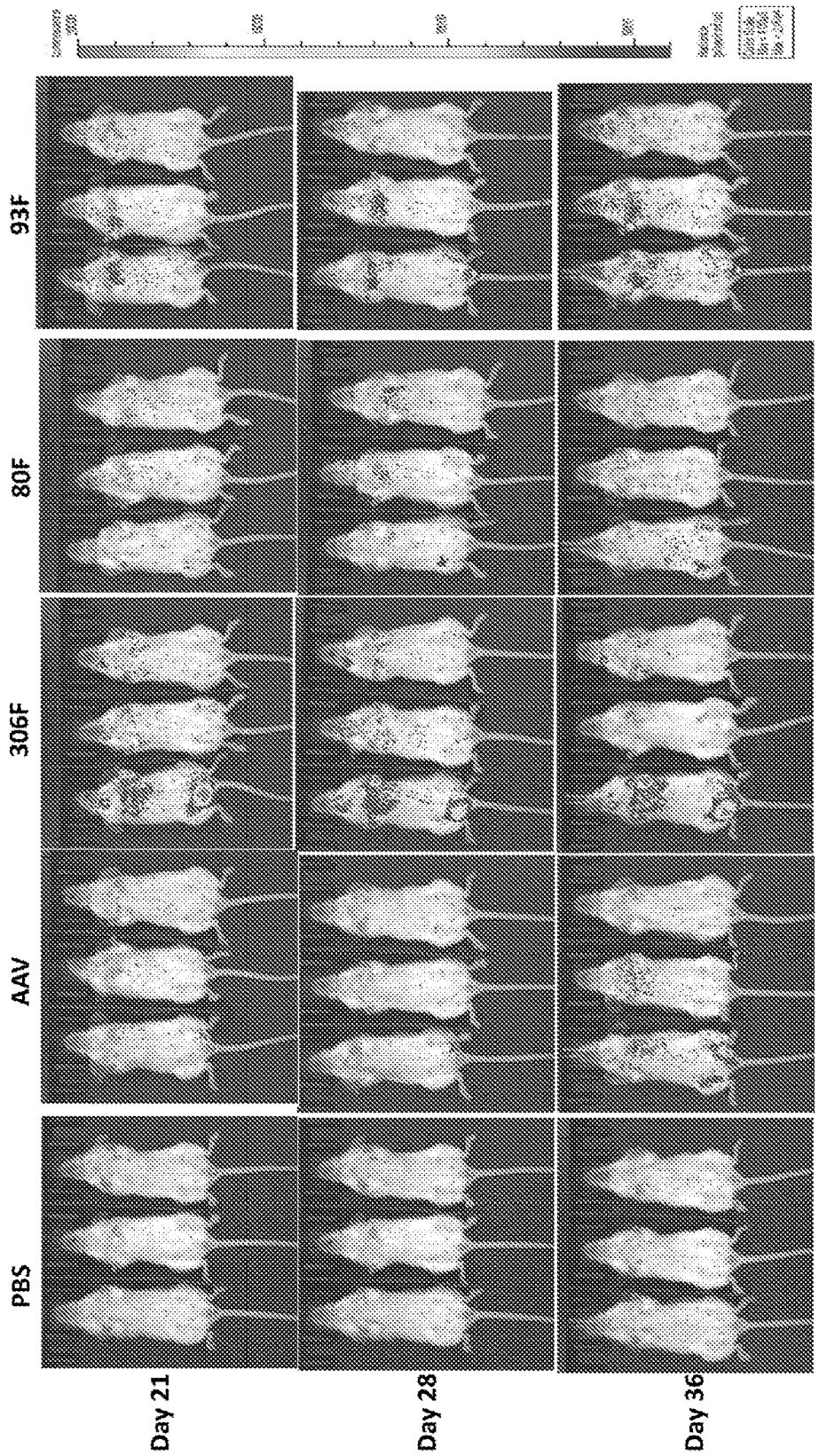
Figure 18B:
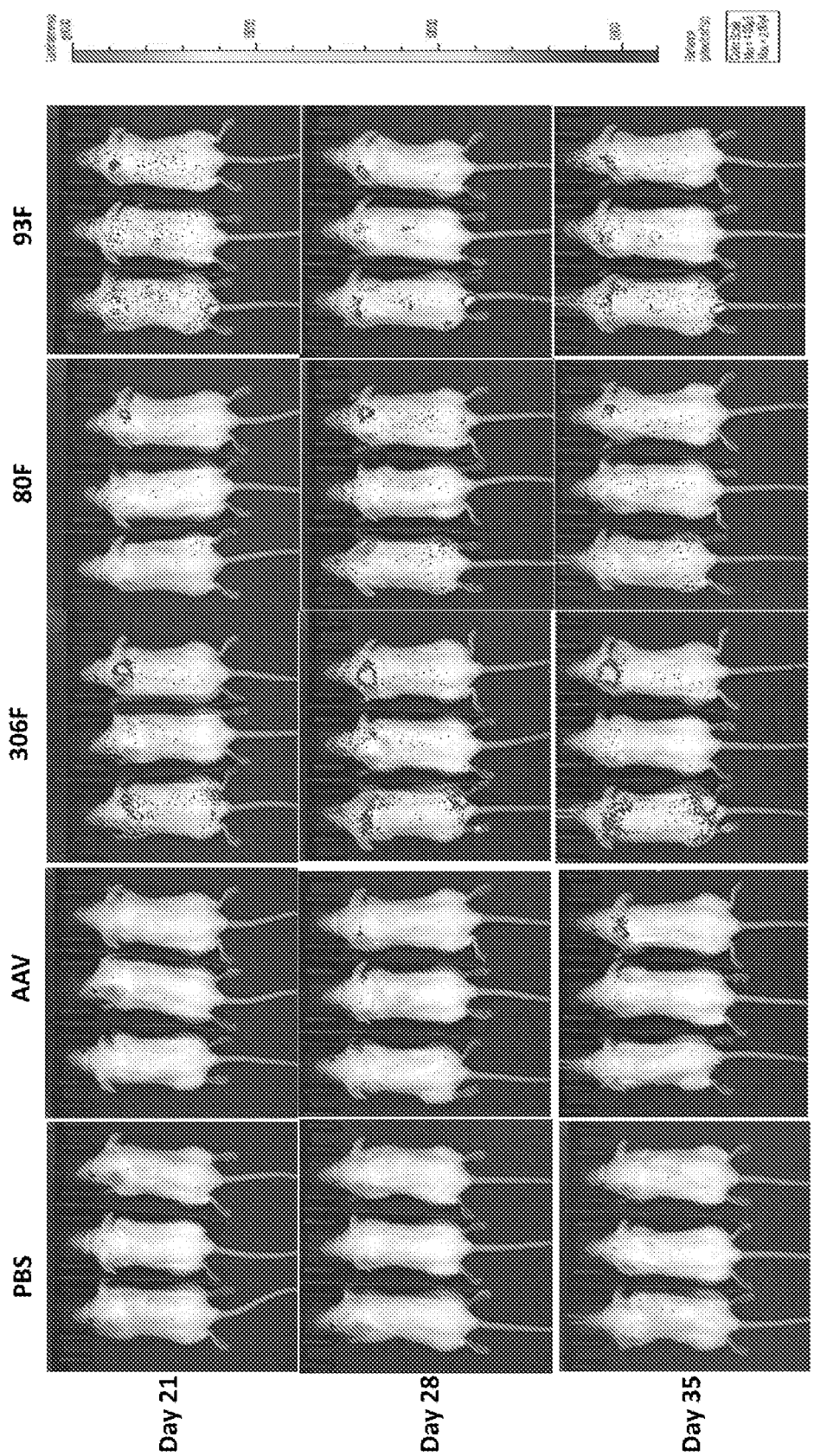
Figure 18C:
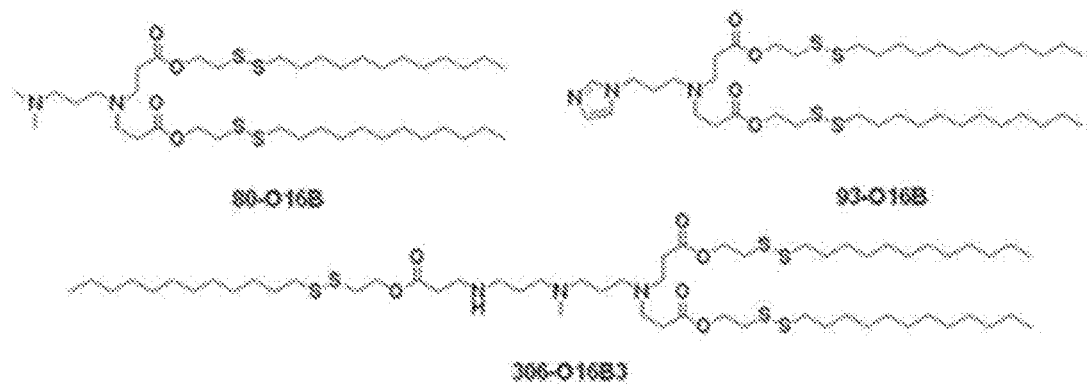
Figure 18D:
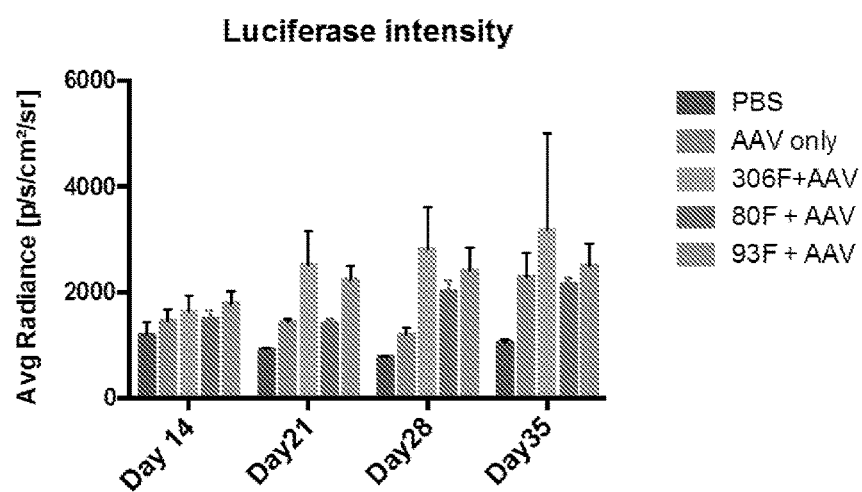
Figure 18E:
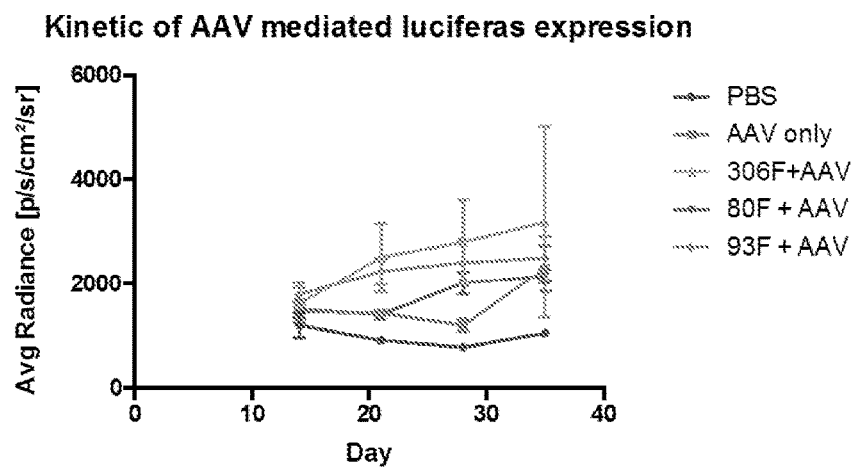

FIG. 18A-18E shows luciferase expression detected in mice. FIG. 18A-B: Luciferase AAV vector administered alone or formulated with lipid 306F, lipid 80F, or lipid 93F. FIG. 18C: Structures of lipids 306F, 80F and 93F; FIG. 18D: Luciferase activity quantified in vivo by IVIS; FIG. 18E: Kinetics of AAV mediated luciferase expression.

The following detailed description, given by way of example, but not intended to limit the invention solely to the specific embodiments described, may best be understood in conjunction with the accompanying drawings.

DETAILED DESCRIPTION OF THE INVENTION

In certain embodiments, the CRISPR system is derived advantageously from a type II CRISPR system. In some embodiments, one or more elements of a CRISPR system is derived from a particular organism comprising an endogenous CRISPR system, such as *Streptococcus pyogenes*. In preferred embodiments of the invention, the CRISPR system is a type II CRISPR system and the Cas enzyme is Cas9, which catalyzes DNA cleavage. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof.

In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is about no more than 25%, 10%, 5%, 1%, 0.1%, 0.01%, or less of the DNA cleavage activity of the non-mutated form of the enzyme; an example can be when the DNA cleavage activity of the mutated form is nil or negligible as compared with the non-mutated form. Where the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other Cas9s, residues corresponding to SpCas9 D10 and H840 are also preferred. Orthologs of SpCas9 can be used in the practice of the invention. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9 (*S. pyogenes* Cas9) or saCas9 (*S. aureus* Cas9). StCas9" refers to wild type Cas9 from *S. thermophilus*, the protein sequence of which is given in the SwissProt database under accession number G3ECR1. Similarly, *S pyogenes* Cas9 or spCas9 is included in SwissProt under accession number Q99ZW2. By derived, Applicants mean that the derived enzyme is largely based, in the sense of having a high degree of sequence homology with, a wildtype enzyme, but that it has been mutated (modified) in some way as described herein. It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptococcus pyogenes*. However, it will be appreciated that this invention includes many more Cas9s from other species of microbes, such as SpCas9, SaCa9, StCas9 and so forth. Enzymatic action by Cas9 derived from *Streptococcus pyogenes* or any closely related Cas9 generates double stranded breaks at target site sequences which hybridize to 20 nucleotides of the guide sequence and that have a protospacer-adjacent motif (PAM) sequence (examples include NGG/NRG or a PAM that can be determined as described herein) following the 20 nucleotides of the target sequence. CRISPR activity through Cas9 for site-specific DNA recognition and cleavage is defined by the guide sequence, the tracr sequence that hybridizes in part to the guide sequence and the PAM sequence. More aspects of the CRISPR system are described in Karginov and Hannon, The CRISPR system: small RNA-guided defence in bacteria and archaea, Mole Cell 2010 January 15; 37 (1): 7. The type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps. First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA: tracrRNA complex directs Cas9 to the DNA target comprising, consisting essentially of, or consisting of the protospacer and the corresponding PAM via heteroduplex formation between the spacer region of the crRNA and the protospacer DNA. Finally, Cas9 mediates cleavage of target DNA upstream of PAM to create a DSB within the protospacer. A pre-crRNA array comprising, consisting essentially of, or consisting of a single spacer flanked by two direct repeats (DRs) is also encompassed by the term "tracr-mate sequences"). In certain embodiments, Cas9 may be constitutively present or inducibly present or conditionally present or administered or delivered. Cas9 optimization may be used to enhance function or to develop new functions, one can generate chimeric Cas9 proteins. And Cas9 may be used as a generic DNA binding protein.

In an advantageous embodiment, the present invention encompasses effector proteins identified in a Type V CRISPR-Cas loci, e.g. a Cpf1-encoding loci denoted as subtype V-A. Presently, the subtype V-A loci encompasses cas1, cas2, a distinct gene denoted cpf1 and a CRISPR array. Cpf1 (CRISPR-associated protein Cpf1, subtype PRE-FRAN) is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in all Cas9 proteins, and the RuvC-like domain is contiguous in the Cpf1 sequence, in contrast to Cas9 where it contains long inserts including the HNH domain. Accordingly, in particular embodiments, the CRISPR-Cas enzyme comprises only a RuvC-like nuclease domain.

The Cpf1 gene is found in several diverse bacterial genomes, typically in the same locus with cas1, cas2, and cas4 genes and a CRISPR cassette (for example, FNFX1_1431-FNFX1_1428 of *Francisella* cf. *novicida* Fx1). Thus, the layout of this novel CRISPR-Cas system appears to be similar to that of type II-B. Furthermore, similar to Cas9, the Cpf1 protein contains a readily identifiable C-terminal region that is homologous to the transposon ORF—B and includes an active RuvC-like nuclease, an arginine-rich region, and a Zn finger (absent in Cas9). However, unlike Cas9, Cpf1 is also present in several genomes without a CRISPR-Cas context and its relatively high similarity with ORF—B suggests that it might be a transposon component. It was suggested that if this was a genuine CRISPR-Cas system and Cpf1 is a functional analog of Cas9 it would be a novel CRISPR-Cas type, namely type V (See Annotation and Classification of CRISPR-Cas Systems. Makarova K S, Koonin E V. Methods Mol Biol. 2015; 1311:47-75). However, as described herein, Cpf1 is denoted to be in subtype V-A to distinguish it from C2c1p which does not have an identical domain structure and is hence denoted to be in subtype V-B.

The nucleic acid-targeting system may be derived advantageously from a Type VI CRISPR system. In some embodiments, one or more elements of a nucleic acid-targeting system is derived from a particular organism comprising an endogenous RNA-targeting system. In particular embodiments, the Type VI RNA-targeting Cas enzyme is C2c2. In an embodiment of the invention, there is provided a effector protein which comprises an amino acid sequence having at least 80% sequence homology to the wild-type sequence of any of Leptotrichia shahii C2c2, Lachnospiraceae bacterium MA2020 C2c2, Lachnospiraceae bacterium NK4A179 C2c2, *Clostridium aminophilum* (DSM 10710) C2c2, Carnobacterium *gallinarum* (DSM 4847) C2c2, Paludibacter propionicigenes (WB4) C2c2, *Listeria* weihenstephanensis (FSL R9-0317) C2c2, Listeriaceae bacterium (FSL M6-0635) C2c2, *Listeria* newyorkensis (FSL M6-0635) C2c2, Leptotrichia *wadei* (F0279) C2c2, *Rhodobacter capsulatus* (SB 1003) C2c2, *Rhodobacter capsulatus* (R121) C2c2, *Rhodobacter capsulatus* (DE442) C2c2, Leptotrichia *wadei* (Lw2) C2c2, or *Listeria* seeligeri C2c2.

In an embodiment of the invention, the effector protein comprises at least one HEPN domain, including but not limited to HEPN domains described herein, HEPN domains known in the art, and domains recognized to be HEPN domains by comparison to consensus sequences and motifs.

Delivery Generally

Vector delivery, e.g., plasmid, viral delivery: The CRISPR enzyme, for instance a Cas9, and/or any of the present RNAs, for instance a guide RNA, can be delivered using any suitable vector, e.g., plasmid or viral vectors, such as adeno associated virus (AAV), lentivirus, adenovirus or other viral vector types, or combinations thereof. Cas9 and one or more guide RNAs can be packaged into one or more vectors, e.g., plasmid or viral vectors. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON-S PHARMACEUTICAL SCIENCES (Mack Pub. Co., N.J. 1991) which is incorporated by reference herein.

In an embodiment herein the delivery is via an adenovirus, which may be at a single booster dose containing at least $1 \times 10^5$ particles (also referred to as particle units, pu) of adenoviral vector. In an embodiment herein, the dose preferably is at least about $1 \times 10^6$ particles (for example, about $1 \times 10^6 - 1 \times 10^{12}$ particles), more preferably at least about $1 \times 10^7$ particles, more preferably at least about $1 \times 10^8$ particles (e.g., about $1 \times 10^8 - 1 \times 10^{11}$ particles or about $1 \times 10^8 - 1 \times 10^{12}$ particles), and most preferably at least about $1 \times 10^9$ particles (e.g., about $1 \times 10^9 - 1 \times 10^{10}$ particles or about $1 \times 10^9 - 1 \times 10^{12}$ particles), or even at least about $1 \times 10^{10}$ particles (e.g., about $1 \times 10^{10} - 1 \times 10^{12}$ particles) of the adenoviral vector. Alternatively, the dose comprises no more than about $1\times10^{14}$ particles, preferably no more than about $1\times10^{13}$ particles, even more preferably no more than about $1\times10^{12}$ particles, even more preferably no more than about $1\times10^{11}$ particles, and most preferably no more than about $1\times10^{10}$ particles (e.g., no more than about $1\times10^{9}$ articles). Thus, the dose may contain a single dose of adenoviral vector with, for example, about $1\times10^{6}$ particle units (pu), about $2\times10^{6}$ pu, about $4\times10^{6}$ pu, about $1\times10^{7}$ pu, about $2\times10^{7}$ pu, about $4\times10^{7}$ pu, about $1\times10^{8}$ pu, about $2\times10^{8}$ pu, about $4\times10^{8}$ pu, about $1\times10^{9}$ pu, about $2\times10^{9}$ pu, about $4\times10^{9}$ pu, about $1\times10^{10}$ pu, about $2\times10^{10}$ pu, about $4\times10^{10}$ pu, about $1\times10^{11}$ pu, about $2\times10^{11}$ pu, about $4\times10^{11}$ pu, about $1\times10^{12}$ pu, about $2\times10^{12}$ pu, or about $4\times10^{12}$ pu of adenoviral vector. See, for example, the adenoviral vectors in U.S. Pat. No. 8,454,972 $B_2$ to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1\times10^{10}$ to about $1\times10^{10}$ functional AAV/ml solution. The dosage may be adjusted to balance the therapeutic benefit against any side effects. In an embodiment herein, the AAV dose is generally in the range of concentrations of from about $1\times10^{5}$ to $1\times10^{50}$ genomes AAV, from about $1\times10^{8}$ to $1\times10^{20}$ genomes AAV, from about $1\times10^{10}$ to about $1\times10^{16}$ genomes, or about $1\times10^{11}$ to about $1\times10^{16}$ genomes AAV. A human dosage may be about $1\times10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 $B_2$ to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 µg to about 10 µg per 70 kg individual. Plasmids of the invention will generally comprise (i) a promoter; (ii) a sequence encoding a CRISPR enzyme, operably linked to said promoter; (iii) a selectable marker; (iv) an origin of replication; and (v) a transcription terminator downstream of and operably linked to (ii). The plasmid can also encode the RNA components of a CRISPR complex, but one or more of these may instead be encoded on a different vector.

The doses herein are based on an average 70 kg individual. The frequency of administration is within the ambit of the medical or veterinary practitioner (e.g., physician, veterinarian), or scientist skilled in the art. It is also noted that mice used in experiments are typically about 20g and from mice experiments one can scale up to a 70 kg individual.

In some embodiments the RNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference. Delivery systems aimed specifically at the enhanced and improved delivery of siRNA into mammalian cells have been developed, (see, for example, Shen et al FEBS Let. 2003, 539: 111-114; Xia et al., Nat. Biotech. 2002, 20:1006-1010; Reich et al., Mol. Vision. 2003, 9:210-216; Sorensen et al., J. Mol. Biol. 2003, 327:761-766; Lewis et al., Nat. Gen. 2002, 32:107-108 and Simeoni et al., NAR 2003, 31, 11:2717-2724) and may be applied to the present invention. siRNA has recently been successfully used for inhibition of gene expression in primates (see for example. Tolentino et al., Retina 24 (4): 660 which may also be applied to the present invention.

Indeed, RNA delivery is a useful method of in vivo delivery. It is possible to deliver Cas9 and gRNA (and, for instance, HR repair template) into cells using liposomes or particles. Thus delivery of the CRISPR enzyme, such as a Cas9 and/or delivery of the RNAs of the invention may be in RNA form and via microvesicles, liposomes or particles. For example, Cas9 mRNA and gRNA can be packaged into liposomal particles for delivery in vivo. Liposomal transfection reagents such as lipofectamine from Life Technologies and other reagents on the market can effectively deliver RNA molecules into the liver.

Means of delivery of RNA also preferred include delivery of RNA via particles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19:3112-3118, 2010) or exosomes (Schroeder, A., Levins, C., Cortez, C., Langer, R., and Anderson, D., Lipid-based nanotherapeutics for siRNA delivery, Journal of Internal Medicine, 267:9-21, 2010, PMID: 2005961). Indeed, exosomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December; 7 (12): 2112-26. doi: 10.1038/nprot.2012.131. Epub 2012 Nov. 15.) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purify and characterized from transfected cell supernatant, then RNA is loaded into the exosomes. Delivery or administration according to the invention can be performed with exosomes, in particular but not limited to the brain. Vitamin E (α-tocopherol) may be conjugated with CRISPR Cas and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain. Mice were infused via Osmotic minipumps (model 1007D; Alzet, Cupertino, CA) filled with phosphate-buffered saline (PBS) or free TocsiBACE or Toc-siBACE/HDL and connected with Brain Infusion Kit 3 (Alzet). A brain-infusion cannula was placed about 0.5 mm posterior to the bregma at midline for infusion into the dorsal third ventricle. Uno et al. found that as little as 3 nmol of Toc-siRNA with HDL could induce a target reduction in comparable degree by the same ICV infusion method. A similar dosage of CRISPR Cas conjugated to α-tocopherol and co-administered with HDL targeted to the brain may be contemplated for humans in the present invention, for example, about 3 nmol to about 3 µmol of CRISPR Cas targeted to the brain may be contemplated. Zou et al. ((HUMAN GENE THERAPY 22:465-475 (April 2011)) describes a method of lentiviral-mediated delivery of short-hairpin RNAs targeting PKCγ for in vivo gene silencing in the spinal cord of rats. Zou et al. administered about 10 µl of a recombinant lentivirus having a titer of $1 \times 10^9$ transducing units (TU)/ml by an intrathecal catheter. A similar dosage of CRISPR Cas expressed in a lentiviral vector targeted to the brain may be contemplated for humans in the present invention, for example, about 10-50 ml of CRISPR Cas targeted to the brain in a lentivirus having a titer of $1 \times 10^9$ transducing units (TU)/ml may be contemplated.

Anderson et al. (US20170079916) provides a modified dendrimer nanoparticle for the delivery of therapeutic, prophylactic and/or diagnostic agents to a subject, comprising: one or more zero to seven generation alkylated dendrimers; one or more amphiphilic polymers; and one or more therapeutic, prophylactic and/or diagnostic agents encapsulated therein. One alkylated dendrimer may be selected from the group consisting of poly(ethyleneimine), poly(polypropylenimine), diaminobutane amine polypropylenimine tetramine and poly(amido amine). The therapeutic, prophylactic and diagnostic agent may be selected from the group consisting of proteins, peptides, carbohydrates, nucleic acids, lipids, small molecules and combinations thereof.

Anderson et al. (US20160367686) provides a compound of Formula (I):

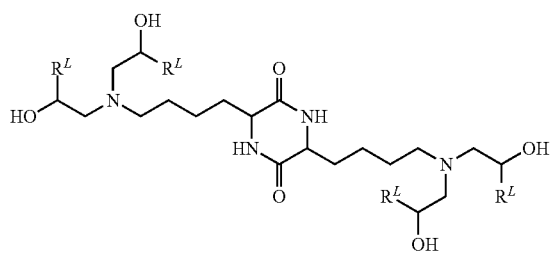

and salts thereof, wherein each instance of R L is independently optionally substituted $C_6$-$C_{40}$ alkenyl, and a composition for the delivery of an agent to a subject or cell comprising the compound, or a salt thereof; an agent; and optionally, an excipient. The agent may be an organic molecule, inorganic molecule, nucleic acid, protein, peptide, polynucleotide, targeting agent, an isotopically labeled chemical compound, vaccine, an immunological agent, or an agent useful in bioprocessing. The composition may further comprise cholesterol, a PEGylated lipid, a phospholipid, or an apolipoprotein.

Anderson et al. (US20150232883) provides a delivery particle formulations and/or systems, preferably nanoparticle delivery formulations and/or systems, comprising (a) a CRISPR-Cas system RNA polynucleotide sequence; or (b) Cas9; or (c) both a CRISPR-Cas system RNA polynucleotide sequence and Cas9; or (d) one or more vectors that contain nucleic acid molecule(s) encoding (a), (b) or (c), wherein the CRISPR-Cas system RNA polynucleotide sequence and the Cas9 do not naturally occur together. The delivery particle formulations may further comprise a surfactant, lipid or protein, wherein the surfactant may comprise a cationic lipid.

Anderson et al. (US20050123596) provides examples of microparticles that are designed to release their payload when exposed to acidic conditions, wherein the microparticles comprise at least one agent to be delivered, a pH triggering agent, and a polymer, wherein the polymer is selected from the group of polymethacrylates and polyacrylates.

Anderson et al (US20020150626) provides lipid-protein-sugar particles for delivery of nucleic acids, wherein the polynucleotide is encapsulated in a lipid-protein-sugar matrix by contacting the polynucleotide with a lipid, a protein, and a sugar; and spray drying mixture of the polynucleotide, the lipid, the protein, and the sugar to make microparticles.

In terms of local delivery to the brain, this can be achieved in various ways. For instance, material can be delivered intrastriatally e.g., by injection. Injection can be performed stereotactically via a craniotomy.

Enhancing NHEJ or HR efficiency is also helpful for delivery. It is preferred that NHEJ efficiency is enhanced by co-expressing end-processing enzymes such as Trex2 (Dumitrache et al. Genetics. 2011 August; 188 (4): 787-797). It is preferred that HR efficiency is increased by transiently inhibiting NHEJ machineries such as Ku70 and Ku86. HR efficiency can also be increased by co-expressing prokaryotic or eukaryotic homologous recombination enzymes such as RecBCD, RecA.

Packaging and Promoters Generally

Ways to package Cas9 coding nucleic acid molecules, e.g., DNA, into vectors, e.g., viral vectors, to mediate genome modification in vivo include:
  To achieve NHEJ-mediated gene knockout:
    Single virus vector:
    Vector containing two or more expression cassettes:
    Promoter-Cas9 coding nucleic acid molecule-terminator
    Promoter-gRNA1-terminator
    Promoter-gRNA2-terminator
    Promoter-gRNA (N)-terminator (up to size limit of vector)
  Double virus vector:
    Vector 1 containing one expression cassette for driving the expression of Cas9
    Promoter-Cas9 coding nucleic acid molecule-terminator
    Vector 2 containing one more expression cassettes for driving the expression of one or more guideRNAs
    Promoter-gRNA1-terminator
    Promoter-gRNA (N)-terminator (up to size limit of vector)
  To mediate homology-directed repair.
    In addition to the single and double virus vector approaches described above, an additional vector is used to deliver a homology-direct repair template.

The promoter used to drive Cas9 coding nucleic acid molecule expression can include:
  AAV ITR can serve as a promoter: this is advantageous for eliminating the need for an additional promoter element (which can take up space in the vector). The additional space freed up can be used to drive the expression of additional elements (gRNA, etc.). Also, ITR activity is relatively weaker, so can be used to reduce potential toxicity due to over expression of Cas9.
  For ubiquitous expression, can use promoters: CMV, CAG, CBh, PGK, SV40, Ferritin heavy or light chains, etc.
  For brain or other CNS expression, can use promoters: SynapsinI for all neurons, CaMKIIalpha for excitatory neurons, GAD67 or GAD65 or VGAT for GABAergic neurons, etc.
  For liver expression, can use Albumin promoter.
  For lung expression, can use SP-B.
  For endothelial cells, can use ICAM.

For hematopoietic cells can use IFNbeta or CD45.
For Osteoblasts can use OG-2.
The promoter used to drive guide RNA can include: Pol III promoters such as U6 or H1
Use of Pol II promoter and intronic cassettes to express gRNA Adeno Associated Virus (AAV)

Cas9 and one or more guide RNA can be delivered using adeno associated virus (AAV), lentivirus, adenovirus or other plasmid or viral vector types, in particular, using formulations and doses from, for example, U.S. Pat. No. 8,454,972 (formulations, doses for adenovirus), 8,404,658 (formulations, doses for AAV) and 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual (e.g., a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into the tissue of interest. For cell-type specific genome modification, the expression of Cas9 can be driven by a cell-type specific promoter. For example, liver-specific expression might use the Albumin promoter and neuron-specific expression (e.g., for targeting CNS disorders) might use the Synapsin I promoter.

In terms of in vivo delivery, AAV is advantageous over other viral vectors for a couple of reasons:

Low toxicity (this may be due to the purification method not requiring ultra centrifugation of cell particles that can activate the immune response) and.

Low probability of causing insertional mutagenesis because it doesn't integrate into the host genome.

AAV has a packaging limit of 4.5 or 4.75 Kb. This means that Cas9 as well as a promoter and transcription terminator have to be all fit into the same viral vector. Constructs larger than 4.5 or 4.75 Kb will lead to significantly reduced virus production. SpCas9 is quite large, the gene itself is over 4.1 Kb, which makes it difficult for packing into AAV. Therefore embodiments of the invention include utilizing homologs of Cas9 that are shorter. For example:

| Species | Cas9 Size (nt) |
| --- | --- |
| Corynebacter diphtheriae | 3252 |
| Eubacterium ventriosum | 3321 |
| Streptococcus pasteurianus | 3390 |
| Lactobacillus farciminis | 3378 |
| Sphaerochaeta globus | 3537 |
| Azospirillum B510 | 3504 |
| Gluconacetobacter diazotrophicus | 3150 |
| Neisseria cinerea | 3246 |
| Roseburia intestinalis | 3420 |
| Parvibaculum lavamentivorans | 3111 |
| Staphylococcus aureus | 3159 |

-continued

| Species | Cas9 Size (nt) |
| --- | --- |
| Nitratifractor salsuginis DSM 16511 | 3396 |
| Campylobacter lari CF89-12 | 3009 |
| Campylobacter jejuni | 2952 |
| Streptococcus thermophilus LMD-9 | 3396 | rAAV vectors are preferably produced in insect cells, e.g., Spodoptera frugiperda Sf9 insect cells, grown in serum-free suspension culture. Serum-free insect cells can be purchased from commercial vendors, e.g., Sigma Aldrich (EX-CELL 405).

These species are therefore, in general, preferred Cas9 species.

Lentivirus

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 μg of lentiviral transfer plasmid (pCasES10) and the following packaging plasmids: 5 μg of pMD2.G (VSV-g pseudotype), and 7.5ug of psPAX2 (gag/pol/rev/tat). Transfection was done in 4 mL OptiMEM with a cationic lipid delivery agent (50 uL Lipofectamine 2000 and 100ul Plus reagent). After 6 hours, the media was changed to antibiotic-free DMEM with 10% fetal bovine serum. These methods use serum during cell culture, but serum-free methods are preferred.

Lentivirus may be purified as follows. Viral supernatants were harvested after 48 hours. Supernatants were first cleared of debris and filtered through a 0.45 um low protein binding (PVDF) filter. They were then spun in an ultracentrifuge for 2 hours at 24,000 rpm. Viral pellets were resuspended in 50ul of DMEM overnight at 4C. They were then aliquoted and immediately frozen at −80° C.

In another embodiment, minimal non-primate lentiviral vectors based on the equine infectious anemia virus (EIAV) are also contemplated, especially for ocular gene therapy (see, e.g., Balagaan, J Gene Med 2006; 8:275-285). In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) and this vector may be modified for the CRISPR-Cas system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2: 36ra43) may be used/and or adapted to the CRISPR-Cas system of the present invention. A minimum of $2.5 \times 10^6$ CD34+ cells per kilogram patient weight may be collected and prestimulated for 16 to 20 hours in X-VIVO 15 medium (Lonza) containing 2 μmol/L-glutamine, stem cell factor (100 ng/ml), Flt-3 ligand (Flt-3L) (100 ng/ml), and thrombopoietin (10 ng/ml) (Cell-Genix) at a density of 2× $10^6$ cells/ml. Prestimulated cells may be transduced with lentiviral at a multiplicity of infection of 5 for 16 to 24 hours in 75-$cm^2$ tissue culture flasks coated with fibronectin (25 mg/$cm^2$) (RetroNectin, Takara Bio Inc.).

Lentiviral vectors have been disclosed as in the treatment for Parkinson-s Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and US Patent No. U.S. Pat. No. 7,259,015.

RNA Delivery

RNA delivery: The CRISPR enzyme, for instance a Cas9, and/or any of the present RNAs, for instance a guide RNA, can also be delivered in the form of RNA. Cas9 mRNA can be generated using in vitro transcription. For example, Cas9 mRNA can be synthesized using a PCR cassette containing the following elements: T7_promoter-kozak sequence (GCCACC)-Cas9-3' UTR from beta globin-poly A tail (a string of 120 or more adenines). The cassette can be used for transcription by T7 polymerase. Guide RNAs can also be transcribed using in vitro transcription from a cassette containing T7_promoter-GG-guide RNA sequence.

To enhance expression and reduce possible toxicity, the CRISPR enzyme-coding sequence and/or the guide RNA can be modified to include one or more modified nucleoside e.g., using pseudo-U or 5-Methyl-C.

mRNA delivery methods are especially promising for liver delivery currently.

Much clinical work on RNA delivery has focused on RNAi or antisense, but these systems can be adapted for delivery of RNA for implementing the present invention. References below to RNAi etc. should be read accordingly.

Particles

Liu et al. (US20110212179) provides bimodal porous polymer microspheres comprising a base polymer, wherein the particle comprises macropores having a diameter ranging from about 20 to about 500 microns and micropores having a diameter ranging from about 1 to about 70 microns, and wherein the microspheres have a diameter ranging from about 50 to about 1100 microns.

Berg et al. (US20160174546) a nanolipid delivery system, in particular a nano-particle concentrate, comprising: a composition comprising a lipid, oil or solvent, the composition having a viscosity of less than 100 cP at 25. degree. C. and a Kauri Butanol solvency of greater than 25 Kb; and at least one amphipathic compound selected from the group consisting of an alkoxylated lipid, an alkoxylated fatty acid, an alkoxylated alcohol, a heteroatomic hydrophilic lipid, a heteroatomic hydrophilic fatty acid, a heteroatomic hydrophilic alcohol, a diluent, and combinations thereof, wherein the compound is derived from a starting compound having a viscosity of less than 1000 cP at 50. degree. C., wherein the concentrate is configured to provide a stable nano emulsion having a D50 and a mean average particle size distribution of less than 100 nm when diluted.

Liu et al. (US20140301951) provides a protocell nanostructure comprising: a porous particle core comprising a plurality of pores; and at least one lipid bilayer surrounding the porous particle core to form a protocell, wherein the protocell is capable of loading one or more cargo components to the plurality of pores of the porous particle core and releasing the one or more cargo components from the porous particle core across the surrounding lipid bilayer.

Chromy et al. (US20150105538) provides methods and systems for assembling, solubilizing and/or purifying a membrane associated protein in a nanolipoprotein particle, which comprise a temperature transition cycle performed in presence of a detergent, wherein during the temperature transition cycle the nanolipoprotein components are brought to a temperature above and below the gel to liquid crystalling transition temperature of the membrane forming lipid of the nanolipoprotein particle.

Bader et al. (US20150250725), provides a method for producing a lipid particle comprising the following: i) providing a first solution comprising denatured apolipoprotein, ii) adding the first solution to a second solution comprising at least two lipids and a detergent but no apolipoprotein, and iii) removing the detergent from the solution obtained in ii) and thereby producing a lipid particle.

Mirkin et al., (US20100129793) provides a method of preparing a composite particle comprising the steps of (a) admixing a dielectric component and a magnetic component to form a first intermediate, (b) admixing the first intermediate and gold seeds to form a second intermediate, and (c) forming a gold shell on the second intermediate by admixing the second intermediate with a gold source and a reducing agent to form said composite particle.

CRISPR enzyme mRNA and guide RNA may be delivered simultaneously using nanoparticles or lipid envelopes.

For example, Su X, Fricke J, Kavanagh D G, Irvine D J ("In vitro and in vivo mRNA delivery using lipid-enveloped pH-responsive polymer nanoparticles" Mol Pharm. 2011 Jun. 6; 8 (3): 774-87. doi: 10.1021/mp100390w. Epub 2011 Apr. 1) describes biodegradable core-shell structured nanoparticles with a poly(β-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

In one embodiment, nanoparticles based on self assembling bioadhesive polymers are contemplated, which may be applied to oral delivery of peptides, intravenous delivery of peptides and nasal delivery of peptides, all to the brain. Other embodiments, such as oral absorption and ocular delivery of hydrophobic drugs are also contemplated. The molecular envelope technology involves an engineered polymer envelope which is protected and delivered to the site of the disease (see, e.g., Mazza, M. et al. ACSNano, 2013. 7 (2): 1016-1026; Siew, A., et al. Mol Pharm, 2012. 9 (1): 14-28; Lalatsa, A., et al. J Contr Rel, 2012. 161 (2): 523-36; Lalatsa, A., et al., Mol Pharm, 2012. 9 (6): 1665-80; Lalatsa, A., et al. Mol Pharm, 2012. 9 (6): 1764-74; Garrett, N. L., et al. J Biophotonics, 2012. 5 (5-6): 458-68; Garrett, N. L., et al. J Raman Spect, 2012. 43 (5): 681-688; Ahmad, S., et al. J Royal Soc Interface 2010. 7: S423-33; Uchegbu, I.F. Expert Opin Drug Deliv, 2006. 3 (5): 629-40; Qu, X.,et al. Biomacromolecules, 2006. 7 (12): 3452-9 and Uchegbu, I. F., et al. Int J Pharm, 2001. 224:185-199). Doses of about 5 mg/kg are contemplated, with single or multiple doses, depending on the target tissue.

In one embodiment, nanoparticles that can deliver RNA to a cancer cell to stop tumor growth developed by Dan Anderson's lab at MIT may be used/and or adapted to the CRISPR Cas system of the present invention. In particular, the Anderson lab developed fully automated, combinatorial systems for the synthesis, purification, characterization, and formulation of new biomaterials and nanoformulations. See, e.g., Alabi et al., Proc Natl Acad Sci USA. 2013 Aug. 6; 110 (32): 12881-6; Zhang et al., Adv Mater. 2013 Sep. 6; 25 (33): 4641-5; Jiang et al., Nano Lett. 2013 Mar. 13; 13 (3): 1059-64; Karagiannis et al., ACS Nano. 2012 Oct. 23; 6 (10): 8484-7; Whitehead et al., ACS Nano. 2012 Aug. 28; 6 (8): 6922-9 and Lee et al., Nat Nanotechnol. 2012 Jun. 3; 7 (6): 389-93.

The lipid particles developed by the Qiaobing Xu's lab at Tufts University may be used/adapted to the present delivery system for cancer therapy. See Wang et al., *J. Control Release,* 2017 Jan. 31. pii: S0168-3659 (17) 30038-X. doi: 10.1016/j.jconrel.2017.01.037. [Epub ahead of print]; Altinoğlu et al., *Biomater Sci.,* 4 (12): 1773-80, Nov. 15, 2016; Wang et al., *PNAS,* 113 (11): 2868-73 Mar. 15, 2016; Wang et al., *PloS One,* 10 (11): e0141860. doi: 10.1371/journal.pone.0141860. eCollection 2015 Nov. 3, 2015; Takeda et al., *Neural Regen Res.* 10 (5): 689-90, May 2015; Wang et al., *Adv. Healthc Mater.,* 3 (9): 1398-403, September 2014; and Wang et al., *Agnew Chem Int Ed Engl.,* 53 (11): 2893-8, Mar. 10, 2014.

U.S. patent application No. 20110293703 relates to lipidoid compounds are also particularly useful in the administration of polynucleotides, which may be applied to deliver the CRISPR Cas system of the present invention. In one aspect, the aminoalcohol lipidoid compounds are combined with an agent to be delivered to a cell or a subject to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Publication No. 20110293703 also provides methods of preparing the aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30-100° C., preferably at approximately 50-90° C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

US Patent Publication No. 20110293703 also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

US Patent Publication No. 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering. The teachings of US Patent Publication No. 20130302401 may be applied to the CRISPR Cas system of the present invention.

In another embodiment, lipid nanoparticles (LNPs) are contemplated. An antitransthyretin small interfering RNA has been encapsulated in lipid nanoparticles and delivered to humans (see, e.g., Coelho et al., N Engl J Med 2013; 369:819-29), and such a system may be adapted and applied to the CRISPR Cas system of the present invention. Doses of about 0.01 to about 1 mg per kg of body weight administered intravenously are contemplated. Medications to reduce the risk of infusion-related reactions are contemplated, such as dexamethasone, acetampinophen, diphenhydramine or cetirizine, and ranitidine are contemplated. Multiple doses of about 0.3 mg per kilogram every 4 weeks for five doses are also contemplated.

Zhu et al. (US20140348900) provides for a process for preparing liposomes, lipid discs, and other lipid nanoparticles using a multi-port manifold, wherein the lipid solution stream, containing an organic solvent, is mixed with two or more streams of aqueous solution (e.g., buffer). In some aspects, at least some of the streams of the lipid and aqueous solutions are not directly opposite of each other. Thus, the process does not require dilution of the organic solvent as an additional step. In some embodiments, one of the solutions may also contain an active pharmaceutical ingredient (API). This invention provides a robust process of liposome manufacturing with different lipid formulations and different payloads. Particle size, morphology, and the manufacturing scale can be controlled by altering the port size and number of the manifold ports, and by selecting the flow rate or flow velocity of the lipid and aqueous solutions.

Cullis et al. (US20140328759) provides limit size lipid nanoparticles with a diameter from 10-100 nm, in particular comprising a lipid bilayer surrounding an aqueous core. Methods and apparatus for preparing such limit size lipid nanoparticles are also disclosed.

Manoharan et al. (US20140308304) provides cationic lipids of formula (I)

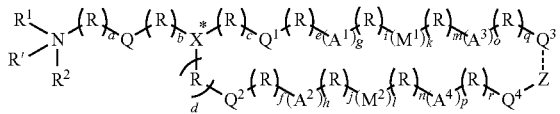

Formula (1)

or a salt thereof, wherein X is N or P; R' is absent, hydrogen, or alkyl; with respect to $R^1$ and $R^2$, (i) $R^1$ and $R^2$ are each, independently, optionally substituted alkyl, alkenyl, alkynyl, cycloalkyl, cycloalkylalkyl, heterocycle or $R^{10}$; (ii) $R^1$ and $R^2$, together with the nitrogen atom to which they are attached, form an optionally substituted heterocylic ring; or (iii) one of $R^1$ and $R^2$ is optionally substituted alkyl, alkenyl, alkynyl, cycloalkyl, cycloalkylalkyl, or heterocycle, and the other forms a 4-10 member heterocyclic ring or heteroaryl with (a) the adjacent nitrogen atom and (b) the (R) a group adjacent to the nitrogen atom; each occurrence of R is, independently, —($CR^3R^4$)—; each occurrence of $R^3$ and $R^4$ are, independently H, halogen, OH, alkyl, alkoxy, —$NH_2$, alkylamino, or dialkylamino; or $R^3$ and $R^4$, together with the carbon atom to which they are directly attached, form a cycloalkyl group, wherein no more than three R groups in each chain attached to the atom X* are cycloalkyl; each occurrence of $R^{10}$ is independently selected from PEG and polymers based on poly(oxazoline), poly(ethylene oxide), poly(vinyl alcohol), poly(glycerol), poly(N-vinylpyrrolidone), poly [N-(2-hydroxypropyl) methacrylamide] and poly(amino acid) s, wherein (i) the PEG or polymer is linear or branched, (ii) the PEG or polymer is polymerized by n subunits, (iii) n is a number-averaged degree of polymerization between 10 and 200 units, and (iv) wherein the compound of formula has at most two $R^{10}$ groups; Q is absent or is—O—, —NH—, —S—, —C(O)O—, —OC(O)—, —C(O) N($R^4$)—, —N($R^5$) C(O)—, —S—S—, —OC(O)O—, —O—N.dbd.C($R^5$)—, —C($R^5$).dbd.N—O—, —OC (O) N($R^5$)—, —N($R^5$) C(O) N($R^5$)—, —N($R^5$) C(O) O—, —C(O)S—, —C(S)O— or —C($R^5$).dbd.N— O—C(O)—; $Q^1$ and $Q^2$ are each, independently, absent, —O—, —S—, —OC(O)—, —C(O)O—, —SC(O)—, —C(O)S—, —OC(S)—, —C(S)O—, —S—S—, —C(O) (NR$^5$)—, —N($R^5$) C(O)—, —C(S) (NR$^5$)—, —N($R^5$) C(O)—, —N($R^5$) C(O) N($R^5$)—, or —OC(O)O—; $Q^3$ and $Q^4$ are each, independently, H, —($CR^3R^4$)—, aryl, or a cholesterol moiety; each occurrence of $A^1$, $A^2$, $A^3$ and $A^4$ is, independently, —($CR^5R^5$—$CR^5$.dbd.$CR^5$)—; each occurrence of $R^5$ is, independently, H or alkyl; $M^1$ and $M^2$ are each, independently, a biodegradable group (e.g., —OC (O)—, —C(O)O—, —SC(O)—, —C(O)S—, —OC (S)—, —C(S)O—, —S—S—, —C($R^5$).dbd.N—, —N.dbd.C($R^5$)—, —C($R^5$).dbd.N—O—, —O—N.dbd.C($R^5$)—, —C(O) (NR$^5$)—, —N($R^5$) C(O)—, —C(S) (NR$^5$)—, —N($R^5$) C(O)—, —N($R^5$) C(O) N($R^5$)—, —OC(O)O—, —OSi ($R^5$) .sub.20--, —C(O) ($CR^3R^4$) C(O)O—, or —OC(O) ($CR^3R^4$) C(O)—); Z is absent, alkylene or —O—P (O) (OH)—O—; each attached to Z is an optional bond, such that when Z is absent, $Q^3$ and $Q^4$ are not directly covalently bound together; a is 1, 2, 3, 4, 5 or 6; b is 0, 1, 2, or 3; c, d, e, f, i, j, m, n, q and r are each, independently, 0, 1, 2, 3, 4, 5, 6, 7, 8, 9, or 10; g and h are each, independently, 0, 1 or 2; k and l are each, independently, 0 or 1, where at least one of k and l is 1; and o and p are each, independently, 0, 1 or 2, wherein $Q^3$ and $Q^4$ are each, independently, separated from the tertiary atom marked with an asterisk (X*) by a chain of 8 or more atoms. The cationic lipid can be used with other lipid components such as cholesterol and PEG-lipids to form lipid nanoparticles with oligonucleotides, to facilitate the cellular uptake and endosomal escape, and to knockdown target mRNA both in vitro and in vivo.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding CRISPR Cas to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, *Molecular Therapy*, vol. 19, no. 12, pages 1286-220 December 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethyl-ammonium-propane (DLinDAP), 1,2-dilinoleyloxy-3-N,N- dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, *Molecular Therapy*, vol. 19, no. 12, pages 1286-220 December 2011). A dosage of 1 µg/ml of LNP or CRISPR-Cas RNA in or associated with the LNP may be contemplated, especially for a formulation containing DLinKC2-DMA.

Preparation of LNPs and CRISPR Cas encapsulation may be used/and or adapted from Rosin et al, *Molecular Therapy*, vol. 19, no. 12, pages 1286-220 December 2011). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-0-[2"-(methoxypolyethyleneglycol 2000) succinoyl]-1,2-dimyristoyl-sn-glycol (PEG-S-DMG), and R-3-[(ω-methoxy-poly(ethylene glycol) 2000) carbamoyl]-1,2-dimyristyloxlpropyl-3-amine (PEG-C-DOMG) may be provided by Tekmira Pharmaceuticals (Vancouver, Canada) or synthesized. Cholesterol may be purchased from Sigma (St Louis, MO). The specific CRISPR Cas RNA may be encapsulated in LNPs containing DLinDAP, DLinDMA, DLinK-DMA, and DLinKC2-DMA (cationic lipid: DSPC: CHOL: PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid: DSPC: cholesterol: PEG-c-DOMG (40:10:40:10 molar ratio) in ethanol to a final lipid concentration of 10 mmol/l. This ethanol solution of lipid may be added drop-wise to 50 mmol/l citrate, pH 4.0 to form multilamellar vesicles to produce a final concentration of 30% ethanol vol/vol. Large unilamellar vesicles may be formed following extrusion of multilamellar vesicles through two stacked 80 nm Nuclepore polycarbonate filters using the Extruder (Northern Lipids, Vancouver, Canada). Encapsulation may be achieved by adding RNA dissolved at 2 mg/ml in 50 mmol/l citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Nanoparticle size distribution may be determined by dynamic light scattering using a NICOMP 370 particle sizer, the vesicle/intensity modes, and Gaussian fitting (Nicomp Particle Sizing, Santa Barbara, CA). The particle size for all three LNP systems may be ~70 nm in diameter. RNA encapsulation efficiency may be determined by removal of free RNA using VivaPureD MiniH columns (Sartorius Stedim Biotech) from samples collected before and after dialysis. The encapsulated RNA may be extracted from the eluted nanoparticles and quantified at 260 nm. RNA to lipid ratio was determined by measurement of cholesterol content in vesicles using the Cholesterol E enzymatic assay from Wako Chemicals USA (Richmond, VA). In conjunction with the herein discussion of LNPs and PEG lipids, PEGylated liposomes or LNPs are likewise suitable for delivery of a CRISPR-Cas system or components thereof.

Preparation of large LNPs may be used/and or adapted from Rosin et al, Molecular Therapy, vol. 19, no. 12, pages 1286-220 December 2011. A lipid premix solution (20.4 mg/ml total lipid concentration) may be prepared in ethanol containing DLinKC2-DMA, DSPC, and cholesterol at 50:10:38.5 molar ratios. Sodium acetate may be added to the lipid premix at a molar ratio of 0.75:1 (sodium acetate: DLinKC2-DMA). The lipids may be subsequently hydrated by combining the mixture with 1.85 volumes of citrate buffer (10 mmol/l, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano ZS, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at an RNA to total lipid ratio of approximately 1:10 (wt: wt), followed by incubation for 30 minutes at 37° C. to form loaded LNPs. The mixture may be subsequently dialyzed overnight in PBS and filtered with a 0.45-µm syringe filter.

Liposomes

In one aspect, the invention provides a particle delivery system comprising a composite virus particle, wherein the composite virus particle comprises a lipid, a virus capsid protein, and a protein or peptide. The peptide or protein can be up to one megadalton in size.

In one embodiment, the particle delivery system comprises a virus particle adsorbed to a liposome. In one embodiment, the liposome comprises a cationic lipid.

In one embodiment, the liposome of the particle delivery system comprises the CRISPR-Cas system component.

In one aspect, the invention provides a delivery system comprising one or more hybrid virus capsid proteins in combination with a lipid particle, wherein the hybrid virus capsid protein comprises at least a portion of a virus capsid protein attached to at least a portion of a non-capsid protein.

In one embodiment, the virus capsid protein of the delivery system is attached to the surface of the lipid particle. In one embodiment, the virus capsid protein is attached to the surface of the lipid particle by an electrostatic interaction or by hydrophobic interaction.

In one embodiment, the lipid particle has a dof 50-1000 nm, preferably 100-1000 nm.

In one embodiment, the delivery system comprises a protein or peptide, wherein the protein or peptide has a molecular weight of up to a megadalton. In one embodiment, the protein or peptide has a molecular weight in the range of 110 to 160 kDa.

In one embodiment, the delivery system comprises a protein or peptide, wherein the protein or peptide comprises a CRISPR protein or peptide. In one embodiment, the protein or peptide comprises a Cas9, a Cpf1 or a C2c2.

In one embodiment, the lipid, lipid particle or lipid layer of the delivery system comprises at least one cationic lipid.

In one embodiment, the lipid compound is preferably a bio-reducible material, e.g., a bio-reducible polymer and a bio-reducible lipid-like compound.

In one aspect, the lipid or lipid-like compound comprises a hydrophilic head, a hydrophobic tail, and a linker.

In one embodiment, the hydrophilic head contains one or more hydrophilic functional groups, e.g., hydroxyl, carboxyl, amino, sulfhydryl, phosphate, amide, ester, ether, carbamate, carbonate, carbamide and phosphodiester. These groups can form hydrogen bonds and are optionally positively or negatively charged.

In one embodiment, the hydrophobic tail is a saturated or unsaturated, linear or branched, acyclic or cyclic, aromatic or nonaromatic hydrocarbon moiety containing a disulfide bond and 8-24 carbon atoms. One or more of the carbon atoms can be replaced with a heteroatom, such as N, O, P, B, S, Si, Sb, Al, Sn, As, Se, and Ge. The lipid or lipid-like compounds containing disulfide bond can be bioreducible.

In one embodiment, the linker of the lipid or lipid-like compound links the hydrophilic head and the hydrophobic tail. The linker can be any chemical group that is hydrophilic or hydrophobic, polar or non-polar, e.g., O, S, Si, amino, alkylene, ester, amide, carbamate, carbamide, carbonate phosphate, phosphite, sulfate, sulfite, and thiosulfate.

The lipid or lipid-like compounds described above include the compounds themselves, as well as their salts and solvates, if applicable. A salt, for example, can be formed between an anion and a positively charged group (e.g., amino) on a lipid-like compound. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group (e.g., carboxylate) on a lipid-like compound. Suitable cations include sodium ion, potassium ion, magnesium ion, calcium ion, and an ammonium cation such as tetramethylammonium ion. The lipid-like compounds also include those salts containing quaternary nitrogen atoms. A solvate refers to a complex formed between a lipid-like compound and a pharmaceutically acceptable solvent. Examples of pharmaceutically acceptable solvents include water, ethanol, isopropanol, ethyl acetate, acetic acid, and ethanolamine.

Delivery or administration according to the invention can be performed with liposomes. Liposomes are spherical vesicle structures composed of a uni- or multilamellar lipid bilayer surrounding internal aqueous compartments and a relatively impermeable outer lipophilic phospholipid bilayer. Liposomes have gained considerable attention as drug delivery carriers because they are biocompatible, non-toxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi: 10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi: 10.1155/2011/469679 for review).

Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. Further, liposomes are prepared from hydrogenated egg phosphatidylcholine or egg phosphatidylcholine, cholesterol, and dicetyl phosphate, and their mean vesicle sizes were adjusted to about 50 and 100 nm. (see, e.g., Spuch and Navarro, Journal of Drug Delivery, vol. 2011, Article ID 469679, 12 pages, 2011. doi: 10.1155/2011/469679 for review).

A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside. Since this formulation is made up of phospholipids only, liposomal formulations have encountered many challenges, one of the ones being the instability in plasma. Several attempts to overcome these challenges have been made, specifically in the manipulation of the lipid membrane. One of these attempts focused on the manipulation of cholesterol. Addition of cholesterol to conventional formulations reduces rapid release of the encapsulated bioactive compound into the plasma or 1,2-dioleoyl-sn-glycero-3-phosphoethanolamine (DOPE) increases the stability (see, e.g., Spuch and Navarro, Journal of Drug Delivery, vol. 2011, Article ID 469679, 12 pages, 2011. doi: 10.1155/2011/469679 for review).

In a particularly advantageous embodiment, Trojan Horse liposomes (also known as Molecular Trojan Horses) are desirable and protocols may be found at cshprotocols.cshlp.org/content/2010/4/pdb.prot5407.long. These particles allow delivery of a transgene to the entire brain after an intravascular injection. Without being bound by limitation, it is believed that neutral lipid particles with specific antibodies conjugated to surface allow crossing of the blood brain barrier via endocytosis. Applicant postulates utilizing Trojan Horse Liposomes to deliver the CRISPR family of nucleases to the brain via an intravascular injection, which would allow whole brain transgenic animals without the need for embryonic manipulation. About 1-5 g of DNA or RNA may be contemplated for in vivo administration in liposomes.

In another embodiment, the CRISPR Cas system may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of a specific CRISPR Cas targeted in a SNALP are contemplated. The daily treatment may be over about three days and then weekly for about five weeks. In another embodiment, a specific CRISPR Cas encapsulated SNALP) administered by intravenous injection to at doses of about 1 or 2.5 mg/kg are also contemplated (see, e.g., Zimmerman et al., Nature Letters, Vol. 441, 4 May 2006). The SNALP formulation may contain the lipids 3-N-[(wmethoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio (see, e.g., Zimmerman et al., Nature Letters, Vol. 441, 4 May 2006).

In another embodiment, stable nucleic-acid-lipid particles (SNALPs) have proven to be effective delivery molecules to highly vascularized HepG2-derived liver tumors but not in poorly vascularized HCT-116 derived liver tumors (see, e.g., Li, Gene Therapy (2012) 19, 775-780). The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/ PEG-C-DMA. The resulted SNALP liposomes are about 80-100 nm in size.

In yet another embodiment, a SNALP may comprise synthetic cholesterol (Sigma-Aldrich, St Louis, MO, USA), dipalmitoylphosphatidylcholine (Avanti Polar Lipids, Alabaster, AL, USA), 3-N-[(w-methoxy poly(ethylene glycol) 2000) carbamoyl]-1,2-dimyrestyloxypropylamine, and cationic 1,2-dilinoleyloxy-3-N,Ndimethylaminopropane (see, e.g., Geisbert et al., Lancet 2010; 375:1896-905). A dosage of about 2 mg/kg total CRISPR Cas per dose administered as, for example, a bolus intravenous infusion may be contemplated.

In yet another embodiment, a SNALP may comprise synthetic cholesterol (Sigma-Aldrich), 1,2-distearoyl-sn-glycero-3-phosphocholine (DSPC; Avanti Polar Lipids Inc.), PEG-CDMA, and 1,2-dilinoleyloxy-3-(N;N-dimethyl)aminopropane (DLinDMA) (see, e.g., Judge, *J. Clin. Invest.* 119:661-673 (2009)). Formulations used for in vivo studies may comprise a final lipid/RNA mass ratio of about 9:1.

The safety profile of RNAi nanomedicines has been reviewed by Barros and Gollob of Alnylam Pharmaceuticals (see, e.g., Advanced Drug Delivery Reviews 64 (2012) 1730-1737). The stable nucleic acid lipid particle (SNALP) is comprised of four different lipids—an ionizable lipid (DLinDMA) that is cationic at low pH, a neutral helper lipid, cholesterol, and a diffusible polyethylene glycol (PEG)-lipid. The particle is approximately 80 nm in diameter and is charge-neutral at physiologic pH. During formulation, the ionizable lipid serves to condense lipid with the anionic RNA during particle formation. When positively charged under increasingly acidic endosomal conditions, the ionizable lipid also mediates the fusion of SNALP with the endosomal membrane enabling release of RNA into the cytoplasm. The PEG-lipid stabilizes the particle and reduces aggregation during formulation, and subsequently provides a neutral hydrophilic exterior that improves pharmacokinetic properties.

To date, two clinical programs have been initiated using SNALP formulations with RNA. Tekmira Pharmaceuticals recently completed a phase I single-dose study of SNALP-ApoB in adult volunteers with elevated LDL cholesterol. ApoB is predominantly expressed in the liver and jejunum and is essential for the assembly and secretion of VLDL and LDL. Seventeen subjects received a single dose of SNALP-ApoB (dose escalation across 7 dose levels). There was no evidence of liver toxicity (anticipated as the potential dose-limiting toxicity based on preclinical studies). One (of two) subjects at the highest dose experienced flu-like symptoms consistent with immune system stimulation, and the decision was made to conclude the trial.

Alnylam Pharmaceuticals has similarly advanced ALN-TTR01, which employs the SNALP technology described above and targets hepatocyte production of both mutant and wild-type TTR to treat TTR amyloidosis (ATTR). Three ATTR syndromes have been described: familial amyloidotic polyneuropathy (FAP) and familial amyloidotic cardiomyopathy (FAC)—both caused by autosomal dominant mutations in TTR; and senile systemic amyloidosis (SSA) cause by wildtype TTR. A placebo-controlled, single dose-escalation phase I trial of ALN-TTR01 was recently completed in patients with ATTR. ALN-TTR01 was administered as a 15-minute IV infusion to 31 patients (23 with study drug and 8 with placebo) within a dose range of 0.01 to 1.0 mg/kg (based on siRNA). Treatment was well tolerated with no significant increases in liver function tests. Infusion-related reactions were noted in 3 of 23 patients at ≥0.4 mg/kg; all responded to slowing of the infusion rate and all continued on study. Minimal and transient elevations of serum cytokines IL-6, IP-10 and IL-Ira were noted in two patients at the highest dose of 1 mg/kg (as anticipated from preclinical and NHP studies). Lowering of serum TTR, the expected pharmacodynamics effect of ALN-TTR01, was observed at 1 mg/kg.

In yet another embodiment, a SNALP may be made by solubilizing a cationic lipid, DSPC, cholesterol and PEG-lipid e.g., in ethanol, e.g., at a molar ratio of 40:10:40:10, respectively (see, Semple et al., Nature Niotechnology, Volume 28 Number 2 Feb. 2010, pp. 172-177). The lipid mixture was added to an aqueous buffer (50 mM citrate, pH 4) with mixing to a final ethanol and lipid concentration of 30% (vol/vol) and 6.1 mg/ml, respectively, and allowed to equilibrate at 22° C. for 2 min before extrusion. The hydrated lipids were extruded through two stacked 80 nm pore-sized filters (Nuclepore) at 22° C. using a Lipex Extruder (Northern Lipids) until a vesicle diameter of 70-90 nm, as determined by dynamic light scattering analysis, was obtained. This generally required 1-3 passes. The siRNA (solubilized in a 50 mM citrate, pH 4 aqueous solution containing 30% ethanol) was added to the pre-equilibrated (35° C.) vesicles at a rate of ~5 ml/min with mixing. After a final target siRNA/lipid ratio of 0.06 (wt/wt) was reached, the mixture was incubated for a further 30 min at 35° C. to allow vesicle reorganization and encapsulation of the siRNA. The ethanol was then removed and the external buffer replaced with PBS (155 mM NaCl, 3 mM $Na_2HPO_4$, 1 mM $KH_2PO_4$, pH 7.5) by either dialysis or tangential flow diafiltration. siRNA were encapsulated in SNALP using a controlled step-wise dilution method process. The lipid constituents of KC2-SNALP were DLin-KC2-DMA (cationic lipid), dipalmitoylphosphatidylcholine (DPPC; Avanti Polar Lipids), synthetic cholesterol (Sigma) and PEG-C-DMA used at a molar ratio of 57.1:7.1:34.3:1.4. Upon formation of the loaded particles, SNALP were dialyzed against PBS and filter sterilized through a 0.2 μm filter before use. Mean particle sizes were 75-85 nm and 90-95% of the siRNA was encapsulated within the lipid particles. The final siRNA/lipid ratio in formulations used for in vivo testing was ~0.15 (wt/wt). LNP-siRNA systems containing Factor VII siRNA were diluted to the appropriate concentrations in sterile PBS immediately before use and the formulations were administered intravenously through the lateral tail vein in a total volume of 10 ml/kg. This method and these delivery systems may be extrapolated to the CRISPR Cas system of the present invention.

Other Lipids

Other cationic lipids, such as amino lipid 2,2-dilinoleyl-4-dimethylaminoethyl-[1,3]-dioxolane (DLin-KC2-DMA) may be utilized to encapsulate CRISPR Cas or components thereof or nucleic acid molecule(s) coding therefor e.g., similar to SiRNA (see, e.g., Jayaraman, *Angew. Chem. Int. Ed.* 2012, 51, 8529-8533), and hence may be employed in the practice of the invention. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol) 2000) propylcarbamate (PEG-lipid) in the molar ratio 40/10/40/10, respectively, and a FVII siRNA/ total lipid ratio of approximately 0.05 (w/w). To ensure a narrow particle size distribution in the range of 70-90 nm and a low polydispersity index of 0.11±0.04 (n=56), the particles may be extruded up to three times through 80 nm membranes prior to adding the CRISPR Cas RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Michael S D Kormann et al. ("Expression of therapeutic proteins after delivery of chemically modified mRNA in mice: Nature Biotechnology, Volume: 29, Pages: 154-157 (2011)) describes the use of lipid envelopes to deliver RNA. Use of lipid envelopes is also preferred in the present invention.

In another embodiment, lipids may be formulated with the CRISPR Cas system of the present invention to form lipid nanoparticles (LNPs). Lipids include, but are not limited to, DLin-KC2-DMA4, C12-200 and colipids distearoylphosphatidylcholine, cholesterol, and PEG-DMG may be formulated with CRISPR Cas instead of siRNA (see, e.g., Novobrantseva, Molecular Therapy-Nucleic Acids (2012) 1, e4; doi: 10.1038/mtna.2011.3) using a spontaneous vesicle formation procedure. The component molar ratio may be about 50/10/38.5/1.5 (DLin-KC2-DMA or $C_{12-200}$/distearoylphosphatidylcholine/cholesterol/PEG-DMG). The final lipid: siRNA weight ratio may be ~12:1 and 9:1 in the case of DLin-KC2-DMA and C12-200 lipid nanoparticles (LNPs), respectively. The formulations may have mean particle diameters of ~80 nm with >90% entrapment efficiency. A 3 mg/kg dose may be contemplated.

Tekmira has a portfolio of approximately 95 patent families, in the U.S. and abroad, that are directed to various aspects of LNPs and LNP formulations (see, e.g., U.S. Pat. Nos. 7,982,027; 7,799,565; 8,058,069; 8,283,333; 7,901, 708; 7,745,651; 7,803,397; 8,101,741; 8,188,263; 7,915, 399; 8,236,943 and 7,838,658 and European Pat. Nos 1766035; 1519714; 1781593 and 1664316), all of which may be used and/or adapted to the present invention.

The CRISPR Cas system or components thereof or nucleic acid molecule(s) coding therefor may be delivered encapsulated in PLGA Microspheres such as that further described in US published applications Ser. No. 20/130, 252281 and 20130245107 and 20130244279 (assigned to Moderna Therapeutics) which relate to aspects of formulation of compositions comprising modified nucleic acid molecules which may encode a protein, a protein precursor, or a partially or fully processed form of the protein or a protein precursor. The formulation may have a molar ratio 50:10: 38.5:1.5-3.0 (cationic lipid: fusogenic lipid: cholesterol: PEG lipid). The PEG lipid may be selected from, but is not limited to PEG-c-DOMG, PEG-DMG. The fusogenic lipid may be DSPC. See also, Schrum et al., Delivery and Formulation of Engineered Nucleic Acids, US published application No. 20120251618.

Nanomerics' technology addresses bioavailability challenges for a broad range of therapeutics, including low molecular weight hydrophobic drugs, peptides, and nucleic acid based therapeutics (plasmid, siRNA, miRNA). Specific administration routes for which the technology has demonstrated clear advantages include the oral route, transport across the blood-brain-barrier, delivery to solid tumours, as well as to the eye. See, e.g., Mazza et al., 2013, *ACS Nano.* 2013 Feb. 26; 7 (2): 1016-26; Uchegbu and Siew, 2013, J Pharm Sci. 102 (2): 305-10 and Lalatsa et al., 2012, J Control Release. 2012 Jul. 20; 161 (2): 523-36.

US Patent Publication No. 20050019923 describes cationic dendrimers for delivering bioactive molecules, such as polynucleotide molecules, peptides and polypeptides and/or pharmaceutical agents, to a mammalian body. The dendrimers are suitable for targeting the delivery of the bioactive molecules to, for example, the liver, spleen, lung, kidney or heart (or even the brain). Dendrimers are synthetic 3-dimensional macromolecules that are prepared in a step-wise fashion from simple branched monomer units, the nature and functionality of which can be easily controlled and varied. Dendrimers are synthesised from the repeated addition of building blocks to a multifunctional core (divergent approach to synthesis), or towards a multifunctional core (convergent approach to synthesis) and each addition of a 3-dimensional shell of building blocks leads to the formation of a higher generation of the dendrimers. Polypropylenimine dendrimers start from a diaminobutane core to which is added twice the number of amino groups by a double Michael addition of acrylonitrile to the primary amines followed by the hydrogenation of the nitriles. This results in a doubling of the amino groups. Polypropylenimine dendrimers contain 100% protonable nitrogens and up to 64 terminal amino groups (generation 5, DAB 64). Protonable groups are usually amine groups which are able to accept protons at neutral pH. The use of dendrimers as gene delivery agents has largely focused on the use of the polyamidoamine. and phosphorous containing compounds with a mixture of amine/amide or N—P ($O_2$) S as the conjugating units respectively with no work being reported on the use of the lower generation polypropylenimine dendrimers for gene delivery. Polypropylenimine dendrimers have also been studied as pH sensitive controlled release systems for drug delivery and for their encapsulation of guest molecules when chemically modified by peripheral amino acid groups. The cytotoxicity and interaction of polypropylenimine dendrimers with DNA as well as the transfection efficacy of DAB 64 has also been studied.

US Patent Publication No. 20050019923 is based upon the observation that, contrary to earlier reports, cationic dendrimers, such as polypropylenimine dendrimers, display suitable properties, such as specific targeting and low toxicity, for use in the targeted delivery of bioactive molecules, such as genetic material. In addition, derivatives of the cationic dendrimer also display suitable properties for the targeted delivery of bioactive molecules. See also, Bioactive Polymers, US published application No. 20080267903, which discloses "Various polymers, including cationic polyamine polymers and dendrimeric polymers, are shown to possess anti-proliferative activity, and may therefore be useful for treatment of disorders characterised by undesirable cellular proliferation such as neoplasms and tumours, inflammatory disorders (including autoimmune disorders), psoriasis and atherosclerosis. The polymers may be used alone as active agents, or as delivery vehicles for other therapeutic agents, such as drug molecules or nucleic acids for gene therapy. In such cases, the polymers' own intrinsic anti-tumour activity may complement the activity of the agent to be delivered." The disclosures of these patent publications may be employed in conjunction with herein teachings for delivery of CRISPR Cas system(s) or component(s) thereof or nucleic acid molecule(s) coding therefor.

In an aspect the invention provides a (non-naturally occurring or engineered) inducible CRISPR protein according to the invention as described herein (CRISPR-Cas system), comprising: a first CRISPR protein fusion construct attached to a first half of an inducible dimer and a second CRISPR protein fusion construct attached to a second half of the inducible dimer, wherein the first Cpf1 fusion construct is operably linked to one or more nuclear localization signals, wherein the second CRISPR protein fusion construct is operably linked to one or more nuclear export signals, wherein contact with an inducer energy source brings the first and second halves of the inducible dimer together, wherein bringing the first and second halves of the inducible dimer together allows the first and second CRISPR protein fusion constructs to constitute a functional CRISPR protein (optionally wherein the CRISPR-Cas system comprises a guide RNA (gRNA) comprising a guide sequence capable of hybridizing to a target sequence in a genomic locus of interest in a cell, and wherein the functional CRISPR-Cas system binds to the target sequence and, optionally, edits the genomic locus to alter gene expression).

In an aspect of the invention in the inducible CRISPR-Cas system, the inducible dimer is or comprises or consists essentially of or consists of an inducible heterodimer. In an aspect, in inducible CRISPR-Cas system, the first half or a first portion or a first fragment of the inducible heterodimer is or comprises or consists of or consists essentially of an FKBP, optionally FKBP12. In an aspect of the invention, in the inducible CRISPR-Cas system, the second half or a second portion or a second fragment of the inducible heterodimer is or comprises or consists of or consists essentially of FRB. In an aspect of the invention, in the inducible CRISPR-Cas system, the arrangement of the first CRISPR fusion construct is or comprises or consists of or consists essentially of N' terminal CRISPR part-FRB-NES. In an aspect of the invention, in the inducible CRISPR-Cas system, the arrangement of the first CRISP fusion construct is or comprises or consists of or consists essentially of NES-N' terminal CRISP part-FRB-NES. In an aspect of the invention, in the inducible CRISPR-Cas system, the arrangement of the second CRISP fusion construct is or comprises or consists essentially of or consists of C' terminal CRISP part-FKBP-NLS. In an aspect the invention provides in the inducible Cpf1 CRISPR-Cas system, the arrangement of the second CRISP fusion construct is or comprises or consists of or consists essentially of NLS-C' terminal CRISP part-FKBP-NLS. In an aspect, in inducible CRISPR-Cas system there can be a linker that separates the CRISP part from the half or portion or fragment of the inducible dimer. In an aspect, in the inducible CRISPR-Cas system, the inducer energy source is or comprises or consists essentially of or consists of rapamycin. In an aspect, in inducible CRISPR-Cas system, the inducible dimer is an inducible homodimer. In an aspect, in an inducible Cpf1 CRISPR-Cas system, the Cpf1 is AsCpf1, LbCpf1 or FnCpf1.

In an aspect, the invention provides a (non-naturally occurring or engineered) inducible CRISPR-Cas system, comprising:

a first CRISPR fusion construct attached to a first half of an inducible heterodimer and a second CRISPR fusion construct attached to a second half of the inducible heterodimer, wherein the first CRISPR fusion construct is operably linked to one or more nuclear localization signals, wherein the second CRISPR fusion construct is operably linked to a nuclear export signal, wherein contact with an inducer energy source brings the first and second halves of the inducible heterodimer together, wherein bringing the first and second halves of the inducible heterodimer together allows the first and second CRISPR fusion constructs to constitute a functional CRISPR (optionally wherein the CRISPR-Cas system comprises a guide RNA (gRNA) comprising a guide sequence capable of hybridizing to a target sequence in a genomic locus of interest in a cell, and wherein the functional CRISPR-Cas system edits the genomic locus to alter gene expression).

Accordingly, the invention comprehends inter alia homodimers as well as heterodimers, dead-CRISPR or CRISPR protein having essentially no nuclease activity, e.g., through mutation, systems or complexes wherein there is one or more NLS and/or one or more NES; functional domain(s) linked to split Cas9; methods, including methods of treatment, and uses.

An inducer energy source may be considered to be simply an inducer or a dimerizing agent. The term 'inducer energy source' is used herein throughout for consistency. The inducer energy source (or inducer) acts to reconstitute the enzyme. In some embodiments, the inducer energy source brings the two parts of the enzyme together through the action of the two halves of the inducible dimer. The two halves of the inducible dimer therefore are brought tougher in the presence of the inducer energy source. The two halves of the dimer will not form into the dimer (dimerize) without the inducer energy source.

Thus, the two halves of the inducible dimer cooperate with the inducer energy source to dimerize the dimer. This in turn reconstitutes the CRISPR by bringing the first and second parts of the CRISPR together.

The CRISPR protein fusion constructs each comprise one part of the split CRISPR protein. These are fused, preferably via a linker such as a GlySer linker described herein, to one of the two halves of the dimer. The two halves of the dimer may be substantially the same two monomers that together that form the homodimer, or they may be different monomers that together form the heterodimer. As such, the two monomers can be thought of as one half of the full dimer.

The CRISPR protein is split in the sense that the two parts of the CRISPR protein enzyme substantially comprise a functioning CRISPR protein. That CRISPR protein may function as a genome editing enzyme (when forming a complex with the target DNA and the guide), such as a nickase or a nuclease (cleaving both strands of the DNA), or it may be a dead-CRISPR protein which is essentially a DNA-binding protein with very little or no catalytic activity, due to typically mutation(s) in its catalytic domains.

The two parts of the split CRISPR protein can be thought of as the N' terminal part and the C' terminal part of the split CRISPR protein. The fusion is typically at the split point of the CRISPR protein. In other words, the C' terminal of the N' terminal part of the split CRISPR protein is fused to one of the dimer halves, whilst the N' terminal of the C' terminal part is fused to the other dimer half.

The CRISPR protein does not have to be split in the sense that the break is newly created. The split point is typically designed in silico and cloned into the constructs. Together, the two parts of the split CRISPR protein, the N' terminal and C' terminal parts, form a full CRISPR protein, comprising preferably at least 70% or more of the wildtype amino acids (or nucleotides encoding them), preferably at least 80% or more, preferably at least 90% or more, preferably at least 95% or more, and most preferably at least 99% or more of the wildtype amino acids (or nucleotides encoding them). Some trimming may be possible, and mutants are envisaged. Non-functional domains may be removed entirely. What is important is that the two parts may be brought together and that the desired CRISPR protein function is restored or reconstituted. The dimer may be a homodimer or a heterodimer.

One or more, preferably two, NLSs may be used in operable linkage to the first CRISPR protein construct. One or more, preferably two, NESs may be used in operable linkage to the first Cpf1 construct. The NLSs and/or the NESs preferably flank the split Cpf1-dimer (i.e., half dimer) fusion, i.e., one NLS may be positioned at the N' terminal of the first CRISPR protein construct and one NLS may be at the C' terminal of the first CRISPR protein construct. Similarly, one NES may be positioned at the N' terminal of the second CRISPR construct and one NES may be at the C' terminal of the second CRISPR construct. Where reference is made to N' or C' terminals, it will be appreciated that these correspond to 5' ad 3' ends in the corresponding nucleotide sequence.

A preferred arrangement is that the first CRISPR protein construct is arranged 5'-NLS-(N' terminal CRISPR protein part)-linker-(first half of the dimer)-NLS-3'. A preferred arrangement is that the second CRISPR protein construct is arranged 5'-NES--(second half of the dimer)-linker-(C' terminal CRISPR protein part)-NES-3'. A suitable promoter is preferably upstream of each of these constructs. The two constructs may be delivered separately or together.

In some embodiments, one or all of the NES(s) in operable linkage to the second CPf1 construct may be swapped out for an NLS. However, this may be typically not preferred and, in other embodiments, the localization signal in operable linkage to the second Cpf1 construct is one or more NES(s).

It will also be appreciated that the NES may be operably linked to the N' terminal fragment of the split CRISPR protein and that the NLS may be operably linked to the C' terminal fragment of the split CRISPR protein. However, the arrangement where the NLS is operably linked to the N' terminal fragment of the split Cpf1 and that the NES is operably linked to the C' terminal fragment of the split CRISPR protein may be preferred.

The NES functions to localize the second CRISPR protein fusion construct outside of the nucleus, at least until the inducer energy source is provided (e.g., at least until an energy source is provided to the inducer to perform its function). The presence of the inducer stimulates dimerization of the two CRISPR protein fusions within the cytoplasm and makes it thermodynamically worthwhile for the dimerized, first and second, CRISPR protein fusions to localize to the nucleus. Without being bound by theory, Applicants believe that the NES sequesters the second CRISPR protein fusion to the cytoplasm (i.e., outside of the nucleus). The NLS on the first CRISPR protein fusion localizes it to the nucleus. In both cases, Applicants use the NES or NLS to shift an equilibrium (the equilibrium of nuclear transport) to a desired direction. The dimerization typically occurs outside of the nucleus (a very small fraction might happen in the nucleus) and the NLSs on the dimerized complex shift the equilibrium of nuclear transport to nuclear localization, so the dimerized and hence reconstituted CRISPR protein enters the nucleus.

Beneficially, Applicants are able to reconstitute function in the split CRISPR protein. Transient transfection is used to prove the concept and dimerization occurs in the background in the presence of the inducer energy source. No activity is seen with separate fragments of the CRISPR protein. Stable expression through lentiviral delivery is then used to develop this and show that a split CRISPR protein approach can be used.

This present split CRISPR protein approach is beneficial as it allows the CRISPR protein activity to be inducible, thus allowing for temporal control. Furthermore, different localization sequences may be used (i.e., the NES and NLS as preferred) to reduce background activity from auto-assembled complexes. Tissue specific promoters, for example one for each of the first and second CRISPR protein fusion constructs, may also be used for tissue-specific targeting, thus providing spatial control. Two different tissue specific promoters may be used to exert a finer degree of control if required. The same approach may be used in respect of stage-specific promoters or there may a mixture of stage and tissue specific promoters, where one of the first and second Cpf1 fusion constructs is under the control of (i.e. operably linked to or comprises) a tissue-specific promoter, whilst the other of the first and second Cpf1 fusion constructs is under the control of (i.e. operably linked to or comprises) a stage-specific promoter.

The inducible CRISPR protein CRISPR-Cas system comprises one or more nuclear localization sequences (NLSs), as described herein, for example as operably linked to the first CRISPR protein fusion construct. These nuclear localization sequences are ideally of sufficient strength to drive accumulation of said first CRISPR protein fusion construct in a detectable amount in the nucleus of a eukaryotic cell. Without wishing to be bound by theory, it is believed that a nuclear localization sequence is not necessary for CRISPR-Cas complex activity in eukaryotes, but that including such sequences enhances activity of the system, especially as to targeting nucleic acid molecules in the nucleus, and assists with the operation of the present 2-part system.

Equally, the second CRISPR protein fusion construct is operably linked to a nuclear export sequence (NES). Indeed, it may be linked to one or more nuclear export sequences. In other words, the number of export sequences used with the second CRISPR protein fusion construct is preferably 1 or 2 or 3. Typically 2 is preferred, but 1 is enough and so is preferred in some embodiments. Suitable examples of NLS and NES are known in the art. For example, a preferred nuclear export signal (NES) is human protein tyrosine kinase 2. Preferred signals will be species specific.

Where the FRB and FKBP system are used, the FKBP is preferably flanked by nuclear localization sequences (NLSs). Where the FRB and FKBP system are used, the preferred arrangement is N' terminal CRISPR protein-FRB-NES: C' terminal Cpf1-FKBP-NLS. Thus, the first CRISPR protein fusion construct would comprise the C' terminal CRISPR protein part and the second CRISPR protein fusion construct would comprise the N' terminal CRISPR protein part.

Another beneficial aspect to the present invention is that it may be turned on quickly, i.e. that is has a rapid response. It is believed, without being bound by theory, that CRISPR protein activity can be induced through dimerization of existing (already present) fusion constructs (through contact with the inducer energy source) more rapidly than through the expression (especially translation) of new fusion constructs. As such, the first and second CRISPR protein fusion constructs may be expressed in the target cell ahead of time, i.e. before CRISPR protein activity is required. CRISPR protein activity can then be temporally controlled and then quickly constituted through addition of the inducer energy source, which ideally acts more quickly (to dimerize the heterodimer and thereby provide CRISPR protein activity) than through expression (including induction of transcription) of CRISPR protein delivered by a vector, for example.

Applicants demonstrate that CRISPR protein can be split into two components, which reconstitute a functional nuclease when brought back together. Employing rapamycin sensitive dimerization domains, Applicants generate a chemically inducible CRISPR protein for temporal control of CRISPR protein-mediated genome editing and transcription modulation. Put another way, Applicants demonstrate that CRISPR protein can be rendered chemically inducible by being split into two fragments and that rapamycin-sensitive dimerization domains may be used for controlled reassembly of the CRISPR protein. Applicants show that the re-assembled CRISPR protein may be used to mediate genome editing (through nuclease/nickase activity) as well as transcription modulation (as a DNA-binding domain, the so-called "dead CRISPR protein").

As such, the use of rapamycin-sensitive dimerization domains is preferred. Reassembly of the CRISPR protein is preferred. Reassembly can be determined by restoration of binding activity. Where the CRISPR protein is a nickase or induces a double-strand break, suitable comparison percentages compared to a wildtype are described herein.

Rapamycin treatments can last 12 days. The dose can be 200 nM. This temporal and/or molar dosage is an example of an appropriate dose for Human embryonic kidney 293 FT (HEK293FT) cell lines and this may also be used in other cell lines. This figure can be extrapolated out for therapeutic use in vivo into, for example, mg/kg. However, it is also envisaged that the standard dosage for administering rapamycin to a subject is used here as well. By the "standard dosage", it is meant the dosage under rapamycin's normal therapeutic use or primary indication (i.e. the dose used when rapamycin is administered for use to prevent organ rejection).

It is noteworthy that the preferred arrangement of CRISPR protein-FRB/FKBP pieces are separate and inactive until rapamycin-induced dimerization of FRB and FKBP results in reassembly of a functional full-length CRISPR protein nuclease. Thus, it is preferred that first CRISPR protein fusion construct attached to a first half of an inducible heterodimer is delivered separately and/or is localized separately from the second Cpf1 fusion construct attached to a first half of an inducible heterodimer.

To sequester the CRISPR protein (N)—FRB fragment in the cytoplasm, where it is less likely to dimerize with the nuclear-localized Cpf1 (C)-FKBP fragment, it is preferable to use on CRISPR protein (N)—FRB a single nuclear export sequence (NES) from the human protein tyrosine kinase 2 (CRISPR protein (N)—FRB-NES). In the presence of rapamycin, CRISPR protein (N)—FRB-NES dimerizes with CRISPR protein (C)-FKBP-2×NLS to reconstitute a complete CRISPR protein, which shifts the balance of nuclear trafficking toward nuclear import and allows DNA targeting.

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents EP 2 784 162 B1 and EP 2 771 468 B1; European Patent Applications EP 2 771 468 (EP13818570.7), EP 2 764 103 (EP13824232.6), and EP 2 784 162 (EP1170383.5); and PCT Patent Publications PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO 2014/093701 (PCT/US2013/074800), WO 2014/018423 (PCT/US2013/05118), WO 2014/204723 (PCT/US2014/01790), WO 2014/204724 (PCT/US2014/01800), WO 2014/204725 (PCT/US2014/01803), WO 2014/204726 (PCT/US2014/01804), WO 2014/204727 (PCT/US2014/01806), WO 2014/204728 (PCT/US2014/01808), WO 2014/204729 (PCT/US2014/01809). Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/01803, PCT/US2014/01800, PCT/US2014/01809, PCT/US2014/01804 and PCT/US2014/01806, each filed Jun. 10, 2014 6/10/14; PCT/US2014/01808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055,484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/1806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to US provisional patent application U.S. Ser. No. 61/980, 012 filed Apr. 15, 2014. Reference is made to PCT application designating, inter alia, the United States, application No. PCT/US14/1806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12-Dec.-14, PROTECTED GUIDE RNAS (PGRNAS); U.S. application 62/096,708, 24-Dec.-14, PROTECTED GUIDE RNAS (PGRNAS); U.S. application 62/091,462, 12-Dec.-14, DEAD GUIDES FOR CRISPR TRANSCRIPTION FACTORS; U.S. application 62/096,324, 23-Dec.-14, DEAD GUIDES FOR CRISPR TRANSCRIPTION FACTORS; U.S. application 62/091,456, 12-Dec.-14, ESCORTED AND FUNCTIONALIZED GUIDES FOR CRISPR-CAS SYSTEMS; U.S. application 62/091,461, 12-Dec.-14, DELIVERY, USE AND THERAPEUTIC APPLICATIONS OF THE CRISPR-CAS SYSTEMS AND COMPOSITIONS FOR GENOME EDITING AS TO HEMATOPOETIC STEM CELLS (HSCs); U.S. application 62/094,903, 19-Dec.-14, UNBIASED IDENTIFICATION OF DOUBLE-STRAND BREAKS AND GENOMIC REARRANGEMENT BY GENOME-WIDE INSERT CAPTURE SEQUENCING; U.S. application 62/096,761, 24-Dec.-14, ENGINEERING OF SYSTEMS, METHODS AND OPTIMIZED ENZYME AND GUIDE SCAFFOLDS FOR SEQUENCE MANIPULATION; U.S. application 62/098,059, 30-Dec.-14, RNA-TARGETING SYSTEM; U.S. application 62/096,656, 24-Dec.-14, CRISPR HAVING OR ASSOCIATED WITH DESTABILIZATION DOMAINS; U.S. application 62/096,697, 24-Dec.-14, CRISPR HAVING OR ASSOCIATED WITH AAV; U.S. application 62/098,158, 30-Dec.-14, ENGINEERED CRISPR COMPLEX INSERTIONAL TARGETING SYSTEMS; U.S. application 62/151,052, 22-Apr.-15, CELLULAR TARGETING FOR EXTRACELLULAR EXOSOMAL REPORTING; U.S. application 62/054,490, 24-Sep.-14, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25-Sep.-14, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4-Dec.-14, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24-Sep.-14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23-Oct.-14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24-Sep.-14, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24-Sep.-14, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25-Sep.-14, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25-Sep.-14, MULTIFUNCTIONAL-CRISPR COMPLEXES AND/OR OPTIMIZED ENZYME LINKED FUNCTIONAL-CRISPR COMPLEXES; U.S. application 62/087,475, 4-Dec.-14, FUNCTIONAL SCREENING WITH OPTIMIZED FUNCTIONAL CRISPR-CAS SYSTEMS; U.S. application 62/055,487, 25-Sep.-14, FUNCTIONAL SCREENING WITH OPTIMIZED FUNCTIONAL CRISPR-CAS SYSTEMS; U.S. application 62/087,546, 4-Dec.-14, MULTIFUNCTIONAL CRISPR COMPLEXES AND/OR OPTIMIZED ENZYME LINKED FUNCTIONAL-CRISPR COMPLEXES; and U.S. application 62/098,285, 30-Dec.-14, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR/Cas systems. Cong, L., Ran, F.A., Cox, D., Lin, S., Barretto, R., Habib, N., Hsu, P.D., Wu, X., Jiang, W., Marraffini, L.A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol Mar; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR Cas9 for Enhanced Genome Editing Specificity. Ran, FA., Hsu, PD., Lin, CY., Gootenberg, J S., Konermann, S., Trevino, AE., Scott, DA., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, FA., Konermann, S., Agarwala, V., $L_1$, Y., Fine, E., Wu, X., Shalem, O., Cradick, TJ., Marraffini, LA., Bao, G., & Zhang, F. Nat Biotechnol doi:10.1038/nbt.2647 (2013);

Genome engineering using the CRISPR-Cas9 system. Ran, FA., Hsu, PD., Wright, J., Agarwala, V., Scott, DA., Zhang, F. Nature Protocols November; 8(11):2281-308 (2013-B);

Genome-Scale CRISPR-Cas9 Knockout Screening in Human Cells. Shalem, O., Sanjana, NE., Hartenian, E., Shi, X., Scott, DA., Mikkelson, T., Heckl, D., Ebert, BL., Root, DE., Doench, JG., Zhang, F. Science December 12. (2013). [Epub ahead of print];

Crystal structure of cas9 in complex with guide RNA and target DNA. Nishimasu, H., Ran, FA., Hsu, PD., Konermann, S., Shehata, SI., Dohmae, N., Ishitani, R., Zhang, F., Nureki, 0. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas 0, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh 00, Barcena C, Hsu P D, Habib N, Gootenberg J S, Nishimasu H, Nureki 0, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem 0, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem 0, Wu X, Makarova K S, Koonin E V, Sharp P A, Zhang F., (published online 1 Apr. 2015), Nature. April 9; 520(7546):186-91(2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR/Cas9 cleavage of viral DNA efficiently suppresses hepatitis B virus," Scientific Reports 5:10833. doi: 10.1038/srep10833 (Jun. 2, 2015).

Nishimasu et al., "Crystal Structure of *Staphylococcus aureus* Cas9," Cell 162, 1113-1126 (Aug. 27, 2015).

Zetsche et al. (2015), "Cpf1 is a single RNA-guided endonuclease of a class 2 CRISPR-Cas system," Cell 163, 759-771 (Oct. 22, 2015) doi: 10.1016/j.cell.2015.09.038. Epub Sep. 25, 2015.

Shmakov et al. (2015), "Discovery and Functional Characterization of Diverse Class 2 CRISPR-Cas Systems," Molecular Cell 60, 385-397 (Nov. 5, 2015) doi: 10.1016/j.molcel.2015.10.008. Epub Oct. 22, 2015.

Dahlman et al., "Orthogonal gene control with a catalytically active Cas9 nuclease," Nature Biotechnology 33, 1159-1161 (November, 2015).

Gao et al, "Engineered Cpf1 Enzymes with Altered P A M Specificities," bioRxiv 091611; doi: http://dx.doi.org/10.1101/091611 Epub Dec. 4, 2016.

Smargon et al. (2017), "Cas13b Is a Type VI-B CRISPR-Associated RNA-Guided R Nase Differentially Regulated by Accessory Proteins Csx27 and Csx28," Molecular Cell 65, 618-630 (Feb. 16, 2017) doi: 10.1016/j.molcel.2016.12.023. Epub Jan. 5, 2017.

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of Streptococcuspneumoniae and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in S. pneumoniae, nearly 100% of cells that were recovered using the described approach contained the desired mutation, and in E. coli, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knock-out (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of Streptococcuspyogenes Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays. Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Shalem et al. (2015) described ways in which catalytically inactive Cas9 (dCas9) fusions are used to synthetically repress (CRISPRi) or activate (CRISPRa) expression, showing advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al(2015) demonstrated cleavage of viral episomal DNA (cccDNA) in infected cells. The HBV genome exists in the nuclei of infected hepatocytes as a 3.2kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Zetsche et al. (2015) reported the characterization of Cpf1, a putative class 2 CRISPR effector. It was demonstrated that Cpf1 mediates robust DNA interference with features distinct from Cas9. Identifying this mechanism of interference broadens our understanding of CRISPR-Cas systems and advances their genome editing applications.

Shmakov et al. (2015) reported the characterization of three distinct Class 2 CRISPR-Cas systems. The effectors of two of the identified systems, C2c1 and C2c3, contain RuvC like endonuclease domains distantly related to Cpf1. The third system, C2c2, contains an effector with two predicted HEPN RNase domains.

Gao et al. (2016) reported using a structure-guided saturation mutagenesis screen to increase the targeting range of Cpf1. AsCpf1 variants were engineered with the mutations S542R/K607R and S542R/K548V/N552R that can cleave target sites with TYCV/CCCC and TATV PAMs, respectively, with enhanced activities in vitro and in human cells.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

In addition, mention is made of PCT application PCT/US14/70057, and BI-2013/107 entitled "DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS (claiming priority from one or more or all of US provisional patent applications: 62/054,490, filed Sep. 24, 2014; 62/010,441, filed Jun. 10, 2014; and 61/915,118, 61/915,215 and 61/915,148, each filed on Dec. 12, 2013) ("the Particle Delivery PCT"), incorporated herein by reference, and of PCT application PCT/US14/70127, and BI-2013/101 entitled "DELIVERY, USE AND THERAPEUTIC APPLICATIONS OF THE CRISPR-CAS SYSTEMS AND COMPOSITIONS FOR GENOME EDITING" (claiming priority from one or more or all of US provisional patent applications: 61/915,176; 61/915,192; 61/915,215; 61/915,107, 61/915,145; 61/915,148; and 61/915,153 each filed Dec. 12, 2013) ("the Eye PCT"), incorporated herein by reference, with respect to a method of preparing an sgRNA-and-Cas9 protein containing particle comprising admixing a mixture comprising an sgRNA and Cas9 protein (and optionally HDR template) with a mixture comprising or consisting essentially of or consisting of surfactant, phospholipid, biodegradable polymer, lipoprotein and alcohol; and particles from such a process. For example, wherein Cas9 protein and sgRNA were mixed together at a suitable, e.g., 3:1 to 1:3 or 2:1 to 1:2 or 1:1 molar ratio, at a suitable temperature, e.g., 15-30C, e.g., 20-25C, e.g., room temperature, for a suitable time, e.g., 15-45, such as 30 minutes, advantageously in sterile, nuclease free buffer, e.g., 1×PBS. Separately, particle components such as or comprising: a surfactant, e.g., cationic lipid, e.g., 1,2-dioleoyl-3-trimethylammonium-propane (DOTAP); phospholipid, e.g., dimyristoylphosphatidylcholine (DMPC); biodegradable polymer, such as an ethylene-glycol polymer or PEG, and a lipoprotein, such as a low-density lipoprotein, e.g., cholesterol were dissolved in an alcohol, advantageously a $C_{1-6}$ alkyl alcohol, such as methanol, ethanol, isopropanol, e.g., 100% ethanol. The two solutions were mixed together to form particles containing the Cas9-sgRNA complexes. Accordingly, sgRNA may be pre-complexed with the Cas9 protein, before formulating the entire complex in a particle. Formulations may be made with a different molar ratio of different components known to promote delivery of nucleic acids into cells (e.g. 1,2-dioleoyl-3-trimethylammonium-propane (DOTAP), 1,2-ditetradecanoyl-sn-glycero-3-phosphocholine (DMPC), polyethylene glycol (PEG), and cholesterol) For example DOTAP: DMPC: PEG: Cholesterol Molar Ratios may be DOTAP 100, DMPC 0, PEG 0, Cholesterol 0; or DOTAP 90, DMPC 0, PEG 10, Cholesterol 0; or DOTAP 90, DMPC 0, PEG 5, Cholesterol 5. DOTAP 100, DMPC 0, PEG 0, Cholesterol 0. That application accordingly comprehends admixing sgRNA, Cas9 protein and components that form a particle; as well as particles from such admixing. Aspects of the instant invention can involve particles; for example, particles using a process analogous to that of the Particle Delivery PCT or that of the Eye PCT, e.g., by admixing a mixture comprising sgRNA and/or Cas9 as in the instant invention and components that form a particle, e.g., as in the Particle Delivery PCT or in the Eye PCT, to form a particle and particles from such admixing (or, of course, other particles involving sgRNA and/or Cas9 as in the instant invention).

The subject invention may be used as part of a research program wherein there is transmission of results or data. A computer system (or digital device) may be used to receive, transmit, display and/or store results, analyze the data and/or results, and/or produce a report of the results and/or data and/or analysis. A computer system may be understood as a logical apparatus that can read instructions from media (e.g. software) and/or network port (e.g. from the internet), which can optionally be connected to a server having fixed media. A computer system may comprise one or more of a CPU, disk drives, input devices such as keyboard and/or mouse, and a display (e.g. a monitor). Data communication, such as transmission of instructions or reports, can be achieved through a communication medium to a server at a local or a remote location. The communication medium can include any means of transmitting and/or receiving data. For example, the communication medium can be a network connection, a wireless connection, or an internet connection. Such a connection can provide for communication over the World Wide Web. It is envisioned that data relating to the present invention can be transmitted over such networks or connections (or any other suitable means for transmitting information, including but not limited to mailing a physical report, such as a print-out) for reception and/or for review by a receiver. The receiver can be but is not limited to an individual, or electronic system (e.g. one or more computers, and/or one or more servers). In some embodiments, the computer system comprises one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other suitable storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc. A client-server, relational database architecture can be used in embodiments of the invention. A client-server architecture is a network architecture in which each computer or process on the network is either a client or a server. Server computers are typically powerful computers dedicated to managing disk drives (file servers), printers (print servers), or network traffic (network servers). Client computers include PCs (personal computers) or workstations on which users run applications, as well as example output devices as disclosed herein. Client computers rely on server computers for resources, such as files, devices, and even processing power. In some embodiments of the invention, the server computer handles all of the database functionality. The client computer can have software that handles all the front-end data management and can also receive data input from users. A machine readable medium comprising computer-executable code may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution. Accordingly, the invention comprehends performing any method herein-discussed and storing and/or transmitting data and/or results therefrom and/or analysis thereof, as well as products from performing any method herein-discussed, including intermediates.

Throughout this disclosure there has been mention of CRISPR or CRISPR-Cas complexes or systems. CRISPR systems or complexes can target nucleic acid molecules, e.g., CRISPR-Cas9 complexes can target and cleave or nick or simply sit upon a target DNA molecule (depending if the Cas9 has mutations that render it a nickase or "dead"). Such systems or complexes are amenable for achieving tissue-specific and temporally controlled targeted deletion of candidate disease genes. Examples include but are not limited to genes involved in cholesterol and fatty acid metabolism, amyloid diseases, dominant negative diseases, latent viral infections, among other disorders. Accordingly, target sequences for such systems or complexes can be in candidate disease genes, e.g.:

| Disease | GENE | SPACER | PAM | Mechanism | References |
|---|---|---|---|---|---|
| Hypercholesterolemia | HMG-CR | GCCAAATTG GACGACCCT CG | CGG | Knockout | Fluvastatin: a review of its pharmacology and use in the management of hypercholesterolaemia. (Plosker GL et al. Drugs 1996, 51(3):433-459) |
| Hypercholesterolemia | SQLE | CGAGGAGAC CCCCGTTTC GG | TGG | Knockout | Potential role of nonstatin cholesterol lowering agents (Trapani et al. IUBMB Life, Volume 63, Issue 11, pages 964-971, November 2011) |
| Hyperlipidemia | DGAT1 | CCCGCCGCC GCCGTGGCT CG | AGG | Knockout | DGAT1 inhibitors as anti-obesity and anti-diabetic agents. (Birch AM et al. Current Opinion in Drug Discovery & Development [2010, 13(4):489-496) |
| Leukemia | BCR-ABL | TGAGCTCTA CGAGATCCA CA | AGG | Knockout | Killing of leukemic cells with a BCR/ABL fusion gene by RNA interference (RNAi). (Fuchs et al. Oncogene 2002, 21(37):5716-5724) |

Thus, the present invention, with regard to CRISPR or CRISPR-Cas complexes contemplates correction of hematopoietic disorders. For example, Severe Combined Immune Deficiency (SCID) results from a defect in lymphocytes T maturation, always associated with a functional defect in lymphocytes B (Cavazzana-Calvo et al., Annu. Rev. Med., 2005, 56, 585-602; Fischer et al., Immunol. Rev., 2005, 203, 98-109). In the case of Adenosine Deaminase (ADA) deficiency, one of the SCID forms, patients can be treated by injection of recombinant Adenosine Deaminase enzyme. Since the ADA gene has been shown to be mutated in SCID patients (Giblett et al., Lancet, 1972, 2, 1067-1069), several other genes involved in SCID have been identified (Cavazzana-Calvo et al., Annu. Rev. Med., 2005, 56, 585-602; Fischer et al., Immunol. Rev., 2005, 203, 98-109). There are four major causes for SCID: (i) the most frequent form of SCID, SCID-X1 (X-linked SCID or X-SCID), is caused by mutation in the IL2RG gene, resulting in the absence of mature T lymphocytes and NK cells. IL2RG encodes the gamma C protein (Noguchi, et al., Cell, 1993, 73, 147-157), a common component of at least five interleukin receptor complexes. These receptors activate several targets through the JAK3 kinase (Macchi et al., Nature, 1995, 377, 65-68), which inactivation results in the same syndrome as gamma C inactivation; (ii) mutation in the ADA gene results in a defect in purine metabolism that is lethal for lymphocyte precursors, which in turn results in the quasi absence of B, T and NK cells; (iii) V(D)J recombination is an essential step in the maturation of immunoglobulins and T lymphocytes receptors (TCRs). Mutations in Recombination Activating Gene 1 and 2 (RAG1 and RAG2) and Artemis, three genes involved in this process, result in the absence of mature T and B lymphocytes; and (iv) Mutations in other genes such as CD45, involved in T cell specific signaling have also been reported, although they represent a minority of cases (Cavazzana-Calvo et al., Annu. Rev. Med., 2005, 56, 585-602; Fischer et al., Immunol. Rev., 2005, 203, 98-109). In aspect of the invention, relating to CRISPR or CRISPR-Cas complexes contemplates system, the invention contemplates that it may be used to correct ocular defects that arise from several genetic mutations further described in Genetic Diseases of the Eye, Second Edition, edited by Elias I. Traboulsi, Oxford University Press, 2012. Non-limiting examples of ocular defects to be corrected include macular degeneration (MD), retinitis pigmentosa (RP). Non-limiting examples of genes and proteins associated with ocular defects include but are not limited to the following proteins: (ABCA4) ATP-binding cassette, sub-family A (ABC1), member 4 ACHM1 achromatopsia (rod monochromacy) 1 ApoE Apolipoprotein E (ApoE) C1QTNF5 (CTRP5) C1q and tumor necrosis factor related protein 5 (C1QTNF5) C2 Complement component 2 (C2) C3 Complement components (C3) CCL2 Chemokine (C—C motif) Ligand 2 (CCL2) CCR2 Chemokine (C—C motif) receptor 2 (CCR2) CD36 Cluster of Differentiation 36 CFB Complement factor B CFH Complement factor CFH H CFHR1 complement factor H-related 1 CFHR3 complement factor H-related 3 CNGB3 cyclic nucleotide gated channel beta 3 CP ceruloplasmin (CP) CRP C reactive protein (CRP) CST3 cystatin C or cystatin 3 (CST3) CTSD Cathepsin D (CTSD) CX3CR1 chemokine (C-X3-C motif) receptor 1 ELOVL4 Elongation of very long chain fatty acids 4 ERCC6 excision repair cross-complementing rodent repair deficiency, complementation group 6 FBLN5 Fibulin-5 FBLN5 Fibulin 5 FBLN6 Fibulin 6 FSCN2 fascin (FSCN2) HMCN1 Hemicentin 1 HMCN1 hemicentin 1 HTRA1 HtrA serine peptidase 1 (HTRA1) HTRA1 HtrA serine peptidase 1 IL-6 Interleukin 6 IL-8 Interleukin 8 LOC387715 Hypothetical protein PLEKHA1 Pleckstrin homology domain-containing family A member 1 (PLEKHA1) PROM1 Prominin 1(PROM1 or CD133) PRPH2 Peripherin-2 RPGR retinitis pigmentosa GTPase regulator SERPING1 serpin peptidase inhibitor, clade G, member 1 (C1-inhibitor) TCOF1 Treacle TIMP3 Metalloproteinase inhibitor 3 (TIMP3) TLR3 Toll-like receptor 3 The present invention, with regard to CRISPR or CRISPR-Cas complexes contemplates also contemplates delivering to the heart. For the heart, a myocardium tropic adeno-associated virus (AAVM) is preferred, in particular AAVM1 which showed preferential gene transfer in the heart (see, e.g., Lin-Yanga et al., PNAS, Mar. 10, 2009, vol. 106, no. 10). For example, US Patent Publication No. 20110023139, describes use of zinc finger nucleases to genetically modify cells, animals and proteins associated with cardiovascular disease. Cardiovascular diseases generally include high blood pressure, heart attacks, heart failure, and stroke and TIA. By way of example, the chromosomal sequence may comprise, but is not limited to, IL1B (interleukin 1, beta), XDH (xanthine dehydrogenase), TP53 (tumor protein p53), PTGIS (prostaglandin 12 (prostacyclin) synthase), MB (myoglobin), IL4 (interleukin 4), ANGPT1 (angiopoietin 1), ABCG8 (ATP-binding cassette, sub-family G (WHITE), member 8), CTSK (cathepsin K), PTGIR (prostaglandin 12 (prostacyclin) receptor (IP)), KCNJ11 (potassium inwardly-rectifying channel, subfamily J, member 11), INS (insulin), CRP (C-reactive protein, pentraxin-related), PDGFRB (platelet-derived growth factor receptor, beta polypeptide), CCNA2 (cyclin A2), PDGFB (platelet-derived growth factor beta polypeptide (simian sarcoma viral (v-sis) oncogene homolog)), KCNJ5 (potassium inwardly-rectifying channel, subfamily J, member 5), KCNN3 (potassium intermediate/small conductance calcium-activated channel, subfamily N, member 3), CAPN10 (calpain 10), PTGES (prostaglandin E synthase), ADRA2B (adrenergic, alpha-2B-, receptor), ABCG5 (ATP-binding cassette, sub-family G (WHITE), member 5), PRDX2 (peroxiredoxin 2), CAPN5 (calpain 5), PARP14 (poly(ADP-ribose) polymerase family, member 14), MEX3C (mex-3 homolog C (*C. elegans*)), ACE angiotensin I converting enzyme (peptidyl-dipeptidase A) 1), TNF (tumor necrosis factor (TNF superfamily, member 2)), IL6 (interleukin 6 (interferon, beta 2)), STN (statin), SERPINE1 (serpin peptidase inhibitor, clade E (nexin, plasminogen activator inhibitor type 1), member 1), ALB (albumin), ADIPOQ (adiponectin, C1Q and collagen domain containing), APOB (apolipoprotein B (including Ag(x) antigen)), APOE (apolipoprotein E), LEP (leptin), MTHFR (5,10-methylenetetrahydrofolate reductase (NADPH)), APOA1 (apolipoprotein A-I), EDN1 (endothelin 1), NPPB (natriuretic peptide precursor B), NOS3 (nitric oxide synthase 3 (endothelial cell)), PPARG (peroxisome proliferator-activated receptor gamma), PLAT (plasminogen activator, tissue), PTGS2 (prostaglandin-endoperoxide synthase 2 (prostaglandin G/H synthase and cyclooxygenase)), CETP (cholesteryl ester transfer protein, plasma), AGTR1 (angiotensin II receptor, type 1), HMGCR (3-hydroxy-3-methylglutaryl-Coenzyme A reductase), IGF1 (insulin-like growth factor 1 (somatomedin C)), SELE (selectin E), REN (renin), PPARA (peroxisome proliferator-activated receptor alpha), PON1 (paraoxonase 1), KNG1 (kininogen 1), CCL2 (chemokine (C—C motif) ligand 2), LPL (lipoprotein lipase), VWF (von Willebrand factor), F2 (coagulation factor II (thrombin)), ICAM1 (intercellular adhesion molecule 1), TGFB1 (transforming growth factor, beta 1), NPPA (natriuretic peptide precursor A), IL10 (interleukin 10), EPO (erythropoietin), SOD1 (superoxide dismutase 1, soluble), VCAM1 (vascular cell adhesion molecule 1), IFNG (interferon, gamma), LPA (lipoprotein, Lp(a)), MPO (myeloperoxidase), ESR1 (estrogen receptor 1), MAPK1 (mitogen-activated protein kinase 1), HP (haptoglobin), F3 (coagulation factor III (thromboplastin, tissue factor)), CST3 (cystatin C), COG2 (component of oligomeric golgi complex 2), MMP9 (matrix metallopeptidase 9 (gelatinase B, 92 kDa gelatinase, 92 kDa type IV collagenase)), SERPINC1 (serpin peptidase inhibitor, clade C (antithrombin), member 1), F8 (coagulation factor VIII, procoagulant component), HMOX1 (heme oxygenase (decycling) 1), APOC3 (apolipoprotein C—III), IL8 (interleukin 8), PROK1 (prokineticin 1), CBS (cystathionine-beta-synthase), NOS2 (nitric oxide synthase 2, inducible), TLR4 (toll-like receptor 4), SELP (selectin P (granule membrane protein 140 kDa, antigen CD62)), ABCA1 (ATP-binding cassette, sub-family A (ABC1), member 1), AGT (angiotensinogen (serpin peptidase inhibitor, clade A, member 8)), LDLR (low density lipoprotein receptor), GPT (glutamic-pyruvate transaminase (alanine aminotransferase)), VEGFA (vascular endothelial growth factor A), NR3C2 (nuclear receptor subfamily 3, group C, member 2), IL18 (interleukin 18 (interferon-gamma-inducing factor)), NOS1 (nitric oxide synthase 1 (neuronal)), NR3C1 (nuclear receptor subfamily 3, group C, member 1 (glucocorticoid receptor)), FGB (fibrinogen beta chain), HGF (hepatocyte growth factor (hepapoietin A; scatter factor)), IL1A (interleukin 1, alpha), RETN (resistin), AKT1 (v-akt murine thymoma viral oncogene homolog 1), LIPC (lipase, hepatic), HSPD1 (heat shock 60 kDa protein 1 (chaperonin)), MAPK14 (mitogen-activated protein kinase 14), SPP1 (secreted phosphoprotein 1), ITGB3 (integrin, beta 3 (platelet glycoprotein 111a, antigen CD61)), CAT (catalase), UTS2 (urotensin 2), THBD (thrombomodulin), F10 (coagulation factor X), CP (ceruloplasmin (ferroxidase)), TNFRSF11B (tumor necrosis factor receptor superfamily, member 11b), EDNRA (endothelin receptor type A), EGFR (epidermal growth factor receptor (erythroblastic leukemia viral (v-erb-b) oncogene homolog, avian)), MMP2 (matrix metallopeptidase 2 (gelatinase A, 72 kDa gelatinase, 72 kDa type IV collagenase)), PLG (plasminogen), NPY (neuropeptide Y), RHOD (ras homolog gene family, member D), MAPK8 (mitogen-activated protein kinase 8), MYC (v-myc myelocytomatosis viral oncogene homolog (avian)), FN1 (fibronectin 1), CMA1 (chymase 1, mast cell), PLAU (plasminogen activator, urokinase), GNB3 (guanine nucleotide binding protein (G protein), beta polypeptide 3), ADRB2 (adrenergic, beta-2-, receptor, surface), APOA5 (apolipoprotein A-V), SOD2 (superoxide dismutase 2, mitochondrial), F5 (coagulation factor V (proaccelerin, labile factor)), VDR (vitamin D (1,25-dihydroxyvitamin D3) receptor), ALOX5 (arachidonate 5-lipoxygenase), HLA-DRB1 (major histocompatibility complex, class II, DR beta 1), PARP1 (poly (ADP-ribose) polymerase 1), CD40LG (CD40 ligand), PON2 (paraoxonase 2), AGER (advanced glycosylation end product-specific receptor), IRS1 (insulin receptor substrate 1), PTGS1 (prostaglandin-endoperoxide synthase 1 (prostaglandin G/H synthase and cyclooxygenase)), ECE1 (endothelin converting enzyme 1), F7 (coagulation factor VII (serum prothrombin conversion accelerator)), URN (interleukin 1 receptor antagonist), EPHX2 (epoxide hydrolase 2, cytoplasmic), IGFBP1 (insulin-like growth factor binding protein 1), MAPK10 (mitogen-activated protein kinase 10), FAS (Fas (TNF receptor superfamily, member 6)), ABCB1 (ATP-binding cassette, sub-family B (MDR/TAP), member 1), JUN (jun oncogene), IGFBP3 (insulin-like growth factor binding protein 3), CD14 (CD14 molecule), PDE5A (phosphodiesterase 5A, cGMP-specific), AGTR2 (angiotensin II receptor, type 2), CD40 (CD40 molecule, TNF receptor superfamily member 5), LCAT (lecithin-cholesterol acyltransferase), CCR5 (chemokine (C—C motif) receptor 5), MMP1 (matrix metallopeptidase 1 (interstitial collagenase)), TIMP1 (TIMP metallopeptidase inhibitor 1), ADM (adrenomedullin), DYT10 (dystonia 10), STAT3 (signal transducer and activator of transcription 3 (acute-phase response factor)), MMP3 (matrix metallopeptidase 3 (stromelysin 1, progelatinase)), ELN (elastin), USF1 (upstream transcription factor 1), CFH (complement factor H), HSPA4 (heat shock 70 kDa protein 4), MMP12 (matrix metallopeptidase 12 (macrophage elastase)), MME (membrane metallo-endopeptidase), F2R (coagulation factor II (thrombin) receptor), SELL (selectin L), CTSB (cathepsin B), ANXA5 (annexin A5), ADRB1 (adrenergic, beta-i-, receptor), CYBA (cytochrome b-245, alpha polypeptide), FGA (fibrinogen alpha chain), GGT1 (gamma-glutamyltransferase 1), LIPG (lipase, endothelial), HIF1A (hypoxia inducible factor 1, alpha subunit (basic helix-loop-helix transcription factor)), CXCR4 (chemokine (C—X—C motif) receptor 4), PROC (protein C (inactivator of coagulation factors Va and VIIIa)), SCARB1 (scavenger receptor class B, member 1), CD79A (CD79a molecule, immunoglobulin-associated alpha), PLTP (phospholipid transfer protein), ADD1 (adducin 1 (alpha)), FGG (fibrinogen gamma chain), SAA1 (serum amyloid A1), KCNH2 (potassium voltage-gated channel, subfamily H (eag-related), member 2), DPP4 (dipeptidyl-peptidase 4), G6PD (glucose-6-phosphate dehydrogenase), NPR1 (natriuretic peptide receptor A/guanylate cyclase A (atrionatriuretic peptide receptor A)), VTN (vitronectin), KIAA0101 (KIAA0101), FOS (FBJ murine osteosarcoma viral oncogene homolog), TLR2 (toll-like receptor 2), PPIG (peptidylprolyl isomerase G (cyclophilin G)), IL,1R1 (interleukin 1 receptor, type I), AR (androgen receptor), CYP1A1 (cytochrome P450, family 1, subfamily A, polypeptide 1), SERPINAl (serpin peptidase inhibitor, clade A (alpha-1 antiproteinase, antitrypsin), member 1), MTR (5-methyltetrahydrofolate-homocysteine methyltransferase), RBP4 (retinol binding protein 4, plasma), APOA4 (apolipoprotein A-IV), CDKN2A (cyclin-dependent kinase inhibitor 2A (melanoma, p16, inhibits CDK4)), FGF2 (fibroblast growth factor 2 (basic)), EDNRB (endothelin receptor type B), ITGA2 (integrin, alpha 2 (CD49B, alpha 2 subunit of VLA-2 receptor)), CABINI (calcineurin binding protein 1), SHBG (sex hormone-binding globulin), HMGB1 (high-mobility group box 1), HSP90B2P (heat shock protein 90 kDa beta (Grp94), member 2 (pseudogene)), CYP3A4 (cytochrome P450, family 3, subfamily A, polypeptide 4), GJA1 (gap junction protein, alpha 1, 43 kDa), CAV1 (caveolin 1, caveolae protein, 22 kDa), ESR2 (estrogen receptor 2 (ER beta)), LTA (lymphotoxin alpha (TNF superfamily, member 1)), GDF15 (growth differentiation factor 15), BDNF (brain-derived neurotrophic factor), CYP2D6 (cytochrome P450, family 2, subfamily D, polypeptide 6), NGF (nerve growth factor (beta polypeptide)), SP1 (Spl transcription factor), TGIF1 (TGFB-induced factor homeobox 1), SRC (v-src sarcoma (Schmidt-Ruppin A-2) viral oncogene homolog (avian)), EGF (epidermal growth factor (beta-urogastrone)), PIK3CG (phosphoinositide-3-kinase, catalytic, gamma polypeptide), HLA-A (major histocompatibility complex, class I, A), KCNQ1 (potassium voltage-gated channel, KQT-like subfamily, member 1), CNR1 (cannabinoid receptor 1 (brain)), FBN1 (fibrillin 1), CHKA (choline kinase alpha), BEST1 (bestrophin 1), APP (amyloid beta (A4) precursor protein), CTNNB1 (catenin (cadherin-associated protein), beta 1, 88 kDa), TL2 (interleukin 2), CD36 (CD36 molecule (thrombospondin receptor)), PRKAB1 (protein kinase, AMP-activated, beta 1 non-catalytic subunit), TPO (thyroid peroxidase), ALDH7A1 (aldehyde dehydrogenase 7 family, member A1), CX3CR1 (chemokine (C-X3-C motif) receptor 1), TH (tyrosine hydroxylase), F9 (coagulation factor IX), GH1 (growth hormone 1), TF (transferrin), HFE (hemochromatosis), IL17A (interleukin 17A), PTEN (phosphatase and tensin homolog), GSTM1 (glutathione S-transferase mu 1), DMD (dystrophin), GATA4 (GATA binding protein 4), F13A1 (coagulation factor XIII, A1 polypeptide), TTR (transthyretin), FABP4 (fatty acid binding protein 4, adipocyte), PON3 (paraoxonase 3), APOC1 (apolipoprotein C—I), INSR (insulin receptor), TNFRSF 1B (tumor necrosis factor receptor superfamily, member 1i), HTR2A (5-hydroxytryptamine (serotonin) receptor 2A), CSF3 (colony stimulating factor 3 (granulocyte)), CYP2C9 (cytochrome P450, family 2, subfamily C, polypeptide 9), TXN (thioredoxin), CYP11B2 (cytochrome P450, family 11, subfamily B, polypeptide 2), PTH (parathyroid hormone), CSF2 (colony stimulating factor 2 (granulocyte-macrophage)), KDR (kinase insert domain receptor (a type III receptor tyrosine kinase)), PLA2G2A (phospholipase A2, group IIA (platelets, synovial fluid)), B2M (beta-2-microglobulin), THBS1 (thrombospondin 1), GCG (glucagon), RHOA (ras homolog gene family, member A), ALDH2 (aldehyde dehydrogenase 2 family (mitochondrial)), TCF7L2 (transcription factor 7-like 2 (T-cell specific, HMG-box)), BDKRB2 (bradykinin receptor B2), NFE2L2 (nuclear factor (erythroid-derived 2)-like 2), NOTCHI (Notch homolog 1, translocation-associated (*Drosophila*)), UGT1A1 (UDP glucuronosyltransferase 1 family, polypeptide A1), IFNA1 (interferon, alpha 1), PPARD (peroxisome proliferator-activated receptor delta), SIRT1 (sirtuin (silent mating type information regulation 2 homolog) 1 (*S. cerevisiae*)), GNRH1 (gonadotropin-releasing hormone 1 (luteinizing-releasing hormone)), PAPPA (pregnancy-associated plasma protein A, pappalysin 1), ARR3 (arrestin 3, retinal (X-arrestin)), NPPC (natriuretic peptide precursor C), AHSP (alpha hemoglobin stabilizing protein), PTK2 (PTK2 protein tyrosine kinase 2), IL13 (interleukin 13), MTOR (mechanistic target of rapamycin (serine/threonine kinase)), ITGB2 (integrin, beta 2 (complement component 3 receptor 3 and 4 subunit)), GSTT 1 (glutathione S-transferase theta 1), IL6ST (interleukin 6 signal transducer (gp130, oncostatin M receptor)), CPB2 (carboxypeptidase B2 (plasma)), CYP1A2 (cytochrome P450, family 1, subfamily A, polypeptide 2), HNF4A (hepatocyte nuclear factor 4, alpha), SLC6A4 (solute carrier family 6 (neurotransmitter transporter, serotonin), member 4), PLA2G6 (phospholipase A2, group VI (cytosolic, calcium-independent)), TNFSF11 (tumor necrosis factor (ligand) superfamily, member 11), SLC8A1 (solute carrier family 8 (sodium/calcium exchanger), member 1), F2RL1 (coagulation factor II (thrombin) receptor-like 1), AKR1A1 (aldo-keto reductase family 1, member A1 (aldehyde reductase)), ALDH9A1 (aldehyde dehydrogenase 9 family, member A1), BGLAP (bone gamma-carboxyglutamate (gla) protein), MTTP (microsomal triglyceride transfer protein), MTRR (5-methyltetrahydrofolate-homocysteine methyltransferase reductase), SULT1A3 (sulfotransferase family, cytosolic, 1A, phenol-preferring, member 3), RAGE (renal tumor antigen), C4B (complement component 4B (Chido blood group), P2RY12 (purinergic receptor P2Y, G-protein coupled, 12), RNLS (renalase, FAD-dependent amine oxidase), CREB1 (cAMP responsive element binding protein 1), POMC (proopiomelanocortin), RAC1 (ras-related C3 botulinum toxin substrate 1 (rho family, small GTP binding protein Rac1)), LMNA (lamin NC), CD59 (CD59 molecule, complement regulatory protein), SCN5A (sodium channel, voltage-gated, type V, alpha subunit), CYP1B1 (cytochrome P450, family 1, subfamily B, polypeptide 1), MIF (macrophage migration inhibitory factor (glycosylation-inhibiting factor)), MMP13 (matrix metallopeptidase 13 (collagenase 3)), TTMP2 (TTMP metallopeptidase inhibitor 2), CYP19A1 (cytochrome P450, family 19, subfamily A, polypeptide 1), CYP21A2 (cytochrome P450, family 21, subfamily A, polypeptide 2), PTPN22 (protein tyrosine phosphatase, non-receptor type 22 (lymphoid)), MYH14 (myosin, heavy chain 14, non-muscle), MBL2 (mannose-binding lectin (protein C) 2, soluble (opsonic defect)), SELPLG (selectin P ligand), AOC3 (amine oxidase, copper containing 3 (vascular adhesion protein 1)), CTSL1 (cathepsin $L_1$), PCNA (proliferating cell nuclear antigen), IGF2 (insulin-like growth factor 2 (somatomedin A)), ITGB1 (integrin, beta 1 (fibronectin receptor, beta polypeptide, antigen CD29 includes MDF2, MSK12)), CAST (calpastatin), CXCL 12 (chemokine (C—X—C motif) ligand 12 (stromal cell-derived factor 1)), IGHE (immunoglobulin heavy constant epsilon), KCNE1 (potassium voltage-gated channel, Isk-related family, member 1), TFRC (transferrin receptor (p90, CD71)), COL1A1 (collagen, type I, alpha 1), COL1A2 (collagen, type I, alpha 2), IL2RB (interleukin 2 receptor, beta), PLA2G10 (phospholipase A2, group X), ANGPT2 (angiopoietin 2), PROCR (protein C receptor, endothelial (EPCR)), NOX4 (NADPH oxidase 4), HAMP (hepcidin antimicrobial peptide), PTPN11 (protein tyrosine phosphatase, non-receptor type 11), SLC2A1 (solute carrier family 2 (facilitated glucose transporter), member 1), IL2RA (interleukin 2 receptor, alpha), CCL5 (chemokine (C—C motif) ligand 5), IRF1 (interferon regulatory factor 1), CFLAR (CASP8 and FADD-like apoptosis regulator), CALCA (calcitonin-related polypeptide alpha), EIF4E (eukaryotic translation initiation factor 4E), GSTP1 (glutathione S-transferase pi 1), JAK2 (Janus kinase 2), CYP3A5 (cytochrome P450, family 3, subfamily A, polypeptide 5), HSPG2 (heparan sulfate proteoglycan 2), CCL3 (chemokine (C—C motif) ligand 3), MYD88 (myeloid differentiation primary response gene (88)), VIP (vasoactive intestinal peptide), SOAT1 (sterol O-acyltransferase 1), ADRBK1 (adrenergic, beta, receptor kinase 1), NR4A2 (nuclear receptor subfamily 4, group A, member 2), MMP8 (matrix metallopeptidase 8 (neutrophil collagenase)), NPR2 (natriuretic peptide receptor B/guanylate cyclase B (atrionatriuretic peptide receptor B)), GCH1 (GTP cyclohydrolase 1), EPRS (glutamyl-prolyl-tRNA synthetase), PPARGC1A (peroxisome proliferator-activated receptor gamma, coactivator 1 alpha), F12 (coagulation factor XII (Hageman factor)), PECAM1 (platelet/endothelial cell adhesion molecule), CCL4 (chemokine (C—C motif) ligand 4), SERPINA3 (serpin peptidase inhibitor, clade A (alpha-1 antiproteinase, antitrypsin), member 3), CASR (calcium-sensing receptor), GJA5 (gap junction protein, alpha 5, 40 kDa), FABP2 (fatty acid binding protein 2, intestinal), TTF2 (transcription termination factor, RNA polymerase II), PROS1 (protein S (alpha)), CTF1 (cardiotrophin 1), SGCB (sarcoglycan, beta (43 kDa dystrophin-associated glycoprotein)), YME1L1 (YME1-like 1 (S. cerevisiae)), CAMP (cathelicidin antimicrobial peptide), ZC3H12A (zinc finger CCCH-type containing 12A), AKR1B1 (aldo-keto reductase family 1, member B1 (aldose reductase)), DES (desmin), MMP7 (matrix metallopeptidase 7 (matrilysin, uterine)), AHR (aryl hydrocarbon receptor), CSF1 (colony stimulating factor 1 (macrophage)), HDAC9 (histone deacetylase 9), CTGF (connective tissue growth factor), KCNMA1 (potassium large conductance calcium-activated channel, subfamily M, alpha member 1), UGT1A (UDP glucuronosyltransferase 1 family, polypeptide A complex locus), PRKCA (protein kinase C, alpha), COMT (catechol-.beta.-methyltransferase), S100B (S100 calcium binding protein B), EGR1 (early growth response 1), PRL (prolactin), 1I15 (interleukin 15), DRD4 (dopamine receptor D4), CAMK2G (calcium/calmodulin-dependent protein kinase II gamma), SLC22A2 (solute carrier family 22 (organic cation transporter), member 2), CCL11 (chemokine (C—C motif) ligand 11), PGF (B321 placental growth factor), THPO (thrombopoietin), GP6 (glycoprotein VI (platelet)), TACR1 (tachykinin receptor 1), NTS (neurotensin), HNF1A (HNF1 homeobox A), SST (somatostatin), KCND1 (potassium voltage-gated channel, Shal-related subfamily, member 1), LOC646627 (phospholipase inhibitor), TBXAS1 (thromboxane A synthase 1 (platelet)), CYP2J2 (cytochrome P450, family 2, subfamily J, polypeptide 2), TBXA2R (thromboxane A2 receptor), ADH1C (alcohol dehydrogenase 1C (class I), gamma polypeptide), ALOX12 (arachidonate 12-lipoxygenase), AHSG (alpha-2-HS-glycoprotein), BHMT (betaine-homocysteine methyltransferase), GJA4 (gap junction protein, alpha 4, 37 kDa), SLC25A4 (solute carrier family 25 (mitochondrial carrier; adenine nucleotide translocator), member 4), ACLY (ATP citrate lyase), ALOX5AP (arachidonate 5-lipoxygenase-activating protein), NUMA1 (nuclear mitotic apparatus protein 1), CYP27B1 (cytochrome P450, family 27, subfamily B, polypeptide 1), CYSLTR2 (cysteinyl leukotriene receptor 2), SOD3 (superoxide dismutase 3, extracellular), LTC4S (leukotriene C4 synthase), UCN (urocortin), GHRL (ghrelin/obestatin prepropeptide), APOC2 (apolipoprotein C-II), CLEC4A (C-type lectin domain family 4, member A), KBTBD10 (kelch repeat and BTB (POZ) domain containing 10), TNC (tenascin C), TYMS (thymidylate synthetase), SHC1 (SHC (Src homology 2 domain containing) transforming protein 1), LRP1 (low density lipoprotein receptor-related protein 1), SOCS3 (suppressor of cytokine signaling 3), ADH1B (alcohol dehydrogenase 1B (class I), beta polypeptide), KLK3 (kallikrein-related peptidase 3), HSD11B1 (hydroxysteroid (11-beta) dehydrogenase 1), VKORC1 (vitamin K epoxide reductase complex, subunit 1), SERPINB2 (serpin peptidase inhibitor, clade B (ovalbumin), member 2), TNS1 (tensin 1), RNF19A (ring finger protein 19A), EPOR (erythropoietin receptor), ITGAM (integrin, alpha M (complement component 3 receptor 3 subunit)), PITX2 (paired-like homeodomain 2), MAPK7 (mitogen-activated protein kinase 7), FCGR3A (Fc fragment of IgG, low affinity 1IIa, receptor (CD16a)), LEPR (leptin receptor), ENG (endoglin), GPX1 (glutathione peroxidase 1), GOT2 (glutamic-oxaloacetic transaminase 2, mitochondrial (aspartate aminotransferase 2)), HRH1 (histamine receptor H1), NR1I2 (nuclear receptor subfamily 1, group I, member 2), CRH (corticotropin releasing hormone), HTR1A (5-hydroxytryptamine (serotonin) receptor 1A), VDAC1 (voltage-dependent anion channel 1), HPSE (heparanase), SFTPD (surfactant protein D), TAP2 (transporter 2, ATP-binding cassette, subfamily B (MDR/TAP)), RNF123 (ring finger protein 123), PTK2B (PTK2B protein tyrosine kinase 2 beta), NTRK2 (neurotrophic tyrosine kinase, receptor, type 2), IL6R (interleukin 6 receptor), ACHE (acetylcholinesterase (Yt blood group)), GLP1R (glucagon-like peptide 1 receptor), GHR (growth hormone receptor), GSR (glutathione reductase), NQO1 (NAD(P)H dehydrogenase, quinone 1), NR5A1 (nuclear receptor subfamily 5, group A, member 1), GJB2 (gap junction protein, beta 2, 26 kDa), SLC9A1 (solute carrier family 9 (sodium/hydrogen exchanger), member 1), MAOA (monoamine oxidase A), PCSK9 (proprotein convertase subtilisin/kexin type 9), FCGR2A (Fc fragment of IgG, low affinity IIa, receptor (CD32)), SERPINF1 (serpin peptidase inhibitor, clade F (alpha-2 antiplasmin, pigment epithelium derived factor), member 1), EDN3 (endothelin 3), DHFR (dihydrofolate reductase), GAS6 (growth arrestspecific 6), SMPD1 (sphingomyelin phosphodiesterase 1, acid lysosomal), UCP2 (uncoupling protein 2 (mitochondrial, proton carrier)), TFAP2A (transcription factor AP-2 alpha (activating enhancer binding protein 2 alpha)), C4BPA (complement component 4 binding protein, alpha), SERPINF2 (serpin peptidase inhibitor, clade F (alpha-2 antiplasmin, pigment epithelium derived factor), member 2), TYMP (thymidine phosphorylase), ALPP (alkaline phosphatase, placental (Regan isozyme)), CXCR2 (chemokine (C—X—C motif) receptor 2), SLC39A3 (solute carrier family 39 (zinc transporter), member 3), ABCG2 (ATP-binding cassette, sub-family G (WHITE), member 2), ADA (adenosine deaminase), JAK3 (Janus kinase 3), HSPA1A (heat shock 70 kDa protein 1A), FASN (fatty acid synthase), FGF1 (fibroblast growth factor 1 (acidic)), F11 (coagulation factor XI), ATP7A (ATPase, Cu++transporting, alpha polypeptide), CR1 (complement component (3b/4b) receptor 1 (Knops blood group)), GFAP (glial fibrillary acidic protein), ROCK1 (Rho-associated, coiled-coil containing protein kinase 1), MECP2 (methyl CpG binding protein 2 (Rett syndrome)), MYLK (myosin light chain kinase), BCHE (butyrylcholinesterase), LIPE (lipase, hormone-sensitive), PRDX5 (peroxiredoxin 5), ADORA1 (adenosine A1 receptor), WRN (Werner syndrome, RecQ helicase-like), CXCR3 (chemokine (C—X—C motif) receptor 3), CD81 (CD81 molecule), SMAD7 (SMAD family member 7), LAMC2 (laminin, gamma 2), MAP3K5 (mitogen-activated protein kinase kinase kinase 5), CHGA (chromogranin A (parathyroid secretory protein 1)), IAPP (islet amyloid polypeptide), RHO (rhodopsin), ENPP1 (ectonucleotide pyrophosphatase/phosphodiesterase 1), PTHLH (parathyroid hormone-like hormone), NRG1 (neuregulin 1), VEGFC (vascular endothelial growth factor C), ENPEP (glutamyl aminopeptidase (aminopeptidase A)), CEBPB (CCAAT/enhancer binding protein (C/EBP), beta), NAGLU (N-acetylglucosaminidase, alpha-), F2RL3 (coagulation factor II (thrombin) receptor-like 3), CX3CL1 (chemokine (C-X3-C motif) ligand 1), BDKRB1 (bradykinin receptor B1), ADAMTS13 (ADAM metallopeptidase with thrombospondin type 1 motif, 13), ELANE (elastase, neutrophil expressed), ENPP2 (ectonucleotide pyrophosphatase/phosphodiesterase 2), CISH (cytokine inducible SH2-containing protein), GAST (gastrin), MYOC (myocilin, trabecular meshwork inducible glucocorticoid response), ATP1A2 (ATPase, Na+/K+transporting, alpha 2 polypeptide), NF1 (neurofibromin 1), GJB1 (gap junction protein, beta 1, 32 kDa), MEF2A (myocyte enhancer factor 2A), VCL (vinculin), BMPR2 (bone morphogenetic protein receptor, type II (serine/threonine kinase)), TUBB (tubulin, beta), CDC42 (cell division cycle 42 (GTP binding protein, 25 kDa)), KRT18 (keratin 18), HSF1 (heat shock transcription factor 1), MYB (v-myb myeloblastosis viral oncogene homolog (avian)), PRKAA2 (protein kinase, AMP-activated, alpha 2 catalytic subunit), ROCK2 (Rho-associated, coiled-coil containing protein kinase 2), TFPI (tissue factor pathway inhibitor (lipoprotein-associated coagulation inhibitor)), PRKG1 (protein kinase, cGMP-dependent, type I), BMP2 (bone morphogenetic protein 2), CTNND1 (catenin (cadherin-associated protein), delta 1), CTH (cystathionase (cystathionine gamma-lyase)), CTSS (cathepsin S), VAV2 (vav 2 guanine nucleotide exchange factor), NPY2R (neuropeptide Y receptor Y2), IGFBP2 (insulin-like growth factor binding protein 2, 36 kDa), CD28 (CD28 molecule), GSTA1 (glutathione S-transferase alpha 1), PPIA (peptidylprolyl isomerase A (cyclophilin A)), APOH (apolipoprotein H (beta-2-glycoprotein I)), S100A8 (S100 calcium binding protein A8), IL11 (interleukin 11), ALOX15 (arachidonate 15-lipoxygenase), FBLN1 (fibulin 1), NR1H3 (nuclear receptor subfamily 1, group H, member 3), SCD (stearoyl-CoA desaturase (delta-9-desaturase)), GIP (gastric inhibitory polypeptide), CHGB (chromogranin B (secretogranin 1)), PRKCB (protein kinase C, beta), SRD5A1 (steroid-5-alpha-reductase, alpha polypeptide 1 (3-oxo-5 alpha-steroid delta 4-dehydrogenase alpha 1)), HSD11B2 (hydroxysteroid (11-beta) dehydrogenase 2), CALCRL (calcitonin receptor-like), GALNT2 (UDP-N-acetyl-alpha-D-galactosamine.polypeptide N-acetylgalactosaminyltransferase 2 (GalNAc-T2)), ANGPTL4 (angiopoietin-like 4), KCNN4 (potassium intermediate/small conductance calcium-activated channel, subfamily N, member 4), PIK3C2A (phosphoinositide-3-kinase, class 2, alpha polypeptide), HBEGF (heparin-binding EGF-like growth factor), CYP7A1 (cytochrome P450, family 7, subfamily A, polypeptide 1), HLA-DRB5 (major histocompatibility complex, class II, DR beta 5), BNIP3 (BCL2/adenovirus E1B 19 kDa interacting protein 3), GCKR (glucokinase (hexokinase 4) regulator), S100A12 (S100 calcium binding protein A12), *PADI4* (peptidyl arginine deiminase, type IV), HSPA14 (heat shock 70 kDa protein 14), CXCR1 (chemokine (C—X—C motif) receptor 1), H19 (H19, imprinted maternally expressed transcript (non-protein coding)), KRTAP19-3 (keratin associated protein 19-3), IDDM2 (insulin-dependent diabetes mellitus 2), RAC2 (ras-related C3 botulinum toxin substrate 2 (rho family, small GTP binding protein Rac2)), RYR1 (ryanodine receptor 1 (skeletal)), CLOCK (clock homolog (mouse)), NGFR (nerve growth factor receptor (TNFR superfamily, member 16)), DBH (dopamine beta-hydroxylase (dopamine beta-monooxygenase)), CHRNA4 (cholinergic receptor, nicotinic, alpha 4), CACNA1C (calcium channel, voltage-dependent, L type, alpha 1C subunit), PRKAG2 (protein kinase, AMP-activated, gamma 2 non-catalytic subunit), CHAT (choline acetyltransferase), PTGDS (prostaglandin D2 synthase 21 kDa (brain)), NR1H2 (nuclear receptor subfamily 1, group H, member 2), TEK (TEK tyrosine kinase, endothelial), VEGFB (vascular endothelial growth factor B), MEF2C (myocyte enhancer factor 2C), MAPKAPK2 (mitogen-activated protein kinase-activated protein kinase 2), TNFRSF11A (tumor necrosis factor receptor superfamily, member 11a, NFKB activator), HSPA9 (heat shock 70 kDa protein 9 (mortalin)), CYSLTR1 (cysteinyl leukotriene receptor 1), MAT1A (methionine adenosyltransferase I, alpha), OPRL1 (opiate receptor-like 1), IMPA1 (inositol(myo)-1(or 4)-monophosphatase 1), CLCN2 (chloride channel 2), DLD (dihydrolipoamide dehydrogenase), PSMA6 (proteasome (prosome, macropain) subunit, alpha type, 6), PSMB8 (proteasome (prosome, macropain) subunit, beta type, 8 (large multifunctional peptidase 7)), CHI3L 1 (chitinase 3-like 1 (cartilage glycoprotein-39)), ALDH1B1 (aldehyde dehydrogenase 1 family, member B1), PARP2 (poly(ADP-ribose) polymerase 2), STAR (steroidogenic acute regulatory protein), LBP (lipopolysaccharide binding protein), ABCC6 (ATP-binding cassette, sub-family C(CFTR/MRP), member 6), RGS2 (regulator of G-protein signaling 2, 24 kDa), EFNB2 (ephrin-B2), GJB6 (gap junction protein, beta 6, 30 kDa), APOA2 (apolipoprotein A-II), AMPD1 (adenosine monophosphate deaminase 1), DYSF (dysferlin, limb girdle muscular dystrophy 2B (autosomal recessive)), FDFT1 (farnesyl-diphosphate farnesyltransferase 1), EDN2 (endothelin 2), CCR6 (chemokine (C—C motif) receptor 6), GJB3 (gap junction protein, beta 3, 31 kDa), IL1RL1 (interleukin 1 receptor-like 1), ENTPD1 (ectonucleoside triphosphate diphosphohydrolase 1), BBS4 (Bardet-Biedl syndrome 4), CELSR2 (cadherin, EGF LAG seven-pass G-type receptor 2

(flamingo homolog, *Drosophila*)), F11R (F11 receptor), RAPGEF3 (Rap guanine nucleotide exchange factor (GEF) 3), HYAL1 (hyaluronoglucosaminidase 1), ZNF259 (zinc finger protein 259), ATOX1 (ATX1 antioxidant protein 1 homolog (yeast)), ATF6 (activating transcription factor 6), KHK (ketohexokinase (fructokinase)), SAT1 (spermidine/spermine N1-acetyltransferase 1), GGH (gamma-glutamyl hydrolase (conjugase, folylpolygammaglutamyl hydrolase)), TIMP4 (TIMP metallopeptidase inhibitor 4), SLC4A4 (solute carrier family 4, sodium bicarbonate cotransporter, member 4), PDE2A (phosphodiesterase 2A, cGMP-stimulated), PDE3B (phosphodiesterase 3B, cGMP-inhibited), FADS1 (fatty acid desaturase 1), FADS2 (fatty acid desaturase 2), TMSB4X (thymosin beta 4, X-linked), TXNIP (thioredoxin interacting protein), LIMS1 (LIM and senescent cell antigen-like domains 1), RHOB (ras homolog gene family, member B), LY96 (lymphocyte antigen 96), FOXO1 (forkhead box 01), PNPLA2 (patatin-like phospholipase domain containing 2), TRH (thyrotropin-releasing hormone), GJC1 (gap junction protein, gamma 1, 45 kDa), SLC17A5 (solute carrier family 17 (anion/sugar transporter), member 5), FTO (fat mass and obesity associated), GJD2 (gap junction protein, delta 2, 36 kDa), PSRC1 (proline/serine-rich coiled-coil 1), CASP12 (caspase 12 (gene/pseudogene)), GPBAR1 (G protein-coupled bile acid receptor 1), PXK (PX domain containing serine/threonine kinase), IL33 (interleukin 33), TRIB1 (tribbles homolog 1 (*Drosophila*)), PBX4 (pre-B-cell leukemia homeobox 4), NUPR1 (nuclear protein, transcriptional regulator, 1), 15-Sep(15 kDa selenoprotein), CILP2 (cartilage intermediate layer protein 2), TERC (telomerase RNA component), GGT2 (gamma-glutamyltransferase 2), MT-CO1 (mitochondrially encoded cytochrome c oxidase I), and UOX (urate oxidase, pseudogene). In an additional embodiment, the chromosomal sequence may further be selected from Pon1 (paraoxonase 1), LDLR (LDL receptor), ApoE (Apolipoprotein E), Apo B-100 (Apolipoprotein B-100), ApoA (Apolipoprotein(a)), ApoA1 (Apolipoprotein A1), CBS (Cystathionine B-synthase), Glycoprotein I Ib/IIb, MTHRF (5,10-methylenetetrahydrofolate reductase (NADPH), and combinations thereof. In one iteration, the chromosomal sequences and proteins encoded by chromosomal sequences involved in cardiovascular disease may be chosen from CacnalC, Sod1, Pten, Ppar(alpha), Apo E, Leptin, and combinations thereof. The text herein accordingly provides exemplary targets as to CRISPR or CRISPR-Cas systems or complexes.

Although the present invention and its advantages have been described in detail, it should be understood that various changes, substitutions and alterations can be made herein without departing from the spirit and scope of the invention as defined in the appended claims. The present invention will be further illustrated in the following Examples which are given for illustration purposes only and are not intended to limit the invention in any way.

EXAMPLES

Example 1: Exemplary Lipid Particles

A lipid particle of the invention can be prepared as follows. Compound 80-O14B is prepared using N,N'-dimethylpropane-1,3-diamine and 2-(decyldisulfanyl)ethyl acrylate. In a 5-mL Teflon-lined glass screw-top vial, the acrylate with disulfide bonds is added to the amine at a molar ratio of 2.4:1. The mixture is stirred at 90° C. for two days. After cooling, the lipid-like compound formed may be used without purification or purified using flash chromatography on silica gel. The prepared compound optionally is characterized by proton nuclear magnetic resonance.

The lipid-like compound prepared above is dissolved in sodium acetate solution (25 mM, pH=5.5) at a concentration of 1 mg/mL. Optionally, cholesterol and 1,2-dioleoyl-sn-glycero-3-phosphoethanolamine ("DOPE") is also included.

A synthetic lipid nanoparticle, comprising either pure synthetic lipid or synthetic lipid in combination with an excipient, such as cholesterol, PEGylated lipid or DOPE, at a particular concentration (for example, 0.1 mg/ml-2 mg/ml), is mixed with a viral particles (for example, an AAV viral particle). In a typical experiment, the AAV concentration is 109 AAV/µg lipid nanoparticle. After mixing, the mixture is left at room temperature for 15 min. Before imaging, the sample is mixed using vortex for 1 min.

In one embodiment, an AAV composition, comprising AAV capsids or capsid subunit proteins is introduced into the resulting mixture and incubated for 15 minutes at room temperature. (The AAV capsids and capsid subunit proteins can be wild type capsid subunits or further contain hybrid AAV capsid subunits comprising heterologous proteins or peptides.) The weight ratio between the lipid-like compound and AVV component is varied, for example 5:1, 10:1, 20:1, or 50:1. The complex composition thus prepared is ready for use in cells.

Example 2: Hybrid A AV-Lipid Particle

Hybrid A AV-lipid particles were formulated by mixing AAV8 vector with lipid nanoparticles encasing purified negatively supercharged CRE recombinase protein (10' AAV virions per µg lipid). The hybrid AAV-lipid particles were used to infect HEK293T cells. Protein delivery of CRE by the hybrid AAV-lipid particle was compared to lipid-CRE formulation 48 hours post transfection using a DsRed reporter for CRE activity. (FIG. 16).

Example 3: Exterior Cas9

Construct A encodes AAV9.eSpCas9.(G4S)3. Construct B encodes AAV9 capsid. Equal moles of construct A and construct B were transfected in HEK293 cells, along with cis genome and adenoviral helper plasmid pDF6 (Puresyn Inc.), and purified by iodixanol-based ultracentrifugation. Cas9 incorporation in ~1.4 g/cc iodixanol fractions was tested by western blotting for VP (AAV capsid proteins VP1-3) and Cas9. The ratio of the constructs A and B is changed to vary the proportion of wt capsid:hybrid capsid in AAV particles.

```
Construct A encodes AAV9.eSpCas9.(G4S)3
GTCGACGGTATCGGGGGAGCTCGCAGGGTCTCCATTTTGAAGCGGGAGGTT

TGAACGCGCAGCCGCCATGCCGGGGTTTTACGAGATTGTGATTAAGGTCCC

CAGCGACCTTGACGAGCATCTGCCCGGCATTTCTGACAGCTTTGTGAACTG

GGTGGCCGAGAAGGAATGGGAGTTGCCGCCAGATTCTGACATGGATCTGAA

TCTGATTGAGCAGGCACCCCTGACCGTGGCCGAGAAGCTGCAGCGCGACTT

TCTGACGGAATGGCGCCGTGTGAGTAAGGCCCCGGAGGCTCTTTTCTTTGT

GCAATTTGAGAAGGGAGAGAGCTACTTCCACATGCACGTGCTCGTGGAAAC

CACCGGGGTGAAATCCATGGTTTTGGGACGTTTCCTGAGTCAGATTCGCGA

AAAACTGATTCAGAGAATTTACCGCGGGATCGAGCCGACTTTGCCAAACTG
```

-continued

```
GTTCGCGGTCACAAAGACCAGAAATGGCGCCGGAGGCGGGAACAAGGTGGT
GGATGAGTGCTACATCCCCAATTACTTGCTCCCCAAAACCCAGCCTGAGCT
CCAGTGGGCGTGGACTAATATGGAACAGTATTTAAGCGCCTGTTTGAATCT
CACGGAGCGTAAACGGTTGGTGGCGCAGCATCTGACGCACGTGTCGCAGAC
GCAGGAGCAGAACAAAGAGAATCAGAATCCCAATTCTGATGCGCCGGTGAT
CAGATCAAAAACTTCAGCCAGGTACATGGAGCTGGTCGGGTGGCTCGTGGA
CAAGGGGATTACCTCGGAGAAGCAGTGGATCCAGGAGGACCAGGCCTCATA
CATCTCCTTCAATGCGCCTCCAACTCGCGGTCCCAAATCAAGGCTGCCTT
GGACAATGCGGGAAAGATTATGAGCCTGACTAAAACCGCCCCCGACTACCT
GGTGGGCCAGCAGCCCGTGGAGGACATTTCCAGCAATCGGATTTATAAAT
TTTGGAACTAAACGGGTACGATCCCCAATATGCGGCTTCCGTCTTTCTGGG
ATGGGCCACGAAAAAGTTCGGCAAGAGGAACACCATCTGGCTGTTTGGGCC
TGCAACTACCGGGAAGACCAACATCGCGGAGGCCATAGCCCACACTGTGCC
CTTCTACGGGTGCGTAAACTGGACCAATGAGAACTTTCCCTTCAACGACTG
TGTCGACAAGATGGTGATCTGGTGGGAGGAGGGGAAGATGACCGCCAAGGT
CGTGGAGTCGGCCAAAGCCATTCTCGGAGGAAGCAAGGTGCGCGTGGACCA
GAAATGCAAGTCCTCGGCCCAGATAGACCCGACTCCCGTGATCGTCACCTC
CAACACCAACATGTGCGCCGTGATTGACGGGAACTCAACGACCTTCGAACA
CCAGCAGCCGTTGCAAGACCGGATGTTCAAATTTGAACTCACCCGCCGTCT
GGATCATGACTTTGGGAAGGTCACCAAGCAGGAAGTCAAAGACTTTTTCCG
GTGGGCAAAGGATCACGTGGTTGAGGTGGAGCATGAATTCTACGTCAAAAA
GGGTGGAGCCAAGAAAAGACCCGCCCCCAGTGACGCAGATATAAGTGAGCC
CAAACGGGTGCGCGAGTCAGTTGCGCAGCCATCGACGTCAGACGCGGAAGC
TTCGATCAACTACGCGGACAGGTACCAAAACAAATGTTCTCGTCACGTGGG
CATGAATCTGATGCTGTTTCCCTGCAGACAATGCGAGAGACTGAATCAGAA
TTCAAATATCTGCTTCACTCACGGTGTCAAAGACTGTTTAGAGTGCTTTCC
CGTGTCAGAATCTCAACCCGTTTCTGTCGTCAAAAAGGCGTATCAGAAACT
GTGCTACATTCATCACATCATGGGAAAGGTGCCAGACGCTTGCACTGCTTG
CGACCTGGTCAATGTGGACTTGGATGACTGTGTTTCTGAACAATAAATGAC
TTAAACCAGGTATGAGTCGGCTGGATAAATCTAAAGTCATAAACGGCGCTC
TGGAATTACTCAATGAAGTCGGTATCGAAGGCCTGACGACAAGGAAACTCG
CTCAAAAGCTGGGAGTTGAGCAGCCTACCCTGTACTGGCACGTGAAGAACA
AGCGGGCCCTGCTGATGCCCTGGCCATCGAGATGCTGGACAGGCATCATA
CCCACTTCTGCCCCCTGGAAGGCGAGTCATGGCAAGACTTTCTGCGGAACA
ACGCCAAGTCATTCCGCTGTGCTCTCCTCTCACATCGCGACGGGGCTAAAG
TGCATCTCGGCACCCGCCCAACAGAGAAACAGTACGAAACCCTGGAAATC
AGCTCGCGTTCCTGTGTCAGCAAGGCTTCTCCCTGGAGAACGCACTGTACG
CTCTGTCCGCCGTGGGCCACTTTACACTGGGCTGCGTATTGGAGGAACAGG
AGCATCAAGTAGCAAAAGAGGAAAGAGAGACACCTACCACCGATTCTATGC
CCCCACTTCTGAGACAAGCAATTGAGCTGTTCGACCGGCAGGGAGCCGAAC
CTGCCTTCCTTTTCGGCCTGGAACTAATCATATGTGGCCTGGAGAAACAGC
```

```
TAAAGTGCGAAAGCGGCGGGCCGGCCGACGCCCTTGACGATTTTGACTTAG
ACATGCTCCCAGCCGATGCCCTTGACGACTTTGACCTTGATATGCTGCCTG
CTGACGCTCTTGACGATTTTGACCTTGACATGCTCCCCGGGTAAATGCATG
AATTCGATCTAGAGGGCCCTATTCTATAGTGTCACCTAAATGCTAGAGCTC
GCTGATCAGCCTCGACTGTGCCTTCTAGTTGCCAGCCATCTGTTGTTTGCC
CCTCCCCCGTGCCTTCCTTGACCCTGGAAGGTGCCACTCCCACTGTCCTTT
CCTAATAAAATGAGGAAATTGCATCGCATTGTCTGAGTAGGTGTCATTCTA
TTCTGGGGGGTGGGGTGGGGCAGGACAGCAAGGGGGAGGATTGGGAAGACA
ATAGCAGGCATGCTGGGGATGCGGTGGGCTCTATGGCTTCTGAGGCGGAAA
GAACCAGCTGGGGCTCGAATCAAGCTATCAAGTGCCACCTGACGTCTCCCT
ATCAGTGATAGAGAAGTCGACACGTCTCGAGCTCCCTATCAGTGATAGAGA
AGGTACGTCTAGAACGTCTCCCTATCAGTGATAGAGAAGTCGACACGTCTC
GAGCTCCCTATCAGTGATAGAGAAGGTACGTCTAGAACGTCTCCCTATCAG
TGATAGAGAAGTCGACACGTCTCGAGCTCCCTATCAGTGATAGAGAAGGTA
CGTCTAGAACGTCTCCCTATCAGTGATAGAGAAGTCGACACGTCTCGAGCT
CCCTATCAGTGATAGAGAAGGTACCCCCTATATAAGCAGAGAGATCTGTTC
AAATTTGAACTGACTAAGCGGCTCCCGCCAGATTTTGGCAAGATTACTAAG
CAGGAAGTCAAGGACTTTTTTGCTTGGGCAAAGGTCAATCAGGTGCCGGTG
ACTCACGAGTTTAAAGTTCCCAGGGAATTGGCGGGAACTAAAGGGGCGGAG
AAATCTCTAAAACGCCCACTGGGTGACGTCACCAATACTAGCTATAAAAGT
CTGGAGAAGCGGGCCAGGCTCTCATTTGTTCCCGAGACGCCTCGCAGTTCA
GACGTGACTGTTGATCCCGCTCCTCTGCGACCGCTAGCTTCGATCAACTAC
GCGGACAGGTACCAAAACAAATGTTCTCGTCACGTGGGCATGAATCTGATG
CTGTTTCCCTGAGACAATGCGAGAGACTGAATCAGAATTCAAATATCTGC
TTCACTCACGGTGTCAAAGACTGTTTAGAGTGCTTTCCCGTGTCAGAATCT
CAACCCGTTTCTGTCGTCAAAAAGGCGTATCAGAAACTGTGCTACATTCAT
CACATCATGGGAAAGGTGCCAGACGCTTGCACTGCTTGCGACCTGGTCAAT
GTGGACTTGGATGACTGTGTTTCTGAACAATAAATGACTTAAACCAGGTAT
GGCTGCCGATGGTTATCTTCCAGATTGGCTCGAGGACAACCTTAGTGAAGG
AATTCGCGAGTGGTGGGCTTTGAAACCTGGAGCCCCTCAACCCAAGGCAAA
TCAACAACATCAAGACAACGCTCGAGGTCTTGTGCTTCCGGGTTACAAATA
CCTTGGACCCGGCAACGGACTCGACAAGGGGGAGCCGGTCAACGCAGCAGA
CGCGGCGGCCCTCGAGCACGACAAGGCCTACGACCAGCAGCTCAAGGCCGG
AGACAACCCGTACCTCAAGTACAACCACGCCGACGCCGAGTTCCAGGAGCG
GCTCAAAGAAGATACGTCTTTTGGGGGCAACCTCGGGCGAGCAGTCTTCCA
GGCCAAAAAGAGGCTTCTTGAACCTCTTGGTCTGGTTGAGGAAGCGGCTAA
GACGGCTCCTGGAAAGAAGAGGCCTGTAGAGCAGTCCTCAGGAACCGGA
CTCCTCCGCGGGTATTGGCAAATCGGGTGCACAGCCCGCTAAAAAGAGACT
CAATTTCGGTCAGACTGGCGACACAGAGTCAGTCCCAGACCCTCAACCAAT
CGGAGAACCTCCCGCAGCCCCCTCAGGTGTGGGATCTCTTACAATGGCTTC
```

-continued
```
AGGTGGTGGCGCACCAGTGGCAGACAATAACGAAGGTGCCGATGGAGTGGG
TAGTTCCTCGGGAAATTGGCATTGCGATTCCCAATGGCTGGGGGACAGAGT
CATCACCACCAGCACCCGAACCTGGGCCCTGCCCACCTACAACAATCACCT
CTACAAGCAAATCTCCAACAGCACATCTGGAGGATCTTCAAATGACAACGC
CTACTTCGGCTACAGCACCCCCTGGGGGTATTTTGACTTCAACAGATTCCA
CTGCCACTTCTCACCACGTGACTGGCAGCGACTCATCAACAACAACTGGGG
ATTCCGGCCTAAGCGACTCAACTTCAAGCTCTTCAACATTCAGGTCAAAGA
GGTTACGGACAACAATGGAGTCAAGACCATCGCCAATAACCTTACCAGCAC
GGTCCAGGTCnCACGGACTCAGACTATCAGCTCCCGTACGTGCTCGGGTCG
GCTCACGAGGGCTGCCTCCCGCCGTTCCCAGCGGACGTTTTCATGATTCCT
CAGTACGGGTATCTGACGCTTAATGATGGAAGCCAGGCCGTGGGTCGTTCG
TCCTTTTACTGCCTGGAATATTTCCCGTCGCAAATGCTAAGAACGGGTAAC
AACTTCCAGTTCAGCTACGAGTTTGAGAACGTACCTTTCCATAGCAGCTAC
GCTCACAGCCAAAGCCTGGACCGACTAATGAATCCACTCATCGACCAATAC
TTGTACTATCTCTAGAACTATTAACGGTTCTGGACAGAATCAACAAACG
CTAAAATTCAGTGTGGCCGGACCCAGCAACATGGCTGTCCAGGGAAGAAAC
TACATACCTGGACCCAGCTACCGACAACAACGTGTCTCAACCACTGTGACT
CAAAACAACAACAGCGAATTTGCTTGGCCTGGAGCTTCTTCTTGGGCTCTC
AATGGACGTAATAGCTTGATGAATCCTGGACCTGCTATGGCCAGCCACAAA
GAAGGAGAGGACCGTTTCTTTCCTTTGTCTGGATCTTTAATTTTTGGCAAA
CAAGGTACCGGCAGAGACAACGTGGATGCGGACAAGTCATGATAACCAACG
AAGAAGAAATTAAAACTACTAACCCGGTAGCAACGGAGTCCTATGGACAAG
TGGCCACAAACCACCAGAGTGCCCAAGGAGGGGGAGGATCAGGCGGTGGAG
GTAGTGGAGGAGGCGGGAGCCATCACCACCACCATCACATGGCCCCAAAGA
AGAAGCGGAAGGTCGGTATCCACGGAGTCCCAGCAGCCGACAAGAAGTACA
GCATCGGCCTGGACATCGGCACCAACTCTGTGGGCTGGGCCGTGATCACCG
ACGAGTACAAGGTGCCCAGCAAGAAATTCAAGGTGCTGGGCAACACCGACC
GGCACAGCATCAAGAAGAACCTGATCGGAGCCCTGCTGTTCGACAGCGGCG
AAACAGCCGAGGCCACCCGGCTGAAGAGAACCGCCAGAAGAAGATACACCA
GACGGAAGAACCGGATCTGCTATCTGCAAGAGATCTTCAGCAACGAGATGG
CCAAGGTGGACGACAGCTTCTTCCACAGACTGGAAGAGTCCTTCCTGGTGG
AAGAGGATAAGAAGCACGAGCGGCACCCCATCTTCGGCAACATCGTGGACG
AGGTGGCCTACCACGAGAAGTAGCCCACCATCTACCACCTGAGAAAGAAAC
TGGTGGACAGCACCGACAAGGCCGACCTGCGGCTGATCTATCTGGCCCTGG
CCCACATGATCAAGTTCCGGGGCCACTTCCTGATCGAGGGCGACCTGAACC
CCGACAACAGCGACGTGGACAAGCTGTTCATCCAGCTGGTGCAGACCTACA
ACCAGCTGTTCGAGGAAAACCCCATCAACGCCAGCGGCGTGGACGCCAAGG
CCATCCTGTCTGCCAGACTGAGCAAGAGCAGACGGCTGGAAAATCTGATCG
CCCAGCTGCCCGGCGAGAAGAAGAATGGCCTGTTCGGAAACCTGATTGCCC
TGAGCCTGGGCCTGACCCCCAACTTCAAGAGCAACTTCGACCTGGCCGAGG
ATGCCAAACTGCAGCTGAGCAAGGACACCTACGACGACGACCTGGACAAGC
TGCTGGCCCAGATCGGCGACCAGTACGCCGACCTGTTTCTGGCCGCCAAGA
ACCTGTCCGACGCCATCCTGCTGAGCGACATCCTGAGAGTGAACACCGAGA
TCACCAAGGCCCCCCTGAGCGCCTCTATGATCAAGAGATACGACGAGCACC
ACCAGGACCTGACCCTGCTGAAAGCTCTCGTGCGGCAGCAGCTGCCTGAGA
AGTACAAAGAGATTTTCTTCGACCAGAGCAAGAACGGCTACGCCGGCTACA
TTGACGGCGGAGCCAGCCAGGAAGAGTTCTACAAGTTCATCAAGCCCATCC
TGGAAAAGATGGACGGCACCGAGGAACTGCTCGTGAAGCTGAACAGAGAGG
ACCTGCTGCGGAAGCAGCGGACCTTCGACAACGGCAGCATCCCCCACCAGA
TCCACCTGGGAGAGCTGCACGCCATTCTGCGGCGGCAGGAAGATTTTTACC
CATTCCTGAAGGACAACCGGGAAAAGATCGAGAAGATCCTGACCTTCCGCA
TCCCCTACTACGTGGGCCCTCTGGCCAGGGGAAACAGCAGATTCGCCTGGA
TGACCAGAAAGAGCGAGGAAACCATCACCCCCTGGAACTTCGAGGAAGTGG
TGGACAAGGGCGCTTCCGCCCAGAGCTTCATCGAGCGGATGACCAACTTCG
ATAAGAACCTGCCCAACGAGAAGGTGCTGCCCAAGCACAGCCTGCTGTACG
AGTACTTCACCGTGTATAACGAGCTGACCAAAGTGAAATACGTGACCGAGG
GAATGAGAAAGCCCGCCTTCCTGAGCGGCGAGCAGAAAAAGGCCATCGTGG
ACCTGCTGTTCAAGACCAACCGGAAAGTGACCGTGAAGCAGCTGAAAGAGG
ACTACTTCAAGAAAATCGAGTGCTTCGACTCCGTGGAAATCTCCGGCGTGG
AAGATCGGTTCAACGCCTCCCTGGGCACATACCACGATCTGCTGAAAATTA
TCAAGGACAAGGACTTCCTGGACAATGAGGAAAACGAGGACATTCTGGAAG
ATATCGTGCTGACCCTGACACTGTTTGAGGACAGAGAGATGATCGAGGAAC
GGCTGAAAACCTATGCCCACCTGTTCGACGACAAAGTGATGAAGCAGCTGA
AGCGGCGGAGATACACCGGCTGGGGCAGGCTGAGCCGGAAGCTGATCAACG
GCATCCGGGACAAGCAGTCCGGCAAGACAATCCTGGATTTCCTGAAGTCCG
ACGGCTTCGCCAACAGAAACTTCATGCAGCTGATCCACGACGACAGCCTGA
CCTTTAAAGAGGACATCCAGAAAGCCCAGGTGTCCGGCCAGGGCGATAGCC
TGCACGAGCACATTGCCAATCTGGCCGGCAGCCCCGCCATTAAGAAGGGCA
TCCTGCAGACAGTGAAGGTGGTGGACGAGCTCGTGAAAGTGATGGGCCGGC
ACAAGCCCGAGAACATCGTGATCGAAATGGCCAGAGAGAACCAGACCACCC
AGAAGGGAGAGAAGAACAGCGGCGAGAGAATGAAGCGGATGGAAGAGGGCA
TCAAAGAGCTGGGCAGCCAGATCCTGAAAGAACACCCCGTGGAAAACACCC
AGCTGCAGAACGAGAAGCTGTACCTGTACTACCTGCAGAATGGGCGGGATA
TGTACGTGGACCAGGAACTGGACATCAACCGGCTGTCCGACTACGATGTGG
ACCATATCGTGCCTCAGAGCTTTCTGGCGGACGACTCCATCGACAACAAGG
TGCTGACCAGAAGCGACAAGAACCGGGGCAAGAGCGACAACGTGCCCTCCG
AAGAGGTCGTGAAGAAGATGAAGAACTACTGGCGGCAGCTGCTGAACGCCA
AGCTGATTACCCAGAGAAAGTTCGACAATCTGACCAAGGCCGAGAGAGGCG
GCCTGAGCGAACTGGATAAGGCCGGCTTCATCAAGAGACAGCTGGTGGAAA
CCCGGCAGATCACAAAGCACGTGGCACAGATCCTGGACTCCCGGATGAACA
CTAAGTACGACGAGAATGACAAGCTGATCCGGGAAGTGAAAGTGATCACCC
```

-continued

```
TGAAGTCCAAGCTGGTGTCCGATTTCCGGAAGGATTTCCAGTTTTACAAAG
TGCGCGAGATCAACAACTACCACCACGCCCACGACGCCTACCTGAACGCCG
TCGTGGGAACCGCCCTGATCAAAAAGTACCCTGCGCTGGAAAGCGAGTTCG
TGTACGGCGACTACAAGGTGTACGACGTGCGGAAGATGATCGCCAAGAGCG
AGCAGGAAATCGGCAAGGCTACCGCCAAGTACTTCTTCTACAGCAACATCA
TGAACTTTTTCAAGACCGAGATTACCCTGGCCAACGGCGAGATCCGGAAGG
CGCCTCTGATCGAGACAAACGGCGAAACCGGGGAGATCGTGTGGGATAAGG
GCCGGGATTTTGCCACCGTGCGGAAAGTGCTGAGCATGCCCCAAGTGAATA
TCGTGAAAAAGACCGAGGTGCAGACAGGCGGCTTCAGCAAAGAGTCTATCC
TGCCCAAGAGGAACAGCGATAAGCTGATCGCCAGAAAGAAGGACTGGGACC
CTAAGAAGTACGGCGGCTTCGACAGCCCCACCGTGGCCTATTCTGTGCTGG
TGGTGGCCAAAGTGGAAAAGGGCAAGTCCAAGAAACTCTAAGAGTGTGAAA
GAGCTGCTGGGGATCACCATCATGGAAAGAAGCAGCTTCGAGAAGAATCCC
TATCGACTTTCTGGAAGCCAAGGGCTACAAAGAAGTGAAAAAGGACCTGAT
CATCAAGCTGCCTAAGTACTCCCTGTTCGAGCTGGAAAACGGCCGGAAGAG
AATGCTGGCCTCTGCCGGCGAACTGCAGAAGGGAAACGAACTGGCCCTGCC
CTCCAAATATGTGAACTTCCTGTACCTGGCCAGCCACTATGAGAAGCTGAA
GGGCTCCCCCGAGGATAATGAGCAGAAACAGCTGTTTGTGGAACAGCACAA
GCACTACCTGGACGAGATCATCGAGCAGATCAGCGAGTTCTCCAAGAGAGT
GATCCTGGCCGACGCTAATCTGGACAAAGTGCTGTCCGCCTTACAACAAGC
ACCGGGATAAGCCCATCAGAGAGCAGGCCGAGAATATCATCCACCTGTTTA
CCCTGACCAATCTGGGAGCCCCTGCCGCCTTCAAGTACTTTGACACCACCA
TCGACCGGAAGAGGTACACCAGCACCAAAGAGGTGCTGGACGCCACCCTGA
TCCACCAGAGCATCACCGGCCTGTACGAGACACGGATCGACCTGTCTCAGC
TGGGAGGCGACAAAAGGCCGGCGGCCACGAAAAAGGCCGGCCAGGCAAAAA
AGAAAAAGGGAGGGGGAGGATCAGGCGGTGGAGGTAGTGGAGGAGGCGGGA
GCGCACAGGCGCAGACCGGTTGGGTTCAAAACCAAGGAATACTTCCGGGTA
TGGTTTGGCAGGACAGAGATGTGTACCTGCAAGGACCCATTTGGGCCAAAA
TTCCTCACACGGACGGCAACTTTCACCCTTCTCCGCTGATGGGAGGGTTTG
GAATGAAGCACCCGCCTCCTCAGATCCTCATCAAAAACACACCTGTACCTG
CGGATCCTCCAACGGCCTTCAACAAGGACAAGCTGAACTCTTTCATCACCC
AGTATTCTACTGGCCAAGTCAGCGTGGAGATCGAGTGGGAGCTGCAGAAGG
AAAACAGCAAGCGCTGGAACCCGGAGATCCAGTACACTTCCAACTATTACA
AGTCTAATAATGTTGAATTTGCTGTTAATACTGAAGGTGTATATAGTGAAC
CCCGCCCCATTGGCACCAGATACCTGACTCGTAATCGTAATTGCTTGTTA
ATCAATAAACCGTTTAATTCGTTTCAGTTGAACTTTGGTCTCTGCGAAGGG
CGAATTCGTTTAAACCTGCAGGACTAGAGGTCCTGTATTAGAGGTCACGTG
AGTGTTTTGCGACATTTTGCGACACCATGTGGTCACGCTGGGTATTTAAGC
CCGAGTGAGCACGCAGGGTCTCCATTTTGAAGCGGGAGGTTTGAACGCGCA
GCCGCCAAGCCGAATTCTGCAGATATCCATCACACTGGCGGCCGCTCGACT
AGAGCGGCCGCCACCGCGGTGGAGCTCCAGCTTTTGTTCCCTTTAGTGAGG
```

-continued

```
GTTAATTGCGCGCTTGGCGTAATCATGGTCATAGCTGTTTCCTGTGTGAAA
TTGTTATCCGCTCACAATTCCACACAACATACGAGCCGGAAGCATAAAGTG
TAAAGCCTGGGGTGCCTAATGAGTGAGCTAACTCACATTAATTGCGTTGCG
CTCACTGCCCGCTTTCCAGTCGGGAAACCTGTCGTGCCAGCTGCATTAATG
AATCGGCCAACGCGCGGGGAGAGGCGGTTTGCGTATTGGGCGCTCTTCCGC
TTCCTCGCTCACTGACTCGCTGCGCTCGGTCGTTCGGCTGCGGCGAGCGGT
ATCAGCTCACTCAAAGGCGGTAATACGGTTATCCACAGAATCAGGGGATAA
CGCAGGAAAGAACATGTGAGCAAAAGGCCAGCAAAAGGCCAGGAACCGTAA
AAAGGCCGCGTTGCTGGCGTTTTTCCATAGGCTCCGCCCCCCTGACGAGCA
TCACAAAAATCGACGCTCAAGTCAGAGGTGGCGAAACCCGACAGGACTATA
AAGATACCAGGCGTTTCCCCCTGGAAGCTCCCTCGTGCGCTCTCCTGTTCC
GACCCTGCCGCTTACCGGATACCTGTCCGCCTTTCTCCCTTCGGGAAGCGT
GGCGCTTTCTCATAGCTCACGCTGTAGGTATCTCAGTTCGGTGTAGGTCGT
TCGCTCCAAGCTGGGCTGTGTGCACGAACCCCCCGTTCAGCCCGACCGCTG
CGCCTTATCCGGTAACTATCGTCTTGAGTCCAACCCGGTAAGACACGACTT
ATCGCCACTGGCAGCAGCCACTGGTAACAGGATTAGCAGAGCGAGGTATGT
AGGCGGTGCTACAGAGTTCTTGAAGTGGTGGCCTAACTACGGCTACACTAG
AAGAACAGTATTTGGTATCTGCGCTCTGCTGAAGCCAGTTACCTTCGGAAA
AAGAGTTGGTAGCTCTTGATCCGGCAAACAAACCACCGCTGGTAGCGGTGG
TTTTTTTGTTTGCAAGCAGCAGATTACGCGCAGAAAAAAAGGATCTCAAGA
AGATCCTTTGATCTTTTCTACGGGGTCTGACGCTCAGTGGAACGAAAACTC
ACGTTAAGGGATTTTGGTCATGAGATTATCAAAAAGGATCTTCACCTAGAT
CCTTTTAAATTAAAAATGAAGTTTTAAATCAATCTAAAGTATATATGAGTA
AACTTGGTCTGACAGTTACCAATGCTTAATCAGTGAGGCACCTATCTCAGC
GATCTGTCTATTTCGTTCATCCATAGTTGCCTGACTCCCCGTCGTGTAGAT
AACTACGATACGGGAGGGCTTACCATCTGGCCCCAGTGCTGCAATGATACC
GCGAGACCCACGCTCACCGGCTCCAGATTTATCAGCAATAAACCAGCCAGC
CGGAAGGGCCGAGCGCAGAAGTGGTCCTGCAACTTTATCCGCCTCCATCCA
GTCTATTAATTGTTGCCGGGAAGCTAGAGTAAGTAGTTCGCCAGTTAATAG
TTTGCGCAACGTTGTTGCCATTGCTACAGGCATCGTGGTGTCACGCTCGTC
GTTTGGTATGGCTTCATTCAGCTCCGGTTCCCAACGATCAAGGCGAGTTAC
ATGATCCCCCATGTTGTGCAAAAAAGCGGTTAGCTCCTTCGGTCCTCCGAT
CGTTGTCAGAAGTAAGTTGGCCGCAGTGTTATCACTCATGGTTATGGCAGC
ACTGCATAATTCTCTTACTGTCATGCCATCCGTAAGATGCTTTTCTGTGAC
TGGTGAGTACTCAACCAACTTCATTCTGAGAATAGTGTATGCGGCGACCGA
GTTGCTCTTGCCCGGCGTCAATACGGGATAATACCGCGCCACATAGCAGAA
CTTTAAAAGTGCTCATCATTGGAAAACGTTCTTCGGGGCGAAAACTCTCAA
GGATCTTACCGCTGTTGAGATCCAGTTCGATGTAACCCACTCGTGCACCCA
ACTGATCTTCAGCATCTTTTACTTTCACCAGCGTTTCTGGGTGAGCAAAAA
CAGGAAGGCAAAATGCCGCAAAAAAGGGAATAAGGGCGACACGGAAATGTT
```

```
GAATACTCATACTCTTCCTTTTTCAATATTATTGAAGCATTTATCAGGGTT
ATTGTCTCATGAGCGGATACATATTTGAATGTATTTAGAAAAATAAACAAA
TAGGGGTTCCGCGCACATTTCCCCGAAAAGTGCCACCTAAATTGTAAGCGT
TAATATTTTGTTAAAATTCGCGTTAAATTTTTGTTAAATCAGCTCATTTTT
TAACCAATAGGCCGAAATCGGCAAAATCCCTTATAAATCAAAAGAATAGAC
CGAGATAGGGTTGAGTGTTGTTCCAGTTTGGAACAAGAGTCCACTATTAAA
GAACGTGGACTCCAACGTCAAAGGGCGAAAAACCGTCTATCAGGGCGATGG
CCCACTACGTGAACCATCACCCTAATCAAGTTTTTTGGGGTCGAGGTGCCG
TAAAGCACTAAATCGGAACCCTAAAGGGAGCCCCCGATTTAGAGCTTGACG
GGGAAAGCCGGCGAACGTGGCGAGAAAGGAAGGGAAGAAAGCGAAAGGAGC
GGGCGCTAGGGCGCTGGCAAGTGTAGCGGTCACGCTGCGCGTAACCACCAC
ACCCGCCGCGCTTAATGCGCCGCTACAGGGCGCGTCCCATTCGCCATTCAG
GCTGCGCAACTGTTGGGAAGGGCGATCGGTGCGGGCCTCTTCGCTATTACG
CCAGCTGGCGAAAGGGGGATGTGCTGCAAGGCGATTAAGTTGGGTAACGCC
AGGGTTTTCCCAGTCACGACGTTGTAAAACGACGGCCAGTGAGCGCGCGTA
ATACGACTCACTATAGGGCGAATTGGGTACCGGGCCCCCCCTCGATCGAG
Construct_B encodes AAV9 capsid:
ATGGCGGGGTTTTACGAGATTGTGATTAAGGTCCCCAGCGACCTTGACGAG
CATCTGCCCGGCATTTCTGACAGCTTTGTGAACTGGGTGGCCGAGAAGGAA
TGGGAGTTGCCGCCAGATTCTGACATGGATCTGAATCTGATTGAGCAGGCA
CCCCTGACCGTGGCCGAGAAGCTGCAGCGCGACTTTCTGACGGAATGGCGC
CGTGTGAGTAAGGCCCCGGAGGCTCTTTTCTTTGTGCAATTTGAGAAGGGA
GAGAGCTACTTCCACATGCACGTGCTCGTGGAAACCACCGGGGTGAAATCC
ATGGTTTTGGGACGTTTCCTGAGTCAGATTCGCGAAAAACTGATTCAGAGA
ATTTACCGCGGGATCGAGCCGACTTTGCCAAACTGGTTCGCGGTCACAAAG
ACCAGAAATGGCGCCGGAGGCGGGAACAAGGTGGTGGATGAGTGCTACATC
CCCAATTACTTGCTCCCCAAAACCCAGCCTGAGCTCAGTGGGCGTGGACT
AATATGGAACAGTATTTAAGCGCCTGTTTGAATCTCACGGAGCGTAAACGG
TTGGTGGCGCAGCATCTGACGCACGTGTCGCAGACGCAGGAGCAGAACAAA
GAGAATCAGAATCCCAATTCTGATGCGCCGGTGATCAGATCAAAAACTTCA
GCCAGGTACATGGAGCTGGTCGGGTGGCTCGTGGACAAGGGGATTACCTCG
GAGAAGCAGTGGATCCAGGAGGACCAGGCCTCATACATCTCCTTCAATGCG
GCCTCCAACTCGCGGTCCCAAATCAAGGCTGCCTTGGACAATGCGGGAAAG
ATTATGAGCCTGACTAAAACCGCCCCCGACTACCTGGTGGGCCAGCAGCCC
GTGGAGGACATTTCCAGCAATCGGATTTATAAAATTTTGGAACTAAACGGG
TACGATCCCCAATATGCGGCTTCCGTCTTTCTGGGATGGGCCACGAAAAAG
TTCGGCAAGAGGAACACCATCTGGCTGTTTGGGCCTGCAACTACCGGGAAG
ACCAACATCGCGGAGGCCATAGCCCACACTGTGCCGTTCTACGGGTGCGTA
AACTGGACCAATGAGAACTTTCCCTTCAACGACTGTGTCGACAAGATGGTG
ATCTGGTGGGAGGAGGGGAAGATGACCGCCAAGGTCGTGGAGTCGGCCAAA
GCCATTCTCGGAGGAAGCAAGGTGCGCGTGGACCAGAAATGCAAGTCCTCG
```
```
GCCCAGATAGACCCGACTCCCGTGATCGTCACCTCCAACACCAACATGTGC
GCCGTGATTGACGGGAACTCAACGACCTTCGAACACCAGCAGCCGGTTGCAA
GACCGGATGTTCAAATTTGAACTCACCCGCCGTCTGGATCATGACTTTGGG
AAGGTCACCAAGCAGGAAGTCAAAGACTTTTTCCGGTGGGCAAAGGATCAC
GTGGTTGAGGTGGAGCATGAATTCTACGTCAAAAAGGGTGGAGCCAAGAAA
AGACCCGCCCCCAGTGACGCAGATATAAGTGAGCCCAAACGGGTGCGCGAG
TCAGTTGCGCAGCCATCGACGTCAGACGCGGAAGCTTCGATCAACTACGCG
GACAGGTACCAAAACAAATGTTCTCGTCACGTGGGCATGAATCTGATGCTG
TTTCCCTGCAGACAATGCGAGAGACTGAATCAGAATTCAAATATCTGCTTC
ACTCACGGTGTCAAAGACTGTTTAGAGTGCTTTCCCGTGTCAGAATCTCAA
CCCGTTTCTGTCGTCAAAAAGGCGTATCAGAAACTGTGCTACATTCATCAC
ATCATGGGAAAGGTGCCAGACGCTTGCACTGCTTGCGACCTGGTCAATGTG
GACTTGGATGACTGTGTTTCTGAACAATAAATGACTTAAACCAGGTATGAG
TCGGCTGGATAAATCTAAAGTCATAAACGGCGCTCTGGAATTACTCAATGA
AGTCGGTATCGAAGGCCTGACGACAAGGAAACTCGCTCAAAAGCTGGGAGT
TGAGCAGCCTACCCTGTACTGGCACGTGAAGAACAAGCGGGCCCTGCTCGA
TGCCGTGGCCATCGAGATGCTGGACAGGCATCATACCCACTTCTGCCCCCT
GGAAGGCGAGTCATGGCAAGACTTTCTGCGGAACAACGCCAAGTCATTCCG
CTGTGCTCTCCTCTCACATCGCGACGGGGCTAAAGTGCATCTCGGCACCCG
CCCAACAGAGAAACAGTACGAAACCCTGGAAAATCAGCTCGCGTTCCTGTG
TCAGCAAGGCTTCTCCCTGGAGAACGCACTGTACGCTCTGTCCGCCGTGGG
CCACTTTACACTGGGCTGCGTATTGGAGGAACAGGAGCATCAAGTAGCAAA
AGAGGAAAGAGAGACACCTACCACCGATTCTATGCCCCCACTTCTGAGACA
AGCAATTGAGCTGTTCGACCGGCAGGGAGCCGAACCTGCCTTCCTTTTCGG
CCTGGAACTAATCATATGTGGCCTGGAGAAACAGCTAAAGTGCGAAAGCGG
CGGGCCGGCCGACGCCCTTGACGATTTTGACTTAGACATGCTCCCAGCCGA
TGCCCTTGACGACTTTGACCTTGATATGCTGCCTGCTGACGCTCTTGACGA
TTTTGACCTTGACATGCTCCCCGGGTAAATGCATGAATTCGATCTAGAGGG
CCCTATTCTATAGTGTCACCTAAATGCTAGAGCTCGCTGATCAGCCTCGAC
TGTGCCTTCTAGTTGCCAGCCATCTGTTGTTTGCCCCTCCCCCGTGCCTTC
CTTGACCCTGGAAGGTGCCACTCCCACTGTCCTTTCCTAATAAAATGAGGA
AATTGCATCGCATTGTCTGAGTAGGTGTCATTCTATTCTGGGGGGTGGGGT
GGGGCAGGACAGCAAGGGGGAGGATTGGGAAGACAATAGCAGGCATGCTGG
GGATGCGGTGGGCTCTATGGCTTCTGAGGCGGAAAGAACCAGCTGGGGCTC
GAATCAAGCTATCAAGTGCCACCTGACGAAGGTACGTCTAGAACGTCTCCC
TATCAGTGATAGAGAAGTCGACACGTCTCGAGCTCCCTATCAGTGATAGAG
AAGGTACGTCTAGAACGTCTCCCTATCAGTGATAGAGAAGTCGACACGTCT
CGAGCTCCCTATCAGTGATAGAGAAGGTACGTCTAGAACGTCTCCCTATCA
GTGATAGAGAAGTCGACACGTCTCGAGCTCCCTATCAGTGATAGAGAAGGT
ACCCCCTATATAAGCAGAGAGATCTGTTCAAATTTGAACTGACTAAGCGGC
TCCCGCCAGATTTTGGCAAGATTACTAAGCAGGAAGTCAAGGACTTTTTTG
```

CTTGGGCAAAGGTCAATCAGGTGCCGGTGACTCACGAGTTTAAAGTTCCCA
GGGAATTGGCGGGAACTAAAGGGGCGGAGAAATCTCTAAAACGCCCACTGG
GTGACGTCACCAATACTAGCTATAAAAGTCTGGAGAAGCGGGCCAGGCTCT
CATTTGTTCCCGAGACGCCTCGCAGTTCAGACGTGACTGTTGATCCCGCTC
CTCTGCGACCGCTAGCTTCGATCAACTACGCGGACAGGTACCAAAACAAAT
GTTCTCGTCACGTGGGCATGAATCTGATGCTGTTTCCCTGCAGACAATGCG
AGAGACTGAATCAGAATTCAAATATCTGCTTCACTCACGGTGTCAAAGACT
GTTTAGAGTGCTTTCCCGTGTCAGAATCTCAACCCGTTTCTGTCGTCAAAA
AGGCGTATCAGAAACTGTGCTACATTCATCACATCATGGGAAAGGTGCCAG
ACGCTTGCACTGCTTGCGACCTGGTCAATGTGGACTTGGATGACTGTGTTT
CTGAACAATAAATGACTTAAACCAGGTATGGCTGCCGATGGTTATCTTCCA
GATTGGCTCGAGGACAACCTTAGTGAAGGAATTCGCGAGTGGTGGGCTTTG
AAACCTGGAGCCCCTCAACCCAAGGCAAATCAACAACATCAAGACAACGCT
CGAGGTCTTGTGCTTCCGGGTTACAAATACCTTGGACCCGGCAACGGACTC
GACAAGGGGAGCCGGTCAACGCAGCAGACGCGGCGGCCCTCGAGCACGAC
AAGGCCTACGACCAGCAGCTCAAGGCCGGAGACAACCCGTACGTCAAGTAC
AACCACGCCGACGCCGAGTTCCAGGAGCGGCTCAAAGAAGATACGTCTTTT
GGGGGCAACCTCGGGCGAGCAGTCTTCCAGGCCAAAAAGAGGCTTCTTGAA
CCTCTTGGTCTGGTTGAGGAAGCGGCTAAGACGGCTCCTGGAAAGAAGAGG
CCTGTAGAGCAGTCTCCTCAGGAACCGGACTCCTCCGCGGGTATTGGCAAA
TCGGGTGCACAGCCCGCTAAAAAGAGACTCAATTTCGGTCAGACTGGCGAC
ACAGAGTCAGTCCCAGACCCTCAACCAATCGGAGAACCTCCCGCAGCCCCC
TCAGGTGTGGGATCTCTTACAATGGCTTCAGGTGGTGGCGCACCAGTGGCA
GACAATAACGAAGGTGCCGATGGAGTGGGTAGTTCCTCGGGAAATTGGCAT
TGCGATTCCCAATGGCTGGGGACAGAGTCATCACCACCAGCACCCGAACC
TGGGCCCTGCCCACCTACAACAATCACCTCTACAAGCAAATCTCCAACAGC
ACATCTGGAGGATCTTCAAATGACAACGCCTACTTCGGCTACAGCACCCCC
TGGGGGTATTTTGACTTCAACAGATTCCACTGCCACTTCTCACCACGTGAC
TGGCAGCGACTCATCAACAACAACTGGGGATTCCGGCCTAAGCGACTCAAC
TTCAAGCTCTTCAACATTCAGGTCAAAGAGGTTACGGACAACAATGGAGTC
AAGACCATCGCCAATAACCTTACCAGCACGGTCCAGGTCTTCACGGACTCA
GACTATCAGCTCCCGTACGTGCTCGGGTCGGCTCACGAGGGCTGCCTCCCG
CCGTTCCCAGCGGACGTTTTCATGATTCCTCAGTACGGGTATCTGACGCTT
AATGATGGAAGCCAGGCCGTGGGTCGTTCGTCCTTTTACTGCCTGGAATAT
TTCCCGTCGCAAATGCTAAGAACGGGTAACAACTTCCAGTTCAGCTACGAG
TTTGAGAACGTACCTTTCCATAGCAGCTACGCTCACAGCCAAAGCCTGGAC
CGACTAATGAATCCACTCATCGACCAATACTTGTACTATCTCTCAAAGACT
ATTAACGGTTCTGGACAGAATCAACAAACGCTAAAATTCAGTGTGGCCGGA
CCCAGCAACATGGCTGTCCAGGGAAGAAACTACATACCTGGACCCAGCTAC
CGACAACAACGTGTCTCAACCACTGTGACTCAAAACAACAACAGCGAATTT

GCTTGGCCTGGAGCTTCTTCTTGGGCTCTCAATGGACGTAATAGCTTGATG
AATCCTGGACCTGCTATGGCCAGCCACAAAGAAGGAGAGGACCGTTTCTTT
CCTTTGTCTGGATCTTTAATTTTTGGCAAACAAGGAACTGGAAGAGACAAC
GTGGATGCGGACAAACTCATGATAACCAACGAAGAAGAAATTAAAACTACT
AACCCGGTAGCAACGGAGTCCTATGGACAAGTGGCCACAAACCACCAGAGT
GCCCAAGCACAGGCGCAGACCGGCTGGGTTCAAAACCAAGGAATACTTCCG
GGTATGGTTTGGCAGGACAGAGATGTGTACCTGCAAGGACCCATTTGGGCC
AAAATTCCTCACACGGACGGCAACTTTCACCCTTCTCCGCTGATGGGAGGG
TTTGGAATGAAGCACCCGCCTCCTCAGATCCTCATCAAAAACACACCTGTA
CCTGCCGGATCCTCCAACGGCCTTCAACAAGGACAAGCTGAACTCTTTCATC
ACCCAGTATTCTACTGGCCAAGTCAGCGTGGAGATCGAGTGGGAGCTGCAG
AAGGAAAACAGCAAGCGCTGGAACCCGGAGATCCAGTACACTTCCAACTAT
TACAAGTCTAATAATGTTGAATTTGCTGTTAATACTGAAGGTGTATATAGT
GAACCCCGCCCCATTGGCACCAGATACCTGACTCGTAATCTGTAATTGCTT
GTTAATCAATAAACCGTTTAATTCGTTTCAGTTGAACTTTGGTCTCTGCGA
AGGGCGAATTCGTTTAAACCTGCAGGACTAGAGGTCCTGTATTAGAGGTCA
CGTGAGTGTTTTGCGACATTTTGCGACACCATGTGGTCACGCTGGGTATTT
AAGCCCGAGTGAGCACGCAGGGTCTCCATTTTGAAGCGGGAGGTTTGAACG
CGCAGCCGCCAAGCCGAATTCTGCAGATATCCATCACACTGGCGGCCGCTC
GACTAGAGCGGCCGCCACCGCGGTGGAGCTCCAGCTTTTGTTCCCTTTAGT
GAGGGTTAATTGCGCGCTTGGCGTAATCATGGTCATAGCTGTTTCCTGTGT
GAAATTGTTATCCGCTCACAATTCCACACAACATACGAGCCGGAAGCATAA
AGTGTAAAGCCTGGGGTGCCTAATGAGTGAGCTAACTCACATTAATTGCGT
TGCGCTCACTGCCCGCTTTCCAGTCGGGAAACCTGTCGTGCCAGCTGCATT
AATGAATCGGCCAACGCGCGGGGAGAGGCGGTTTGCGTATTGGGCGCTCTT
CCGCTTCCTCGCTCACTGACTCGCTGCGCTCGGTCGTTCGGCTGCGGCGAG
CGGTATCAGCTCACTCAAAGGCGGTAATACGGTTATCCACAGAATCAGGGG
ATAACGCAGGAAAGAACATGTGAGCAAAAGGCCAGCAAAAGGCCAGGAACC
GTAAAAAGGCCGCGTTGCTGGCGTTTTTCCATAGGCTCCGCCCCCCTGACG
AGCATCACAAAAATCGACGCTCAAGTCAGAGGTGGCGAAACCCGACAGGAC
TATAAAGATACCAGGCGTTTCCCCCTGGAAGCTCCCTCGTGCGCTCTCCTG
TTCCGACCCTGCCGCTTACCGGATACCTGTCCGCCTTTCTCCCTTCGGGAA
GCGTGGCGCTTTCTCATAGCTCACGCTGTAGGTATCTCAGTTCGGTGTAGG
TCGTTCGCTCCAAGCTGGGCTGTGTGCACGAACCCCCCGTTCAGCCCGACC
GCTGCGCCTTATCCGGTAACTATCGTCTTGAGTCCAACCCGGTAAGACACG
ACTTATCGCCACTGGCAGCAGCCACTGGTAACAGGATTAGCAGAGCGAGGT
ATGTAGGCGGTGCTACAGAGTTCTTGAAGTGGTGGCCTAACTACGGCTACA
CTAGAAGAACAGTATTTGGTATCTGCGCTCTGCTGAAGCCAGTTACCTTCG
GAAAAAGAGTTGGTAGCTCTTGATCCGGCAAACAAACCACCGCTGGTAGCG
GTGGTTTTTTTGTTTGCAAGCAGCAGATTACGCGCAGAAAAAAAGGATCTC
AAGAAGATCCTTTGATCTTTTCTACGGGGTCTGACGCTCAGTGGAACGAAA

```
ACTCACGTTAAGGGATTTTGGTCATGAGATTATCAAAAAGGATCTTCACCT

AGATCCTTTTAAATTAAAAATGAAGTTTTAAATCAATCTAAAGTATATATG

AGTAAACTTGGTCTGACAGTTACCAATGCTTAATCAGTGAGGCACCTATCT

CAGCGATCTGTCTATTTCGTTCATCCATAGTTGCCTGACTCCCCGTCGTGT

AGATAACTACGATACGGGTAGGGCTTACCATCTGGCCCCAGTGCTGCAATG

ATACCGCGAGACCCACGCTCACCGGCTCCAGATTTATCAGCAATAAACCAG

CCAGCCGGAAGGGCCGAGCGCAGAAGTGGTCCTGCAACTTTATCCGCCTCC

ATCCAGTCTATTAATTGTTGCCGGGAAGCTAGAGTAAGTAGTTCGCCAGTT

AATAGTTTGCGCAACGTTGTTGCCATTGCTACAGGCATCGTGGTGTCACGC

TCGTCGTTTGGTATGGCTTCATTCAGCTCCGGTTCCCAACGATCAAGGCGA

GTTACATGATCCCCATGTTGTGCAAAAAAGCGGTTAGCTCCTTCGGTCCT

CCGATCGTTGTCAGAAGTAAGTTGGCCGCAGTGTTATCACTCATGGTTATG

GCAGCACTGCATAATTCTCTTACTGTCATGCCATCCGTAAGATGCTTTTCT

GTGACTGGTGAGTACTCAACCAAGTCATTCTGAGAATAGTGTATGCGGCGA

CCGAGTTGCTCTTGCCCGCGTCAATACGGGATAATACCGCGCCACATAG

CAGAACTTTAAAAGTGCTCATCATTGGAAAACGTTCTTCGGGGCGAAACT

CTCAAGGATCTTACCGCTGTTGAGATCCAGTTCGATGTAACCCACTCGTGC

ACCCAACTGATCTTCAGCATCTTTTACTTTCACCAGCGTTTCTGGGTGAGC

AAAAACAGGAAGGCAAAATGCCGCAAAAAAGGGAATAAGGGCGACACGGAA

ATGTTGAATACTCATACTCTTCCTTTTTCAATATTATTGAAGCATTTATCA

GGGTTATTGTCTCATGAGCGGATACATATTTGAATGTATTTAGAAAAATAA
```

```
ACAAATAGGGGTTCCGCGCACATTTCCCCGAAAAGTGCCACCTAAATTGTA

AGCGTTAATATTTTGTTAAAATTCGCGTTAAATTTTTGTTAAATCAGCTCA

TTTTTTAACCAATAGGCCGAAATCGGCAAAATCCCTTATAAATCAAAAGAA

TAGACCGAGATAGGGTTGAGTGTTGTTCCAGTTTGGAACAAGAGTCCACTA

TTAAAGAACGTGGACTCCAACGTCAAAGGGCGAAAAACCGTCTATCAGGGC

GATGGCCCACTACGTGAACCATCACCCTAATCAAGTTTTTTGGGGTCGAGG

TGCCGTAAAGCACTAAATCGGAACCCTAAAGGGAGCCCCCGATTTAGAGCT

TGACGGGGAAAGCCGGCGAACGTGGCGAGAAAGGAAGGGAAGAAAGCGAAA

GGAGCGGGCGCTAGGGCGCTGGCAAGTGTAGCGGTCACGCTGCGCGTAACC

ACCACACCCGCCGCGCTTAATGCGCCGCTACAGGGCGCGTCCCATTCGCCA

TTCAGGCTGGGCAACTGTTGGGAAGGGCGATCGGTGCGGGCCTCTTCGCTA

TTACGCCAGCTGGCGAAAGGGGGATGTGCTGCAAGGCGATTAAGTTGGGTA

ACGCCAGGGTTTTCCCAGTCACGACGTTGTAAAACGACGGCCAGTGAGCGC

GCGTAATACGACTCACTATAGGGCGAATTGGGTACCGGGCCCCCCCTCGAT

CGAGGTCGACGGTATCGGGGGAGCTCGCAGGGTCTCCATTTTGAAGCGGGA

GGTTTGAACGCGCAGCCGCC
```

Example 4: Interior Cas9

Construct C encodes AAV9_VP3_loop3-eSpCas9). Construct D encodes AAV9-VP3. Various molar ratios of construct C and construct D were transfected in HEK293 cells, along with adenoviral helper plasmid pDF6 (Puresyn Inc.), and purified by iodixanol-based ultracentrifugation. CRE incorporation in ~1.4 g/cc iodixanol fractions was tested by western blotting for VP (AAV capsid proteins VP1-3) and CRE.

```
Construct_C:_tTA.iCAP.AAV9_only_VP3_loop3_eSpCas9
ATGCCGGGGTTTTACGAGATTGTGATTAAGGTCCCCAGCGACCTTGACGA

GCATCTGCCCGGCATTTCTGACAGCTTTGTGAACTGGGTGGCCGAGAAGGAATGGG

AGTTGCCGCCAGATTCTGACATGGATCTGAATCTGATTGAGCAGGCACCCCTGACCG

TGGCCGAGAAGCTGCAGCGCGACTTTCTGACGGAATGGCGCCGTGTGAGTAAGGCC

CCGGAGGCTCTTTTCTTTGTGCAATTTGAGAAGGGAGAGAGCTACTTCCACATGCAC

GTGCTCGTGGAAACCACCGGGGTGAAATCCATGGTTTTGGGACGTTTCCTGAGTCAG

ATTCGCGAAAAACTGATTCAGAGAATTTACCGCGGGATCGAGCCGACTTTGCCAAA

CTGGTTCGCGGTCACAAAGACCAGAAATGGCGCCGGAGGCGGGAACAAGGTGGTGG

ATGAGTGCTACATCCCCAATTACTTGCTCCCCAAAACCCAGCCTGAGCTCCAGTGGG

CGTGGACTAATATGGAACAGTATTTAAGCGCCTGTTTGAATCTCACGGAGCGTAAAC

GGTTGGTGGCGCAGCATCTGACGCACGTGTCGCAGACGCAGGAGCAGAACAAAGAG

AATCAGAATCCCAATTCTGATGCGCCGGTGATCAGATCAAAAACTTCAGCCAGGTAC

ATGGAGCTGGTCGGGTGGCTCGTGGACAAGGGGATTACCTCGGAGAAGCAGTGGAT

CCAGGAGGACCAGGCCTCATACATCTCCTTCAATGCGGCCTCCAACTCGCGGTCCCA

AATCAAGGCTGCCTTGGACAATGCGGGAAAGATTATGAGCCTGACTAAAACCGCCC

CCGACTACCTGGTGGGCCAGCAGCCCGTGGAGGACATTTCCAGCAATCGGATTTATA

AAATTTTGGAACTAAACGGGTACGATCCCCAATATGCGGCTTCCGTCTTTCTGGGAT
```

-continued

```
GGGCCACGAAAAAGTTCGGCAAGAGGAACACCATCTGGCTGTTTGGGCCTGCAACT

ACCGGGAAGACCAACATCGCGGAGGCCATAGCCCACACTGTGCCCTTCTACGGGTG

CGTAAACTGGACCAATGAGAACTTTCCCTTCAACGACTGTGTCGACAAGATGGTGAT

CTGGTGGGAGGAGGGGAAGATGACCGCCAAGGTCGTGGAGTCGGCCAAAGCCATTC

TCGGAGGAAGCAAGGTGCGCGTGGACCAGAAATGCAAGTCCTCGGCCCAGATAGAC

CCGACTCCCGTGATCGTCACCTCCAACACCAACATGTGCGCCGTGATTGACGGGAAC

TCAACGACCTTCGAACACCAGCAGCCGTTGCAAGACCGGATGTTCAAATTTGAACTC

ACCCGCCGTCTGGATCATGACTTTGGGAAGGTCACCAAGCAGGAAGTCAAAGACTT

TTTCCGGTGGGCAAAGGATCACGTGGTTGAGGTGGAGCATGAATTCTACGTCAAAA

AGGGTGGAGCCAAGAAAAGACCCGCCCCCAGTGACGCAGATATAAGTGAGCCCAA

ACGGGTGCGCGAGTCAGTTGCGCAGCCATCGACGTCAGACGCGGAAGCTTCGATCA

ACTACGCGGACAGGTACCAAAACAAATGTTCTCGTCACGTGGGCATGAATCTGATG

CTGTTTCCCTGCAGACAATGCGAGAGACTGAATCAGAATTCAAATATCTGCTTCACT

CACGGTGTCAAAGACTGTTTAGAGTGCTTTCCCGTGTCAGAATCTCAACCCGTTTCT

GTCGTCAAAAAGGCGTATCAGAAACTGTGCTACATTCATCACATCATGGGAAAGGT

GCCAGACGCTTGCACTGCTTGCGACCTGGTCAATGTGGACTTGGATGACTGTGTTTC

TGAACAATAAATGACTTAAACCAGGTATGAGTCGGCTGGATAAATCTAAAGTCATA

AACGGCGCTCTGGAATTACTCAATGAAGTCGGTATCGAAGGCCTGACGACAAGGAA

ACTCGCTCAAAAGCTGGGAGTTGAGCAGCCTACCCTGTACTGGCACGTGAAGAACA

AGCGGGCCCTGCTCGATGCCCTGGCCATCGAGATGCTGGACAGGCATCATACCCACT

TCTGCCCCCTGGAAGGCGAGTCATGGCAAGACTTTCTGCGGAACAACGCCAAGTCA

TTCCGCTGTGCTCTCCTCTCACATCGCGACGGGCTAAAGTGCATCTCGGCACCCGC

CCAACAGAGAAACAGTACGAAACCCTGGAAAATCAGCTCGCGTTCCTGTGTCAGCA

AGGCTTCTCCCTGGAGAACGCACTGTACGCTCTGTCCGCCGTGGGCCACTTTACACT

GGGCTGCGTATTGGAGGAACAGGAGCATCAAGTAGCAAAAGAGGAAAGAGAGACA

CCTACCACCGATTCTATGCCCCCACTTCTGAGACAAGCAATTGACCTGTTCGACGGG

CAGGGAGCCGAACCTGCCTTCCTTTTCGGCCTGGAACTAATCATATGTGGCCTGGAG

AAACAGCTAAAGTGCGAAAGCGGCGGGCCGGCCGACGCCCTTGACGATTTTGACTT

AGACATGCTCCCAGCCGATGCCCTTGACGACTTTGACCTTGATATGCTGCCTGCTGA

CGCTCTTGACGATTTTGACCTTGACATGCTCCCCGGGTAAATGCATGAATTCGATCT

AGAGGGCCCTATTCTATAGTGTCACCTAAATGCTAGAGCTCGCTGATCAGCCTCGAC

TGTGCCTTCTAGTTGCCAGCCATCTGTTGTTTGCCCCTCCCCCGTGCCTTCCTTGACC

CTGGAAGGTGCCACTCCCACTGTCCTTTCCTAATAAAATGAGGAAATTGCATCGCAT

TGTCTGAGTAGGTGTCATTCTATTCTGGGGGGTGGGGTGGGCAGGACAGCAAGGG

GGAGGATTGGGAAGACAATAGCAGGCATGCTGGGGATGCGGTGGGCTCTATGGCTT

CTGAGGCGGAAAGAACCAGCTGGGGCTCGAATCAAGCTATCAAGTGCCACCTGACG

TCTCCCTATCAGTGATAGAGAAGTCGACACGTCTCGAGCTCCCTATCAGTGATAGAG

AAGGTACGTCTAGAACGTCTCCCTATCAGTGATAGAGAAGTCGACACGTCTCGAGCT

CCCTATCAGTGATAGAGAAGGTACGTCTAGAACGTCTCCCTATCAGTGATAGAGAA

GTCGACACGTCTCGAGCTCCCTATCAGTGATAGAGAAGGTACGTCTAGAACGTCTCC
```

-continued

```
CTATCAGTGATAGAGAAGTCGACACGTCTCGAGCTCCCTATCAGTGATAGAGAAGG

TACCCCCTATATAAGCAGAGAGATCTGTTCAAATTTGAACTGACTAAGCGGCTCCCG

CCAGATTTTGGCAAGATTACTAAGCAGGAAGTCAAGGACTTTTTTGCTTGGGCAAAG

GTCAATCAGGTGCCGGTGACTCACGAGTTTAAAGTTCCCAGGGAATTGGCGGGAAC

TAAAGGGGCGGAGAAATCTCTAAAACGCCCACTGGGTGACGTCACCAATACTAGCT

ATAAAAGTCTGGAGAAGCGGGCCAGGCTCTCATTTGTTCCCGAGACGCCTCGCAGTT

CAGACGTGACTGTTGATCCCGCTCCTCTGCGACCGCTAGCTTCGATCAACTACGCGG

ACAGGTACCAAAACAAATGTTCTCGTCACGTGGGCATGAATCTGATGCTGTTTCCCT

GCAGACAATGCGAGAGACTGAATCAGAATTCAAATATCTCCTTCACTCACGGTGTCA

AAGACTGTTTAGAGTGCTTTCCCGTGTCAGAATCTCAACCCGTTTCTGTCGTCAAAA

AGGCGTATCAGAAACTGTGCTACATTCATCACATCATGGGAAAGGTGCCAGACGCTT

GCACTGCTTGCGACCTGGTCAATGTGGACTTGGATGACTGTGTTTCTGAACAATAAA

TGACTTAAACCAGGTTTAGCTGCCGATGGTTATCTTCCAGATTGGCTCGAGGACAAC

CTTAGTGAAGGAATTCGCGAGTGGTGGGCTTTGAAACCTGGAGCCCCTCAACCCAA

GGCAAATCAACAACATCAAGACAACGCTCGAGGTCTTGTGCTTCCGGGTTACAAAT

ACCTTGGACCCGGCAACGGACTCGACAAGGGGGAGCCGGTCAACGCAGCAGACGC

GGCGGCCCTCGAGCACGACAAGGCCTACGACCAGCAGCTCAAGGCCGGAGACAACC

CGTACCTCAAGTACAACCACGCCGACGCCGAGTTCCAGGAGCGGCTCAAAGAAGAT

ACGTCTTTTGGGGGCAACCTCGGGCGAGCAGTCTTCCAGGCCAAAAAGAGGCTTCTT

GAACCTCTTGGTCTGGTTGAGGAAGCGGCTAAGGCCGCTCCTGGAAAGAAGAGGCC

TGTAGAGCAGTCTCCTCAGGAACCGGACTCCTCCGCGGGTATTGGCAAATCGGGTGC

ACAGCCCGCTAAAAAGAGACTCAATTTCGGTCAGACTGGCGACACAGAGTCAGTCC

CAGACCCTCAACCAATCGGAGAACCTCCCGCAGCCCCCTCAGGTGTGGGATCTCTTA

CAATGGCTTCAGGTGGTGGCGCACCAGTGGCAGACAATAACGAAGGTGCCGATGGA

GTGGGTAGTTCCTCGGGAAATTGGCATTGCGATTCCCAATGGCTGGGGACAGAGTC

ATCACCACCAGCACCCGAACCTGGGCCCTGCCCACCTACAACAATCACCTCTACAAG

CAAATCTCCAACAGCACATCTGGAGGATCTTCAAATGACAACGCCTACTTCGGCTAC

AGCACCCCCTGGGGGTATTTTGACTTCAACAGATTCCACTGCCACTTCTCACCACGT

GACTGGCAGCGACTCATCAACAACAACTGGGGATTCCGGCCTAAGCGACTCAACTT

CAAGCTCTTCAACATTCAGGTCAAAGAGGTTACGGACAACAATGGAGTCAAGACCA

TCGCCAATAACCTTACCAGCACGGTCCAGGTCTTCACGGACTCAGACTATCAGCTCC

CGTACGTGCTCGGGTCGGCTCACGAGGGCTGCCTCCCGCCGTTCCCAGCGGACGTTT

TCATGATTCCTCAGTACGGGTATCTGACGCTTAATGATGGAAGCCAGGCCGTGGGTC

GTTCGTCCTTTTACTGCCTGGAATATTTCCCGTCGCAAATGCTAAGAACGGGTAACA

ACTTCCAGTTCAGCTACGAGTTTGAGAACGTACCTTTCCATAGCAGCTACGCTCACA

GCCAAAGCCTGGACCGACTAATGAATCCACTCATCGACCAATACTTGTACTATCTCT

CAAAGACTATTAACGGTTCTGGACAGAATCAACAAACGCTAAAATTCAGTGTGGCC

GGACCCAGCAACATGGCTGTCCAGGGAAGAAACTACATACCTGGACCCAGCTACCG

ACAACAACGTGTCTCAACCACTGTGACTCAAAACAACAACAGCGAATTTGCTTGGC

CTGGAGCTTCTTCTTGGGCTCTCAATGGACGTAATAGCTTGATGAATCCTGGACCTG

CTATGGCCAGCCACAAAGAAGGAGAGGACCGTTTCTTTCCTTTGTCTGGATCTTTAA
```

-continued

```
TTTTTGGCAAACAAGGAACTGGAAGAGACAACGTGGATGCGGACAAAGTCATGATA

ACCAACGAAGAAGAAATTAAAACTACTAACCCGGTAGCAACGGAGTCCTATGGACA

AGTGGCCACAAACCACCAGAGTGCCCAAGCACAGGCGCAGACCGGCTGGGTTCAAA

ACCAAGGAATACTTCCGGGTATGGTTTGGCAGGACAGAGATGTGTACCTGCAAGGA

CCCATTTGGGCCAAAATTCCTCACACGGACGAGGGGGAGGATCAGGCGGTGGAGGT

AGTGGAGGAGGCGGGAGCCATCACCACCACCATCACATGGCCCCAAAGAAGAAGC

GGAAGGTCGGTATCCACGGAGTCCCAGCAGCCGACAAGAAGTACAGCATCGGCCTG

GACATCGGCACCAACTCTGTGGGCTGGGCCGTGATCACCGACGAGTACAAGGTGCC

CAGCAAGAAATTCAAGGTGCTGGGCAACACCGACCGGCACAGCATCAAGAAGAAC

CTGATCGGAGCCCTGCTGTTCGACAGCGGCGAAACAGCCGAGGCCACCCGGCTGAA

GAGAACCGCCAGAAGAAGATACACCAGACGGAAGAACCGGATCTGCTATCTGCAA

GAGATCTTCAGCAACGAGATGGCCAAGGTGGACGACAGCTTCTTCCACAGACTGGA

AGAGTCCTTCCTGGTGGAAGAGGATAAGAAGCACGAGCGGCACCCCATCTTCGGCA

ACATCGTGGACGAGGTGGCCTACCACGAGAAGTACCCCACCATCTACCACCTGAGA

AAGAAACTGGTGGACAGCACCGACAAGGCCGACCTGCGGCTGATCTATCTGGCCCT

GGCCCACATGATCAAGTTCCGGGGCCACTTCCTGATCGAGGGCGACCTGAACCCCG

ACAACAGCGACGTGGACAAGCTGTTCATCCAGCTGGTGCAGACCTACAACCAGCTG

TTCGAGGAAAACCCCATCAACGCCAGCGGCGTGGACGCCAAGGCCATCCTGTCTGC

CAGACTGAGCAAGAGCAGACGGCTGGAAAATCTGATCGCCCAGCTGCCCGGCGAGA

AGAAGAATGGCCTGTTCGGAAACCTGATTGCCCTGAGCCTGGGCCTGACCCCCAACT

TCAAGAGCAACTTCGACCTGGCCGAGGATGCCAAACTGCAGCTGAGCAAGGACACC

TACGACGACGACCTGGACAACCTGCTGGCCCAGATCGGCGACCAGTACGCCGACCT

GTTTCTGGCCGCCAAGAACCTGTCCGACGCCATCCTGCTGAGCGACATCCTGAGAGT

GAACACCGAGATCACCAAGGCCCCCCTGAGCGCCTCTATGATCAAGAGATACGACG

AGCACCACCAGGACCTGACCCTGCTGAAAGCTCTCGTGCGGCAGCAGCTGCCTGAG

AAGTACAAAGAGATTTTCTTCGACCAGAGCAAGAACGGCTACGCCGGCTACATTGA

CGGCGGAGCCAGCCAGGAAGAGTTCTACAAGTTCATCAAGCCCATCCTGGAAAAGA

TGGACGGCACCGAGGAACTGCTCGTGAAGCTGAACAGAGAGGACCTGCTGCGGAAG

CAGCGGACCTTCGACAACGGCAGCATCCCCCACCAGATCCACCTGGGAGAGCTGCA

CGCCATTCTGCGGCGGCAGGAAGATTTTTACCCATTCCTGAAGGACAACCGGGAAA

AGATCGAGAAGATCCTGACCTTCCGCATCCCCTACTACGTGGGCCCTCTGGCCAGGG

GAAACAGCAGATTCGCCTGGATGACCAGAAAGAGCGAGGAAACCATCACCCCCTGG

AACTTCGAGGAAGTGGTGGACAAGGGCGCTTCCGCCCAGAGCTTCATCGAGCGGAT

GACCAACTTCGATAAGAACCTGCCCAACGAGAAGGTGCTGCCCAAGCACAGCCTGC

TGTACGAGTACTTCACCGTGTATAACGAGCTGACCAAAGTGAAATACGTGACCGAG

GGAATGAGAAAGCCCGCCTTCCTGAGCGGCGAGCAGAAAAAGGCCATCGTGGACCT

GCTGTTCAAGACCAACCGGAAAGTGACCGTGAAGCAGCTGAAAGAGGACTACTTCA

AGAAAATCGAGTGCTTCGACTCCGTGGAAATCTCCGGCGTGGAAGATCGGTTCAAC

GCCTCCCTGGGCACATACCACGATCTGCTGAAAATTATCAAGGACAAGGACTTCCTG

GACAATGAGGAAAACGAGGACATTCTGGAAGATATCGTGCTGACCCTGACACTGTT
```

-continued

```
TGAGGACAGAGAGATGATCGAGGAACGGCTGAAAACCTATGCCCACCTGTTCGACG

ACAAAGTGATGAAGCAGCTGAAGCGGCGGAGATACACCGGCTGGGGCAGGCTGAG

CCGGAAGCTGATCAACGGCATCCGGGACAAGCAGTCCGGCAAGACAATCCTGGATT

TCCTGAAGTCCGACGGCTTCGCCAACAGAAACTTCATGCAGCTGATCCACGACGAC

AGCCTGACCTTTAAAGAGGACATCCAGAAAGCCCAGGTGTCCGGCCAGGGCGATAG

CCTGCACGAGCACATTGCCAATCTGGCCGGCAGCCCCGCCATTAAGAAGGGCATCC

TGCAGACAGTGAAGGTGGTGGACGAGCTCGTGAAAGTGATGGGCCGGCACAAGCCC

GAGAACATCGTGATCGAAATGGCCAGAGAGAACCAGACCACCCAGAAGGGACAGA

AGAACAGCCGCGAGAGAATGAAGCGGATCGAAGAGGGCATCAAAGAGCTGGGCAG

CCAGATCCTGAAAGAACACCCCGTGGAAAACACCCAGCTGCAGAACGAGAAGCTGT

ACCTGTACTACCTGCAGAATGGGCGGGATATGTACGTGGACCAGGAACTGGACATC

AACCGGCTGTCCGACTACGATGTGGACCATATCGTGCCTCAGAGCTTTCTGGCGGAC

GACTCCATCGACAACAAGGTGCTGACCAGAAGCGACAAGAACCGGGGCAAGAGCG

ACAACGTGCCCTCCGAAGAGGTCGTGAAGAAGATGAAGAACTACTGGCGGCAGCTG

CTGAACGCCAAGCTGATTACCCAGAGAAAGTTCGACAATCTGACCAAGGCCGAGAG

AGGCGGCCTGAGCGAACTGGATAAGGCCGGCTTCATCAAGAGACAGCTGGTGGAAA

CCCGGCAGATCACAAAGCACGTGGCACAGATCCTGGACTCCCGGATGAACACTAAG

TACGACGAGAATGACAAGCTGATCCGGGAAGTGAAAGTGATCACCCTGAAGTCCAA

GCTGGTGTCCGATTTCCGGAAGGATTTCCAGTTTTACAAAGTGCGCGAGATCAACAA

CTACCACCACGCCCACGACGCCTACCTGAACGCCGTCGTGGGAACCGCCCTGATCA

AAAAGTACCCTGCGCTGGAAAGCGAGTTCGTGTACGGCGACTACAAGGTGTACGAC

GTGCGGAAGATGATCGCCAAGAGCGAGCAGGAAATCGGCAAGGCTACCGCCAAGT

ACTTCTTCTACAGCAACATCATGAACTTTTTCAAGACCGAGATTACCCTGGCCAACG

GCGAGATCCGGAAGGCGCCTCTGATCGAGACAAACGGCGAAACCGGGGAGATCGT

GTGGGATAAGGGCCGGGATTTTGCCACCGTGCGGAAAGTGCTGAGCATGCCCCAAG

TGAATATCGTGAAAAAGACCGAGGTGCAGACAGGCGGCTTCAGCAAAGAGTCTATC

CTGCCCAAGAGGAACAGCGATAAGCTGATCGCCAGAAAGAAGGACTGGGACCCTA

AGAAGTACGGCGGCTTCGACAGCCCCACCGTGGCCTATTCTGTGCTGGTGGTGGCCA

AAGTGGAAAAGGGCAAGTCCAAGAAACTGAAGAGTGTGAAAGAGCTGCTGGGGAT

CACCATCATGGAAAGAAGCAGCTTCGAGAAGAATCCCATCGACTTTCTGGAAGCCA

AGGGCTACAAAGAAGTGAAAAAGGACCTGATCATCAAGCTGCCTAAGTACTCCCTG

TTCGAGCTGGAAAACGGCCGGAAGAGAATGCTGGCCTCTGCCGGCGAACTGCAGAA

GGGAAACGAACTGGCCCTGCCCTCCAAATATGTGAACTTCCTGTACCTGGCCAGCCA

CTATGAGAAGCTGAAGGGCTCCCCCGAGGATAATGAGCAGAAACAGCTGTTTGTGG

AACAGCACAAGCACTACCTGGACGAGATCATCGAGCAGATCAGCGAGTTCTCCAAG

AGAGTGATCCTGGCCGACGCTAATCTGGACAAAGTGCTGTCCGCCTACAACAAGCA

CCGGGATAAGCCCATCAGAGAGCAGGCCGAGAATATCATCCACCTGTTTACCCTGA

CCAATCTGGGAGCCCCTGCCGCCTTCAAGTACTTTGACACCACCATCGACCGGAAGA

GGTACACCAGCACCAAAGAGGTGCTGGACGCCACCCTGATCCACCAGAGCATCACC

GGCCTGTACGAGACACGGATCGACCTGTCTCAGCTGGGAGGCGACAAAAGGCCGGC

GGCCACGAAAAAGGCCGGCCAGGCAAAAAAGAAAAAGGGAGGGGGAGGATCAGG
```

-continued

```
CGGTGGAGGTAGTGGAGGAGGCGGGAAAAAGGCCGGCGGCCACGAAAAAGGCCGG
CCAGGCAAAAAGAAAAAGTACCCATACGATGTTCCAGATTACGCTGGAGGGGAG
GATCAGGCGGTGGAGGTAGTGGAGGAGGCGGGAGCGGCAACTTTCACCCTTCTCCG
CTGATGGGAGGGTTTGGAATGAAGCACCCGCCTCCTCAGATCCTCATCAAAAACAC
ACCTGTACCTGCGGATCCTCCAACGGCCTTCAACAAGGACAAGCTGAACTCTTTCAT
CACCCAGTATTCTACTGGCCAAGTCAGCGTGGAGATCGAGTGGGAGCTGCAGAAGG
AAAACAGCAAGCGCTGGAACCCGGAGATCCAGTACACTTCCAACTATTACAAGTCT
AATAATGTTGAATTTGCTGTTAATACTGAAGGTGTATATAGTGAACCCCGCCCCATT
GGCACCAGATACCTGACTCGTAATCTGTAATTGCTTGTTAATCAATAAACCGTTTAA
TTCGTTTCAGTTGAACTTTGGTCTCTGCGAAGGGCGAATTCGTTTAAACCTGCAGGA
CTAGAGGTCCTGTATTAGAGGTCACGTGAGTGTTTTGCGACATTTTGCGACACCATG
TGGTCACGCTGGGTATTTAAGCCCGAGTGAGCACGCAGGGTCTCCATTTTGAAGCGG
GAGGTTTGAACGCGCAGCCGCCAAGCCGAATTCTGCAGATATCCATCACACTGGCG
GCCGCTCGACTAGAGCGGCCGCCACCGCGGTGGAGCTCCAGCTTTTGTTCCCTTTAG
TGAGGGTTAATTGCGCGCTTGGCGTAATCATGGTCATAGCTGTTTCCTGTGTGAAAT
TGTTATCCGCTCACAATTCCACACAACATACGAGCCGGAAGCATAAAGTGTAAAGC
CTGGGGTGCCTAATGAGTGAGCTAACTCACATTAATTGCGTTGCGCTGACTGCCCGC
TTTCCAGTCGGGAAACCTGTCGTGCCAGCTGCATTAATGAATCGGCCAACGCGCGGG
GAGAGGCGGTTTGCGTATTGGGCGCTCTTCCGCTTCCTCGCTCACTGACTCGCTGCG
CTCGGTCGTTCGGCTGCGGCGAGCGGTATCAGCTCACTCAAAGGCGGTAATACGGTT
ATCCACAGAATCAGGGGATAACGCAGGAAAGAACATGTGAGCAAAAGGCCAGCAA
AAGGCCAGGAACCGTAAAAAGGCCGCGTTGCTGGCGTTTTTCCATAGGCTCCGCCCC
CCTGACGAGCATCACAAAAATCGACGCTCAAGTCAGAGGTGGCGAAACCCGACAGG
ACTATAAAGATACCAGGCGTTTCCCCCTGGAAGCTCCCTCGTGCGCTCTCCTGTTCC
GACCCTGCCGCTTACCGGATACCTGTCCGCCTTTCTCCCTTCGGGAAGCGTGGCGCT
TTCTCATAGCTCACGCTGTAGGTATCTCAGTTCGGTGTAGGTCGTTCGCTCCAAGCTG
GGCTGTGTGCACGAACCCCCCGTTCAGCCCGACCGCTGCGCCTTATCCGGTAACTAT
CGTCTTGAGTCCAACCCGGTAAGACACGACTTATCGCCACTGGCAGCAGCCACTGGT
AACAGGATTAGCAGAGCGAGGTATGTAGGCGGTGCTACAGAGTTCTTGAAGTGGTG
GCCTAACTACGGCTACACTAGAAGAACAGTATTTGGTATCTGCGCTCTGCTGAAGCC
AGTTACCTTCGGAAAAAGAGTTGGTAGCTCTTGATCCGGCAAACAAACCACCGCTG
GTAGCGGTGGTTTTTTTGTTTGCAAGCAGCAGATTACGCGCAGAAAAAAAGGATCTC
AAGAAGATCCTTTGATCTTTTCTACGGGGTCTGACGCTCAGTGGAACGAAAACTCAC
GTTAAGGGATTTTGGTCATGAGATTATCAAAAAGGATCTTCACCTAGATCCTTTTAA
ATTAAAAATGAAGTTTTAAATCAATCTAAAGTATATATGAGTAAACTTGGTCTGACA
GTTACCAATGCTTAATCAGTGAGGCACCTATCTCAGCGATCTGTCTATTTCGTTCATC
CATAGTTGCCTGACTCCCCGTCGTGTAGATAACTACGATACGGGAGGGCTTACCATC
TGGCCCCAGTGCTGCAATGATACCGCGAGACCCACGCTCACCGGCTCCAGATTTATC
AGCAATAAACCAGCCAGCCGGAAGGGCCGAGCGCAGAAGTGGTCCTGCAACTTTAT
CCGCCTCCATCCAGTCTATTAATTGTTGCCGGGAAGCTAGAGTAAGTAGTTCGCCAG
```

```
TTAATAGTTTGCGCAACGTTGTTGCCATTGCTACAGGCATCGTGGTGTCACGCTCGTC
GTTTGGTATGGCTTCATTCAGCTCCGGTTCCCAACGATCAAGGCGAGTTACATGATC
CCCCATGTTGTGCAAAAAAGCGGTTAGCTCCTTCGGTCCTCCGATCGTTGTCAGAAG
TAAGTTGGCCGCAGTGTTATCACTCATGGTTATGGCAGCACTGCATAATTCTCTTACT
GTCATGCCATCCGTAAGATGCTTTTCTGTGACTGGTGAGTACTCAACCAAGTCATTCT
GAGAATAGTGTATGCGGCGACCGAGTTGCTCTTGCCCGGCGTCAATACGGGATAAT
ACCGCGCCACATAGCAGAACTTTAAAAGTGCTCATCATTGGAAAACGTTCTTCGGGG
CGAAAACTCTCAAGGATCTTACCGCTGTTGAGATCCAGTTCGATGTAACCCACTCGT
GCACCCAACTGATCTTCAGCATCTTTTACTTTCACCAGCGTTTCTGGGTGAGCAAAA
ACAGGAAGGCAAAATGCCGCAAAAAAGGGAATAAGGGCGACACGGAAATGTTGAA
TACTCATACTCTTCCTTTTTCAATATTATTGAAGCATTTATCAGGGTTATTGTCTCATG
AGCGGATACATATTTGAATGTATTTAGAAAAATAAACAAATAGGGGTTCCGCGCAC
ATTTCCCCGAAAAGTGCCACCTAAATTGTAAGCGTTAATATTTTGTTAAAATTCGCG
TTAAATTTTTGTTAAATCAGCTCATTTTTTAACCAATAGGCCGAAATCGGCAAAATC
CCTTATAAATCAAAAGAATAGACCGAGATAGGGTTGAGTGTTGTTCCAGTTTGGAAC
AAGAGTCCACTATTAAAGAACGTGGACTCCAACGTCAAAGGGCGAAAAACCGTCTA
TCAGGGCGATGGCCCACTACGTGAACCATCACCCTAATCAAGTTTTTTGGGGTCGAG
GTGCCGTAAAGCACTAAATCGGAACCCTAAAGGGAGCCCCCGATTTAGAGCTTGAC
GGGGAAAGCCGGCGAACGTGGCGAGAAAGGAAGGGAAGAAAGCGAAAGGAGCGG
GCGCTAGGGCGCTGGCAAGTGTAGCGGTCACGCTGCGCGTAACCACCACACCCGCC
GCGCTTAATGCGCCGCTACAGGGCGCGTCCCATTCGCCATTCAGGCTGCGCAACTGT
TGGGAAGGGCGATCGGTGCGGGCCTCTTCGCTATTACGCCAGCTGGCGAAAGGGGG
ATGTGCTGCAAGGCGATTAAGTTGGGTAACGCCAGGGTTTTCCCAGTCACGACGTTG
TAAAACGACGGCCAGTGAGCGCGCGTAATACGACTCACTATAGGGCGAATTGGGTA
CCGGGCCCCCCCTCGATCGAGGTCGACGGTATCGGGGGAGCTCGCAGGGTCTCCATT
TTGAAGCGGGAGGTTTGAACGCGCAGCCGCC
>Construct_D:_tTA.iCAP.AAV9_only_VP3
ATGCCGGGGTTTTACGAGATTGTGATTAAGGTCCCCAGCGACCTTGACGAGCATCTG
CCCGGCATTTCTGACAGCTTTGTGAACTGGGTGGCCGAGAAGGAATGGGAGTTGCC
GCCAGATTCTGACATGGATCTGAATCTGATTGAGCAGGCACCCCTGACCGTGGCCGA
GAAGCTGCAGCGCGACTTTCTGACGGAATGGCGCCGTGTGAGTAAGGCCCCGGAGG
CTCTTTTCTTTGTGCAATTTGAGAAGGGAGAGAGCTACTTCCACATGCACGTGCTCG
TGGAAACCACCGGGGTGAAATCCATGGTTTTGGGACGTTTCCTGAGTCAGATTCGCG
AAAAACTGATTCAGAGAATTTACCGCGGGATCGAGCCGACTTTGCCAAACTGGTTCG
CGGTCACAAAGACCAGAAATGGCGCCGGAGGCGGGAACAAGGTGGTGGATGAGTG
CTACATCCCCAATTACTTGCTCCCCAAAACCCAGCCTGAGCTCCAGTGGGCGTGGAC
TAATATGGAACAGTATTTAAGCGCCTGTTTGAATCTCACGGAGCGTAAACGGTTGGT
GGCGCAGCATCTGACGCACGTGTCGCAGACGCAGGAGCAGAACAAAGAGAATCAG
AATCCCAATTCTGATGCGCCGGTGATCAGATCAAAAACTTCAGCCAGGTACATGGA
GCTGGTCGGGTGGCTCGTGGACAAGGGGATTACCTCGGAGAAGCAGTGGATCCAGG
AGGACCAGGCCTCATACATCTCCTTCAATGCGGCCTCCAACTCGCGGTCCCAAATCA
```

-continued
```
AGGCTGCCTTGGACAATGCGGGAAAGATTATGAGCCTGACTAAAACCGCCCCCGAC

TACCTGGTGGGCCAGCAGCCCGTGGAGGACATTTCCAGCAATCGGATTTATAAAATT

TTGGAACTAAACGGGTACGATCCCCAATATGCGGCTTCCGTCTTTCTGGGATGGGCC

ACGAAAAAGTTCGGCAAGAGGAACACCATCTGGCTGTTTGGGCCTGCAACTACCGG

GAAGACCAACATCGCGGAGGCCATAGCCCACACTGTGCCCTTCTACGGGTGCGTAA

ACTGGACCAATGAGAACTTTCCCTTCAACGACTGTGTCGACAAGATGGTGATCTGGT

GGGAGGAGGGGAAGATGACCGCCAAGGTCGTGGAGTCGGCCAAAGCCATTCTCGGA

GGAAGCAAGGTGCGCGTGGACCAGAAATGCAAGTCCTCGGCCCAGATAGACCCGAC

TCCCGTGATCGTCACCTCCAACACCAACATGTGCGCCGTGATTGACGGGAACTCAAC

GACCTTCGAACACCAGCAGCCGTTGCAAGACCGGATGTTCAAATTTGAACTCACCCG

CCGTCTGGATCATGACTTTGGGAAGGTCACCAAGCAGGAAGTCAAAGACTTTTTCCG

GTGGGCAAAGGATCACGTGGTTGAGGTGGAGCATGAATTCTACGTCAAAAAGGGTG

GAGCCAAGAAAAGACCCGCCCCCAGTGACGCAGATATAAGTGAGCCCAAACGGGT

GCGCGAGTCAGTTGCGCAGCCATCGACGTCAGACGCGGAAGCTTCGATCAACTACG

CGGACAGGTACCAAAACAAATGTTCTCGTCACGTGGGCATGAATCTGATGCTGTTTC

CCTGCAGACAATGCGAGAGACTGAATCAGAATTCAAATATCTGCTTCACTCACGGTG

TCAAAGACTGTTTAGAGTGCTTTCCCGTGTCAGAATCTCAACCCGTTTCTGTCGTCAA

AAAGGCGTATCAGAAACTGTGCTACATTCATCACATCATGGGAAAGGTGCCAGACG

CTTGCACTGCTTGCGACCTGGTCAATGTGGACTTGGATGACTGTGTTTCTGAACAAT

AAATGACTTAAACCAGGTATGAGTCGGCTGGATAAATCTAAAGTCATAAACGGCGC

TCTGGAATTACTCAATGAAGTCGGTATCGAAGGCCTGACGACAAGGAAACTCGCTC

AAAAGCTGGGAGTTGAGCAGCCTACCCTGTACTGGCACGTGAAGAACAAGCGGGCC

CTGCTCGATGCCCTGGCCATCGAGATGCTGGACAGGCATCATACCCACTTCTGCCCC

CTGGAAGGCGAGTCATGGCAAGACTTTCTGCGGAACAACGCCAAGTCATTCCGCTGT

GCTCTCCTCTCACATCGCGACGGGGCTAAAGTGCATCTCGGCACCCGCCCAACAGAG

AAACAGTACGAAACCCTGGAAAATCAGCTCGCGTTCCTGTGTCAGCAAGGCTTCTCC

CTGGAGAACGCACTGTACGCTCTGTCCGCCGTGGGCCACTTTACACTGGGCTGCGTA

TTGGAGGAACAGGAGCATCAAGTAGCAAAGAGGAAAGAGAGACACCTACCACCG

ATTCTATGCCCCCACTTCTGAGACAAGCAATTGAGCTGTTCGACCGGCAGGGAGCCG

AACCTGCCTTCCTTTTCGGCCTGGAACTAATCATATGTGGCCTGGAGAAACAGCTAA

AGTGCGAAAGCGGCGGGCCGGCCGACGCCCTTGACGATTTTGACTTAGACATGCTC

CCAGCCGATGCCCTTGACGACTTTGACCTTGATATGCTGCCTGCTGACGCTCTTGAC

GATTTTGACCTTGACATGCTCCCCGGGTAAATGCATGAATTCGATCTAGAGGGCCCT

ATTCTATAGTGTCACCTAAATGCTAGAGCTCGCTGATCAGCCTCGACTGTGCCTTCTA

GTTGCCAGCCATCTGTTGTTTGCCCCTCCCCCGTGCCTTCCTTGACCCTGGAAGGTGC

CACTCCCACTGTCCTTTCCTAATAAAATGAGGAAATTGCATCGCATTGTCTGAGTAG

GTGTCATTCTATTCTGGGGGGTGGGGTGGGGCAGGACAGCAAGGGGGAGGATTGGG

AAGACAATAGCAGGCATGCTGGGGATGCGGTGGGCTCTATGGCTTCTGAGGCGGAA

AGAACCAGCTGGGGCTCGAATCAAGCTATCAAGTGCCACCTGACGTCTCCCTATCAG

TGATAGAGAAGTCGACACGTCTCGAGCTCCCTATCAGTGATAGAAGGTACGTCT

AGAACGTCTCCCTATCAGTGATAGAGAAGTCGACACGTCTCGAGCTCCCTATCAGTG
```

```
ATAGAGAAGGTACGTCTAGAACGTCTCCCTATCAGTGATAGAGAAGTCGACACGTC

TCGAGCTCCCTATCAGTGATAGAGAAGGTACGTCTAGAACGTCTCCCTATCAGTGAT

AGAGAAGTCGACACGTCTCGAGCTCCCTATCAGTGATAGAGAAGGTACCCCCTATAT

AAGCAGAGAGATCTGTTCAAATTTGAACTGACTAAGCGGCTCCCGCCAGATTTTGGC

AAGATTACTAAGCAGGAAGTCAAGGACTTTTTTGCTTGGGCAAAGGTCAATCAGGT

GCCGGTGACTCACGAGTTTAAAGTTCCCAGGGAATTGGCGGGAACTAAAGGGGCGG

AGAAATCTCTAAAACGCCCACTGGGTGACGTCACCAATACTAGCTATAAAAGTCTG

GAGAAGCGGGCCAGGCTCTCATTTGTTCCCGAGACGCCTCGCAGTTCAGACGTGACT

GTTGATCCCGCTCCTCTGCGACCGCTAGCTTCGATCAACTACGCGGACAGGTACCAA

AACAAATGTTCTCGTCACGTGGGCATGAATCTGATGCTGTTTCCCTGCAGACAATGC

GAGAGACTGAATCAGAATTCAAATATCTGCTTCACTCACGGTGTCAAAGACTGTTTA

GAGTGCTTTCCCGTGTCAGAATCTCAACCCGTTTCTGTCGTCAAAAAGGCGTATCAG

AAACTGTGCTACATTCATCACATCATGGGAAAGGTGCCAGACGCTTGCACTGCTTGC

GACCTGGTCAATGTGGACTTGGATGACTGTGTTTCTGAACAATAAATGACTTAAACC

AGGTTTAGCTGCCGATGGTTATCTTCCAGATTGGCTCGAGGACAACCTTAGTGAAGG

AATTCGCGAGTGGTGGGCTTTGAAACCTGGAGCCCCTCAACCCAAGGCAAATCAAC

AACATCAAGACAACGCTCGAGGTCTTGTGCTTCCGGGTTACAAATACCTTGGACCCG

GCAACGGACTCGACAAGGGGGAGCCGGTCAACGCAGCAGACGCGGCGGCCCTCGA

GCACGACAAGGCCTACGACCAGCAGCTCAAGGCCGGAGACAACCCGTACCTGAAGT

ACAACCACGCCGACGCCGAGTTCCAGGAGCGGCTCAAAGAAGATACGTCTTTTGGG

GGCAACCTCGGGCGAGCAGTCTTGCAGGCCAAAAAGAGGCTTCTTGAACCTCTTGGT

CTGGTTGAGGAAGCGGCTAAGGCCGCTCCTGGAAAGAAGAGGCCTGTAGAGCAGTC

TCCTCAGGAACCGGACTCCTCCGCGGGTATTGGCAAATCGGGTGCACAGCCCGCTA

AAAAGAGACTCAATTTCGGTCAGACTGGCGACACAGAGTCAGTCCCAGACCCTCAA

CCAATCGGAGAACCTCCCGCAGCCCCCTCAGGTGTGGGATCTCTTACAATGGCTTCA

GGTGGTGGCGCACCAGTGGCAGACAATAACGAAGGTGCCGATGGAGTGGGTAGTTC

CTCGGGAAATTGGCATTGCGATTCCCAATGGCTGGGGACAGAGTCATCACCACCA

GCACCCGAACCTGGGCCCTGCCCACCTACAACAATCACCTCTACAAGCAAATCTCCA

ACAGCACATCTGGAGGATCTTCAAATGACAACGCCTACTTCGGCTACAGCACCCCCT

GGGGGTATTTTGACTTCAACAGATTCCACTGCCACTTCTCACCACGTGACTGGCAGC

GACTCATCAACAACAACTGGGGATTCCGGCCTAAGCGACTCAACTTCAAGCTCTTCA

ACATTCAGGTCAAAGAGGTTACGGACAACAATGGAGTCAAGACCATCGCCAATAAC

CTTACCAGCACGGTCCAGGTCTTCACGGACTCAGACTATCAGCTCCCGTACGTGCTC

GGGTCGGCTCACGAGGGCTGCCTCCCGCCGTTCCCAGCGGACGTTTTCATGATTCCT

CAGTACGGGTATCTGACGCTTAATGATGGAAGCCAGGCCGTGGGTCGTTCGTCCTTT

TACTGCCTGGAATATTTCCCGTCGCAAATGCTAAGAACGGGTAACAACTTCCAGTTC

AGCTACGAGTTTGAGAACGTACCTTTCCATAGCAGCTACGCTCACAGCCAAAGCCTG

GACCGACTAATGAATCCACTCATCGACCAATACTTGTACTATCTCTCAAAGACTATT

AACGGTTCTGGACAGAATCAACAAACGCTAAAATTCAGTGTGGCCGGACCCAGCAA

CATGGCTGTCCAGGGAAGAAACTACATACCTGGACCCAGCTACCGACAACAACGTG
```

-continued

```
TCTCAACCACTGTGACTCAAAACAACAACAGCGAATTTGCTTGGCCTGGAGCTTCTT

CTTGGGCTCTCAATGGACGTAATAGCTTGATGAATCCTGGACCTGCTATGGCCAGCC

ACAAAGAAGGAGAGGACCGTTTCTTTCCTTTGTCTGGATCTTTAATTTTTGGCAAAC

AAGGAACTGGAAGAGACAACGTGGATGCGGACAAAGTCATGATAACCAACGAAGA

AGAAATTAAAACTACTAACCCGGTAGCAACGGAGTCCTATGGACAAGTGGCCACAA

ACCACCAGAGTGCCCAAGCACAGGCGCAGACCGGCTGGGTTCAAAACCAAGGAATA

CTTCCGGGTATGGTTTGGCAGGACAGAGATGTGTACCTGCAAGGACCCATTTGGGCC

AAAATTCCTCACACGGACGGCAACTTTCACCCTTCTCCGCTGATGGGAGGGTTTGGA

ATGAAGCACCCGCCTCCTCAGATCCTCATCAAAAACACACCTGTACCTGCGGATCCT

CCAACGGCCTTCAACAAGGACAAGCTGAACTCTTTCATCACCCAGTATTCTACTGGC

CAAGTCAGCGTGGAGATCGAGTGGGAGCTGCAGAAGGAAAACAGCAAGCGCTGGA

ACCCGGAGATCCAGTACACTTCCAACTATTACAAGTCTAATAATGTTGAATTTGCTG

TTAATACTGAAGGTGTATATAGTGAACCCCGCCCCATTGGCACCAGATACCTGACTC

GTAATCTGTAATTGCTTGTTAATCAATAAACCGTTTAATTCGTTTCAGTTGAACTTTG

GTCTCTGCGAAGGGCGAATTCGTTTAAACCTGCAGGACTAGAGGTCCTGTATTAGAG

GTCACGTGAGTGTTTTGCGACATTTTGCGACACCATGTGGTCACGCTGGGTATTTAA

GCCCGAGTGAGCACGCAGGGTCTCCATTTTGAAGCGGGAGGTTTGAACGCGCAGCC

GCCAAGCCGAATTCTGCAGATATCCATCACACTGGCGGCCGCTCGACTAGAGCGGC

CGCCACCGCGGTGGAGCTCCAGCTTTTGTTCCCTTTAGTGAGGGTTAATTGCGCGCTT

GGCGTAATCATGGTCATAGCTGTTTCCTGTGTGAAATTGTTATCCGCTCACAATTCCA

CACAACATACGAGCCGGAAGCATAAAGTGTAAAGCCTGGGGTGCCTAATGAGTGAG

CTAACTCACATTAATTGCGTTGCGCTCACTGCCCGCTTTCCAGTCGGGAAACCTGTC

GTGCCAGCTGCATTAATGAATCGGCCAACGCGCGGGGAGAGGCGGTTTGCGTATTG

GGCGCTCTTCCGCTTCCTCGCTCACTGACTCGCTGCGCTCGGTCGTTCGGCTGCGGCG

AGCGGTATCAGCTCACTCAAAGGCGGTAATACGGTTATCCACAGAATCAGGGGATA

ACGCAGGAAAGAACATGTGAGCAAAAGGCCAGCAAAAGGCCAGGAACCGTAAAAA

GGCCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGCGT

TTCCCCCTGGAAGCTCCCTCGTGCGCTCTCCTGTTCCGACCCTGCCGCTTACCGGATA

CCTGTCCGCCTTTCTCCCTTCGGGAAGCGTGGCGCTTTCTCATAGCTCACGCTGTAGG

TATCTCAGTTCGGTGTAGGTCGTTCGCTCCAAGCTGGGCTGTGTGCACGAACCCCCC

GTTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGGGAG

GTATGTAGGCGGTGCTACAGAGTTCTTGAAGTGGTGGCCTAACTACGGCTACACTAG

AAGAACAGTATTTGGTATCTGCGCTCTGCTGAAGCCAGTTACCTTCGGAAAAAGAGT

TGGTAGCTCTTGATCCGGCAAACAAACCACCGCTGGTAGCGGTGGTTTTTTTGTTTG

CAAGCAGCAGATTACGCGCAGAAAAAAAGGATCTCAAGAAGATCCTTTGATCTTTT

GCGCGCGTAATACGACTCACTATAGGGCGAATTGGGTACCGGGCCCCCCCTCGATC

GAGGTCGACGGTATCGGGGGAGCTCGCAGGGTCTCCATTTTGAAGCGGGAGGTTTG

AACGCGCAGCCGCC
```

Example 5: Interior SunTag-GFP

Construct E encodes iCAP.AAV9_loop3_SunTag1x. Equal moles of construct E and construct D were transfected in HEK293 cells, along with plasmid containing scFv-sfGFP fusion (construct F, from Addgene), and adenoviral helper plasmid pDF6 (Puresyn Inc.), and purified by iodixanol-based ultracentrifugation. sfGFP incorporation in ~1.4 g/cc iodixanol fractions was tested by western blotting for VP (AAV capsid proteins VP1-3) and GFP.

```
>Construct_E:_tTA.iCAP.AAV9_loop3_SunTag1x
ATGCCGGGGTTTTACGAGATTGTGATTAAGGTCCCCAGCGACCTTGACGA
GCATCTGCCCGGCATTTCTGACAGCTTTGTGAACTGGGTGGCCGAGAAGGAATGGG
AGTTGCCGCCAGATTCTGACATGGATCTGAATCTGATTGAGCAGGCACCCCTGACCG
TGGCCGAGAAGCTGCAGCGCGACTTTCTGACGGAATGGCGCCGTGTGAGTAAGGCC
CCGGAGGCTCTTTTCTTTGTGCAATTTGAGAAGGGAGAGAGCTACTTCCACATGCAC
GTGCTCGTGGAAACCACCGGGGTGAAATCCATGGTTTTGGGACGTTTCCTGAGTCAG
ATTCGCGAAAAACTGATTCAGAGAATTTACCGCGGGATCGAGCCGACTTTGCCAAA
CTGGTTCGCGGTCACAAAGACCAGAAATGGCGCCGGAGGCGGGAACAAGGTGGTGG
ATGAGTGCTACATCCCCAATTACTTGCTCCCCAAAACCCAGCCTGAGCTCCAGTGGG
CGTGGACTAATATGGAACAGTATTTAAGCGCCTGTTTGAATCTCACGGAGCGTAAAC
GGTTGGTGGCGCAGCATCTGACGCACGTGTCGCAGACGCAGGAGCAGAACAAAGAG
AATCAGAATCCCAATTCTGATGCGCCGGTGATCAGATCAAAAACTTCAGCCAGGTAC
ATGGAGCTGGTCGGGTGGCTCGTGGACAAGGGGATTACCTCGGAGAAGCAGTGGAT
CCAGGAGGACCAGGCCTCATACATCTCCTTCAATGCGGCCTCCAACTCGCGGTCCCA
AATCAAGGCTGCCTTGGACAATGCGGGAAAGATTATGAGCCTGACTAAAACCGCCC
CCGACTACCTGGTGGGCCAGCAGCCCGTGGAGGACATTTCCAGCAATCGGATTTATA
AAATTTTGGAACTAAACGGGTACGATCCCCAATATGCGGCTTCCGTCTTTCTGGGAT
GGGCCACGAAAAAGTTCGGCAAGAGGAACACCATCTGGCTGTTTGGGCCTGCAACT
ACCGGGAAGACCAACATCGCGGAGGCCATAGCCCACACTGTGCCCTTCTACGGGTG
CGTAAACTGGACCAATGAGAACTTTCCCTTCAACGACTGTGTCGACAAGATGGTGAT
CTGGTGGGAGGAGGGGAAGATGACCGCCAAGGTCGTGGAGTCGGCCAAAGCCATTC
TCGGAGGAAGCAAGGTGCGCGTGGACCAGAAATGCAAGTCCTCGGCCCAGATAGAC
CCGACTCCCGTGATCGTCACCTCCAACACCAACATGTGCGCCGTGATTGACGGGAAC
TCAACGACCTTCGAACACCAGCAGCCGTTGCAAGACCGGATGTTCAAATTTGAACTC
ACCCGCCGTCTGGATCATGACTTTGGGAAGGTCACCAAGCAGGAAGTCAAAGACTT
TTTCCGGTGGGCAAAGGATCACGTGGTTGAGGTGGAGCATGAATTCTACGTCAAAA
AGGGTGGAGCCAAGAAAAGACCCGCCCCCAGTGACGCAGATATAAGTGAGCCCAA
ACGGGTGCGCGAGTCAGTTGCGCAGCCATCGACGTCAGACGCGGAAGCTTCGATCA
ACTACGCGGACAGGTACCAAAACAAATGTTCTCGTCACGTGGGCATGAATCTGATG
CTGTTTCCCTGCAGACAATGCGAGAGACTGAATCAGAATTCAAATATCTGCTTCACT
CACGGTGTCAAAGACTGTTTAGAGTGCTTTCCCGTGTCAGAATCTCAACCCGTTTCT
GTCGTCAAAAAGGCGTATCAGAAACTGTGCTACATTCATCACATCATGGGAAAGGT
GCCAGACGCTTGCACTGCTTGCGACCTGGTCAATGTGGACTTGGATGACTGTGTTTC
TGAACAATAAATGACTTAAACCAGGTATGAGTCGGCTGGATAAATCTAAAGTCATA
AACGGCGCTCTGGAATTACTCAATGAAGTCGGTATCGAAGGCCTGACGACAAGGAA
ACTCGCTCAAAAGCTGGGAGTTGAGCAGCCTACCCTGTACTGGCACGTGAAGAACA
AGCGGGCCCTGCTCGATGCCCTGGCCATCGAGATGCTGGACAGGCATCATACCCACT
```

-continued

```
TCTGCCCCCTGGAAGGCGAGTCATGGCAAGACTTTCTGCGGAACAACGCCAAGTCA
TTCCGCTGTGCTCTCCTCTCACATCGCGACGGGGCTAAAGTGCATCTCGGCACCCGC
CCAACAGAGAAACAGTACGAAACCCTGGAAAATCAGCTCGCGTTCCTGTGTCAGCA
AGGCTTCTCCCTGGAGAACGCACTGTACGCTCTGTCCGGCGTGGGCCACTTTACACT
GGGCTGCGTATTGGAGGAACAGGAGCATCAAGTAGCAAAAGAGGAAAGAGAGACA
CCTACCACCGATTCTATGCCCCCACTTCTGAGACAAGCAATTGAGCTGTTCGACCGG
CAGGGAGCCGAACCTGCCTTCCTTTTCGGCCTGGAACTAATCATATGTGGCCTGGAG
AAACAGCTAAAGTGCGAAAGCGGCGGGCCGGCCGACGCCCTTGACGATTTTGACTT
AGACATGCTCCCAGCCGATGCCCTTGACGACTTTGACCTTGATATGCTGCCTGCTGA
CGCTCTTGACGATTTTGACCTTGACATGCTCCCCGGGTAAATGCATGAATTCGATCT
AGAGGGCCCTATTCTATAGTGTCACCTAAATGCTAGAGCTCGCTGATCAGCCTCGAC
TGTGCCTTCTAGTTGCCAGCCATCTGTTGTTTGCCCCTCCCCCGTGCCTTCCTTGACC
CTGGAAGGTGCCACTCCCACTGTCCTTTCCTAATAAAATGAGGAAATTGCATCGCAT
TGTCTGAGTAGGTGTCATTCTATTCTGGGGGGTGGGGTGGGGCAGGACAGCAAGGG
GGAGGATTGGGAAGACAATAGCAGGCATGCTGGGGATGCGGTGGGCTCTATGGCTT
CTGAGGCGGAAAGAACCAGCTGGGGCTCGAATCAAGCTATCAAGTGCCACCTGACG
TCTCCCTATCAGTGATAGAGAAGTCGACACGTCTCGAGCTCCCTATCAGTGATAGAG
AAGGTACGTCTAGAACGTCTCCCTATCAGTGATAGAGAAGTCGACACGTCTCGAGCT
CCCTATCAGTGATAGAGAAGGTACGTCTAGAACGTCTCCCTATCAGTGATAGAGAA
GTCGACACGTCTCGAGCTCCCTATCAGTGATAGAGAAGGTACGTCTAGAACGTCTCC
CTATCAGTGATAGAGAAGTCGACACGTCTCGAGCTCCCTATCAGTGATAGAGAAGG
TACCCCCTATATAAGCAGAGAGATCTGTTCAAATTTGAACTGACTAAGCGGCTCCCG
CCAGATTTTGGCAAGATTACTAAGCAGGAAGTCAAGGACTTTTTTGCTTGGGCAAAG
GTCAATCAGGTGCCGGTGACTCACGAGTTTAAAGTTCCCAGGGAATTGGCGGGAAC
TAAAGGGGCGGAGAAATCTCTAAAACGCCCACTGGGTGACGTCACCAATACTAGCT
ATAAAAGTCTGGAGAAGCGGGCCAGGCTCTCATTTGTTCCCGAGACGCCTCGCAGTT
CAGACGTGACTGTTGATCCCGCTCCTCTGCGACCGCTAGCTTCGATCAACTACGCGG
ACAGGTACCAAAACAAATGTTCTCGTCACGTGGGCATGAATCTGATGCTGTTTCCCT
GCAGACAATGCGAGAGACTGAATCAGAATTCAAATATCTGCTTCACTCACGGTGTCA
AAGACTGTTTAGAGTGCTTTCCCGTGTCAGAATCTCAACCCGTTTCTGTCGTCAAAA
AGGCGTATCAGAAACTGTGCTACATTCATCACATCATGGGAAAGGTGCCAGACGCTT
GCACTGCTTGCGACCTGGTCAATGTGGACTTGGATGACTGTGTTTCTGAACAATAAA
TGACTTAAACCAGGTATGGCTGCCGATGGTTATCTTCCAGATTGGCTCGAGGACAAC
CTTAGTGAAGGAATTCGCGAGTGGTGGGCTTTGAAACCTGGAGCCCCTCAACCCAA
GGCAAATCAACAACATCAAGACAACGCTCGAGGTCTTGTGCTTCCGGGTTACAAAT
ACCTTGGACCCGGCAACGGACTCGACAAGGGGGAGCCGGTCAACGCAGCAGACGC
GGCGGCCCTCGAGCACGACAAGGCCTACGACCAGCAGCTCAAGGCCGGAGACAACC
CGTACCTCAAGTACAACCACGCCGACGCCGAGTTCCAGGAGCGGCTCAAAGAAGAT
ACGTCTTTTGGGGGCAACCTCGGGCGAGCAGTCTTCCAGGCCAAAAAGAGGCTTCTT
GAACCTCTTGGTCTGGTTGAGGAAGCGGCTAAGACGGCTCCTGGAAAGAAGAGGCC
```

-continued

```
TGTAGAGCAGTCTCCTCAGGAACCGGACTCCTCCGCGGGTATTGGCAAATCGGGTGC
ACAGCCCGCTAAAAAGAGACTCAATTTCGGTCAGACTGGCGACACAGAGTCAGTCC
CAGACCCTCAACCAATCGGAGAACCTCCCGCAGCCCCCTCAGGTGTGGGATCTCTTA
CAATGGCTTCAGGTGGTGGCGCACCAGTGGCAGACAATAACGAAGGTGCCGATGGA
GTGGGTAGTTCCTCGGGAAATTGGCATTGCGATTCCCAATGGCTGGGGACAGAGTC
ATCACCACCAGCACCCGAACCTGGGCCCTGCCCACCTACAACAATCACCTCTACAAG
CAAATCTCCAACAGCACATCTGGAGGATCTTCAAATGACAACGCCTACTTCGGCTAC
AGCACCCCCTGGGGGTATTTTGACTTCAACAGATTCCACTGCCACTTCTCACCACGT
GACTGGCAGCGACTCATCAACAACAACTGGGGATTCCGGCCTAAGCGACTCAACTT
CAAGCTCTTCAACATTCAGGTCAAAGAGGTTACGGACAACAATGGAGTCAAGACCA
TCGCCAATAACCTTACCAGCACGGTCCAGGTCTTCACGGACTCAGACTATCAGCTCC
CGTACGTGCTCGGGTCGGCTCACGAGGGCTGCCTCCCGCCGTTCCCAGCGGACGTTT
TCATGATTCCTCAGTACGGGTATCTGACGCTTAATGATGGAAGCCAGGCCGTGGGTC
GTTCGTCCTTTTACTGCCTGGAATATTTCCCGTCGCAAATGCTAAGAACGGGTAACA
ACTTCCAGTTCAGCTACGAGTTTGAGAACGTACCTTTCCATAGCAGCTACGCTCACA
GCCAAAGCCTGGACCGACTAATGAATCCACTCATCGACCAATACTTGTACTATCTCT
CAAAGACTATTAACGGTTCTGGACAGAATCAACAAACGCTAAAATTCAGTGTGGCC
GGACCCAGCAACATGGCTGTCCAGGGAAGAAACTACATACCTGGACCCAGCTACCG
ACAACAACGTGTCTCAACCACTGTGACTCAAAACAACAACAGCGAATTTGCTTGGC
CTGGAGCTTCTTCTTGGGCTCTCAATGGACGTAATAGCTTGATGAATCCTGGACCTG
CTATGGCCAGCCACAAAGAAGGAGAGGACCGTTTCTTTCCTTTGTCTGGATCTTTAA
TTTTTGGCAAACAAGGAACTGGAAGAGACAACGTGGATGCGGACAAAGTCATGATA
ACCAACGAAGAAGAAATTAAAACTACTAACCCGGTAGCAACGGAGTCCTATGGACA
AGTGGCCACAAACCACCAGAGTGCCCAAGCACAGGCGCAGACCGGCTGGGTfCAAA
ACCAAGGAATACTTCCGGGTATGGTTTGGCAGGACAGAGATGTGTACCTGCAAGGA
CCCATTTGGGCCAAAATTCCTCACACGGACGAAGAACTTTTGAGCAAGAATTATCAT
CTTGAGAACGAAGTGGCTCGTCTTAAGAAAGGTTCTGGCAGTGGAGGCAACTTTCAC
CCTTCTCCGCTGATGGGAGGGTTTGGAATGAAGCACCCGCCTCCTCAGATCCTCATC
AAAAACACACCTGTACCTGCGGATCCTCCAACGGCCTTCAACAAGGACAAGCTGAA
CTCTTTCATCACCCAGTATTCTACTGGCCAAGTCAGCGTGGAGATCGAGTGGGAGCT
GCAGAAGGAAAACAGCAAGCGCTGGAACCCGGAGATCCAGTACACTTCCAACTATT
ACAAGTCTAATAATGTTGAATTTGCTGTTAATACTGAAGGTGTATATAGTGAACCCC
GCCCCATTGGCACCAGATACCTGACTCGTAATCTGTAATTGCTTGTTAATCAATAAA
CCGTTTAATTCGTTTCAGTTGAACTTTGGTCTCTGCGAAGGGCGAATTCGTTTAAACC
TGCAGGACTAGAGGTCCTGTATTAGAGGTCACGTGAGTGTTTTGCGACATTTTGCGA
CACCATGTGGTCACGCTGGGTATTTAAGCCCGAGTGAGCACGCAGGGTCTCCATTTT
GAAGCGGGAGGTTTGAACGCGCAGCCGCCAAGCCGAATTCTGCAGATATCCATCAC
ACTGGCGGCCGCTCGACTAGAGCGGCCGCCACCGCGGTGGAGCTCCAGCTTTTGTTC
CCTTTAGTGAGGGTTAATTGCGCGCTTGGCGTAATCATGGTCATAGCTGTTTCCTGTG
TGAAATTGTTATCCGCTCACAATTCCACACAACATACGAGCCGGAAGCATAAAGTGT
AAAGCCTGGGGTGCCTAATGAGTGAGCTAACTCACATTAATTGCGTTGCGCTCAGTG
```

```
CCCGCTTTCCAGTCGGGAAACCTGTCGTGCCAGCTGCATTAATGAATCGGCCAACGC

GCGGGGAGAGGCGGTTTGCGTATTGGGCGCTCTTCCGCTTCCTCGCTCACTGACTCG

CTGCGCTCGGTCGTTCGGCTGCGGCGAGCGGTATCAGCTCACTCAAAGGCGGTAATA

CGGTTATCCACAGAATCAGGGGATAACGCAGGAAAGAACATGTGAGCAAAAGGCC

AGCAAAAGGCCAGGAACCGTAAAAAGGCCGCGTTGCTGGCGTTTTTCCATAGGCTC

CGCCCCCCTGACGAGCATCACAAAAATCGACGCTCAAGTCAGAGGTGGCGAAACCC

GACAGGACTATAAAGATACCAGGCGTTTCCCCCTGGAAGCTCCCTCGTGCGCTCTCC

TGTTCCGACCCTGCCGCTTACCGGATACCTGTCCGCCTTTCTCCCTTCGGGAAGCGTG

GCGCTTTCTCATAGCTCACGCTGTAGGTATCTCAGTTCGGTGTAGGTCGTTCGCTCCA

AGCTGGGCTGTGTGCACGAACCCCCCGTTCAGCCCGACCGCTGCGCCTTATCCGGTA

ACTATCGTCTTGAGTCCAACCCGGTAAGACACGACTTATCGCCACTGGCAGCAGCCA

CTGGTAACAGGATTAGCAGAGCGAGGTATGTAGGCGGTGCTACAGAGTTCTTGAAG

TGGTGGCCTAACTACGGCTACACTAGAAGAACAGTATTTGGTATCTGCGCTCTGCTG

AAGCCAGTTACCTTCGGAAAAAGAGTTGGTAGCTCTTGATCCGGCAAACAAACCAC

CGCTGGTAGCGGTGGTTTTTTGTTTGCAAGCAGCAGATTACGCGCAGAAAAAAAGG

ATCTCAAGAAGATCCTTTGATCTTTTCTACGGGGTCTGACGCTCAGTGGAACGAAAA

CTCACGTTAAGGGATTTTGGTCATGAGATTATCAAAAAGGATCTTCACCTAGATCCT

TTTAAATTAAAAATGAAGTTTTAAATCAATCTAAAGTATATATGAGTAAACTTGGTC

TGACAGTTACCAATGCTTAATCAGTGAGGCACCTATCTCAGCGATCTGTCTATTTCGT

TCATCCATAGTTGCCTGACTCCCCGTCGTGTAGATAACTACGATACGGGAGGGCTTA

CCATCTGGCCCCAGTGCTGCAATGATACCGCGAGACCCACGCTCACCGGCTCCAGAT

TTATCAGCAATAAACCAGCCAGCCGGAAGGGCCGAGCGCAGAAGTGGTCCTGCAAC

TTTATCCGCCTCCATCCAGTCTATTAATTGTTGCCGGGAAGCTAGAGTAAGTAGTTC

GCCAGTTAATAGTTTGCGCAACGTTGTTGCCATTGCTACAGGCATCGTGGTGTCACG

CTCGTCGTTTGGTATGGCTTCATTCAGCTCCGGTTCCCAACGATCAAGGCGAGTTAC

ATGATCCCCCATGTTGTGCAAAAAAGCGGTTAGCTCCTTCGGTCCTCCGATCGTTGT

CAGAAGTAAGTTGGCCGCAGTGTTATCACTCATGGTTATGGCAGCACTGCATAATTC

TCTTACTGTCATGCCATCCGTAAGATGCTTTTCTGTGACTGGTGAGTACTCAACCAAG

TCATTCTGAGAATAGTGTATGCGGCGACCGAGTTGCTCTTGCCCGGCGTCAATACGG

GATAATACCGCGCCACATAGCAGAACTTTAAAAGTGCTCATCATTGGAAAACGTTCT

TCGGGGCGAAAACTCTCAAGGATCTTACCGCTGTTGAGATCCAGTTCGATGTAACCC

ACTCGTGCACCCAACTGATCTTCAGCATCTTTTACTTTCACCAGCGTTTCTGGGTGAG

CAAAAACAGGAAGGCAAAATGCCGCAAAAAAGGGAATAAGGGCGACACGGAAATG

TTGAATACTCATACTCTTCCTTTTTCAATATTATTGAAGCATTTATCAGGGTTATTGT

CTCATGAGCGGATACATATTTGAATGTATTTAGAAAAATAAACAAATAGGGGTTCCG

CGCACATTTCCCCGAAAAGTGCCACCTAAATTGTAAGCGTTAATATTTTGTTAAAAT

TCGCGTTAAATTTTTGTTAAATCAGCTCATTTTTTAACCAATAGGCCGAAATCGGCA

AAATCCCTTATAAATCAAAAGAATAGACCGAGATAGGGTTGAGTGTTGTTCCAGTTT

GGAACAAGAGTCCACTATTAAAGAACGTGGACTCCAACGTCAAAGGGCGAAAAACC

GTCTATCAGGGCGATGGCCCACTACGTGAACCATCACCCTAATCAAGTTTTTTGGGG
```

```
-continued
TCGAGGTGCCGTAAAGCACTAAATCGGAACCCTAAAGGGAGCCCCCGATTTAGAGC

TTGACGGGGAAAGCCGGCGAACGTGGCGAGAAAGGAAGGGAAGAAAGCGAAAGGA

GCGGGCGCTAGGGCGCTGGCAAGTGTAGCGGTCACGCTGCGCGTAACCACCACACC

CGCCGCGCTTAATGCGCCGCTACAGGGCGCGTCCCATTCGCCATTCAGGCTGCGCAA

CTGTTGGGAAGGGCGATCGGTGCGGGCCTCTTCGCTATTACGCCAGCTGGCGAAAG

GGGGATGTGCTGCAAGGCGATTAAGTTGGGTAACGCCAGGGTTTTCCCAGTCACGA

CGTTGTAAAACGACGGCCAGTGAGCGCGCGTAATACGACTCACTATAGGGCGAATT

GGGTACCGGGCCCCCCCTCGATCGAGGTCGACGGTATCGGGGGAGCTCGCAGGGTC

TCCATTTTGAAGCGGGAGGTTTGAACGCGCAGCCGCC
```

Example 6: Determination of Particle Size Diameter for AAV/Lipid Nanocomplexes Diameter of the AAV/lipid nanocomplexes in diameter can be determined by imaging the complexes using Transmission Electron Microscopy (TEM). See FIGS. 4, 5, 6, 10.

Example 7: Administration of Luciferase AAV/Lipid Formulation and Detection of Luciferase in Tissues or Intact Mice Non-limiting examples of lipids useful in the invention are depicted in FIG. 17A. LUC AAV2 was mixed with 306-016B-3 lipid (FIG. 17A) in the amounts shown in the table below and administered by IV injection to Balb/C mice.

| Mouse Group | AAV number | Lipid mass (µg) |
|---|---|---|
| PBS | 0 | 0 |
| AAV only | $2.9 \times 10^{11}$ | 0 |
| 1 | $2.9 \times 10^{11}$ | 10 |
| 2 | $2.9 \times 10^{11}$ | 50 |
| 3 | $2.9 \times 10^{11}$ | 100 |

Mice were sacrificed 10 days after treatment. Organs were collected and tested with a Luciferase assay kit to quantify luciferase expression. Up to 15-fold increase in Luciferase expression was observed (FIG. 17B) with the greatest increase observed in heart and liver tissue.

Luciferase AAV2/lipid formulations were produced using lipids 306F, 80F, and 93F and administered to mice by IV injection. Luminance was measured at various time points up to 35 days after administration (FIG. 18A-B) and the time course of luciferase accumulation determined (FIG. 18C-E).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

---

What is claimed is:

1. A particle delivery system comprising a composite virus particle,
wherein the composite virus particle comprises a lipid, at least a portion of a virus capsid protein, and at least a portion of a non-capsid protein or peptide, wherein the composite virus particle is adsorbed to a liposome comprising a targeting moiety,
wherein the lipid is selected from EC16-63; 80-O14B; 80-O16B; 80-O18B; 87-O14B; 87-O16B; 87-O18B; 1-O18B; 80-O14; 80-O16; 80-O18; 87-O14; 87-O16; 87-O18; 1N16; 1-N18; 87-N17; 87-N16; 87-N18; EC 16-1; EC 16-3; EC16-12; EC16-14; and mixtures thereof.

2. The particle delivery system of claim 1, wherein the composite virus particle is adsorbed to a liposome by a hydrophobic interaction or an electrostatic interaction.

3. The particle delivery system of claim 2, wherein the liposome comprises:
a CRISPR system component; or
a CRISPR system component attached to the virus capsid protein.

4. A delivery system comprising one or more hybrid virus capsid proteins in combination with a lipid particle, wherein the one or more hybrid virus capsid proteins comprise at least a portion of a virus capsid protein attached to at least a portion of a non-capsid protein, wherein a virus particle is adsorbed to a liposome comprising a targeting moiety,
wherein the lipid particle is selected from: EC16-63; 80-O14B; 80-O16B; 80-O18B; 87-O14B; 87-O16B; 87-O18B; 1-O18B; 80-O14; 80-O16; 80-O18; 87-O14; 87-O16; 87-O18; 1-N16; 1-N18; 87-N17; 87-N16; 87-N18; EC16-1; EC16-3; EC-16-12; EC16-14; and mixtures thereof.

5. The delivery system of claim 4, wherein the portion of a virus capsid protein is attached to a surface of the lipid particle.

6. The delivery system of claim 5, wherein the portion of the virus capsid protein is attached to the surface of the lipid particle by an electrostatic interaction or a hydrophobic interaction.

7. A delivery system comprising a particle comprising a lipid layer, wherein a hybrid virus capsid protein comprising at least a portion of a virus capsid protein attached to a least a portion of a non-capsid protein is embedded in the lipid layer, wherein the virus capsid protein is adsorbed to a liposome comprising a targeting moiety,
wherein the lipid particle is selected from: EC16-63; 80-O14B; 80-O16B; 80-O18B; 87-O14B; 87-O16B; 87-O18B; 1-O18B; 80-O14; 80-O16; 80-O18; 87-O14; 87-O16; 87-O18; 1-N16; 1-N18; 87-N17; 87-N16; 87-N18; EC16-1; EC16-3; EC-16-12; EC16-14; and mixtures thereof.

8. The delivery system of claim 7, wherein the particle has a diameter of between 100 and 1000 nm.

9. The particle delivery system of claim 1 wherein the non-capsid protein or peptide:
has a molecular weight of up to a megadalton;
has a molecular weight in a range of 110 to 160 kDA;
comprises a CRISPR protein or peptide, or
comprises Cas9, a Cpf1 or a Cas13a.

10. The particle delivery system of claim 1 further comprising a wild-type capsid protein.

11. The particle delivery system of claim 10, wherein a weight ratio of hybrid capsid protein to wild-type capsid protein is from 1:10 to 1:1.

12. The particle delivery system of claim 1, wherein the virus capsid protein comprises an Adenoviridae or a Parvoviridae or a Rhabdoviridae or an enveloped virus having a glycoprotein protein;
an adeno-associated virus (AAV) or an adenovirus or a VSV or a rabies virus;
a retrovirus;
a lentivirus; or
murine leukemia virus (MuMLV).

13. The particle delivery system of claim 1, wherein the virus capsid protein comprises VP1, VP2 or VP3.

14. The particle delivery system of claim 13 wherein the virus capsid protein is VP3, and the non-capsid protein is inserted into, tethered, or connected to VP3 loop 3 or loop 6.

15. The particle delivery system of claim 1, wherein the particle delivery system is configured to deliver a virus to an interior of a cell.

16. The particle delivery system of claim 15, wherein the virus capsid protein and the non-capsid protein are capable of dissociating after delivery into a cell.

17. The particle delivery system of claim 1, wherein the virus capsid protein is attached to the non-capsid protein by a linker.

18. The particle delivery system of claim 17, wherein:
the linker comprises amino acids;
the linker is a chemical linker;
the linker is cleavable;
the linker is biodegradable;
the linker comprises $(GGGGS)_{1-3}$, ENLYFQG, or a disulfide; or
each terminus of the non-capsid protein is attached to the virus capsid protein by the linker.

19. The particle delivery system of claim 1, wherein:
the non-capsid protein is attached to an exterior portion of the virus capsid protein;
the non-capsid protein is attached to an interior portion of the virus capsid protein or is encapsulated within the virus capsid protein;
the virus capsid protein and the non-capsid protein are a fusion protein;
the virus capsid protein and the non-capsid protein are a fusion protein that is attached to a surface of the lipid through an electrostatic interaction;
the non-capsid protein is attached to the virus capsid protein prior to formation of the virus capsid protein; or
the non-capsid protein is attached to the virus capsid protein after formation of the virus capsid protein.

20. The delivery system of claim 4, wherein the one or more hybrid virus capsid comprise a targeting moiety or a receptor ligand.

21. The particle delivery system of claim 1, wherein the non-capsid protein comprises a tag or one or more heterologous nuclear localization signals(s) (NLSs).

22. The particle delivery system of claim 9, wherein the CRISPR protein or peptide is a Type II CRISPR protein or a Type VI CRISPR protein.

23. The particle delivery system of claim 22, further comprising a guide RNA, optionally complexed with the CRISPR protein.

24. The particle delivery system of claim 22 comprising a protease or nucleic acid molecule(s) encoding a protease that is expressed, whereby the protease cleaves a linker.

25. The delivery system of claim 4, comprising a first hybrid virus capsid protein and a second hybrid virus capsid protein, wherein the first hybrid virus capsid protein comprises a virus capsid protein attached to a first part of a non-capsid protein, and wherein the second hybrid virus capsid protein comprises a second virus capsid protein attached to a second part of the non-capsid protein, wherein the first part of the non-capsid protein and the second part of the non-capsid protein are capable of associating to form a functional protein.

26. The delivery system of claim 25, wherein:
the non-capsid protein is a CRISPR protein and the functional protein is a functional CRISPR protein;
the first hybrid virus capsid protein and the second hybrid virus capsid protein form a capsid of a virus particle;
the first hybrid virus capsid protein is located at an interior of a first virus particle and the second hybrid virus capsid protein is located at an interior of a second virus particle;
the first part of the non-capsid protein linked to a first member of a ligand pair, and the second part of the non-capsid protein is linked to a second member of a ligand pair, wherein the first part of the ligand pair is capable of binding to the second part of the ligand pair in a cell,
wherein the first part of the ligand pair inducibly binds to the second part of the ligand pair;
wherein the first part of the non-capsid protein and the second part of the non-capsid protein comprise one or more NLSs; or
wherein the first part or CRISPR protein and the second part of the non-capsid protein or CRISPR protein comprise one or more nuclear export signals (NESs).

27. A particle delivery system comprising a hybrid protein that comprises a virus outer protein attached to at least a portion of a non-virus outer protein,
wherein the hybrid protein is a hybrid virus capsid protein or hybrid viral outer protein coat or hybrid envelope protein, the virus outer protein is a virus capsid or outer protein coat or envelope protein and the non-virus outer protein is a protein that is not a virus outer coat protein, wherein the virus outer protein is adsorbed to a liposome comprising a targeting moiety,
wherein the lipid particle is selected from: EC16-63; 80-O14B; 80-O16B; 80-O18B; 87-O14B; 87-O16B; 87-O18B; 1-O18B; 80-O14; 80-O16; 80-O18; 87-O14; 87-O16; 87-O18; 1-N16; 1-N18; 87-N17; 87-N16; 87-N18; EC16-1; EC16-3; EC-16-12; EC16-14; and mixtures thereof.

28. The particle delivery system of claim 27, comprising a protease or nucleic acid molecule(s) encoding a protease that is expressed, said protease being capable of cleaving a linker, whereby there can be cleavage of the linker.

29. The particle delivery system of claim 27, wherein the non-virus outer protein is a CRISPR protein and each terminus of the CRISPR protein is attached to the virus outer protein by a linker.

30. A virus particle comprising one or more hybrid virus capsid protein or one or more hybrid virus outer protein, wherein the one or more hybrid virus capsid proteins comprise a virus capsid protein attached to a non-capsid protein or a CRISPR protein, and the hybrid outer virus protein comprises a virus outer protein attached to a non-virus outer protein or a CRISPR protein, wherein the virus particle is adsorbed to a liposome comprising a targeting moiety,
wherein the lipid particle is selected from: EC16-63; 80-O14B; 80-O16B; 80-O18B; 87-O14B; 87-O16B; 87-O18B; 1-O18B; 80-O14; 80-O16; 80-O18; 87-O14; 87-O16; 87-O18; 1-N16; 1-N18; 87-N17; 87-N16; 87-N18; EC16-1; EC16-3; EC-16-12; EC16-14; and mixtures thereof.

31. A pharmaceutical composition comprising the particle delivery system or the delivery system or the virus particle of claim 1.

* * * * *

SEQUENCE LISTING

```
<160> NUMBER OF SEQ ID NOS: 13

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Gly Gly Gly Gly Ser
1               5

<210> SEQ ID NO 2
<211> LENGTH: 10
<212> TYPE: PRT
<213> ORGANISM: Artificial Sequence
<220> FEATURE:
<223> OTHER INFORMATION: GGGGSGGGGS

<400> SEQUENCE: 2

Gly Gly Gly Gly Ser Gly Gly Gly Gly Ser
1               5                   10
```

```
<210> SEQ ID NO 3
<211> LENGTH: 15
<212> TYPE: PRT
<213> ORGANISM: Artificial Sequence
<220> FEATURE:
<223> OTHER INFORMATION: Synthetic

<400> SEQUENCE: 3

Gly Gly Gly Gly Ser Gly Gly Gly Gly Ser Gly Gly Gly Gly Ser
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Glu Asn Leu Tyr Phe Gln Gly
1               5

<210> SEQ ID NO 5
<211> LENGTH: 20
<212> TYPE: DNA
<213> ORGANISM: Homo sapiens

<400> SEQUENCE: 5
gccaaattgg acgaccctcg                                              20

<210> SEQ ID NO 6
<211> LENGTH: 20
<212> TYPE: DNA
<213> ORGANISM: Homo sapiens

<400> SEQUENCE: 6
cgaggagacc cccgtttcgg                                              20

<210> SEQ ID NO 7
<211> LENGTH: 20
<212> TYPE: DNA
<213> ORGANISM: Homo sapiens

<400> SEQUENCE: 7
cccgccgccg ccgtggctcg                                              20

<210> SEQ ID NO 8
<211> LENGTH: 20
<212> TYPE: DNA
<213> ORGANISM: Homo sapiens

<400> SEQUENCE: 8
tgagctctac gagatccaca                                              20

<210> SEQ ID NO 9
<211> LENGTH: 13665
<212> TYPE: DNA
<213> ORGANISM: Artificial Sequence
<220> FEATURE:
<223> OTHER INFORMATION: Synthetic

<400> SEQUENCE: 9
gtcgacggta tcgggggagc tcgcagggtc tccattttga agcgggaggt ttgaacgcgc   60
agccgccatg ccggggtttt acgagattgt gattaaggtc cccagcgacc ttgacgagca  120
```

-continued

```
tctgcccggc atttctgaca gctttgtgaa ctgggtggcc gagaaggaat gggagttgcc      180
gccagattct gacatggatc tgaatctgat tgagcaggca cccctgaccg tggccgagaa      240
gctgcagcgc gactttctga cggaatggcg ccgtgtgagt aaggccccgg aggctctttt      300
ctttgtgcaa tttgagaagg gagagagcta cttccacatg cacgtgctcg tggaaaccac      360
cggggtgaaa tccatggttt tgggacgttt cctgagtcag attcgcgaaa aactgattca      420
gagaatttac cgcgggatcg agccgacttt gccaaactgg ttcgcggtca caaagaccag      480
aaatggcgcc ggaggcggga caaggtggt ggatgagtgc tacatcccca attacttgct       540
ccccaaaacc cagcctgagc tccagtgggc gtggactaat atggaacagt atttaagcgc      600
ctgtttgaat ctcacggagc gtaaacggtt ggtggcgcag catctgacgc acgtgtcgca      660
gacgcaggag cagaacaaag agaatcagaa tcccaattct gatgcgccgg tgatcagatc      720
aaaaacttca gccaggtaca tggagctggt cgggtggctc gtggacaagg ggattacctc      780
ggagaagcag tggatccagg aggaccaggc ctcatacatc tccttcaatg cggcctccaa      840
ctcgcggtcc caaatcaagg ctgccttgga caatgcggga aagattatga gcctgactaa      900
aaccgccccc gactacctgg tgggccagca gcccgtggag gacatttcca gcaatcggat      960
ttataaaatt ttggaactaa acgggtacga tccccaatat gcggcttccg tctttctggg     1020
atgggccacg aaaaagttcg gcaagaggaa caccatctgg ctgtttgggc ctgcaactac     1080
cgggaagacc aacatcgcgg aggccatagc ccacactgtg cccttctacg ggtgcgtaaa     1140
ctggaccaat gagaactttc ccttcaacga ctgtgtcgac aagatggtga tctggtggga     1200
ggaggggaag atgaccgcca agtcgtgga gtcggccaaa gccattctcg aggaagcaa       1260
ggtgcgcgtg gaccagaaat gcaagtcctc ggcccagata gaccccgactc ccgtgatcgt    1320
cacctccaac accaacatgt cgccgtgat tgacgggaac tcaacgacct tcaacacca       1380
gcagccgttg caagaccgga tgttcaaatt tgaactcacc cgccgtctgg atcatgactt     1440
tgggaaggtc accaagcagg aagtcaaaga ctttttccgg tgggcaaagg atcacgtggt    1500
tgaggtggag catgaattct acgtcaaaaa gggtggagcc aagaaaagac ccgcccccag    1560
tgacgcagat ataagtgagc ccaaacgggt gcgcgagtca gttgcgcagc catcgacgtc     1620
agacgcggaa gcttcgatca actacgcgga caggtaccaa aacaaatgtt ctcgtcacgt    1680
gggcatgaat ctgatgctgt ttccctgcag acaatgcgag agactgaatc agaattcaaa    1740
tatctgcttc actcacggtg tcaaagactg tttagagtgc tttcccgtgt cagaatctca    1800
acccgttct gtcgtcaaaa aggcgtatca gaaactgtgc tacattcatc acatcatggg     1860
aaaggtgcca gacgcttgca ctgcttgcga cctggtcaat gtggacttgg atgactgtgt    1920
ttctgaacaa taaatgactt aaaccaggta tgagtcggct ggataaatct aaagtcataa    1980
acggcgctct ggaattactc aatgaagtcg gtatcgaagg cctgacgaca aggaaactcg    2040
ctcaaaagct gggagttgag cagcctaccc tgtactggca cgtgaagaac aagcgggccc    2100
tgctcgatgc cctggccatc gagatgctgg acaggcatca tacccacttc tgccccctgg    2160
aaggcgagtc atggcaagac tttctgcgga caacgccaa gtcattccgc tgtgctctcc     2220
tctcacatcg cgacggggct aaagtgcatc tcggcacccg cccaacagag aaacagtacg    2280
aaaccctgga aaatcagctc gcgttcctgt gtcagcaagg cttctccctg gagaacgcac    2340
tgtacgctct gtccgccgtg ggccacttta cactgggctg cgtattggag gaacaggagc    2400
atcaagtagc aaaagaggaa agagagacac ctaccaccga ttctatgccc ccacttctga    2460
gacaagcaat tgagctgttc gaccggcagg gagccgaacc tgccttcctt ttcggcctgg    2520
```

```
aactaatcat atgtggcctg gagaaacagc taaagtgcga aagcggcggg ccggccgacg   2580
cccttgacga ttttgactta gacatgctcc cagccgatgc ccttgacgac tttgaccttg   2640
atatgctgcc tgctgacgct cttgacgatt ttgaccttga catgctcccc gggtaaatgc   2700
atgaattcga tctagagggc cctattctat agtgtcacct aaatgctaga gctcgctgat   2760
cagcctcgac tgtgccttct agttgccagc catctgttgt ttgcccctcc ccgtgccttt   2820
ccttgaccct ggaaggtgcc actcccactg tcctttccta ataaaatgag gaaattgcat   2880
cgcattgtct gagtaggtgt cattctattc tggggggtgg ggtggggcag gacagcaagg   2940
gggaggattg ggaagacaat agcaggcatg ctggggatgc ggtgggctct atggcttctg   3000
aggcggaaag aaccagctgg ggctcgaatc aagctatcaa gtgccacctg acgtctccct   3060
atcagtgata gagaagtcga cacgtctcga gctccctatc agtgatagag aaggtacgtc   3120
tagaacgtct ccctatcagt gatagagaag tcgacacgtc tcgagctccc tatcagtgat   3180
agagaaggta cgtctagaac gtctccctat cagtgataga gaagtcgaca cgtctcgagc   3240
tccctatcag tgatagagaa ggtacgtcta gaacgtctcc ctatcagtga tagagaagtc   3300
gacacgtctc gagctcccta tcagtgatag agaaggtacc ccctatataa gcagagagat   3360
ctgttcaaat ttgaactgac taagcggctc ccgccagatt ttggcaagat tactaagcag   3420
gaagtcaagg actttttttgc ttgggcaaag gtcaatcagg tgccggtgac tcacgagttt   3480
aaagttccca gggaattggc gggaactaaa ggggcggaga atctctaaa cgcccactg   3540
ggtgacgtca ccaatactag ctataaaagt ctggagaagc gggccaggct ctcatttgtt   3600
cccgagacgc ctcgcagttc agacgtgact gttgatcccg ctcctctgcg accgctagct   3660
tcgatcaact acgcggacag gtaccaaaac aaatgttctc gtcacgtggg catgaatctg   3720
atgctgtttc cctgcagaca atgcgagaga ctgaatcaga attcaaatat ctgcttcact   3780
cacggtgtca aagactgttt agagtgcttt cccgtgtcag aatctcaacc cgtttctgtc   3840
gtcaaaaagg cgtatcagaa actgtgctac attcatcaca tcatgggaaa ggtgccagac   3900
gcttgcactg cttgcgacct ggtcaatgtg gacttggatg actgtgtttc tgaacaataa   3960
atgacttaaa ccaggtatgg ctgccgatgg ttatcttcca gattggctcg aggacaacct   4020
tagtgaagga attcgcgagt ggtgggcttt gaaacctgga gcccctcaac ccaaggcaaa   4080
tcaacaacat caagacaacg ctcgaggtct tgtgcttccg ggttacaaat accttggacc   4140
cggcaacgga ctcgacaagg gggagccggt caacgcagca gacgcggcgg ccctcgagca   4200
cgacaaggcc tacgaccagc agctcaaggc cggagacaac ccgtacctca gtacaaccca   4260
cgccgacgcc gagttccagg agcggctcaa agaagatacg tcttttgggg caacctcgg   4320
gcgagcagtc ttccaggcca aaaagaggct tcttgaacct cttggtctgg ttgaggaagc   4380
ggctaagacg gctcctggaa agaagaggcc tgtagagcag tctcctcagg aaccggactc   4440
ctccgcgggt attggcaaat cgggtgcaca gcccgctaaa aagagactca atttcggtca   4500
gactggcgac acagagtcag tcccagaccc tcaaccaatc ggagaacctc cgcagccccg   4560
ctcaggtgtg ggatctctta caatggcttc aggtggtggc gcaccagtgg cagacaataa   4620
cgaaggtgcc gatggagtgg gtagttcctc gggaaattgg cattgcgatt cccaatggct   4680
gggggacaga gtcatcacca ccagcacccg aacctgggcc ctgcccacct acaacaatca   4740
cctctacaag caaatctcca acagcacatc tggaggatct tcaaatgaca acgcctactt   4800
cggctacagc accccctggg ggtatttga cttcaacaga ttccactgcc acttctcacc   4860
```

```
acgtgactgg cagcgactca tcaacaacaa ctggggattc cggcctaagc gactcaactt    4920
caagctcttc aacattcagg tcaaagaggt tacggacaac aatggagtca agaccatcgc    4980
caataacctt accagcacgg tccaggtctt cacggactca gactatcagc tcccgtacgt    5040
gctcgggtcg gctcacgagg gctgcctccc gccgttccca gcggacgttt tcatgattcc    5100
tcagtacggg tatctgacgc ttaatgatgg aagccaggcc gtgggtcgtt cgtcctttta    5160
ctgcctggaa tatttcccgt cgcaaatgct aagaacgggt aacaacttcc agttcagcta    5220
cgagtttgag aacgtacctt tccatagcag ctacgctcac agccaaagcc tggaccgact    5280
aatgaatcca ctcatcgacc aatacttgta ctatctctct agaactatta acggttctgg    5340
acagaatcaa caaacgctaa aattcagtgt ggccggaccc agcaacatgg ctgtccaggg    5400
aagaaactac atacctggac ccagctaccg acaacaacgt gtctcaacca ctgtgactca    5460
aaacaacaac agcgaatttg cttggcctgg agcttcttct tgggctctca atggacgtaa    5520
tagcttgatg aatcctggac ctgctatggc cagccacaaa gaaggagagg accgtttctt    5580
tcctttgtct ggatctttaa ttttggcaa acaaggtacc ggcagagaca acgtggatgc    5640
ggacaaagtc atgataacca acgaagaaga aattaaaact actaacccgg tagcaacgga    5700
gtcctatgga caagtggcca caaaccacca gagtgcccaa ggaggggggag atcaggcgg    5760
tggaggtagt ggaggaggcg ggagccatca ccaccaccat cacatggccc caaagaagaa    5820
gcggaaggtc ggtatccacg gagtcccagc agccgacaag aagtacagca tcggcctgga    5880
catcggcacc aactctgtgg gctgggccgt gatcaccgac gagtacaagg tgcccagcaa    5940
gaaattcaag gtgctgggca acaccgaccg gcacagcatc aagaagaacc tgatcggagc    6000
cctgctgttc gacagcggcg aaacagccga ggccacccgg ctgaagagaa ccgccagaag    6060
aagatacacc agacggaaga accggatctg ctatctgcaa gagatcttca gcaacgagat    6120
ggccaaggtg gacgacagct tcttccacag actggaagag tccttcctgg tggaagagga    6180
taagaagcac gagcggcacc ccatcttcgg caacatcgtg gacgaggtgg cctaccacga    6240
gaagtacccc accatctacc acctgagaaa gaaactggtg gacagcaccg acaaggccga    6300
cctgcggctg atctatctgg ccctggccca catgatcaag ttccggggcc acttcctgat    6360
cgagggcgac ctgaacccccg acaacagcga cgtggacaag ctgttcatcc agctggtgca    6420
gacctacaac cagctgttcg aggaaaaccc catcaacgcc agcggcgtgg acgccaaggc    6480
catcctgtct gccagactga gcaagagcag acggctggaa aatctgatcg cccagctgcc    6540
cggcgagaag aagaatggcc tgttcggaaa cctgattgcc ctgagcctgg gcctgacccc    6600
caacttcaag agcaacttcg acctggccga ggatgccaaa ctgcagctga gcaaggacac    6660
ctacgacgac gacctggaca acctgctggc ccagatcggc gaccagtacg ccgacctgtt    6720
tctggccgcc aagaacctgt ccgacgccat cctgctgagc gacatcctga gtgaacac    6780
cgagatcacc aaggcccccc tgagcgcctc tatgatcaag agatacgacg agcaccacca    6840
ggacctgacc ctgctgaaag ctctcgtgcg gcagcagctg cctgagaagt acaaagagat    6900
tttcttcgac cagagcaaga acggctacgc cggctacatt gacggcggag ccagccagga    6960
agtttctac aagttcatca agcccatcct ggaaaagatg gacggcaccg aggaactgct    7020
cgtgaagctg aacagagagg acctgctgcg gaagcagcgg accttcgaca cggcagcat    7080
cccccaccag atccacctgg gagagctgca cgccattctg cggcggcagg aagatttta    7140
cccattcctg aaggacaacc gggaaaagat cgagaagatc ctgaccttcc gcatccccta    7200
ctacgtgggc cctctggcca ggggaaacag cagattcgcc tggatgacca gaaagagcga    7260
```

```
ggaaaccatc accccctgga acttcgagga agtggtggac aagggcgctt ccgcccagag   7320
cttcatcgag cggatgacca acttcgataa gaacctgccc aacagaaagg tgctgcccaa   7380
gcacagcctg ctgtacgagt acttcaccgt gtataacgag ctgaccaaag tgaaatacgt   7440
gaccgaggga atgagaaagc ccgccttcct gagcggcgca cagaaaaagg ccatcgtgga   7500
cctgctgttc aagaccaacc ggaaagtgac cgtgaagcag ctgaaagagg actacttcaa   7560
gaaaatcgag tgcttcgact ccgtggaaat ctccggcgtg gaagatcggt tcaacgcctc   7620
cctgggcaca taccacgatc tgctgaaaat tatcaaggac aaggacttcc tggacaatga   7680
ggaaaacgag gacattctgg aagatatcgt gctgaccctg acactgtttg aggacagaga   7740
gatgatcgag gaacggctga aaacctatgc ccacctgttc gacgacaaag tgatgaagca   7800
gctgaagcgg cggagataca ccggctgggg caggctgagc cggaagctga tcaacggcat   7860
ccgggacaag cagtccggca agacaatcct ggatttcctg aagtccgacg cttcgccaa    7920 cagaaacttc atgcagctga tccacgacga cagcctgacc tttaaagagg acatccagaa   7980
agcccaggtg tccggccagg gcgatagcct gcacgagcac attgccaatc tggccggcag   8040
ccccgccatt aagaagggca tcctgcagac agtgaaggtg gtggacgagc tcgtgaaagt   8100
gatgggccgg cacaagcccg agaacatcgt gatcgaaatg gccagagaga accagaccac   8160
ccagaaggga cagaagaaca ccgcgagag aatgaagcgg atcgaagagg gcatcaaaga   8220
gctgggcagc cagatcctga agaacaccc cgtggaaaac acccagctgc agaacgagaa   8280
gctgtacctg tactacctgc agaatgggcg ggatatgtac gtggaccagg aactggacat   8340
caaccggctg tccgactacg atgtggacca tatcgtgcct cagagctttc tggcggacga   8400
ctccatcgac aacaaggtgc tgaccagaag cgacaagaac cggggcaaga gcgcaacgt    8460 gccctccgaa gaggtcgtga agaagatgaa gaactactgg cggcagctgc tgaacgccaa   8520
gctgattacc cagagaaagt tcgacaatct gaccaaggcc gagagaggcg gcctgagcga   8580
actggataag gccggcttca tcaagagaca gctggtggaa acccggcaga tcacaaagca   8640
cgtggcacag atcctggact cccgatgaa cactaagtac gacgagatg acaagctgat    8700 ccgggaagtg aaagtgatca ccctgaagtc caagctggtg tccgatttcc ggaaggattt   8760
ccagttttac aaagtgcgcg agatcaacaa ctaccaccac gcccacgacg cctacctgaa   8820
cgccgtcgtg ggaaccgccc tgatcaaaaa gtaccctgcg ctggaaagcg agttcgtgta   8880
cggcgactac aaggtgtacg acgtgcggaa gatgatcgcc aagagcgagc aggaaatcgg   8940
caaggctacc gccaagtact cttctacag caacatcatg aactttttca agaccgagat    9000
taccctggcc aacggcgaga tccggaaggc gcctctgatc gagacaaacg gcgaaaccgg   9060
ggagatcgtg tgggataagg gccgggattt tgccaccgtg cggaaagtgc tgagcatgcc   9120
ccaagtgaat atcgtgaaaa agaccgaggt gcagacaggc ggcttcagca agagtctat    9180 cctgcccaag aggaacagcg ataagctgat cgccagaaag aaggactggg accctaagaa   9240
gtacggcggc ttcgacagcc ccaccgtggc ctattctgtg ctggtggtgg ccaaagtgga   9300
aaagggcaag tccaagaaac tgaagagtgt gaaagagctg ctgggatca ccatcatgga    9360 aagaagcagc ttcgagaaga atcccatcga ctttctggaa gccaagggct acaaagaagt   9420
gaaaaaggac ctgatcatca agctgcctaa gtactccctg ttcgagctgg aaaacggccg   9480
gaagagaatg ctggcctctg ccggcgaact gcagaaggga aacgaactgg ccctgccctc   9540
caaatatgtg aacttcctgt acctggccag ccactatgag aagctgaagg gctcccccga   9600
```

```
ggataatgag cagaaacagc tgtttgtgga acagcacaag cactacctgg acgagatcat   9660
cgagcagatc agcgagttct ccaagagagt gatcctggcc gacgctaatc tggacaaagt   9720
gctgtccgcc tacaacaagc accgggataa gcccatcaga gagcaggccg agaatatcat   9780
ccacctgttt accctgacca atctgggagc ccctgccgcc ttcaagtact ttgacaccac   9840
catcgaccgg aagaggtaca ccagcaccaa agaggtgctg gacgccaccc tgatccacca   9900
gagcatcacc ggcctgtacg agacacggat cgacctgtct cagctgggag gcgacaaaag   9960
gccggcggcc acgaaaaagg ccggccaggc aaaaaagaaa aagggagggg gaggatcagg  10020
cggtggaggt agtggaggag gcgggagcgc acaggcgcag accggttggg ttcaaaacca  10080
aggaatactt ccgggtatgg tttggcagga cagagatgtg tacctgcaag acccatttg  10140
ggccaaaatt cctcacacgg acggcaactt tcacccttct ccgctgatgg agggttttgg  10200
aatgaagcac ccgcctcctc agatcctcat caaaaacaca cctgtacctg cggatcctcc  10260
aacggccttc aacaaggaca agctgaactc tttcatcacc cagtattcta ctggccaagt  10320
cagcgtggag atcgagtggg agctgcagaa ggaaaacagc aagcgctgga acccggagat  10380
ccagtacact tccaactatt acaagtctaa taatgttgaa tttgctgtta atactgaagg  10440
tgtatatagt gaaccccgcc ccattggcac cagatacctg actcgtaatc tgtaattgct  10500
tgttaatcaa taaaccgttt aattcgtttc agttgaactt tggtctctgc gaagggcgaa  10560
ttcgtttaaa cctgcaggac tagaggtcct gtattagagg tcacgtgagt gttttgcgac  10620
attttgcgac accatgtggt cacgctgggt atttaagccc gagtgagcac gcagggtctc  10680
cattttgaag cgggaggttt gaacgcgcag ccgccaagcc gaattctgca gatatccatc  10740
acactggcgg ccgctcgact agagcggccg ccaccgcggt ggagctccag cttttgttcc  10800
ctttagtgag ggttaattgc gcgcttggcg taatcatggt catagctgtt tcctgtgtga  10860
aattgttatc cgctcacaat tccacacaac atacgagccg aagcataaa gtgtaaagcc  10920
tggggtgcct aatgagtgag ctaactcaca ttaattgcgt tgcgctcact gcccgctttc  10980
cagtcgggaa acctgtcgtg ccagctgcat taatgaatcg gccaacgcgc ggggagaggc  11040
ggtttgcgta ttgggcgctc ttccgcttcc tcgctcactg actcgctgcg ctcggtcgtt  11100
cggctgcggc gagcggtatc agctcactca aaggcggtaa tacggttatc cacagaatca  11160
ggggataacg caggaaagaa catgtgagca aaaggccagc aaaaggccag gaaccgtaaa  11220
aaggccgcgt tgctggcgtt tttccatagg ctccgccccc ctgacgagca tcacaaaaat  11280
cgacgctcaa gtcagaggtg gcgaaacccg acaggactat aaagatacca ggcgtttccc  11340
cctggaagct ccctcgtgcg ctctcctgtt ccgaccctgc cgcttaccgg atacctgtcc  11400
gcctttctcc cttcgggaag cgtggcgctt tctcatagct cacgctgtag gtatctcagt  11460
tcggtgtagg tcgttcgctc caagctgggc tgtgtgcacg aaccccccgt tcagcccgac  11520
cgctgcgcct tatccggtaa ctatcgtctt gagtccaacc cggtaagaca cgacttatcg  11580
ccactggcag cagccactgg taacaggatt agcagagcga ggtatgtagg cggtgctaca  11640
gagttcttga agtggtggcc taactacggc tacactagaa gaacagtatt tggtatctgc  11700
gctctgctga agccagttac cttcggaaaa agagttggta gctcttgatc cggcaaacaa  11760
accaccgctg gtagcggtgg ttttttgtt tgcaagcagc agattacgcg cagaaaaaaa  11820
ggatctcaag aagatccttt gatcttttct acggggtctg acgctcagtg gaacgaaaac  11880
tcacgttaag ggattttggt catgagatta tcaaaaagga tcttcaccta gatccttta  11940
aattaaaaat gaagttttaa atcaatctaa agtatatatg agtaaacttg gtctgacagt  12000
```

```
taccaatgct taatcagtga ggcacctatc tcagcgatct gtctatttcg ttcatccata    12060
gttgcctgac tccccgtcgt gtagataact acgatacggg agggcttacc atctggcccc    12120
agtgctgcaa tgataccgcg agacccacgc tcaccggctc cagatttatc agcaataaac    12180
cagccagccg gaagggccga gcgcagaagt ggtcctgcaa ctttatccgc ctccatccag    12240
tctattaatt gttgccggga agctagagta agtagttcgc cagttaatag tttgcgcaac    12300
gttgttgcca ttgctacagg catcgtggtg tcacgctcgt cgtttggtat ggcttcattc    12360
agctccggtt cccaacgatc aaggcgagtt acatgatccc ccatgttgtg caaaaaagcg    12420
gttagctcct tcggtcctcc gatcgttgtc agaagtaagt tggccgcagt gttatcactc    12480
atggttatgg cagcactgca taattctctt actgtcatgc catccgtaag atgcttttct    12540
gtgactggtg agtactcaac caagtcattc tgagaatagt gtatgcggcg accgagttgc    12600
tcttgcccgg cgtcaatacg ggataatacc gcgccacata gcagaacttt aaaagtgctc    12660
atcattggaa aacgttcttc ggggcgaaaa ctctcaagga tcttaccgct gttgagatcc    12720
agttcgatgt aacccactcg tgcacccaac tgatcttcag catcttttac tttcaccagc    12780
gtttctgggt gagcaaaaac aggaaggcaa aatgccgcaa aaaagggaat aagggcgaca    12840
cggaaatgtt gaatactcat actcttcctt tttcaatatt attgaagcat ttatcagggt    12900
tattgtctca tgagcggata catatttgaa tgtatttaga aaataaaca aataggggtt    12960 ccgcgcacat ttccccgaaa agtgccacct aaattgtaag cgttaatatt ttgttaaaat    13020
tcgcgttaaa ttttttgttaa atcagctcat tttttaacca ataggccgaa atcggcaaaa    13080
tcccttataa atcaaaagaa tagaccgaga tagggttgag tgttgttcca gtttggaaca    13140
agagtccact attaaagaac gtggactcca acgtcaaagg gcgaaaaacc gtctatcagg    13200
gcgatggccc actacgtgaa ccatcaccct aatcaagttt ttttggggtcg aggtgccgta    13260 aagcactaaa tcggaaccct aaagggagcc ccgatttag agcttgacgg ggaaagccgg    13320
cgaacgtggc gagaaaggaa gggaagaaag cgaaaggagc gggcgctagg gcgctggcaa    13380
gtgtagcggt cacgctgcgc gtaaccacca cacccgccgc gcttaatgcg ccgctacagg    13440
gcgcgtccca ttcgccattc aggctgcgca actgttggga agggcgatcg gtgcgggcct    13500
cttcgctatt acgccagctg gcgaaagggg gatgtgctgc aaggcgatta agttgggtaa    13560
cgccagggtt ttcccagtca cgacgttgta aaacgacggc cagtgagcgc gcgtaatacg    13620
actcactata gggcgaattg ggtaccgggc cccccctcga tcgag                    13665
```

<210> SEQ ID NO 10
<211> LENGTH: 9357
<212> TYPE: DNA
<213> ORGANISM: Artificial Sequence
<220> FEATURE:
<223> OTHER INFORMATION: Synthetic

<400> SEQUENCE: 10

```
atgccggggt tttacgagat tgtgattaag gtccccagcg accttgacga gcatctgccc      60
ggcatttctg acagctttgt gaactgggtg gccgagaagg aatgggagtt gccgccagat     120
tctgacatga atctgaatct gattgagcag gcacccctga ccgtggccga aagctgcag      180 cgcgactttc tgacggaatg gcgccgtgtg agtaaggccc cggaggctct tttctttgtg     240
caatttgaga agggagagag ctacttccac atgcacgtgc tcgtggaaac caccggggtg     300
aaatccatgg ttttgggacg tttcctgagt cagattcgcg aaaaactgat tcagagaatt     360
```

```
taccgcggga tcgagccgac tttgccaaac tggttcgcgg tcacaaagac cagaaatggc    420
gccggaggcg ggaacaaggt ggtggatgag tgctacatcc ccaattactt gctccccaaa    480
acccagcctg agctccagtg ggcgtggact aatatggaac agtatttaag cgcctgtttg    540
aatctcacgg agcgtaaacg gttggtggcg cagcatctga cgcacgtgtc gcagacgcag    600
gagcagaaca aagagaatca gaatcccaat tctgatgcgc cggtgatcag atcaaaaact    660
tcagccaggt acatggagct ggtcgggtgg ctcgtggaca aggggattac ctcggagaag    720
cagtggatcc aggaggacca ggcctcatac atctccttca atgcggcctc caactcgcgg    780
tcccaaatca aggctgcctt ggacaatgcg ggaaagatta tgagcctgac taaaaccgcc    840
cccgactacc tggtgggcca gcagcccgtg gaggacattt ccagcaatcg gatttataaa    900
attttggaac taaacgggta cgatcccaa tatgcggctt ccgtctttct gggatgggcc    960
acgaaaaagt tcggcaagag gaacaccatc tggctgtttg ggcctgcaac taccgggaag    1020
accaacatcg cggaggccat agcccacact gtgcccttct acgggtgcgt aaactggacc    1080
aatgagaact ttcccttcaa cgactgtgtc gacaagatgg tgatctggtg ggaggagggg    1140
aagatgaccg ccaaggtcgt ggagtcggcc aaagccattc tcggaggaag caaggtgcgc    1200
gtggaccaga aatgcaagtc ctcggcccag atagacccga ctcccgtgat cgtcacctcc    1260
aacaccaaca tgtgcgccgt gattgacggg aactcaacga ccttcgaaca ccagcagccg    1320
ttgcaagacc ggatgttcaa atttgaactc acccgccgtc tggatcatga ctttgggaag    1380
gtcaccaagc aggaagtcaa agactttttc cggtgggcaa aggatcacgt ggttgaggtg    1440
gagcatgaat tctacgtcaa aaagggtgga gccaagaaaa gacccgcccc cagtgacgca    1500
gatataagtg agcccaaacg ggtgcgcgag tcagttgcgc agccatcgac gtcagacgcg    1560
gaagcttcga tcaactacgc ggacaggtac caaaacaaat gttctcgtca cgtgggcatg    1620
aatctgatgc tgtttccctg cagacaatgc gagagactga atcagaattc aaatatctgc    1680
ttcactcacg gtgtcaaaga ctgtttagag tgctttcccg tgtcagaatc tcaacccgtt    1740
tctgtcgtca aaaggcgta tcagaaactg tgctacattc atcacatcat gggaaaggtg    1800
ccagacgctt gcactgcttg cgacctggtc aatgtggact ggatgactg tgtttctgaa    1860 caataaatga cttaaaccag gtatgagtcg gctggataaa tctaaagtca taaacggcgc    1920
tctggaatta ctcaatgaag tcggtatcga aggcctgacg acaaggaaac tcgctcaaaa    1980
gctgggagtt gagcagccta ccctgtactg gcacgtgaag aacaagcggg ccctgctcga    2040
tgccctggcc atcgagatgc tggacaggca tcatacccac ttctgccccc tggaaggcga    2100
gtcatggcaa gactttctgc ggaacaacgc caagtcattc cgctgtgctc tcctctcaca    2160
tcgcgacggg gctaaagtgc atctcggcac ccgcccaaca gagaaacagt acgaaaccct    2220
ggaaaatcag ctcgcgttcc tgtgtcagca aggcttctcc ctggagaacg cactgtacgc    2280
tctgtccgcc gtgggccact ttacactggg ctgcgtattg gaggaacagg agcatcaagt    2340
agcaaaagag gaaagagaga cacctaccac cgattctatg cccccacttc tgagacaagc    2400
aattgagctg ttcgaccggc agggagccga acctgcctt cttttcggcc tggaactaat    2460
catatgtggc ctggagaaac agctaaagtc cgaaagcggc gggccggccg acgcccttga    2520
cgattttgac ttagacatgc tcccagccga tgcccttgac gactttgacc ttgatatgct    2580
gcctgctgac gctcttgacg attttgacct tgacatgctc cccgggtaaa tgcatgaatt    2640
cgatctagag ggccctattc tatagtgtca cctaaatgct agagctcgct gatcagcctc    2700
gactgtgcct tctagttgcc agccatctgt tgtttgcccc tcccccgtgc cttccttgac    2760
```

```
cctggaaggt gccactccca ctgtcctttc ctaataaaat gaggaaattg catcgcattg    2820
tctgagtagg tgtcattcta ttctggggg tggggtgggg caggacagca aggggagga    2880 ttgggaagac aatagcaggc atgctgggga tgcggtgggc tctatggctt ctgaggcgga    2940
aagaaccagc tggggctcga atcaagctat caagtgccac ctgacgtctc cctatcagtg    3000
atagagaagt cgacacgtct cgagctccct atcagtgata gagaaggtac gtctagaacg    3060
tctccctatc agtgatagag aagtcgacac gtctcgagct ccctatcagt gatagagaag    3120
gtacgtctag aacgtctccc tatcagtgat agagaagtcg acacgtctcg agctccctat    3180
cagtgataga gaaggtacgt ctagaacgtc tccctatcag tgatagagaa gtcgacacgt    3240
ctcgagctcc ctatcagtga tagagaaggt accccctata agcagaga gatctgttca    3300 aatttgaact gactaagcgg ctcccgccag attttggcaa gattactaag caggaagtca    3360 aggactttt tgcttgggca aaggtcaatc aggtgccggt gactcacgag tttaaagttc    3420
ccagggaatt ggcgggaact aaaggggcgg agaaatctct aaaacgccca ctgggtgacg    3480
tcaccaatac tagctataaa agtctggaga agcgggccag gctctcattt gttcccgaga    3540
cgcctcgcag ttcagacgtg actgttgatc ccgctcctct gcgaccgcta gcttcgatca    3600
actacgcgga caggtaccaa acaaatgtt ctcgtcacgt gggcatgaat ctgatgctgt    3660
ttccctgcag acaatgcgag agactgaatc agaattcaaa tatctgcttc actcacggtg    3720
tcaaagactg tttagagtgc tttcccgtgt cagaatctca acccgtttct gtcgtcaaaa    3780
aggcgtatca gaaactgtgc tacattcatc acatcatggg aaaggtgcca gacgcttgca    3840
ctgcttgcga cctggtcaat gtggacttgg atgactgtgt ttctgaacaa taaatgactt    3900
aaaccaggta tggctgccga tggttatctt ccagattggc tcgaggacaa ccttagtgaa    3960
ggaattcgcg agtggtgggc tttgaaacct ggagcccctc aacccaaggc aaatcaacaa    4020
catcaagaca acgctcgagg tcttgtgctt ccgggttaca aataccttgg acccggcaac    4080
ggactcgaca aggggagcc ggtcaacgca gcagacgcgg cggccctcga gcacgacaag    4140
gcctacgacc agcagctcaa ggccggagac aacccgtacc tcaagtacaa ccacgccgac    4200
gccgagttcc aggagcggct caaagaagat acgtcttttg ggggcaacct cgggcgagca    4260
gtcttccagg ccaaaaagag gcttcttgaa cctcttggtc tggttgagga agcggctaag    4320
acggctcctg gaaagaagag gcctgtagag cagtctcctc aggaaccgga ctcctccgcg    4380
ggtattggca aatcgggtgc acagcccgct aaaaagagac tcaatttcgg tcagactggc    4440
gacacagagt cagtcccaga ccctcaacca atcggagaac ctcccgcagc cccctcaggt    4500
gtgggatctc ttacaatggc ttcaggtggt ggcgcaccag tggcagacaa taacgaaggt    4560
gccgatggag tgggtagttc ctcgggaaat tggcattgcg attcccaatg ctgggggac    4620 agagtcatca ccaccagcac ccgaacctgg gccctgccca cctacaacaa tcacctctac    4680
aagcaaatct ccaacagcac atctggagga tcttcaaatg acaacgccta cttcggctac    4740
agcaccccct gggggtattt tgacttcaac agattccact gccacttctc accacgtgac    4800
tggcagcgac tcatcaacaa caactgggga ttccggccta gcgactcaa cttcaagctc    4860 ttcaacattc aggtcaaaga ggttacggac aacaatggag tcaagaccat cgccaataac    4920
cttaccagca cggtccaggt cttcacggac tcagactatc agctcccgta cgtgctcggg    4980
tcggctcacg agggctgcct cccgccgttc ccagcggacg ttttcatgat tcctcagtac    5040
gggtatctga cgcttaatga tggaagccag gccgtgggtc gttcgtcctt ttactgcctg    5100
```

```
gaatatttcc cgtcgcaaat gctaagaacg ggtaacaact tccagttcag ctacgagttt    5160
gagaacgtac ctttccatag cagctacgct cacagccaaa gcctggaccg actaatgaat    5220
ccactcatcg accaatactt gtactatctc tcaaagacta ttaacggttc tggacagaat    5280
caacaaacgc taaaattcag tgtggccgga cccagcaaca tggctgtcca gggaagaaac    5340
tacatacctg gacccagcta ccgacaacaa cgtgtctcaa ccactgtgac tcaaaacaac    5400
aacagcgaat tgcttggcc tggagcttct tcttgggctc tcaatggacg taatagcttg    5460
atgaatcctg gacctgctat ggccagccac aaagaaggag aggaccgttt ctttcctttg    5520
tctggatctt taattttgg caaacaagga actggaagag acaacgtgga tgcggacaaa    5580
gtcatgataa ccaacgaaga agaaattaaa actactaacc cggtagcaac ggagtcctat    5640
ggacaagtgg ccacaaacca ccagagtgcc caagcacagg cgcagaccgg ctgggttcaa    5700
aaccaaggaa tacttccggg tatggtttgg caggacagag atgtgtacct gcaaggaccc    5760
atttgggcca aaattcctca cacggacggc aactttcacc cttctccgct gatgggaggg    5820 tttgaatga agcacccgcc tcctcagatc ctcatcaaaa acacacctgt acctgcggat    5880
cctccaacgg ccttcaacaa ggacaagctg aactcttttca tcacccagta ttctactggc    5940
caagtcagcg tggagatcga gtgggagctg cagaaggaaa acagcaagcg ctggaacccg    6000
gagatccagt acacttccaa ctattacaag tctaataatg ttgaatttgc tgttaatact    6060
gaaggtgtat atagtgaacc ccgcccatt ggcaccagat acctgactcg taatctgtaa    6120
ttgcttgtta atcaataaac cgtttaattc gtttcagttg aactttggtc tctgcgaagg    6180
gcgaattcgt ttaaacctgc aggactagag gtcctgtatt agaggtcacg tgagtgtttt    6240
gcgacatttt gcgacaccat gtggtcacgc tgggtattta agcccgagtg agcacgcagg    6300
gtctccattt tgaagcggga ggtttgaacg cgcagccgcc aagccgaatt ctgcagatat    6360
ccatcacact ggcggccgct cgactagagc ggccgccacc gcggtggagc tccagctttt    6420 gttccccttta gtgagggtta attgcgcgct tggcgtaatc atggtcatag ctgtttcctg    6480
tgtgaaattg ttatccgctc acaattccac acaacatacg agccggaagc ataaagtgta    6540
aagcctgggg tgcctaatga gtgagctaac tcacattaat tgcgttgcgc tcactgcccg    6600
ctttccagtc gggaaacctg tcgtgccagc tgcattaatg aatcggccaa cgcgcgggga    6660
gaggcggttt gcgtattggg cgctcttccg cttcctcgct cactgactcg ctgcgctcgg    6720
tcgttcggct gcggcgagcg gtatcagctc actcaaaggc ggtaatacgg ttatccacag    6780 aatcaggggga taacgcagga aagaacatgt gagcaaaagg ccagcaaaag gccaggaacc    6840
gtaaaaaggc cgcgttgctg gcgtttttcc ataggctccg ccccctgac gagcatcaca    6900 aaaatcgacg ctcaagtcag aggtggcgaa acccgacagg actataaaga taccaggcgt    6960
ttccccctgg aagctccctc gtgcgctctc ctgttccgac cctgccgctt accggatacc    7020
tgtccgcctt tctcccttcg ggaagcgtgg cgctttctca tagctcacgc tgtaggtatc    7080
tcagttcggt gtaggtcgtt cgctccaagc tgggctgtgt gcacgaaccc cccgttcagc    7140
ccgaccgctg cgccttatcc ggtaactatc gtcttgagtc aacccggta agacacgact    7200 tatcgccact ggcagcagcc actggtaaca ggattagcag agcgaggtat gtaggcggtg    7260
ctacagagtt cttgaagtgg tggcctaact acggctacac tagaagaaca gtatttggta    7320
tctgcgctct gctgaagcca gttaccttcg gaaaaagagt tggtagctct tgatccggca    7380
aacaaaccac cgctggtagc ggtggttttt tgtttgcaa gcagcagatt acgcgcagaa    7440
aaaaaggatc tcaagaagat cctttgatct tttctacggg gtctgacgct cagtggaacg    7500
```

```
aaaactcacg ttaagggatt ttggtcatga gattatcaaa aaggatcttc acctagatcc    7560 tttaaatta aaaatgaagt tttaaatcaa tctaaagtat atatgagtaa acttggtctg    7620
acagttacca atgcttaatc agtgaggcac ctatctcagc gatctgtcta tttcgttcat    7680
ccatagttgc ctgactcccc gtcgtgtaga taactacgat acgggagggc ttaccatctg    7740
gccccagtgc tgcaatgata ccgcgagacc cacgctcacc ggctccagat ttatcagcaa    7800
taaaccagcc agccggaagg gccgagcgca gaagtggtcc tgcaacttta tccgcctcca    7860
tccagtctat taattgttgc cgggaagcta gagtaagtag ttcgccagtt aatagtttgc    7920
gcaacgttgt tgccattgct acaggcatcg tggtgtcacg ctcgtcgttt ggtatggctt    7980
cattcagctc cggttcccaa cgatcaaggc gagttacatg atcccccatg ttgtgcaaaa    8040
aagcggttag ctccttcggt cctccgatcg ttgtcagaag taagttggcc gcagtgttat    8100
cactcatggt tatggcagca ctgcataatt ctcttactgt catgccatcc gtaagatgct    8160
tttctgtgac tggtgagtac tcaaccaagt cattctgaga atagtgtatg cggcgaccga    8220
gttgctcttg cccggcgtca atacgggata ataccgcgcc acatagcaga actttaaaag    8280
tgctcatcat tggaaaacgt tcttcggggc gaaaactctc aaggatctta ccgctgttga    8340
gatccagttc gatgtaaccc actcgtgcac ccaactgatc ttcagcatct tttactttca    8400
ccagcgtttc tgggtgagca aaaacaggaa ggcaaaatgc cgcaaaaaag ggaataaggg    8460
cgacacggaa atgttgaata ctcatactct tcctttttca atattattga agcatttatc    8520
agggttattg tctcatgagc ggatacatat ttgaatgtat ttagaaaaat aaacaaatag    8580
gggttccgcg cacatttccc cgaaaagtgc cacctaaatt gtaagcgtta atattttgtt    8640
aaaattcgcg ttaaattttt gttaaatcag ctcattttt aaccaatagg ccgaaatcgg    8700
caaaatccct tataaatcaa aagaatagac cgagataggg ttgagtgttg ttccagtttg    8760
gaacaagagt ccactattaa agaacgtgga ctccaacgtc aaagggcgaa aaaccgtcta    8820
tcagggcgat ggcccactac gtgaaccatc accctaatca agttttttgg ggtcgaggtg    8880
ccgtaaagca ctaaatcgga acctaaaagg gagccccga tttagagctt gacggggaaa    8940
gccggcgaac gtggcgagaa aggaagggaa gaaagcgaaa ggagcgggcg ctagggcgct    9000
ggcaagtgta gcggtcacgc tgcgcgtaac caccacaccc gccgcgctta atgcgccgct    9060
acagggcgcg tcccattcgc cattcaggct gcgcaactgt tgggaagggc gatcggtgcg    9120
ggcctcttcg ctattacgcc agctggcgaa aggggggatgt gctgcaaggc gattaagttg    9180
ggtaacgcca gggttttccc agtcacgacg ttgtaaaacg acggccagtg agcgcgcgta    9240
atacgactca ctatagggcg aattgggtac cgggccccc ctcgatcgag gtcgacggta    9300 tcggggagc tcgcagggtc tccattttga agcgggaggt ttgaacgcgc agccgcc       9357
```

<210> SEQ ID NO 11
<211> LENGTH: 13782
<212> TYPE: DNA
<213> ORGANISM: Artificial Sequence
<220> FEATURE:
<223> OTHER INFORMATION: Synthetic

<400> SEQUENCE: 11

```
atgccggggt tttacgagat tgtgattaag gtccccagcg accttgacga gcatctgccc      60
ggcatttctg acagctttgt gaactgggtg gccgagaagg aatgggagtt gccgccagat     120
tctgacatgg atctgaatct gattgagcag gcaccctga ccgtggccga gaagctgcag     180
```

```
cgcgactttc tgacggaatg gcgccgtgtg agtaaggccc cggaggctct tttctttgtg    240
caatttgaga agggagagag ctacttccac atgcacgtgc tcgtggaaac caccggggtg    300
aaatccatgg ttttgggacg tttcctgagt cagattcgcg aaaaactgat tcagagaatt    360
taccgcggga tcgagccgac tttgccaaac tggttcgcgg tcacaaagac cagaaatggc    420
gccggaggcg ggaacaaggt ggtggatgag tgctacatcc ccaattactt gctccccaaa    480
acccagcctg agctccagtg ggcgtggact aatatggaac agtatttaag cgcctgtttg    540
aatctcacgg agcgtaaacg gttggtggcg cagcatctga cgcacgtgtc gcagacgcag    600
gagcagaaca aagagaatca gaatcccaat tctgatgcgc cggtgatcag atcaaaaact    660
tcagccaggt acatggagct ggtcgggtgg ctcgtggaca aggggattac ctcggagaag    720
cagtggatcc aggaggacca ggcctcatac atctccttca atgcggcctc caactcgcgg    780
tcccaaatca aggctgcctt ggacaatgcg ggaaagatta tgagcctgac taaaaccgcc    840
cccgactacc tggtgggcca gcagcccgtg gaggacattt ccagcaatcg gatttataaa    900
attttggaac taaacgggta cgatcccaa tatgcggctt ccgtctttct gggatgggcc    960
acgaaaaagt tcggcaagag gaacaccatc tggctgtttg gcctgcaac taccgggaag    1020 accaacatcg cggaggccat agcccacact gtgcccttct acgggtgcgt aaactggacc    1080
aatgagaact tcccttcaa cgactgtgtc gacaagatgg tgatctggtg ggaggagggg    1140
aagatgaccg ccaaggtcgt ggagtcgcc aaagccattc tcggaggaag caaggtgcgc    1200
gtggaccaga aatgcaagtc ctcggcccag atagacccga ctcccgtgat cgtcacctcc    1260
aacaccaaca tgtgcgccgt gattgacggg aactcaacga ccttcgaaca ccagcagccg    1320
ttgcaagacc ggatgttcaa atttgaactc acccgccgtc tggatcatga ctttgggaag    1380
gtcaccaagc aggaagtcaa agactttttc cggtgggcaa aggatcacgt ggttgaggtg    1440
gagcatgaat tctacgtcaa aaagggtgga gccaagaaaa gacccgcccc cagtgacgca    1500
gatataagtg agcccaaacg ggtgcgcgag tcagttgcgc agccatcgac gtcagacgcg    1560
gaagcttcga tcaactacgc ggacaggtac caaaacaaat gttctcgtca cgtgggcatg    1620
aatctgatgc tgtttccctg cagacaatgc gagagactga atcagaattc aaatatctgc    1680
ttcactcacg gtgtcaaaga ctgtttagag tgctttcccg tgtcagaatc tcaacccgtt    1740
tctgtcgtca aaaaggcgta tcagaaactg tgctacattc atcacatcat gggaaaggtg    1800
ccagacgctt gcactgcttg cgacctggtc aatgtggact tggatgactg tgtttctgaa    1860
caataaatga cttaaaccag gtatgagtcg gctggataaa tctaaagtca taaacgcgcg    1920
tctggaatta ctcaatgaag tcggtatcga aggcctgacg acaaggaaac tcgctcaaaa    1980
gctgggagtt gagcagccta ccctgtactg gcacgtgaag aacaagcggg ccctgctcga    2040
tgccctggcc atcgagatgc tggacaggca tcatacccac ttctgccccc tggaaggcga    2100
gtcatggcaa gactttctgc ggaacaacgc caagtcattc cgctgtgctc tcctctcaca    2160
tcgcgacggg gctaaagtgc atctcggcac ccgcccaaca gagaaacagt acgaaaccct    2220
ggaaaatcag ctcgcgttcc tgtgtcagca aggcttctcc ctggagaacg cactgtacgc    2280
tctgtccgcc gtgggccact ttacactggg ctgcgtattg gaggaacagg agcatcaagt    2340
agcaaaagag gaaagagaga cacctaccac cgattctatg ccccacttc tgagacaagc    2400 aattgagctg ttcgaccggc agggagccga acctgccttc cttttcggcc tggaactaat    2460
catatgtggc ctggagaaac agctaaagtg cgaaagcggc gggccggccg acgcccttga    2520
cgattttgac ttagacatgc tcccagccga tgcccttgac gactttgacc ttgatatgct    2580
```

```
gcctgctgac gctcttgacg attttgacct tgacatgctc cccgggtaaa tgcatgaatt    2640
cgatctagag ggccctattc tatagtgtca cctaaatgct agagctcgct gatcagcctc    2700
gactgtgcct tctagttgcc agccatctgt tgtttgcccc tccccgtgc cttccttgac     2760 cctggaaggt gccactccca ctgtcctttc taataaaat gaggaaattg catcgcattg     2820
tctgagtagg tgtcattcta ttctgggggg tggggtgggg caggacagca aggggagga    2880 ttgggaagac aatagcaggc atgctgggga tgcgtgggc tctatggctt ctgaggcgga     2940
aagaaccagc tgggctcga atcaagctat caagtgccac ctgacgtctc cctatcagtg    3000
atagagaagt cgacacgtct cgagctccct atcagtgata gagaaggtac gtctagaacg    3060
tctccctatc agtgatagag aagtcgacac gtctcgagct ccctatcagt gatagagaag    3120
gtacgtctag aacgtctccc tatcagtgat agagaagtcg acacgtctcg agctccctat    3180
cagtgataga aaggtacgt ctagaacgtc tccctatcag tgatagagaa gtcgacacgt    3240
ctcgagctcc ctatcagtga tagagaaggt accccctata taagcagaga gatctgttca    3300
aatttgaact gactaagcgg ctcccgccag attttggcaa gattactaag caggaagtca    3360 aggactttt tgcttgggca aaggtcaatc aggtgccggt gactcacgag tttaaagttc    3420
ccagggaatt ggcgggaact aaaggggcgg agaaatctct aaaacgccca ctgggtgacg    3480
tcaccaatac tagctataaa agtctggaga agcgggccag gctctcattt gttcccgaga    3540
cgcctcgcag ttcagacgtg actgttgatc ccgctcctct gcgaccgcta gcttcgatca    3600
actacgcgga caggtaccaa aacaaatgtt ctcgtcacgt gggcatgaat ctgatgctgt    3660
ttccctgcag acaatgcgag agactgaatc agaattcaaa tatctgcttc actcacggtg    3720
tcaaagactg tttagagtgc tttcccgtgt cagaatctca acccgtttct gtcgtcaaaa    3780
aggcgtatca gaaactgtgc tacattcatc acatcatggg aaaggtgcca gacgcttgca    3840
ctgcttgcga cctggtcaat gtggacttgg atgactgtgt ttctgaacaa taaatgactt    3900
aaaccaggtt tagctgccga tggttatctt ccagattggc tcgaggacaa ccttagtgaa    3960
ggaattcgcg agtggtgggc tttgaaacct ggagcccctc aacccaaggc aaatcaacaa    4020
catcaagaca acgctcgagg tcttgtgctt ccgggttaca aataccttgg acccggcaac    4080
ggactcgaca aggggagcc ggtcaacgca gcagacgcgg cggccctcga gcacgacaag     4140
gcctacgacc agcagctcaa ggccggagac aacccgtacc tcaagtacaa ccacgccgac    4200
gccgagttcc aggagcggct caaagaagat acgtcttttg ggggcaaccct cgggcgagca   4260 gtcttccagg ccaaaagag gcttcttgaa cctcttggtc tggttgagga agcggctaag    4320
gccgctcctg gaaagaagag gcctgtagag cagtctcctc aggaaccgga ctcctccgcg    4380
ggtattggca aatcgggtgc acagcccgct aaaaagagac tcaatttcgg tcagactggc    4440
gacacagagt cagtcccaga ccctcaacca atcggagaac ctcccgcagc ccctcaggt    4500 gtgggatctc ttacaatggc ttcaggtggt ggcgcaccag tggcagacaa taacgaaggt    4560
gccgatggag tgggtagttc ctcgggaaat tggcattgcg attcccaatg ctgggggac     4620 agagtcatca ccaccagcac ccgaacctgg gccctgccca cctacaacaa tcacctctac    4680
aagcaaatct ccaacagcac atctggagga tcttcaaatg acaacgccta cttcggctac    4740 agcacccct gggggtattt tgacttcaac agattccact gccacttctc accacgtgac    4800
tggcagcgac tcatcaacaa caactgggga ttccggccta gcgactcaa cttcaagctc    4860 ttcaacattc aggtcaaaga ggttacggac aacaatggag tcaagaccat cgccaataac    4920
```

```
cttaccagca cggtccaggt cttcacggac tcagactatc agctcccgta cgtgctcggg    4980
tcggctcacg agggctgcct cccgccgttc ccagcggacg ttttcatgat tcctcagtac    5040
gggtatctga cgcttaatga tggaagccag gccgtgggtc gttcgtcctt ttactgcctg    5100
gaatatttcc cgtcgcaaat gctaagaacg ggtaacaact tccagttcag ctacgagttt    5160
gagaacgtac ctttccatag cagctacgct cacagccaaa gcctggaccg actaatgaat    5220
ccactcatcg accaatactt gtactatctc tcaaagacta ttaacggttc tggacagaat    5280
caacaaacgc taaaattcag tgtggccgga cccagcaaca tggctgtcca gggaagaaac    5340
tacatacctg gacccagcta ccgacaacaa cgtgtctcaa ccactgtgac tcaaaacaac    5400
aacagcgaat ttgcttggcc tggagcttct tcttgggctc tcaatggacg taatagcttg    5460
atgaatcctg gacctgctat ggccagccac aaagaaggag aggaccgttt ctttcctttg    5520
tctggatctt taattttggg caaacaagga actggaagag acaacgtgga tgcggacaaa    5580
gtcatgataa ccaacgaaga agaaattaaa actactaacc cggtagcaac ggagtcctat    5640
ggacaagtgg ccacaaacca ccagagtgcc caagcacagg cgcagaccgg ctgggttcaa    5700
aaccaaggaa tacttccggg tatggtttgg caggacagag atgtgtacct gcaaggaccc    5760
atttgggcca aaattcctca cacggacgag ggggaggatc aggcggtgga ggtagtggag    5820
gaggcgggag ccatcaccac caccatcaca tggccccaaa gaagaagcgg aaggtcggta    5880
tccacggagt cccagcagcc gacaagaagt acagcatcgg cctggacatc ggcaccaact    5940
ctgtgggctg gccgtgatc accgacgagt acaaggtgcc cagcaagaaa ttcaaggtgc    6000
tgggcaacac cgaccggcac agcatcaaga gaaacctgat cggagccctg ctgttcgaca    6060
gcggcgaaac agccgaggcc acccggctga gagaaccgc cagaagaaga tacaccagac    6120
ggaagaaccg gatctgctat ctgcaagaga tcttcagcaa cgagatggcc aaggtggacg    6180
acagcttctt ccacagactg gaagagtcct tcctggtgga agaggataag aagcacgagc    6240
ggcaccccat cttcggcaac atcgtggacg aggtggccta ccacgagaag taccccacca    6300
tctaccacct gagaaagaaa ctggtggaca gcaccgacaa ggccgacctg cggctgatct    6360
atctggccct ggcccacatg atcaagttcc ggggccactt cctgatcgag gcgacctga    6420 accccgacaa cagcgacgtg gacaagctgt tcatccagct ggtgcagacc tacaaccagc    6480
tgttcgagga aaaccccatc aacgccagcg gcgtggacgc caaggccatc ctgtctgcca    6540
gactgagcaa gagcagacgg ctggaaaatc tgatcgccca gctgcccggc gagaagaaga    6600
atggcctgtt cggaaacctg attgcccgga gcctgggcct gaccccaac ttcaagagca    6660 acttcgacct ggccgaggat gccaaactgc agctgagcaa ggacacctac gacgacgacc    6720
tggacaacct gctggcccag atcggcgacc agtacgccga cctgtttctg gccgccaaga    6780
acctgtccga cgccatcctg ctgagcgaca tcctgagagt gaacaccgag atcaccaagg    6840 ccccccctgag cgcctctatg atcaagagat acgacgagca ccaccaggac ctgaccctgc    6900
tgaaagctct cgtgcggcag cagctgcctg agaagtacaa agagatttc ttcgaccaga    6960 gcaagaacgg ctacgccggc tacattgacg gcggagccag ccaggaagag ttctacaagt    7020
tcatcaagcc catcctggaa aagatggacg gcaccgagga actgctcgtg aagctgaaca    7080
gagaggacct gctgcggaag cagcggacct tcgacaacgg cagcatcccc caccagatcc    7140
acctgggaga gctgcacgcc attctgcggc ggcaggaaga tttttaccca ttcctgaagg    7200 acaacccggga aagatcgag aagatcctga ccttccgcat cccctactac gtgggccctc    7260
tggccagggg aaacagcaga ttcgcctgga tgaccagaaa gagcgaggaa accatcaccc    7320
```

```
cctggaactt cgaggaagtg gtggacaagg gcgcttccgc ccagagcttc atcgagcgga   7380
tgaccaactt cgataagaac ctgcccaacg agaaggtgct gcccaagcac agcctgctgt   7440
acgagtactt caccgtgtat aacgagctga ccaaagtgaa atacgtgacc gagggaatga   7500
gaaagcccgc cttcctgagc ggcgagcaga aaaaggccat cgtggacctg ctgttcaaga   7560
ccaaccggaa agtgaccgtg aagcagctga agaggactac cttcaagaaa atcgagtgct   7620
tcgactccgt ggaaatctcc ggcgtggaag atcggttcaa cgcctccctg gcacatacc    7680 acgatctgct gaaaattatc aaggacaagg acttcctgga caatgaggaa aacgaggaca   7740
ttctggaaga tatcgtgctg accctgacac tgtttgagga cagagagatg atcgaggaac   7800
ggctgaaaac ctatgcccac ctgttcgacg acaaagtgat gaagcagctg aagcggcgga   7860
gatacaccgg ctggggcagg ctgagccgga agctgatcaa cggcatccgg acaagcagt    7920 ccggcaagac aatcctggat ttcctgaagt ccgacggctt cgccaacaga aacttcatgc   7980
agctgatcca cgacgacagc ctgacctta aagaggacta ccagaaagcc caggtgtccg    8040
gccagggcga tagcctgcac gagcacattg ccaatctggc cggcagcccc gccattaaga   8100
agggcatcct gcagacagtg aaggtggtgg acgagctcgt gaaagtgatg ggccggcaca   8160
agcccgagaa catcgtgatc gaaatggcca gagagaacca gaccacccag aagggacaga   8220
agaacagccg cgagagaatg aagcggatcg aagagggcat caaagagctg ggcagccaga   8280
tcctgaaaga acacccgtg gaaaacaccc agctgcagaa cgagaagctg tacctgtact    8340
acctgcagaa tgggcgggat atgtacgtgg accaggaact ggacatcaac cggctgtccg   8400
actacgatgt ggaccatatc gtgcctcaga gctttctggc ggacgactcc atcgacaaca   8460
aggtgctgac cagaagcgac aagaaccggg gcaagagcga caacgtgccc tccgaagagg   8520
tcgtgaagaa gatgaagaac tactggcggc agctgctgaa cgccaagctg attacccaga   8580
gaaagttcga caatctgacc aaggccgaga aggcggcct gagcgaactg gataaggccg    8640
gcttcatcaa gagacagctg gtggaaaccc ggcagatcac aaagcacgtg gcacagatcc   8700
tggactcccg gatgaacact aagtacgacg agaatgacaa gctgatccgg gaagtgaaag   8760 tgatcacct gaagtccaag ctggtgtccg atttccggaa ggatttccag ttttacaaag    8820
tgcgcgagat caacaactac caccacgccc acgacgccta cctgaacgcc gtcgtgggaa   8880 ccgcccctgat caaaagtac cctgcgctgg aaagcgagtt cgtgtacggc gactacaagg    8940
tgtacgacgt gcggaagatg atcgccaaga gcgagcagga aatcggcaag gctaccgcca   9000
agtacttctt ctacagcaac atcatgaact ttttcaagac cgagattacc ctggccaacg   9060
gcgagatccg gaaggcgcct ctgatcgaga caaacggcga aaccggggag atcgtgtggg   9120
ataagggccg ggattttgcc accgtgcgga aagtgctgag catgcccaa gtgaatatcg    9180 tgaaaaagac cgaggtgcag acaggcggct tcagcaaaga gtctatcctg cccaagagga   9240
acagcgataa gctgatcgcc agaaagaagg actgggaccc taagaagtac ggcggcttcg   9300
acagccccac cgtggcctat tctgtgctgg tggtggccaa agtggaaaag gcaagtcca    9360 agaaactgaa gagtgtgaaa gagctgctgg ggatcaccat catggaaaga agcagcttcg   9420
agaagaatcc catcgacttt ctggaagcca agggctacaa agaagtgaaa aaggacctga   9480
tcatcaagct gcctaagtac tcctgttcg agctggaaaa cggcggaag agaatgctgg     9540 cctctgccgg cgaactgcag aagggaaacg aactggccct gcctccaaa tatgtgaact    9600 tcctgtacct ggccagccac tatgagaagc tgaagggctc ccccgaggat aatgagcaga   9660
```

| | |
|---|---|
| aacagctgtt tgtggaacag cacaagcact acctggacga gatcatcgag cagatcagcg | 9720 |
| agttctccaa gagagtgatc ctggccgacg ctaatctgga caaagtgctg tccgcctaca | 9780 |
| acaagcaccg ggataagccc atcagagagc aggccgagaa tatcatccac ctgtttaccc | 9840 |
| tgaccaatct gggagcccct gccgccttca agtactttga caccaccatc gaccggaaga | 9900 |
| ggtacaccag caccaaagag gtgctggacg ccaccctgat ccaccagagc atcaccggcc | 9960 |
| tgtacgagac acggatcgac ctgtctcagc tgggaggcga caaaaggccg gcggccacga | 10020 |
| aaaaggccgg ccaggcaaaa agaaaaagg gaggggagg atcaggcggt ggaggtagtg | 10080 |
| gaggaggcgg gaaaaaggcc ggcggccacg aaaaaggccg gccaggcaaa aagaaaaag | 10140 |
| tacccatacg atgttccaga ttacgctgga ggggaggat caggcggtgg aggtagtgga | 10200 |
| ggaggcggga gcggcaactt tcacccttct ccgctgatgg gagggtttgg aatgaagcac | 10260 |
| ccgcctcctc agatcctcat caaaaacaca cctgtacctg cggatcctcc aacggccttc | 10320 |
| aacaaggaca agctgaactc tttcatcacc cagtattcta ctggccaagt cagcgtggag | 10380 |
| atcgagtggg agctgcagaa ggaaaacagc aagcgctgga acccggagat ccagtacact | 10440 |
| tccaactatt acaagtctaa taatgttgaa tttgctgtta atactgaagg tgtatatagt | 10500 |
| gaaccccgcc ccattggcac cagatacctg actcgtaatc tgtaattgct tgttaatcaa | 10560 |
| taaaccgttt aattcgtttc agttgaactt tggtctctgc gaagggcgaa ttcgtttaaa | 10620 |
| cctgcaggac tagaggtcct gtattagagg tcacgtgagt gttttgcgac attttgcgac | 10680 |
| accatgtggt cacgctgggt atttaagccc gagtgagcac gcagggtctc catttttgaag | 10740 |
| cgggaggttt gaacgcgcag ccgccaagcc gaattctgca gatatccatc acactggcgg | 10800 |
| ccgctcgact agagcggccg ccaccgcggt ggagctccag cttttgttcc ctttagtgag | 10860 |
| ggttaattgc gcgcttggcg taatcatggt catagctgtt tcctgtgtga aattgttatc | 10920 |
| cgctcacaat tccacacaac atacgagccg gaagcataaa gtgtaaagcc tggggtgcct | 10980 |
| aatgagtgag ctaactcaca ttaattgcgt tgcgctcact gcccgctttc cagtcggaa | 11040 |
| acctgtcgtg ccagctgcat taatgaatcg gccaacgcgc ggggagaggc ggtttgcgta | 11100 |
| ttgggcgctc ttccgcttcc tcgctcactg actcgctgcg ctcggtcgtt cggctgcggc | 11160 |
| gagcggtatc agctcactca aaggcggtaa tacggttatc cacagaatca ggggataacg | 11220 |
| caggaaagaa catgtgagca aaaggccagc aaaaggccag gaaccgtaaa aaggccgcgt | 11280 |
| tgctggcgtt tttccatagg ctccgccccc ctgacgagca tcacaaaaat cgacgctcaa | 11340 |
| gtcagaggtg gcgaaacccg acaggactat aaagatacca ggcgtttccc cctggaagct | 11400 |
| ccctcgtgcg ctctcctgtt ccgaccctgc cgcttaccgg atacctgtcc gcctttctcc | 11460 |
| cttcgggaag cgtggcgctt tctcatagct cacgctgtag gtatctcagt tcggtgtagg | 11520 |
| tcgttcgctc caagctgggc tgtgtgcacg aaccccccgt tcagcccgac cgctgcgcct | 11580 |
| tatccggtaa ctatcgtctt gagtccaacc cggtaagaca cgacttatcg ccactggcag | 11640 |
| cagccactgg taacaggatt agcagagcga ggtatgtagg cggtgctaca gagttcttga | 11700 |
| agtggtggcc taactacggc tacactagaa gaacagtatt tggtatctgc gctctgctga | 11760 |
| agccagttac cttcggaaaa agagttggta gctcttgatc cggcaaacaa accaccgctg | 11820 |
| gtagcggtgg tttttttgtt tgcaagcagc agattacgcg cagaaaaaaa ggatctcaag | 11880 |
| aagatccttt gatcttttct acggggtctg acgctcagtg gaacgaaaac tcacgttaag | 11940 |
| ggattttggt catgagatta tcaaaaagga tcttcaccta gatcctttta aattaaaaat | 12000 |
| gaagttttaa atcaatctaa agtatatatg agtaaacttg gtctgacagt taccaatgct | 12060 |

```
taatcagtga ggcacctatc tcagcgatct gtctatttcg ttcatccata gttgcctgac    12120
tccccgtcgt gtagataact acgatacggg agggcttacc atctggcccc agtgctgcaa    12180
tgataccgcg agaccacgc tcaccggctc cagatttatc agcaataaac cagccagccg     12240
gaagggccga gcgcagaagt ggtcctgcaa ctttatccgc ctccatccag tctattaatt    12300
gttgccggga agctagagta agtagttcgc cagttaatag tttgcgcaac gttgttgcca    12360
ttgctacagg catcgtggtg tcacgctcgt cgtttggtat ggcttcattc agctccggtt    12420
cccaacgatc aaggcgagtt acatgatccc ccatgttgtg caaaaaagcg gttagctcct    12480
tcggtcctcc gatcgttgtc agaagtaagt tggccgcagt gttatcactc atggttatgg    12540
cagcactgca taattctctt actgtcatgc catccgtaag atgcttttct gtgactggtg    12600
agtactcaac caagtcattc tgagaatagt gtatgcggcg accgagttgc tcttgcccgg    12660
cgtcaatacg ggataatacc gcgccacata gcagaacttt aaaagtgctc atcattggaa    12720
aacgttcttc ggggcgaaaa ctctcaagga tcttaccgct gttgagatcc agttcgatgt    12780
aacccactcg tgcacccaac tgatcttcag catcttttac tttcaccagc gtttctgggt    12840
gagcaaaaac aggaaggcaa aatgccgcaa aaaagggaat aagggcgaca cggaaatgtt    12900
gaatactcat actcttcctt tttcaatatt attgaagcat ttatcagggt tattgtctca    12960
tgagcggata catatttgaa tgtatttaga aaaataaaca aataggggtt ccgcgcacat    13020
ttccccgaaa agtgccacct aaattgtaag cgttaatatt ttgttaaaat tcgcgttaaa    13080
tttttgttaa atcagctcat tttttaacca ataggccgaa atcggcaaaa tcccttataa    13140
atcaaaagaa tagaccgaga tagggttgag tgttgttcca gtttggaaca agagtccact    13200 attaagaac gtggactcca acgtcaaagg gcgaaaaacc gtctatcagg gcgatggccc     13260
actacgtgaa ccatcaccct aatcaagttt tttggggtcg aggtgccgta aagcactaaa    13320
tcggaaccct aaagggagcc ccgatttag agcttgacgg ggaaagccgg cgaacgtggc    13380
gagaaaggaa gggaagaaag cgaaaggagc gggcgctagg gcgctggcaa gtgtagcggt    13440
cacgctgcgc gtaaccacca cacccgccgc gcttaatgcg ccgctacagg gcgcgtccca    13500
ttcgccattc aggctgcgca actgttggga agggcgatcg gtgcgggcct cttcgctatt    13560
acgccagctg gcgaaagggg gatgtgctgc aaggcgatta agttgggtaa cgccagggtt    13620
ttcccagtca cgacgttgta aaacgacggc cagtgagcgc gcgtaatacg actcactata    13680
gggcgaattg ggtaccgggc cccccctcga tcgaggtcga cggtatcggg ggagctcgca    13740
gggtctccat tttgaagcgg gaggtttgaa cgcgcagccg cc                      13782
```

<210> SEQ ID NO 12
<211> LENGTH: 9357
<212> TYPE: DNA
<213> ORGANISM: Artificial Sequence
<220> FEATURE:
<223> OTHER INFORMATION: Synthetic

<400> SEQUENCE: 12

```
atgccgggt tttacgagat tgtgattaag gtccccagcg accttgacga gcatctgccc      60
ggcatttctg acagctttgt gaactgggtg gccgagaagg aatgggagtt gccgccagat    120
tctgacatgg atctgaatct gattgagcag gcaccctga ccgtggccga gaagctgcag     180
cgcgactttc tgacggaatg gcgccgtgtg agtaaggccc cggaggctct tttctttgtg    240
caatttgaga agggagagag ctacttccac atgcacgtgc tcgtggaaac caccggggtg    300
```

-continued

```
aaatccatgg ttttgggacg tttcctgagt cagattcgcg aaaaactgat tcagagaatt    360
taccgcggga tcgagccgac tttgccaaac tggttcgcgg tcacaaagac cagaaatggc    420
gccggaggcg ggaacaaggt ggtggatgag tgctacatcc ccaattactt gctccccaaa    480
acccagcctg agctccagtg ggcgtggact aatatggaac agtatttaag cgcctgtttg    540
aatctcacgg agcgtaaacg gttggtggcg cagcatctga cgcacgtgtc gcagacgcag    600
gagcagaaca agagaatca gaatcccaat tctgatgcgc cggtgatcag atcaaaaact    660
tcagccaggt acatggagct ggtcgggtgg ctcgtggaca aggggattac ctcggagaag    720
cagtggatcc aggaggacca ggcctcatac atctccttca atgcggcctc caactcgcgg    780
tcccaaatca aggctgcctt ggacaatgcg ggaaagatta tgagcctgac taaaaccgcc    840
cccgactacc tggtgggcca gcagcccgtg gaggacattt ccagcaatcg gatttataaa    900
attttggaac taaacgggta cgatccccaa tatgcggctt ccgtctttct gggatgggcc    960
acgaaaaagt tcggcaagag gaacaccatc tggctgtttg ggcctgcaac taccgggaag   1020
accaacatcg cggaggccat agcccacact gtgcccttct acgggtgcgt aaactggacc   1080
aatgagaact ttcccttcaa cgactgtgtc gacaagatgg tgatctggtg ggaggagggg   1140
aagatgaccg ccaaggtcgt ggagtcggcc aaagccattc tcggaggaag caaggtgcgc   1200
gtggaccaga atgcaagtc ctcggcccag atagacccga ctcccgtgat cgtcacctcc   1260
aacaccaaca tgtgcgccgt gattgacggg aactcaacga ccttcgaaca ccagcagccg   1320
ttgcaagacc ggatgttcaa atttgaactc acccgccgtc tggatcatga ctttgggaag   1380
gtcaccaagc aggaagtcaa agactttttc cggtgggcaa aggatcacgt ggttgaggtg   1440
gagcatgaat tctacgtcaa aaagggtgga gccaagaaaa gacccgcccc cagtgacgca   1500
gatataagtg agcccaaacg ggtgcgcgag tcagttgcgc agccatcgac gtcagacgcg   1560
gaagcttcga tcaactacgc ggacaggtac caaaacaaat gttctcgtca cgtgggcatg   1620
aatctgatgc tgtttccctg cagacaatgc gagagactga atcagaattc aaatatctgc   1680
ttcactcacg gtgtcaaaga ctgtttagag tgctttcccg tgtcagaatc tcaacccgtt   1740
tctgtcgtca aaaaggcgta tcagaaactg tgctacattc atcacatcat gggaaaggtg   1800
ccagacgctt gcactgcttg cgacctggtc aatgtggact tggatgactg tgtttctgaa   1860
caataaatga cttaaaccag gtatgagtcg gctggataaa tctaaagtca taaacgcgc    1920 tctggaatta ctcaatgaag tcggtatcga aggcctgacg acaaggaaac tcgctcaaaa   1980
gctgggagtt gagcagccta ccctgtactg gcacgtgaag aacaagcggg ccctgctcga   2040
tgccctggcc atcgagatgc tggacaggca tcatacccac ttctgccccc tggaaggcga   2100
gtcatggcaa gactttctgc ggaacaacgc caagtcattc cgctgtgctc tcctctcaca   2160
tcgcgacggg gctaaagtgc atctcggcac ccgcccaaca gagaaacagt acgaaaccct   2220
ggaaaatcag ctcgcgttcc tgtgtcagca aggcttctcc ctggagaacg cactgtacgc   2280
tctgtccgcc gtgggccact ttacactggg ctgcgtattg gaggaacagg agcatcaagt   2340
agcaaaagag gaaagagaga cacctaccac cgattctatg cccccacttc tgagacaagc   2400
aattgagctg ttcgaccggc agggagccga acctgcttc cttttcggcc tggaactaat    2460
catatgtggc ctggagaaac agctaaagtg cgaaagcggc gggccggccg acgcccttga   2520
cgattttgac ttagacatgc tcccagccga tgcccttgac gactttgacc ttgatatgct   2580
gcctgctgac gctcttgacg attttgacct tgacatgctc cccgggtaaa tgcatgaatt   2640
cgatctagag ggccctattc tatagtgtca cctaaatgct agagctcgct gatcagcctc   2700
```

```
gactgtgcct tctagttgcc agccatctgt tgtttgcccc tccccgtgc cttccttgac    2760 cctggaaggt gccactccca ctgtcctttc ctaataaaat gaggaaattg catcgcattg    2820
tctgagtagg tgtcattcta ttctgggggg tggggtgggg caggacagca aggggagga    2880 ttgggaagac aatagcaggc atgctgggga tgcggtgggc tctatggctt ctgaggcgga    2940
aagaaccagc tggggctcga atcaagctat caagtgccac ctgacgtctc cctatcagtg    3000
atagagaagt cgacacgtct cgagctccct atcagtgata gagaaggtac gtctagaacg    3060
tctccctatc agtgatagag aagtcgacac gtctcgagct ccctatcagt gatagagaag    3120
gtacgtctag aacgtctccc tatcagtgat agagaagtcg acacgtctcg agctccctat    3180
cagtgataga gaaggtacgt ctagaacgtc tccctatcag tgatagagaa gtcgacacgt    3240
ctcgagctcc ctatcagtga tagagaaggt accccctata aagcagaga gatctgttca    3300 aatttgaact gactaagcgg ctcccgccag attttggcaa gattactaag caggaagtca    3360 aggactttt tgcttgggca aaggtcaatc aggtgccggt gactcacgag tttaaagttc    3420
ccagggaatt ggcgggaact aaaggggcgg agaaatctct aaaacgccca ctgggtgacg    3480
tcaccaatac tagctataaa agtctggaga agcgggccag gctctcattt gttcccgaga    3540
cgcctcgcag ttcagacgtg actgttgatc ccgctcctct gcgaccgcta gcttcgatca    3600
actacgcgga caggtaccaa aacaaatgtt ctcgtcacgt gggcatgaat ctgatgctgt    3660
ttccctgcag acaatgcgag agactgaatc agaattcaaa tatctgcttc actcacggtg    3720
tcaaagactt tttagagtgc tttcccgtgt cagaatctca acccgtttct gtcgtcaaaa    3780
aggcgtatca gaaactgtgc tacattcatc acatcatggg aaaggtgcca gacgcttgca    3840
ctgcttgcga cctggtcaat gtggacttgg atgactgtgt ttctgaacaa taaatgactt    3900
aaaccaggtt tagctgccga tggttatctt ccagattggc tcgaggacaa ccttagtgaa    3960
ggaattcgcg agtggtgggc tttgaaacct ggagcccctc aacccaaggc aaatcaacaa    4020
catcaagaca acgctcgagg tcttgtgctt ccgggttaca aataccttgg acccggcaac    4080
ggactcgaca aggggggagcc ggtcaacgca gcagacgcgg cggccctcga gcacgacaag    4140
gcctacgacc agcagctcaa ggccggagac aacccgtacc tcaagtacaa ccacgccgac    4200
gccgagttcc aggagcggct caaagaagat acgtcttttg ggggcaacct cgggcgagca    4260
gtcttccagg ccaaaaagag gcttcttgaa cctcttggtc tggttgagga gcggctaag    4320 gccgctcctg gaagaagag gcctgtagag cagtctcctc aggaaccgga ctcctccgcg    4380
ggtattggca aatcgggtgc acagcccgct aaaaagagac tcaatttcgg tcagactggc    4440
gacacagagt cagtcccaga ccctcaacca atcggagaac ctcccgcagc cccctcaggt    4500
gtgggatctc ttacaatggc ttcaggtggt ggcgcaccag tggcagacaa taacgaaggt    4560
gccgatggag tgggtagttc ctcgggaaat tggcattgcg attcccaatg ctgggggac    4620 agagtcatca ccaccagcac ccgaacctgg gccctgccca cctacaacaa tcacctctac    4680
aagcaaatct ccaacagcac atctggagga tcttcaaatg acaacgccta cttcggctac    4740
agcaccccct gggggtattt tgacttcaac agattccact gccacttctc accacgtgac    4800
tggcagcgac tcatcaacaa caactgggga ttccggccta gcgactcaa cttcaagctc    4860 ttcaacattc aggtcaaaga ggttacggac aacaatggag tcaagaccat cgccaataac    4920
cttaccagca cggtccaggt cttcacggac tcagactatc agctcccgta cgtgctcggg    4980
tcggctcacg agggctgcct cccgccgttc ccagcggacg ttttcatgat tcctcagtac    5040
```

```
gggtatctga cgcttaatga tggaagccag gccgtgggtc gttcgtcctt ttactgcctg    5100
gaatatttcc cgtcgcaaat gctaagaacg ggtaacaact tccagttcag ctacgagttt    5160
gagaacgtac cttttccatag cagctacgct cacagccaaa gcctggaccg actaatgaat   5220
ccactcatcg accaatactt gtactatctc tcaaagacta ttaacggttc tggacagaat    5280
caacaaacgc taaaattcag tgtggccgga cccagcaaca tggctgtcca gggaagaaac    5340
tacatacctg gacccagcta ccgacaacaa cgtgtctcaa ccactgtgac tcaaaacaac    5400
aacagcgaat ttgcttggcc tggagcttct tcttgggctc tcaatggacg taatagcttg    5460
atgaatcctg gacctgctat ggccagccac aaagaaggag aggaccgttt ctttcctttg    5520
tctggatctt taatttttgg caaacaagga actggaagag acaacgtgga tgcggacaaa    5580
gtcatgataa ccaacgaaga agaaattaaa actactaacc cggtagcaac ggagtcctat    5640
ggacaagtgg ccacaaacca ccagagtgcc caagcacagg cgcagaccgg ctgggttcaa    5700
aaccaaggaa tacttccggg tatggttttgg caggacagag atgtgtacct gcaaggaccc    5760
atttgggcca aaattcctca cacggacggc aactttcacc cttctccgct gatgggaggg    5820
tttggaatga agcacccgcc tcctcagatc ctcatcaaaa acacacctgt acctgcggat    5880
cctccaacgg ccttcaacaa ggacaagctg aactctttca tcacccagta ttctactggc    5940
caagtcagcg tggagatcga gtgggagctg cagaaggaaa acagcaagcg ctggaacccg    6000
gagatccagt acacttccaa ctattacaag tctaataatg ttgaatttgc tgttaatact    6060
gaaggtgtat atagtgaacc cgcccccatt ggcaccagat acctgactcg taatctgtaa    6120
ttgcttgtta atcaataaac cgtttaattc gtttcagttg aactttggtc tctgcgaagg    6180
gcgaattcgt ttaaacctgc aggactagag gtcctgtatt agaggtcacg tgagtgtttt    6240
gcgacatttt gcgacaccat gtggtcacgc tgggtattta gcccgagtg agcacgcagg    6300
gtctccattt tgaagcggga ggtttgaacg cgcagccgcc aagccgaatt ctgcagatat    6360
ccatcacact ggcggccgct cgactagagc ggccgccacc gcgtggagc tccagctttt    6420
gttcccttta gtgagggtta attgcgcgct tggcgtaatc atggtcatag ctgtttcctg    6480
tgtgaaattg ttatccgctc acaattccac acaacatacg agccggaagc ataaagtgta    6540
aagcctgggg tgcctaatga gtgagctaac tcacattaat tgcgttgcgc tcactgcccg    6600
ctttccagtc gggaaacctg tcgtgccagc tgcattaatg aatcggccaa cgcgcgggga    6660
gaggcggttt gcgtattggg cgctcttccg cttcctcgct cactgactcg ctgcgctcgg    6720
tcgttcggct gcggcgagcg gtatcagctc actcaaaggc ggtaatacgg ttatccacag    6780
aatcagggga taacgcagga aagaacatgt gagcaaaagg ccagcaaaag gccaggaacc    6840
gtaaaaaggc cgcgttgctg gcgtttttcc ataggctccg ccccctgac gagcatcaca    6900
aaaatcgacg ctcaagtcag aggtggcgaa acccgacagg actataaaga taccaggcgt    6960
ttccccctgg aagctccctc gtgcgctctc ctgttccgac cctgccgctt accggatacc    7020
tgtccgcctt tctcccttcg ggaagcgtgg cgctttctca tagctcacgc tgtaggtatc    7080
tcagttcggt gtaggtcgtt cgctccaagc tgggctgtgt gcacgaaccc cccgttcagc    7140
ccgaccgctg cgccttatcc ggtaactatc gtcttgagtc aacccggta agacacgact    7200
tatcgccact ggcagcagcc actggtaaca ggattagcag agcgaggtat gtaggcggtg    7260
ctacagagtt cttgaagtgg tggcctaact acggctacac tagaagaaca gtatttggta    7320
tctgcgctct gctgaagcca gttaccttcg gaaaaagagt tggtagctct tgatccggca    7380
aacaaaccac cgctggtagc ggtggttttt ttgtttgcaa gcagcagatt acgcgcagaa    7440
```

```
aaaaaggatc tcaagaagat cctttgatct tttctacggg gtctgacgct cagtggaacg   7500
aaaactcacg ttaagggatt ttggtcatga gattatcaaa aaggatcttc acctagatcc   7560 tttttaaatta aaaatgaagt tttaaatcaa tctaaagtat atatgagtaa acttggtctg   7620
acagttacca atgcttaatc agtgaggcac ctatctcagc gatctgtcta tttcgttcat   7680
ccatagttgc ctgactcccc gtcgtgtaga taactacgat acgggagggc ttaccatctg   7740
gccccagtgc tgcaatgata ccgcgagacc cacgctcacc ggctccagat ttatcagcaa   7800
taaaccagcc agccggaagg gccgagcgca gaagtggtcc tgcaacttta tccgcctcca   7860
tccagtctat taattgttgc cgggaagcta gagtaagtag ttcgccagtt aatagtttgc   7920
gcaacgttgt tgccattgct acaggcatcg tggtgtcacg ctcgtcgttt ggtatggctt   7980
cattcagctc cggttcccaa cgatcaaggc gagttacatg atcccccatg ttgtgcaaaa   8040
aagcggttag ctccttcggt cctccgatcg ttgtcagaag taagttggcc gcagtgttat   8100
cactcatggt tatggcagca ctgcataatt ctcttactgt catgccatcc gtaagatgct   8160
tttctgtgac tggtgagtac tcaaccaagt cattctgaga atagtgtatg cggcgaccga   8220
gttgctcttg cccggcgtca atacgggata ataccgcgcc acatagcaga actttaaaag   8280
tgctcatcat tggaaaacgt tcttcggggc gaaaactctc aaggatctta ccgctgttga   8340
gatccagttc gatgtaaccc actcgtgcac ccaactgatc ttcagcatct tttactttca   8400
ccagcgtttc tgggtgagca aaaacaggaa ggcaaaatgc cgcaaaaaag ggaataaggg   8460
cgacacggaa atgttgaata ctcatactct ccttttttca atattattga agcatttatc   8520
agggttattg tctcatgagc ggatacatat ttgaatgtat ttagaaaaat aaacaaatag   8580
gggttccgcg cacatttccc cgaaaagtgc cacctaaatt gtaagcgtta atattttgtt   8640
aaaattcgcg ttaaattttt gttaaatcag ctcattttt aaccaatagg ccgaaatcgg   8700
caaaatccct tataaatcaa agaatagac cgagataggg ttgagtgttg ttccagtttg   8760
gaacaagagt ccactattaa agaacgtgga ctccaacgtc aaagggcgaa aaaccgtcta   8820
tcagggcgat ggcccactac gtgaaccatc accctaatca agttttttgg ggtcgaggtg   8880
ccgtaaagca ctaaatcgga acctaaaagg agcccccga tttagagctt gacggggaaa   8940
gccggcgaac gtggcgagaa aggaagggaa gaaagcgaaa ggagcgggcg ctagggcgct   9000
ggcaagtgta gcggtcacgc tgcgcgtaac caccacaccc gccgcgctta atgcgccgct   9060
acagggcgcg tcccattcgc cattcaggct gcgcaactgt tgggaagggc gatcggtgcg   9120
ggcctcttcg ctattacgcc agctggcgaa agggggatgt gctgcaaggc gattaagttg   9180
ggtaacgcca gggttttccc agtcacgacg ttgtaaaacg acggccagtg agcgcgcgta   9240
atacgactca ctatagggcg aattgggtac cgggccccc ctcgatcgag gtcgacggta   9300 tcggggagc tcgcagggtc tccattttga agcgggaggt ttgaacgcgc agccgcc      9357
```

<210> SEQ ID NO 13
<211> LENGTH: 9429
<212> TYPE: DNA
<213> ORGANISM: Artificial Sequence
<220> FEATURE:
<223> OTHER INFORMATION: Synthetic

<400> SEQUENCE: 13

```
atgccggggt tttacgagat tgtgattaag gtccccagcg accttgacga gcatctgccc     60
ggcatttctg acagctttgt gaactgggtg gccgagaagg aatgggagtt gccgccagat    120
```

```
tctgacatgg atctgaatct gattgagcag gcaccctga ccgtggccga gaagctgcag    180
cgcgactttc tgacggaatg gcgccgtgtg agtaaggccc cggaggctct tttctttgtg    240
caatttgaga agggagagag ctacttccac atgcacgtgc tcgtggaaac caccggggtg    300
aaatccatgt ttttgggacg tttcctgagt cagattcgcg aaaaactgat tcagagaatt    360
taccgcggga tcgagccgac tttgccaaac tggttcgcgg tcacaaagac cagaaatggc    420
gccggaggcg ggaacaaggt ggtggatgag tgctacatcc ccaattactt gctccccaaa    480
acccagcctg agctccagtg ggcgtggact aatatggaac agtatttaag cgcctgtttg    540
aatctcacgg agcgtaaacg gttggtggcg cagcatctga cgcacgtgtc gcagacgcag    600
gagcagaaca aagagaatca gaatcccaat tctgatgcgc cggtgatcag atcaaaaact    660
tcagccaggt acatggagct ggtcgggtgg ctcgtggaca agggattac ctcggagaag    720 cagtggatcc aggaggacca ggcctcatac atctccttca atgcggcctc caactcgcgg    780
tcccaaatca aggctgcctt ggacaatgcg ggaaagatta tgagcctgac taaaaccgcc    840
cccgactacc tggtgggcca gcagcccgtg gaggacattt ccagcaatcg gatttataaa    900
attttggaac taaacgggta cgatccccaa tatgcggctt ccgtctttct gggatgggcc    960
acgaaaaagt tcggcaagag gaacaccatc tggctgtttg gcctgcaac taccgggaag    1020 accaacatcg cggaggccat agcccacact gtgcccttct acgggtgcgt aaactggacc    1080
aatgagaact ttcccttcaa cgactgtgtc gacaagatgg tgatctggtg ggaggagggg    1140
aagatgaccg ccaaggtcgt ggagtcggcc aaagccattc tcggaggaag caaggtgcgc    1200
gtggaccaga aatgcaagtc ctcggcccag atagacccga ctcccgtgat cgtcacctcc    1260
aacaccaaca tgtgcgccgt gattgacggg aactcaacga ccttcgaaca ccagcagccg    1320
ttgcaagacc ggatgttcaa atttgaactc acccgccgtc tggatcatga ctttgggaag    1380
gtcaccaagc aggaagtcaa agactttttc cggtgggcaa aggatcacgt ggttgaggtg    1440
gagcatgaat tctacgtcaa aaagggtgga gccaagaaaa gacccgcccc cagtgacgca    1500
gatataagtg agcccaaacg ggtgcgcgag tcagttgcgc agccatcgac gtcagacgcg    1560
gaagcttcga tcaactacgc ggacaggtac caaaacaaat gttctcgtca cgtgggcatg    1620
aatctgatgc tgtttccctg cagacaatgc gagagactga atcagaattc aaatatctgc    1680
ttcactcacg gtgtcaaaga ctgtttagag tgctttcccg tgtcagaatc tcaacccgtt    1740
tctgtcgtca aaaaggcgta tcagaaactg tgctacattc atcacatcat gggaaaggtg    1800
ccagacgctt gcactgcttg cgacctggtc aatgtggact tggatgactg tgtttctgaa    1860
caataaatga cttaaaccag gtatgagtcg gctggataaa tctaaagtca taaacggcgc    1920
tctggaatta ctcaatgaag tcggtatcga aggcctgacg acaaggaaac tcgctcaaaa    1980
gctgggagtt gagcagccta ccctgtactg gcacgtgaag aacaagcggg ccctgctcga    2040
tgccctggcc atcgagatgc tggacaggca tcatacccac ttctgccccc tggaaggcga    2100
gtcatggcaa gactttctgc ggaacaacgc caagtcattc cgctgtgctc tcctctcaca    2160
tcgcgacggg gctaaagtgc atctcggcac ccgcccaaca gagaaacagt acgaaaccct    2220
ggaaaatcag ctcgcgttcc tgtgtcagca aggcttctcc ctggagaacg cactgtacgc    2280
tctgtccgcc gtgggccact ttacactggg ctgcgtattg gaggaacagg agcatcaagt    2340
agcaaaagag gaaagagaga cacctaccac cgattctatg cccccacttc tgagacaagc    2400
aattgagctg ttcgaccggc agggagccga acctgccttc ctttcggcc tggaactaat    2460 catatgtggc ctggagaaac agctaaagtg cgaaagcggc gggccggccg acgcccttga    2520
```

```
cgattttgac ttagacatgc tcccagccga tgcccttgac gactttgacc ttgatatgct    2580
gcctgctgac gctcttgacg attttgacct tgacatgctc cccgggtaaa tgcatgaatt    2640
cgatctagag ggccctattc tatagtgtca cctaaatgct agagctcgct gatcagcctc    2700
gactgtgcct tctagttgcc agccatctgt tgtttgcccc tcccccgtgc cttccttgac    2760
cctggaaggt gccactccca ctgtcctttc ctaataaaat gaggaaattg catcgcattg    2820
tctgagtagg tgtcattcta ttctgggggg tggggtgggg caggacagca agggggagga    2880
ttgggaagac aatagcaggc atgctgggga tgcggtgggc tctatggctt ctgaggcgga    2940
aagaaccagc tggggctcga atcaagctat caagtgccac ctgacgtctc cctatcagtg    3000
atagagaagt cgacacgtct cgagctccct atcagtgata gagaaggtac gtctagaacg    3060
tctccctatc agtgatagag aagtcgacac gtctcgagct ccctatcagt gatagagaag    3120
gtacgtctag aacgtctccc tatcagtgat agagaagtcg acacgtctcg agctccctat    3180
cagtgataga gaaggtacgt ctagaacgtc tccctatcag tgatagagaa gtcgacacgt    3240
ctcgagctcc ctatcagtga tagagaaggt accccctata agcagaga gatctgttca    3300 aatttgaact gactaagcgg ctcccgccag attttggcaa gattactaag caggaagtca    3360 aggactttt tgcttgggca aaggtcaatc aggtgccggt gactcacgag tttaaagttc    3420
ccagggaatt ggcgggaact aaaggggcgg agaaatctct aaaacgccca ctgggtgacg    3480
tcaccaatac tagctataaa agtctggaga agcgggccag gctctcattt gttcccgaga    3540
cgcctcgcag ttcagacgtg actgttgatc ccgctcctct gcgaccgcta gcttcgatca    3600
actacgcgga caggtaccaa acaaatgtt ctcgtcacgt gggcatgaat ctgatgctgt    3660
ttccctgcag acaatgcgag agactgaatc agaattcaaa tatctgcttc actcacggtg    3720
tcaaagactg tttagagtgc tttcccgtgt cagaatctca acccgtttct gtcgtcaaaa    3780
aggcgtatca gaaactgtgc tacattcatc acatcatggg aaaggtgcca gacgcttgca    3840
ctgcttgcga cctggtcaat gtggacttgg atgactgtgt ttctgaacaa taaatgactt    3900
aaaccaggta tggctgccga tggttatctt ccagattggc tcgaggacaa ccttagtgaa    3960
ggaattcgcg agtggtgggc tttgaaacct ggagcccctc aacccaaggc aaatcaacaa    4020
catcaagaca acgctcgagg tcttgtgctt ccgggttaca ataccttgg acccggcaac    4080 ggactcgaca agggggagcc ggtcaacgca gcagacgcgg cggccctcga gcacgacaag    4140
gcctacgacc agcagctcaa ggccggagac aacccgtacc tcaagtacaa ccacgccgac    4200
gccgagttcc aggagcggct caaagaagat acgtcttttg ggggcaacct cgggcgagca    4260
gtcttccagg ccaaaaagag gcttcttgaa cctcttggtc tggttgagga agcggctaag    4320
acggctcctg gaaagaagag gcctgtagag cagtctcctc aggaaccgga ctcctccgcg    4380
ggtattggca aatcgggtgc acagcccgct aaaaagagac tcaatttcgg tcagactggc    4440
gacacagagt cagtcccaga ccctcaacca atcgagaac ctcccgcagc ccctcaggt    4500 gtgggatctc ttacaatggc ttcaggtggt ggcgcaccag tggcagacaa taacgaaggt    4560
gccgatggag tgggtagttc ctcgggaaat tggcattgcg attcccaatg ctgggggac    4620 agagtcatca ccaccagcac ccgaacctgg gccctgccca cctacaacaa tcacctctac    4680
aagcaaatct ccaacagcac atctggagga tcttcaaatg acaacgccta cttcggctac    4740 agcacccct gggggtattt tgacttcaac agattccact gccacttctc accacgtgac    4800
tggcagcgac tcatcaacaa caactgggga ttccggccta agcgactcaa cttcaagctc    4860
```

```
ttcaacattc aggtcaaaga ggttacggac aacaatggag tcaagaccat cgccaataac    4920
cttaccagca cggtccaggt cttcacggac tcagactatc agctcccgta cgtgctcggg    4980
tcggctcacg agggctgcct cccgccgttc ccagcggacg tttcatgat tcctcagtac     5040 gggtatctga cgcttaatga tggaagccag gccgtgggtc gttcgtcctt ttactgcctg    5100
gaatatttcc cgtcgcaaat gctaagaacg ggtaacaact tccagttcag ctacgagttt    5160
gagaacgtac ctttccatag cagctacgct cacagccaaa gcctggaccg actaatgaat    5220
ccactcatcg accaatactt gtactatctc tcaaagacta ttaacggttc tggacagaat    5280
caacaaacgc taaaattcag tgtggccgga cccagcaaca tggctgtcca gggaagaaac    5340
tacatacctg gacccagcta ccgacaacaa cgtgtctcaa ccactgtgac tcaaaacaac    5400
aacagcgaat tgcttggcc tggagcttct tcttgggctc tcaatggacg taatagcttg     5460
atgaatcctg gacctgctat ggccagccac aaagaaggag aggaccgttt ctttcctttg    5520
tctggatctt taattttgg caaacaagga actggaagag acaacgtgga tgcggacaaa     5580
gtcatgataa ccaacgaaga agaaattaaa actactaacc cggtagcaac ggagtcctat    5640
ggacaagtgg ccacaaacca ccagagtgcc caagcacagg cgcagaccgg ctgggttcaa    5700
aaccaaggaa tacttccggg tatggtttgg caggacagag atgtgtacct gcaaggaccc    5760
atttgggcca aaattcctca cacggacgaa gaacttttga gcaagaatta tcatcttgag    5820
aacgaagtgg ctcgtcttaa gaaaggttct ggcagtggag gcaactttca cccttctccg    5880
ctgatgggag ggttgggaat gaagcacccg cctcctcaga tcctcatcaa aaacacacct    5940
gtacctgcgg atcctccaac ggccttcaac aaggacaagc tgaactcttt catcacccag    6000
tattctactg gccaagtcag cgtggagatc gagtgggagc tgcagaagga aaacagcaag    6060
cgctggaacc cggagatcca gtacacttcc aactattaca agtctaataa tgttgaattt    6120
gctgttaata ctgaaggtgt atatagtgaa ccccgcccca ttggcaccag atacctgact    6180
cgtaatctgt aattgcttgt taatcaataa accgtttaat tcgtttcagt tgaactttgg    6240
tctctgcgaa gggcgaattc gtttaaacct gcaggactag aggtcctgta ttagaggtca    6300
cgtgagtgtt ttgcgacatt ttgcgacacc atgtggtcac gctgggtatt taagcccgag    6360
tgagcacgca gggtctccat tttgaagcgg gaggtttgaa cgcgcagccg ccaagccgaa    6420
ttctgcagat atccatcaca ctggcggccg ctcgactaga gcggccgcca ccgcggtgga    6480
gctccagctt tgttcccctt tagtgagggt taattgcgcg cttggcgtaa tcatggtcat    6540
agctgtttcc tgtgtgaaat tgttatccgc tcacaattcc acacaacata cgagccggaa    6600
gcataaagtg taaagcctgg ggtgcctaat gagtgagcta actcacatta attgcgttgc    6660
gctcactgcc cgctttccag tcgggaaacc tgtcgtgcca gctgcattaa tgaatcggcc    6720
aacgcgcggg gagaggcggt ttgcgtattg ggcgctcttc cgcttcctcg ctcactgact    6780
cgctgcgctc ggtcgttcgg ctgcggcgag cggtatcagc tcactcaaag gcggtaatac    6840
ggttatccac agaatcaggg gataacgcag gaaagaacat gtgagcaaaa ggccagcaaa    6900
aggccaggaa ccgtaaaaag gccgcgttgc tggcgttttt ccataggctc cgcccccctg    6960
acgagcatca caaaaatcga cgctcaagtc agaggtggcg aaacccgaca ggactataaa    7020
gataccaggc gtttccccct ggaagctccc tcgtgcgctc tcctgttccg accctgccgc    7080
ttaccggata cctgtccgcc tttctccctt cgggaagcgt ggcgctttct catagctcac    7140
gctgtaggta tctcagttcg gtgtaggtcg ttcgctccaa gctgggctgt gtgcacgaac    7200
cccccgttca gcccgaccgc tgcgccttat ccggtaacta tcgtcttgag tccaacccgg    7260
```

```
taagacacga cttatcgcca ctggcagcag ccactggtaa caggattagc agagcgaggt   7320
atgtaggcgg tgctacagag ttcttgaagt ggtggcctaa ctacggctac actagaagaa   7380
cagtatttgg tatctgcgct ctgctgaagc cagttacctt cggaaaaaga gttggtagct   7440
cttgatccgc aaacaaacc accgctggta gcggtggttt ttttgtttgc aagcagcaga   7500
ttacgcgcag aaaaaaagga tctcaagaag atcctttgat cttttctacg gggtctgacg   7560
ctcagtggaa cgaaaactca cgttaaggga ttttggtcat gagattatca aaaaggatct   7620
tcacctagat ccttttaaat taaaaatgaa gttttaaatc aatctaaagt atatatgagt   7680
aaacttggtc tgacagttac caatgcttaa tcagtgaggc acctatctca gcgatctgtc   7740
tatttcgttc atccatagtt gcctgactcc ccgtcgtgta gataactacg atacgggagg   7800
gcttaccatc tggccccagt gctgcaatga taccgcgaga cccacgctca ccggctccag   7860
atttatcagc aataaaccag ccagccggaa gggccgagcg cagaagtggt cctgcaactt   7920
tatccgcctc catccagtct attaattgtt gccgggaagc tagagtaagt agttcgccag   7980
ttaatagttt gcgcaacgtt gttgccattg ctacaggcat cgtggtgtca cgctcgtcgt   8040
ttggtatggc ttcattcagc tccggttccc aacgatcaag gcgagttaca tgatccccca   8100
tgttgtgcaa aaaagcggtt agctccttcg gtcctccgat cgttgtcaga agtaagttgg   8160
ccgcagtgtt atcactcatg gttatggcag cactgcataa ttctcttact gtcatgccat   8220
ccgtaagatg cttttctgtg actggtgagt actcaaccaa gtcattctga atagtgta     8280 tgcggcgacc gagttgctct tgcccggcgt caatacggga taataccgcg ccacatagca   8340
gaactttaaa agtgctcatc attggaaaac gttcttcggg gcgaaaactc tcaaggatct   8400
taccgctgtt gagatccagt tcgatgtaac ccactcgtgc acccaactga tcttcagcat   8460
cttttacttt caccagcgtt tctgggtgag caaaaacagg aaggcaaaat gccgcaaaaa   8520
agggaataag ggcgacacgg aaatgttgaa tactcatact cttccttttt caatattatt   8580
gaagcattta tcagggttat tgtctcatga gcggatacat atttgaatgt atttagaaaa   8640
ataaacaaat aggggttccg cgcacatttc cccgaaaagt gccacctaaa ttgtaagcgt   8700
taatattttg ttaaaattcg cgttaaattt ttgttaaatc agctcatttt ttaaccaata   8760
ggccgaaatc ggcaaaatcc cttataaatc aaaagaatag accgagatag ggttgagtgt   8820
tgttccagtt tggaacaaga gtccactatt aagaacgtg gactccaacg tcaaagggcg   8880
aaaaaccgtc tatcagggcg atggcccact acgtgaacca tcaccctaat caagtttttt   8940
ggggtcgagg tgccgtaaag cactaaatcg gaaccctaaa gggagccccc gatttagagc   9000
ttgacgggga agccggcga acgtggcgag aaaggaaggg aagaaagcga aaggagcggg   9060
cgctagggcg ctggcaagtg tagcggtcac gctgcgcgta accaccacac ccgccgcgct   9120
taatgcgccg ctacagggcg cgtcccattc gccattcagg ctgcgcaact gttgggaagg   9180
gcgatcggtg cgggcctctt cgctattacg ccagctggcg aaagggggat gtgctgcaag   9240
gcgattaagt tgggtaacgc cagggttttc ccagtcacga cgttgtaaaa cgacggccag   9300
tgagcgcgcg taatacgact cactataggg cgaattgggt accgggcccc ccctcgatcg   9360
aggtcgacgg tatcggggga gctcgcaggg tctccatttt gaagcgggag gtttgaacgc   9420
gcagccgcc                                                          9429
```